US012617774B2

(12) United States Patent
Bestvater et al.

(10) Patent No.: US 12,617,774 B2
(45) Date of Patent: May 5, 2026

(54) SUBSTITUTED INDOLE COMPOUNDS AND METHODS OF USE THEREOF

(71) Applicant: NOVARTIS PHARMA AG, Basel (CH)

(72) Inventors: Brian P. Bestvater, Seattle, WA (US); Jinyue Ding, Seattle, WA (US); Robert Gomez, Seattle, WA (US); Nicholas Anton Mateyko, Seattle, WA (US); Taro Oike, Seattle, WA (US); David Andrew Powell, Seattle, WA (US); Victoria Elizabeth Rose, Seattle, WA (US); Tao Sheng, Seattle, WA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 19/223,498

(22) Filed: May 30, 2025

(65) Prior Publication Data

US 2025/0289804 A1 Sep. 18, 2025

Related U.S. Application Data

(63) Continuation of application No. 18/566,259, filed as application No. PCT/US2022/032042 on Jun. 3, 2022.

(60) Provisional application No. 63/346,120, filed on May 26, 2022, provisional application No. 63/290,019, filed on Dec. 15, 2021, provisional application No. 63/196,339, filed on Jun. 3, 2021.

(51) Int. Cl.

| | |
|---|---|
| *A61K 31/4523* | (2006.01) |
| *A61P 13/12* | (2006.01) |
| *C07D 401/06* | (2006.01) |
| *C07D 401/14* | (2006.01) |
| *C07D 403/06* | (2006.01) |
| *C07D 405/14* | (2006.01) |
| *C07D 491/107* | (2006.01) |

(52) U.S. Cl.

CPC ........ *C07D 401/14* (2013.01); *A61K 31/4523* (2013.01); *A61P 13/12* (2018.01); *C07D 401/06* (2013.01); *C07D 403/06* (2013.01); *C07D 405/14* (2013.01); *C07D 491/107* (2013.01)

(58) Field of Classification Search

CPC .................................................. A61K 31/4523

See application file for complete search history.

(56) References Cited

U.S. PATENT DOCUMENTS

| | | | |
|---|---|---|---|
| 9,468,661 | B2 | 10/2016 | Altmann et al. |
| 2016/0152605 | A1 | 6/2016 | Adams et al. |
| 2020/0165262 | A1 | 5/2020 | Wiles et al. |
| 2023/0286947 | A1 | 9/2023 | Luan et al. |

FOREIGN PATENT DOCUMENTS

| | | | |
|---|---|---|---|
| WO | 2022253997 | A1 | 12/2022 |
| WO | 2022254362 | A1 | 12/2022 |
| WO | 2022268648 | A1 | 12/2022 |
| WO | 2023283256 | A1 | 1/2023 |
| WO | 2023009475 | A1 | 2/2023 |
| WO | 2023072197 | A1 | 5/2023 |
| WO | 2023110869 | A1 | 6/2023 |
| WO | 2023227703 | A1 | 11/2023 |

OTHER PUBLICATIONS

Mainolfi, et al., Discovery of 4-((2S,4S)-4-Ethoxy-1-((5-methoxy-7-methyl-1H-indol-4-yl)methyl)piperidin-2-yl) benzoic Acid (LNP023), a Factor B Inhibitor Specifically Designed To Be Applicable to Treating a Diverse Array of Complement Mediated Diseases, Journal of Medicinal Chemistry, 63, 5697-5722, 2020.

PubChem CID 71530547, created date Jun. 11, 2013.

Schubart, et al., Small-molecule factor B inhibitor for the treatment of complement-mediated diseases, PNAS, 116(16), 7926-7931, Apr. 16, 2019.

Office Action dated Dec. 30, 2024 by Canadian Intellectual Property Office in Canada Application No. 3188363.

(Continued)

*Primary Examiner* — Brian E McDowell

(74) *Attorney, Agent, or Firm* — Francine F. Li

(57) ABSTRACT

Provided herein are substituted indole compounds. In certain embodiments, the compounds are inhibitors of the alternative pathway of the complement system, and in particular, inhibitors of complement factor B (CFB). Also provided are compositions comprising the compounds and methods of use thereof. The compounds provided are useful in the treatment, prevention or amelioration of a disease, condition or disorder through inhibition of the complement alternative pathway.

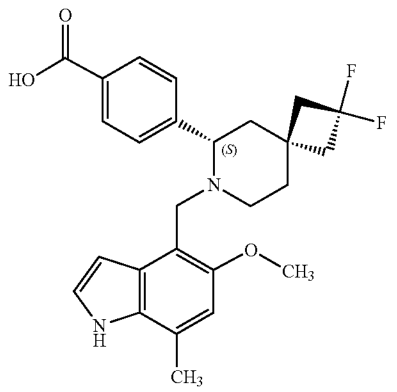

16 Claims, 4 Drawing Sheets

(56) References Cited

OTHER PUBLICATIONS

Response filed Apr. 22, 2025 to Office Action dated Dec. 30, 2024 by Canadian Intellectual Property Office in Canada Application No. 3188363.

Translated Notification of Second Office Action dated May 16, 2025 by China National Intellectual Property Administration in Chinese Application No. 202110898008.4.

Translated Office Action dated Mar. 12, 2025 by Japanese Patent Office in Japanese Application No. 2023-195651.

SUBSTITUTED INDOLE COMPOUNDS AND METHODS OF USE THEREOF

CROSS-REFERENCE TO RELATED APPLICATIONS

This application is a continuation of U.S. Non-Provisional application Ser. No. 18/566,259 filed on Dec. 1, 2023 which is a National Stage application under 35 U.S.C. § 371 of International Application No. PCT/US2022/032042 having an International Filing Date of Jun. 3, 2022, which claims the benefit of U.S. Provisional Patent Application Nos. 63/196,339, filed on Jun. 3, 2021, 63/290,019, filed on Dec. 15, 2021 and 63/346,120, filed on May 26, 2022. The disclosures of each of these applications are incorporated herein by reference in their entireties.

FIELD OF THE INVENTION

Provided herein are substituted indole compounds. In certain embodiments, the compounds are inhibitors of the alternative pathway of the complement system, and in particular, complement factor B (CFB). Also provided are compositions comprising the compounds and methods of use thereof. The compounds provided are useful in the treatment, prevention or amelioration of a disease, condition, or disorder through inhibition of the complement alternative pathway.

BACKGROUND OF THE INVENTION

The complement system is a key component of the innate immunity system with two main functions of host defense against microbial pathogens and clearance of apoptotic cells. Since first discovered by Jules Bordet and Paul Ehrlich in the 1890s, more than a century of research on complement has uncovered its diverse roles in immune response, surveillance, homeostasis, and metabolism (Hajishengallis, Nat Immunol 2017 18: 1288-1298; Sim, Immunobiology 2016 221(10):1037-1045; Ricklin, Nat Immunol 2010 11(9): 785-797). The complement system comprises a large number of soluble proteins that are found in circulation and tissue as inactive zymogens that are activated upon serine protease cleavage. Activation of complement is tightly regulated by both plasma and membrane-bound regulators. Dysregulation of complement activity through genetic mutation, autoantibodies or chronic inflammation has been found to cause tissue damage in various pathological conditions, including autoimmune, inflammatory, neurodegenerative and in a broad range of renal diseases (Zipfel, Nat Rev Immunol 2009 9: 729-749; Holers, Annu Rev Immunol 2014 32: 433-459).

There are three activation pathways: the classical pathway (CP), lectin pathway (LP), and alternative pathway (AP) (Merle, Front Immunol 2015 6: 262). The CP is activated by immunoglobulins (IgG and IgM) and immune complexes through binding of C1q to the Fc domain (Botto, Annu Rev Immunol 2002 205:395-406). The LP is activated by a group of proteins that bind to sugars on the surface of bacteria, for example, mannose binding lectin (MBL) (Garred, Immunol Rev 2016 274(1): 74-97). In contrast to the other two pathways that require specific stimuli for activation, the AP maintains a low level of activation in plasma through a spontaneous hydrolysis process called "tickover" and can also be secondarily activated by the other two complement pathways (Lachmann, Adv Immunol 2009 104: 115-149). The AP forms a rapidly self-amplified loop unless inactivated by factor H and factor I. The three activation pathways generate protease complexes termed "C3 convertases" (C3bBb and C4b2a) to cleave C3, and form C3bBbC3b as C5 convertase. The terminal complement pathway assembles C5b with other complement proteins to form C5b-9 membrane attach complex (MAC), which mediates lysis of pathogens or apoptotic cells (Bhakdi, Immunol Today 1991 12: 318-320). Two soluble fragments of C3 and C5 cleavage products, C3a and C5a, also termed "anaphylatoxins" are potent chemo-attractants that trigger pro-inflammatory responses through their receptors (Klos, Mol Immunol 2009 46(14): 2753-2766).

Complement overactivation and kidney deposition is observed in various chronic kidney diseases (CKDs) including atypical hemolytic uremic syndrome (aHUS), C3 glomerulopathy (C3G), IgA nephropathy (IgAN), membranous nephropathy (MN), ANCA-associated vasculitis (AAV), focal segmental glomerulosclerosis (FSGS) and lupus nephritis (LN) (Harris, Semin Immunopathol 2018 40(1): 125-140; Willows, Clin Med 2020 20(2): 156-160). Preclinical and clinical evidence support the role of complement, especially the AP, in disease initiation and progression. Genetic defects in complement genes, such as CFH, CFI, CFHRs, CFB, C3 and MCP/CD46, have been directly linked to aHUS and C3G (Bu, J Am Soc Nephrol 2014 25(1): 55-64; Marinozzi, J Am Soc Nephrol 2015 25: 2053-2065; Xiao, Semin Thromb Hemost 2014 40(4): 465-471). Complement activation by autoantibodies and immune complexes in the kidney lead to renal injury and contribute to disease progression in multiple glomerular diseases (Corvillo, Front Immunol 2019 10: 886; Marinozzi, J Am Soc Nephrol 2017 28(5): 1603-1613; Seikrit, N Engl J Med 2018 379(25): 2479-2481). Recent studies provide evidence of kidney local production and activation of complement proteins in CKDs such as IgAN and diabetic kidney disease (Mühlig, Front Immunol 2020 11: 1833; Zhou, Clin J Am Soc Nephrol 2021 16(2): 213-224; Kelly Am J Nephrol 2015 41: 48-56). It is believed the local production of complement and the unique microenvironment in the kidney make the organ more susceptible to complement overactivation (Thurman, Clin J Am Soc Nephrol 2020 11:1856).

Significant efforts have been directed towards the development of complement-targeted therapies. Eculizumab is a C5 monoclonal antibody that has been approved for treatment of aHUS. However, when tested in C3G, only a subset of patients who had higher level of C5b-9 (MAC) showed improvement of disease. This is likely due to the contribution of activation fragments at the C3 level upstream of the terminal pathway (Vivarelli, Semin Thromb Hemost 2014 40(4): 472-477). Multiple therapeutic agents targeting different complement pathways are currently in development, each with advantages and limitations (Zipfel, Front Immunol 2019 10: 2166; Thurman, Kidney Int 2016 90(4): 746-752). Nevertheless, there remain needs for potent therapeutic compounds blocking both C3 and C5 levels of the complement system.

As the key enzyme of the AP, CFB provides a highly desirable target to block the central amplification loop and the terminal complement pathway. Knocking out CFB has been shown to be protective in rodent models of C3G (Pickering, Nat Genet 2002 31(4): 424-428), MN (Luo, Front Immunol 2018 9: 1433), ANCA-associated vasculitis (Xiao, Am J Pathol 2007 170(1): 52-64), LN (Watanabe, J Immunol 2000 164(2): 786-794), and multiple renal injury models (Thurman, Am J Physiol Renal Physiol 2012 302: F1529-F1536; Casiraghi, Am J Transplant 2017 17: 2312-2325; Morigi, Sci Rep 2016 6:8445). Genetic deficiency of CFB in these models resulted in reduced proteinuria, protection from renal injury, and prolonged survival. Like many complement proteins, CFB circulates in its native form at high plasma concentration of 300-400 μg/mL. Recently, a selective CFB inhibitor, iptacopan (LNP023), has been shown to bind to active CFB (Schubart Proc Natl Acad Sci USA. 2019 116(16): 7926-7931). In a Phase II clinical trial in C3G, iptacopan demonstrated encouraging efficacy with reduced proteinuria after 12 weeks of treatment (Wong, J Am Soc Nephrol 2020 31: 55A). However, variability in complement activity and patient response was also observed, indicating highly potent compounds with greater and more sustained complement inhibition in vivo could provide greater therapeutic benefit to patients with C3G and a broad range of CKDs.

SUMMARY OF THE INVENTION

In certain embodiments, provided herein are compounds of Formula (I) or a pharmaceutically acceptable salt thereof. In certain embodiments, the compounds are inhibitors of the complement alternative pathway. In certain embodiments, the compounds are inhibitors of complement factor B (CFB). In certain embodiments, the compounds provided herein will confer therapeutic benefits associated with the inhibition of the complement alternative pathway, or CFB, including treating or preventing certain autoimmune disease or disorder, inflammatory disease or disorder, metabolic disease or disorder, neurological disease or disorder, pulmonary disease, respiratory disease or disorder, ophthalmic disease, cardiovascular disease, and kidney disease. Complement-mediated kidney disease includes chronic kidney disease (CKD), diabetic nephropathy, glomerular kidney disease, complement C3 glomerulopathy (C3G), IgA nephropathy (IgAN), membranous nephropathy (MN), focal segmental glomerulosclerosis (FSGS), atypical hemolytic uremic syndrome (aHUS), dense-deposit disease (DDD), minimal change disease (MCD), paroxysmal nocturnal hemoglobinuria (PNH), ANCA-associated vasculitis, lupus nephritis and polycystic kidney disease (PKD).

In certain embodiments, provided herein are compounds of Formula (I):

(I)

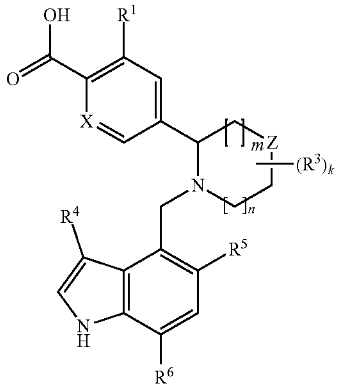

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl, heteroaryl, —C(O)$R^{12}$, —C(O)$NR^{13}R^{14}$ or —$S(O)_tR^{12}$, wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is haloalkyl, —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl;

or $R^{2a}$ and $R^{2b}$, together with the carbon atom to which they are attached, form cycloalkyl or heterocyclyl, wherein the cycloalkyl or heterocyclyl is optionally substituted with one, two or three independently selected $R^{11}$;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl wherein the haloalkyl, deuteroalkyl, —$R_u$-cycloalkyl, —$R_u$-heterocyclyl, cycloalkyl, heterocyclyl or heteroaryl is each optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$R^{12}$, —C(O)$NR^{13}R^{14}$, —$S(O)_tR^{12}$, or —$S(O)_tNR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deuteroC$_{1-3}$alkyl, haloC$_{1-3}$alkyl, cyanoC$_{1-3}$alkyl, hydroxyC$_{1-3}$alkyl, $C_{1-3}$alkoxyC$_{1-3}$alkyl, haloC$_{1-3}$alkoxyC$_{1-3}$alkyl, hydroxyl, $C_{1-3}$alkoxy, haloC$_{1-3}$alkoxy, $C_{1-3}$alkylthio, haloC$_{1-3}$alkylthio, $C_{1-3}$alkylsulfonyl, $C_{1-3}$alkylsulfinyl, or haloC$_{1-3}$alkylsulfinyl; or two $R^{11}$ groups, together with the carbon atom to which they are attached, form $C_{3-5}$cycloalkyl, 3- to 6-membered heterocyclyl or oxo where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1, and n is 1 or 2; and when Z is $CR^{2a}R^{2b}$, m is 1, and $R^{2a}$ and $R^{2b}$, together with the carbon atom to which they are attached, form cycloalkyl, then the cycloalkyl is substituted with at least one $R^{11}$.

Also provided are pharmaceutical compositions formulated for administration by an appropriate route and means containing therapeutically effective concentrations of one or more of the compounds provided herein, or pharmaceutically acceptable salts thereof, and optionally comprising at least one pharmaceutical carrier.

In another aspect, provided herein are methods of treating a disease or disorder mediated by the complement alternative pathway, and particularly by complement factor B, comprising administering to a subject having such disease or disorder, a therapeutically effective amount of one or more compounds disclosed herein, or a pharmaceutically acceptable salt thereof, or the pharmaceutical compositions disclosed herein. In certain embodiments, the disease or disorder is chronic kidney disease (CKD), diabetic nephropathy, glomerular kidney disease, complement C3 glomerulopathy (C3G), IgA nephropathy (IgAN), membranous nephropathy (MN), focal segmental glomerulosclerosis (FSGS), atypical hemolytic uremic syndrome (aHUS), dense-deposit disease (DDD), minimal change disease (MCD), paroxysmal nocturnal hemoglobinuria (PNH), ANCA-associated vasculitis, lupus nephritis, polycystic kidney disease (PKD), autosomal dominant polycystic kidney disease (ADPKD), autosomal recessive polycystic kidney disease (ARPKD), end stage renal disease (ESRD), acute kidney injury, or polycystic liver disease.

Also provided herein are combination therapies using one or more compounds or compositions provided herein, in combination with other pharmaceutical agents for the treatment of the diseases and disorders described herein. These and other aspects of the subject matter described herein will become evident upon reference to the following detailed description and drawings.

DETAILED DESCRIPTION OF THE INVENTION

A. Definitions

Figure 1:
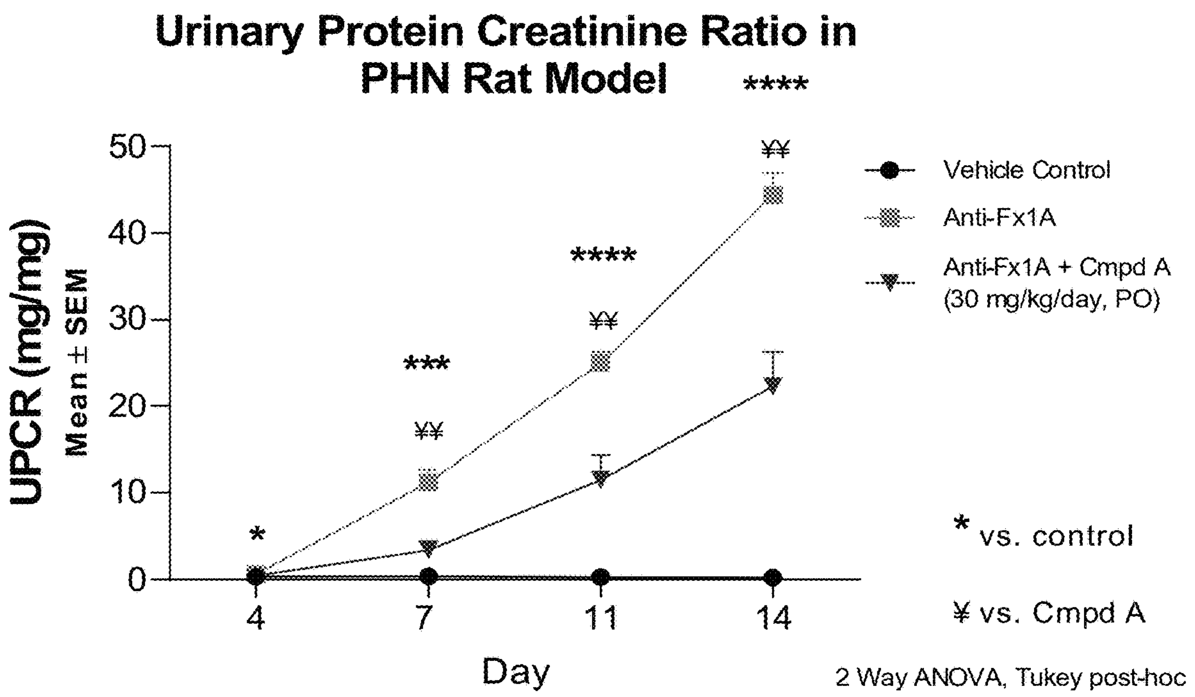
FIG. 1 depicts the impact of therapeutic administration of Compound A of Formula I (dosed orally at 30 mg/kg/day QD) on urinary protein to creatinine ratio (UPCR) in an anti-Fx1a challenged rat model of membranous nephropathy (Passive Heymann Nephritis model or PHN).

Unless defined otherwise, all technical and scientific terms used herein have the same meaning as is commonly understood by one of ordinary skill in the art. In the event that there are a plurality of definitions for a term herein, those in this section prevail unless stated otherwise.

As used herein, when used to refer to modify a numerical value, the term "about" encompasses a range of uncertainty of the numerical value of from 0% to 10% of the numerical value.

The term "alkyl" as used herein and unless otherwise indicated, refers to a saturated hydrocarbon chain that may be a straight chain or branched chain, containing the indicated number of carbon atoms or otherwise having from one to ten, one to eight, one to six, one to four or one to three carbon atoms, and which is attached to the rest of the molecule by a single bond. In certain embodiments, the hydrocarbon chain is optionally deuterated. For example, $C_1$-$C_3$ alkyl indicates that the group may have from 1 to 3 (inclusive) carbon atoms; $C_1$-$C_6$ alkyl indicates that the group may have from 1 to 6 (inclusive) carbon atoms. In some embodiments, an alkyl is a $C_1$-$C_3$ alkyl which represents a straight-chain or branched saturated monovalent hydrocarbon group having 1 to 3 carbon atoms. In some embodiments, an alkyl is a $C_1$-$C_6$ alkyl which represents a straight-chain or branched saturated monovalent hydrocarbon group having 1 to 6 carbon atoms. Examples of alkyl include without limitation methyl, ethyl, n-propyl, isopropyl, n-butyl, isobutyl, sec-butyl, and tert-butyl.

The term "alkoxy" as used herein and unless otherwise indicated, refers to a group of the formula —OR wherein R is alkyl as defined herein. Alkoxy can be, for example, methoxy, ethoxy, n-propoxy, isopropoxy, n-butoxy, iso-butoxy, sec-butoxy, n-pentoxy, 2-pentoxy, 3-pentoxy, or hexyloxy. Likewise, the term "alkylthio" refers to a group of formula —S-(alkyl). The terms "haloalkoxy" and "haloalkylthio" refer to —O-(haloalkyl) and —S-(haloalkyl), respectively.

The term "alkylsulfinyl" as used herein and unless otherwise indicated, refers to the group of the formula —S(O)R wherein R is alkyl as defined herein.

The term "alkylsulfonyl" as used herein and unless otherwise indicated, refers to the group of the formula —$S(O)_2R$ wherein R is alkyl as defined herein.

The term "aryl" as used herein and unless otherwise indicated, is intended to mean any stable monocyclic or bicyclic carbon ring of up to 6 members in each ring, wherein at least one ring is aromatic. Examples of aryl include phenyl, naphthyl, tetrahydronaphthyl, indanyl, or biphenyl.

The term "azolyl" as used herein and unless otherwise indicated, refers to a 5-membered heteroaryl ring system containing at least one nitrogen atom. Examples of azolyl include pyrrole, imidazole, pyrazole, thiazole, isothiazole, oxazole, isoxazole, thiadiazole and oxadiazole.

The term "cycloalkyl" as used herein and unless otherwise indicated, refers to a monocyclic, bicyclic, tricyclic or other polycyclic hydrocarbon group having the indicated number of ring carbon atoms or otherwise having three to ten carbon atoms and which are fully saturated or partially unsaturated (i.e., non-aromatic). Multicyclic cycloalkyl may be fused, bridged and/or spiro-ring systems. Cycloalkyl groups include, but are not limited to, cyclopropyl, cyclobutyl, cyclopentyl, cyclohexyl, cycloheptyl, cyclooctyl, norbornyl, bicyclo[1.1.1]pentane, bicyclo[2.2.1]heptane, bicyclo[3.1.1]heptane, spiro[3.3]heptane, and partially unsaturated hydrocarbon rings such as cyclobutylene, cyclopentene and cyclohexene. In some embodiments, cycloalkyl is a monocyclic $C_3$-$C_8$ cycloalkyl.

The term "deuterium" as used herein and unless otherwise indicated, refers to the heavy isotope of hydrogen represented by the symbol D or $^2$H. As used herein, when a particular position in a compound is designated as "deuterated", as having deuterium or having the prefix "deutero-", it is understood that the compound is an isotopically enriched compound and the presence of deuterium at that position in the compound is substantially greater than its natural abundance of 0.0156%, for example, at least 90% deuterium in the specified position(s).

The term "deuteroalkyl" as used herein and unless otherwise indicated, refers to an alkyl group in which one or more hydrogen atoms of the alkyl are replaced with deuterium in substantially greater abundance than its natural abundance, for example, at least 90% deuterium in the specified position(s).

The term "enantiomerically pure" or "pure enantiomer" as used herein denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of a single enantiomer to the exclusion of its corresponding non-superimposable mirror image. Some embodiments described herein provide a compound that is present as a pure enantiomer. Some embodiments also provide pharmaceutical compositions comprising an enantiomerically pure compound described herein.

The term "halo", "halogen" or "halide" as used herein and unless otherwise indicated, refers to a monovalent fluorine, chlorine, bromine or iodine group.

The term "haloalkyl" as used herein and unless otherwise indicated, refers to a monovalent alkyl group in which at least one hydrogen atom is replaced by a halogen. In some embodiments, more than one hydrogen atom (e.g., 2, 3, 4, 5 or 6) are replaced by independently selected halogens. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halogens (sometimes referred to herein as perhaloalkyl, e.g., perfluoroalkyl, such as trifluoromethyl).

The term "cyano" as used herein and unless otherwise indicated, refers to a —CN group.

The term "cyanoalkyl" as used herein and unless otherwise indicated, refers to an alkyl group in which one hydrogen atom of the alkyl is replaced with a cyano group, as defined herein.

The term "heterocycle", "heterocyclyl" or "heterocyclic" as used herein and unless otherwise indicated, represents a stable 3-, 4-, 5-, 6- or 7-membered monocyclic-, a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e., saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, and/or spiro-bicyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, heterocyclyl is monocyclic having 4 to 7, preferably 4 to 6, ring atoms, of which at least 1 heteroatom is N and the second heteroatom is N, O or S. In certain embodiments, the heterocyclyl is azetidine, pyrrolidine, piperidine, piperazine, morpholine or thiomorpholine. In some embodiments, a heterocyclyl group is bicyclic, and in which case, the first ring (the point of attachment to the remainder of the molecule) is saturated or partially saturated monocyclic heterocyclyl as described herein, and the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, diydrobenzimidazolyl, dihydrobenzoxazole, and dihydrobenzothiazolyl, and N-oxides or sulfones or sulfoxides thereof.

The term "heteroaryl", as used herein and unless otherwise indicated, represents a stable 5-, 6- or 7-membered monocyclic- or stable 9- or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms or a carbon atom of the heteroaryl may optionally be oxidized, and the nitrogen heteroatom may optionally be quaternized. In the case of a "heteroaryl" which is a bicyclic group, the first ring (the point of attachment to the remainder of the molecule) is a monocyclic heteroaryl group as described herein, and the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, pyridinone, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof.

The term "oxo" refers to a carbonyl (C═O) group. When a carbon atom is indicated as being substituted with an oxo group, it is understood that two hydrogen atoms will be removed from the carbon atom and replaced with ═O. Similarly, when a carbon atom is indicated as being substituted by two groups, and may be substituted with an "oxo" group, the two substituents may come together to form the oxo group.

The term "subject" as used herein and unless otherwise indicated, refers to any human or veterinary subject, including mammals such as mice, rats, cows, sheep, pigs, rabbits, goats, horses, monkeys, dogs, cats, and humans, including neonatal, infant, juvenile, adolescent, adult or geriatric patients.

The term "thiol" refers to a group having the formula —SH.

The term "therapeutically effective amount" is an amount sufficient to effect beneficial or desired clinical results. A therapeutically effective amount can be administered in one or more administrations. A therapeutically effective amount is sufficient to palliate, ameliorate, stabilize, reverse, slow or delay the progression of the disease state.

Unless stated otherwise or specifically described, it is understood that substitutions where present can occur on any atom of the alkyl, cycloalkyl, heterocyclyl, aryl or heteroaryl groups, valence permitting.

Unless specifically stated otherwise, where a compound may assume alternative tautomeric or stereoisomeric forms, all alternative isomers are intended to be encompassed within the scope of the claimed subject matter. For example, unless specifically stated otherwise, the compounds provided herein may be stereoisomerically pure (e.g., single enantiomers or diastereomers), or be mixtures of stereoisomers such as racemic or diastereomeric mixtures.

The term "treating", "treat", or "treatment" refers generally to controlling, alleviating, ameliorating, slowing the progress of and/or eliminating a named condition once the condition has been established. In addition to its customary meaning, the term "preventing", "prevent", or "prevention" also refers to delaying the onset of, or reducing the risk of developing a named condition or of a process that can lead to the condition, and/or the recurrence of symptoms of a condition.

In the description herein, if there is any discrepancy between a chemical name and chemical structure, the chemical structure controls.

B. Compounds

In certain embodiments, provided herein are compounds of Formula (I):

(I)

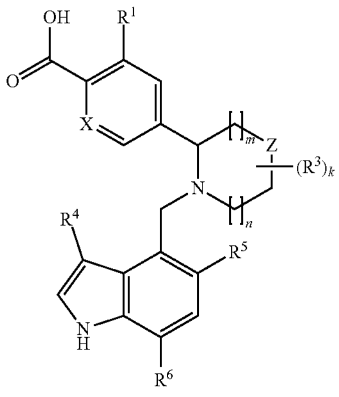

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl, heteroaryl, —C(O)$R^{12}$, —C(O)$NR^{13}R^{14}$ or —$S(O)_tR^{12}$, wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl; or $R^{2a}$ and $R^{2b}$, together with the carbon atom to which they are attached, form cycloalkyl or heterocyclyl, wherein the cycloalkyl or heterocyclyl is optionally substituted with one, two or three independently selected $R^{11}$;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl, wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$R^{12}$, —C(O)$NR^{13}R^{14}$, —$S(O)_tR^{12}$, or —$S(O)_tNR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo, where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1 and n is 1 or 2; and when Z is $CR^{2a}R^{2b}$ and $R^{2a}$ and $R^{2b}$, together with the carbon atom to which they are attached, form cycloalkyl, and m is 1, then the cycloalkyl is substituted with at least one $R^{11}$.

In certain embodiments, provided herein are compounds of Formula (I):

(I)

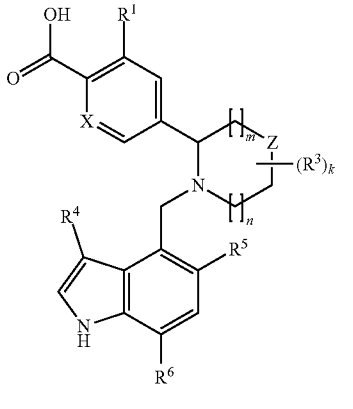

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl, heteroaryl, —C(O)$R^{12}$, —C(O)$NR^{13}R^{14}$ or —$S(O)_tR^{12}$, wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deutero$C_{1-3}$alkyl, or halo$C_{1-3}$alkyl; or $R^{2a}$ and $R^{2b}$, together with the carbon atom to which they are attached, form cycloalkyl or heterocyclyl, wherein the cycloalkyl or heterocyclyl is optionally substituted with one, two or three independently selected $R^{11}$;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl, wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$R^{12}$, —C(O)$NR^{13}R^{14}$, —$S(O)_tR^{12}$, or —$S(O)_tNR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1 and n is 1 or 2; and when Z is $CR^{2a}R^{2b}$ and $R^{2a}$ and $R^{2b}$, together with the carbon atom to which they are attached, form cycloalkyl, and m is 1, then the cycloalkyl is substituted with at least one $R^{11}$.

In certain embodiments, provided herein are compounds of Formula (I):

(I)

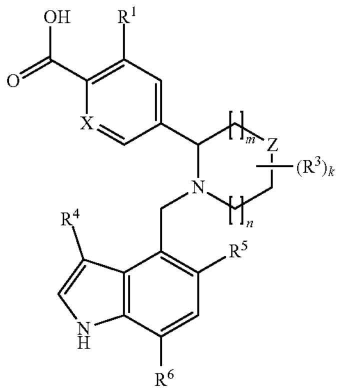

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl, heteroaryl, —C(O)$R^{12}$, —C(O)$NR^{13}R^{14}$ or —S(O)$R^{12}$, wherein the alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl; or $R^{2a}$ and $R^{2b}$, together with the carbon atom to which they are attached, form cycloalkyl substituted with one, two or three independently selected $R^{11}$ or form heterocyclyl, optionally substituted with one, two or three independently selected $R^{11}$;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$R^{12}$, —C(O)$NR^{13}R^{14}$, —S(O)$_t R^{12}$, or —S(O)$_t NR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deuteroC$_{1-3}$alkyl, haloC$_{1-3}$alkyl, cyanoC$_{1-3}$alkyl, hydroxyC$_{1-3}$alkyl, $C_{1-3}$alkoxyC$_{1-3}$alkyl, haloC$_{1-3}$alkoxyC$_{1-3}$alkyl, hydroxyl, $C_{1-3}$alkoxy, haloC$_{1-3}$alkoxy, $C_{1-3}$alkylthio, haloC$_{1-3}$alkylthio, $C_{1-3}$alkylsulfonyl, $C_{1-3}$alkylsulfinyl, or haloC$_{1-3}$alkylsulfinyl; or two $R^{11}$ groups, together with the carbon atom to which they are attached, form $C_{3-5}$cycloalkyl, 3- to 6-membered heterocyclyl or oxo where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2, provided that when Z is $NR^2$, m is 1 and n is 1 or 2.

In certain embodiments, provided herein are compounds of Formula (I):

(I)

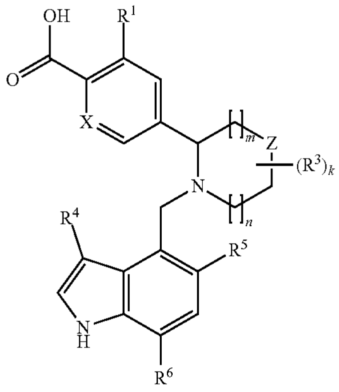

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl, heteroaryl, —C(O)$R^{12}$, —C(O)$NR^{13}R^{14}$ or —S(O)$R^{12}$ wherein the alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl; or $R^{2a}$ and $R^{2b}$, together with the carbon atom to which they are attached, form cycloalkyl substituted with one, two or three independently selected $R^{11}$ or form heterocyclyl, optionally substituted with one, two or three independently selected $R^{11}$;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$R^{12}$, —C(O)$NR^{13}R^{14}$, —S(O)$_t R^{12}$, or —S(O)$_t NR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deuteroC$_{1-3}$alkyl, haloC$_{1-3}$alkyl, cyanoC$_{1-3}$alkyl, hydroxyC$_{1-3}$alkyl, $C_{1-3}$alkoxyC$_{1-3}$alkyl, haloC$_{1-3}$ alkoxyC$_{1-3}$alkyl, hydroxyl, $C_{1-3}$alkoxy, haloC$_{1-3}$ alkoxy, $C_{1-3}$alkylthio, haloC$_{1-3}$alkylthio, $C_{1-3}$alkylsulfonyl, $C_{1-3}$alkylsulfinyl, or haloC$_{1-3}$alkylsulfinyl;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2, provided that when Z is $NR^2$, m is 1 and n is 1 or 2.

In certain embodiments, provided herein are compounds of Formula (I):

(I)

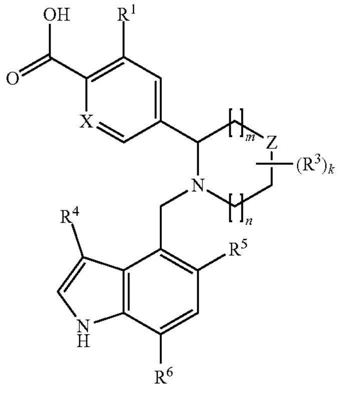

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl, heteroaryl, —C(O)$R^{12}$, —C(O)$NR^{13}R^{14}$ or —S(O)$_t R^{12}$ wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl; or $R^{2a}$ and $R^{2b}$, together with the carbon atom to which they are attached, form cycloalkyl substituted with one, two or three independently selected $R^{11}$ or form heterocyclyl, optionally substituted with one, two or three independently selected $R^{11}$;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is —$R_u$-cycloalkyl, —$R_u$-heterocyclyl, cycloalkyl, heterocyclyl, heteroaryl, —C(O)$R^{12}$, —C(O)$NR^{13}R^{14}$, —S(O)$_t R^{12}$, or —S(O)$_t NR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that when Z is $NR^2$, m is 1 and n is 1 or 2.

In certain embodiments, provided herein are compound of Formula (I) having the Formula (II):

(II)

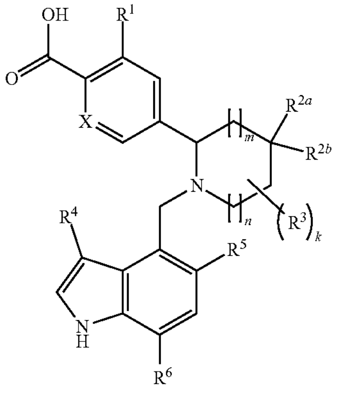

or a pharmaceutically acceptable salt thereof.

In certain embodiments, provided herein are compound of Formula (I) having the Formula (IIa):

(IIa)

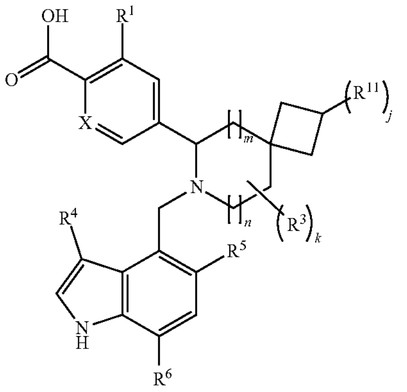

or a pharmaceutically acceptable salt thereof, wherein j is 1 or 2, wherein, when j is 1, the carbon atom connected to $R^{11}$ has a single $R^{11}$ substituent, and when j is 2, the carbon atom connected to $R^{11}$ has two independently selected $R^{11}$ substituents.

In certain embodiments, provided herein are compound of Formula (I) having the Formula (IIb):

(IIb)

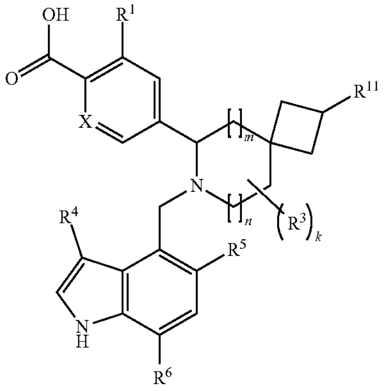

or a pharmaceutically acceptable salt thereof.

In certain embodiments, provided herein are compound of Formula (I) having the Formula (IIc):

(IIc)

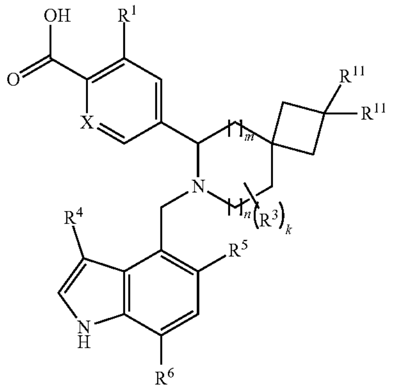

or a pharmaceutically acceptable salt thereof.

In certain embodiments, provided herein are compound of Formula (I) having the Formula (IId):

(IId)

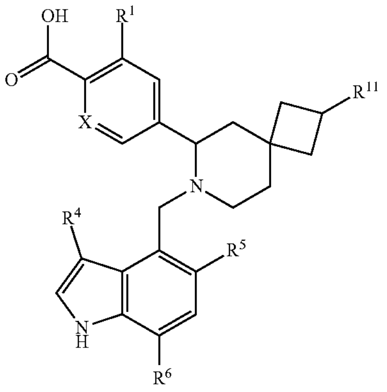

or a pharmaceutically acceptable salt thereof.

In certain embodiments, provided herein is a compound of Formula (I) having the Formula (IIe):

(IIe)

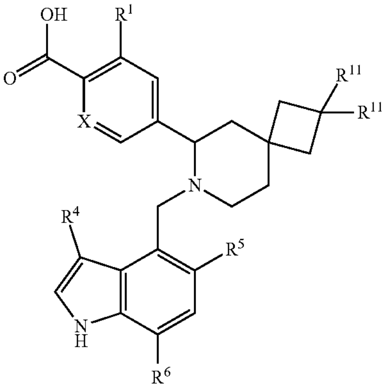

or a pharmaceutically acceptable salt thereof.

In certain embodiments, provided herein is a compound of Formula (I) having the Formula (IIf):

(IIf)

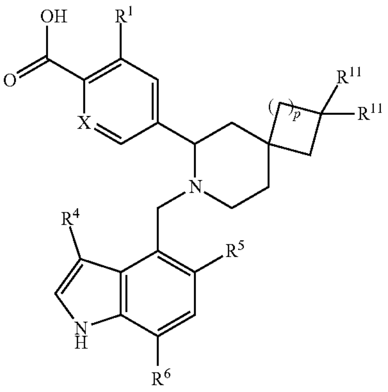

wherein p is 1 or 2; or a pharmaceutically acceptable salt thereof. In certain embodiments, provided herein are compounds of Formula (IIf) wherein each $R^{11}$ is independently halo, and the other variables are as described elsewhere herein for Formula (I) or (IIf). In certain embodiments, provided herein are compounds of Formula (IIf) wherein each $R^{11}$ is fluoro, and the other variables are as described elsewhere herein for Formula (I) or (IIf).

In certain embodiments, provided herein are compounds of Formula (I) having the Formula (III):

(III)

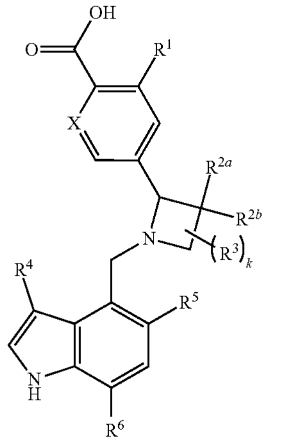

or a pharmaceutically acceptable salt thereof.

In certain embodiments, provided herein are compounds of Formula (I) having the Formula (IIIa):

(IIIa)

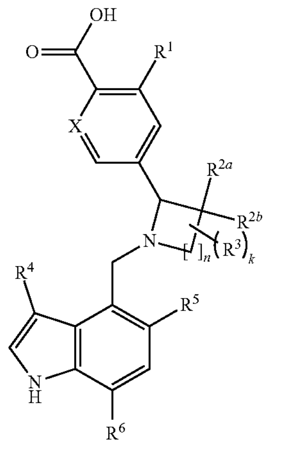

or a pharmaceutically acceptable salt thereof, wherein n is 1 or 2.

In certain embodiments, provided herein are compounds of Formula (I) having the Formula (IV):

(IV)

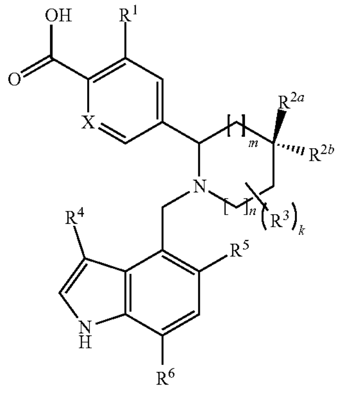

or a pharmaceutically acceptable salt thereof.

In certain embodiments, provided herein are compounds of Formula (IVa):

(IVa)

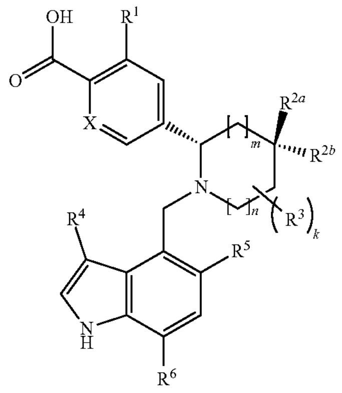

or a pharmaceutically acceptable salt thereof.

In certain embodiments, provided herein are compounds of Formula (I) having the Formula (IVb):

(IVb)

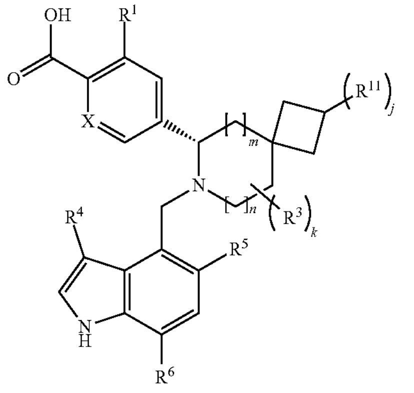

wherein j is 1 or 2; or a pharmaceutically acceptable salt thereof, wherein, when j is 1, the carbon atom connected to $R^{11}$ has a single $R^{11}$ substituent, and when j is 2, the carbon atom connected to $R^{11}$ has two independently selected $R^{11}$ substituents.

In certain embodiments, provided herein are compounds of Formula (I):

(I)

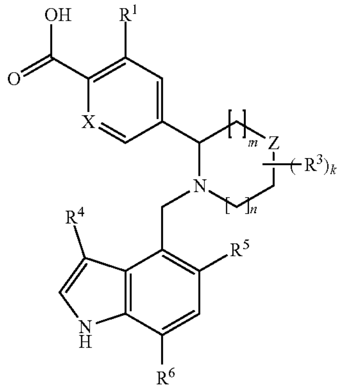

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl, heteroaryl, —C(O)$R^{12}$, —C(O)$NR^{13}R^{14}$ or —$S(O)_tR^{12}$, wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deuteroC$_{1-3}$alkyl, or haloC$_{1-3}$alkyl;

$R^3$ is halo, cyano, $C_{1-3}$alkyl, or haloC$_{1-3}$alkyl;

$R^4$ is hydrogen, halo, cyano, $C_{1-3}$alkyl or haloC$_{1-3}$alkyl;

$R^5$ is halo, $C_{1-3}$alkyl, $C_{3-5}$cycloalkyl, haloC$_{1-3}$alkyl, haloC$_{1-3}$alkoxy or $C_{1-3}$alkoxy;

$R^6$ is halo, cyano, $C_{1-3}$alkyl, $C_{3-5}$cycloalkyl, haloC$_{1-3}$alkyl, $C_{1-3}$alkoxy or haloC$_{1-3}$alkoxy;

$R^7$ is deuteroalkyl, heterocyclyl, or heteroaryl, wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$NR^{13}R^{14}$, —$S(O)_tR^{12}$, or —$S(O)_tNR^{13}R^{14}$, wherein the —$R_u$-cycloalkyl, —$R_u$— heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo, where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1 and n is 1 or 2.

In certain embodiments, provided herein are compounds of Formula (I):

(I)

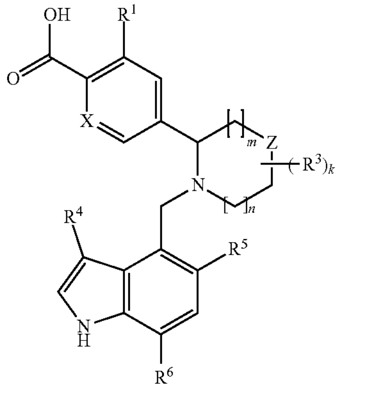

or a pharmaceutically acceptable salt thereof, wherein:

$R^1$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl, heteroaryl, —C(O)$R^{12}$, —C(O)$NR^{13}R^{14}$ or —$S(O)_tR^{12}$, wherein the alkyl, haloalkyl, deuteroalkyl, hydroxyalkyl, alkoxyalkyl, cyanoalkyl, —$R_u$-cycloalkyl, —$R_u$— heterocyclyl, cycloalkyl, heterocyclyl or heteroaryl is optionally substituted with one, two or three independently selected $R^{11}$;

$R^{2a}$ is —$R_u$-cycloalkyl, —$R_u$-heterocyclyl, cycloalkyl, heterocyclyl, aryl, heteroaryl, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deutero$C_{1-3}$alkyl, or halo$C_{1-3}$alkyl;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^7$ is haloalkyl, deuteroalkyl, —$R_u$-cycloalkyl, —$R_u$-heterocyclyl, cycloalkyl, heterocyclyl, or heteroaryl, wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —C(O)$NR^{13}R^{14}$, —$S(O)_tR^{12}$, or —$S(O)_tNR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo, where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1 and n is 1 or 2.

In certain embodiments, provided herein are compounds of Formula (IIa) or (IVb), wherein $R^{11}$ is halo, cyano, or halo$C_{1-3}$alkyl; and the other variables are as described elsewhere herein for Formulae (IIa) and (IVb), respectively. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is halo, cyano, or halo$C_{1-3}$alkyl; j is 1 or 2; k is 0; and m and n are both 1.

In certain embodiments, provided herein are compounds Formula (IIa) or (IVb), wherein $R^{11}$ is fluoro, cyano, or fluoro$C_{1-3}$alkyl; and the other variables are as described elsewhere herein for Formulae (IIa) and (IVb), respectively. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is fluoro, cyano, or fluoro$C_{1-3}$alkyl; j is 1 or 2; k is 0; and m and n are both 1.

In certain embodiments, provided herein are compounds Formulae (IIa) or (IVb), wherein $R^{11}$ is fluoro, cyano, —$CHF_2$ or —$CF_3$; and the other variables are as described elsewhere herein for Formulae (IIa) and (IVb), respectively. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is fluoro, cyano, —$CHF_2$ or —$CF_3$; j is 1 or 2; k is 0; and m and n are both 1.

In certain embodiments, provided herein are compounds of Formula (IIa) or (IVb), wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is halo; j is 2; k is 0 or 1; and m and n are both 1. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is halo; j is 2; k is 0; and m and n are both 1.

In certain embodiments, provided herein are compounds of Formula (IIa) or (IVb), wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is fluoro; j is 2; k is 0 or 1; and m and n are both 1. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is fluoro; j is 2; k is 0; and m and n are both 1.

In certain embodiments, provided herein are compounds of Formula (IIa) or (Ivb), wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is cyano; j is 1; k is 0 or 1; and m and n are both 1. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is cyano; j is 1; k is 0; and m and n are both 1.

In certain embodiments, provided herein are compounds of Formula (IIa) or (IVb), wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is —$CHF_2$ or —$CF_3$; j is 1; k is 0 or 1; and m and n are both 1. In certain embodiments, provided herein are compounds of Formula (IIa) or (IVb), wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is —$CHF_2$ or —$CF_3$; j is 1; k is 0; and m and n are both 1.

In certain embodiments, provided herein are compounds of Formula (I) having the Formula (IVc):

(IVc)

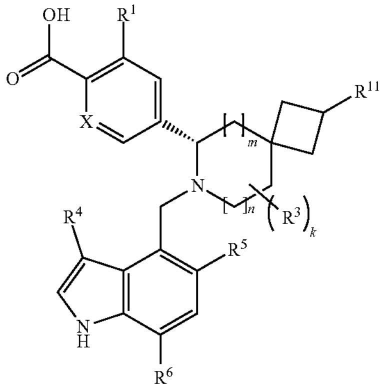

or a pharmaceutically acceptable salt thereof.

In certain embodiments, provided herein are compounds of Formula (I) having the Formula (IVd):

(IVd)

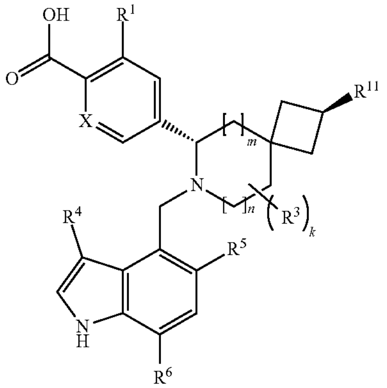

or a pharmaceutically acceptable salt thereof.

In certain embodiments, provided herein are compounds of Formula (I) having the Formula (IVe):

(IVe)

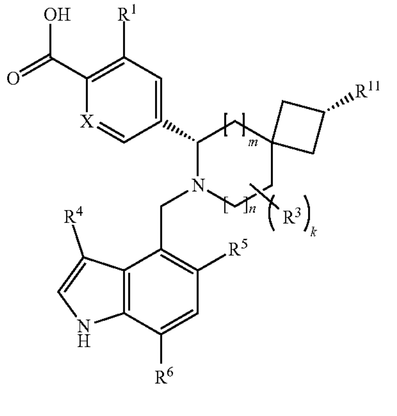

or a pharmaceutically acceptable salt thereof.

In certain embodiments, provided herein are compounds of Formula (I) having the Formula (IVf):

(IVf)

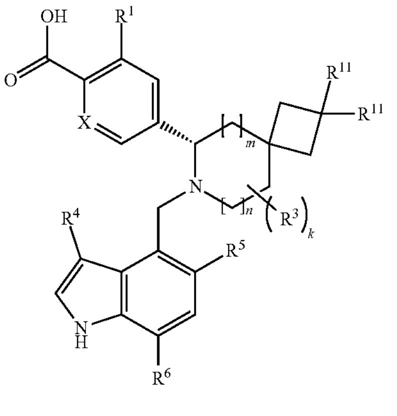

or a pharmaceutically acceptable salt thereof.

In certain embodiments, provided herein are compounds of Formula (IIc) or (IVf) wherein $R^{11}$ is each independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$ alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo; and the remaining variables are as described elsewhere herein for Formulae (IIc) and (IVf), respectively. In certain embodiments, provided herein are compounds of Formula (IIc) or (IVf) wherein $R^{11}$ is each independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$ alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; and the remaining variables are as described elsewhere herein for Formulae (IIc) and (IVf), respectively.

In certain embodiments, provided herein are compounds of Formula (IIc) or (IVf) wherein $R^{11}$ is halo, $C_{1-3}$alkyl, halo$C_{1-3}$alkyl or hydroxyl, and the other variables are as described elsewhere herein for Formulae (IIc) and (IVf), respectively. In certain embodiments, provided herein are compounds of Formula (IIc) or (IVf), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently halo, $C_{1-3}$alkyl, halo$C_{1-3}$alkyl or hydroxyl. In certain embodiments, provided herein are compounds of Formula (IIc) or (IVf), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently halo, $C_{1-3}$alkyl, halo$C_{1-3}$alkyl or hydroxyl.

In certain embodiments, provided herein are compounds of Formula (IIc) or (IVf), or a pharmaceutically acceptable salt thereof, wherein $R^{11a}$ is $C_{1-3}$alkyl or halo$C_{1-3}$alkyl; $R^{11b}$ is hydroxyl, and the remaining variables are as described elsewhere herein for Formula (IIc) and (IVf).

In certain embodiments, provided herein are compounds of Formula (IIc) or (IVf), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently $C_{1-3}$alkyl, halo$C_{1-3}$alkyl or hydroxyl, and the remaining variables are as described elsewhere herein for Formula (IIc) and (IVf). In certain embodiments, provided herein are compounds of Formula (IIc) or (IVf), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently $C_{1-3}$alkyl, halo$C_{1-3}$alkyl or hydroxyl.

In certain embodiments, provided herein are compounds of Formula (IIc) or (I), or a pharmaceutically acceptable salt thereof, wherein $R^{11a}$ is methyl or trifluoromethyl and $R^{11b}$ is hydroxyl, and the remaining variables are as described elsewhere herein for Formulae (IIc) and (IVf). In certain embodiments, provided herein are compounds of Formula (IIc) or (IVf), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11a}$ is methyl or trifluoromethyl and $R^{11b}$ is hydroxyl. In certain embodiments, provided herein are compounds of Formula (IIc) or (IVf), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11a}$ is methyl or trifluoromethyl and $R^{11b}$ is hydroxyl.

In certain embodiments, provided herein are compounds of Formula (IIc) or (IVf), or a pharmaceutically acceptable salt thereof, wherein $R^{11}$ is each independently halo; and the remaining variables are as described elsewhere herein for Formulae (IIc) and (IVf).

In certain embodiments, provided herein are compounds of Formula (IIc) or (IVf), or a pharmaceutically acceptable salt thereof, wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is each independently halo;

k is 0, 1, 2 or 3;

m is 0, 1 or 2; and n is 0, 1 or 2.

In certain embodiments, provided herein are compounds of Formula (IIc) or (IVf), or a pharmaceutically acceptable salt thereof, wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is fluoro;

k is 0, 1, 2 or 3;

m is 0, 1 or 2; and n is 0, 1 or 2. In certain embodiments, provided herein are compounds of Formula (IIc) or (IVf), wherein k is 0, m is 1; n is 1; and the other variables are as described elsewhere herein for Formulae (IIc) and (IVf), respectively.

In certain embodiments, provided herein are compounds of Formula (IIc) or (IVf), or a pharmaceutically acceptable salt thereof, wherein $R^{11}$ is fluoro; and the remaining variables are as described elsewhere herein for Formula (IIc) and (IVf), respectively.

In certain embodiments, provided herein are compounds of Formula (IIc) or (IVf), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is fluoro.

In certain embodiments, provided herein are compounds of Formula (IIc) or (IVf), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is fluoro.

In certain embodiments, provided herein are compounds of Formula (I), (IVb) or (IVc) having the Formula (IVg):

(IVg)

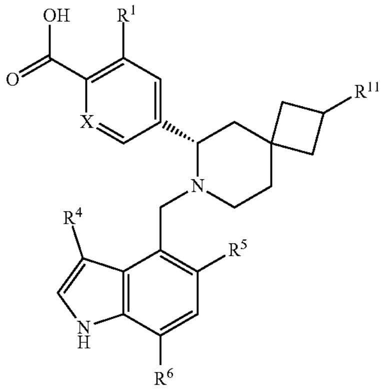

or a pharmaceutically acceptable salt thereof.

In certain embodiments, provided herein are compounds of Formula (I), (IVb) or (IVc) having the Formula (IVh):

(IVh)

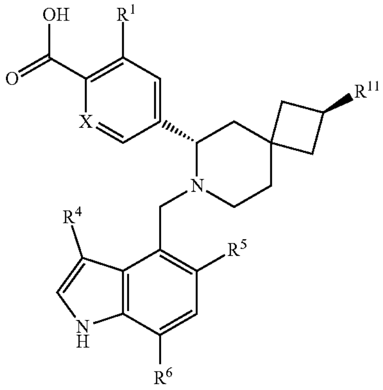

or a pharmaceutically acceptable salt thereof.

In certain embodiments, provided herein are compounds of Formula (I), (IVb) or (IVc) having the Formula (IVi):

(IVi)

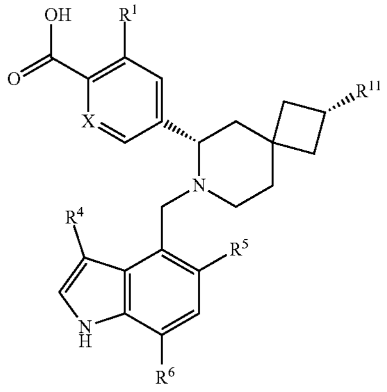

or a pharmaceutically acceptable salt thereof.

In certain embodiments, provided herein are compounds of Formula (IId), (IVg), (IVh) or (IVi), or a pharmaceutically acceptable salt thereof, wherein $R^{11}$ is independently halo, cyano, or halo$C_{1-3}$alkyl; and the remaining variables are as described elsewhere herein for Formulae (IId), (IVg), (IVh) and (IVi). In certain embodiments, provided herein are compounds of Formula (IId), (IVg), (IVh) or (IVi), or a pharmaceutically acceptable salt thereof, wherein $R^{11}$ is cyano or halo$C_{1-3}$alkyl; and the remaining variables are as described elsewhere herein for Formulae (IId), (IVg), (IVh) and (IVi), respectively. In certain embodiments, provided herein are compounds of Formula (IId), (IVg), (IVh) or (IVi), or a pharmaceutically acceptable salt thereof, wherein $R^{11}$ is cyano or fluoro$C_{1-3}$alkyl; and the remaining variables are as described elsewhere herein for Formulae (IId), (IVg), (IVh) and (IVi), respectively. In certain embodiments, provided herein are compounds of Formula (IId), (IVg), (IVh) or (IVi), or a pharmaceutically acceptable salt thereof, wherein $R^{11}$ is cyano, $—CHF_2$ or $—CF_3$; and the remaining variables are as described elsewhere herein for Formulae (IId), (IVg), (IVh) and (IVi), respectively.

In certain embodiments, provided herein are compounds of Formula (IId), (IVg), (IVh) or (IVi), or a pharmaceutically acceptable salt thereof, wherein $R^1$ is hydrogen, fluoro, chloro or methyl; X is N or CH; $R^4$ is hydrogen, halo, cyano, $C_{1-3}$alkyl or halo$C_{1-3}$alkyl; $R^5$ is halo, $C_{1-3}$alkyl, $C_{3-5}$cycloalkyl, halo$C_{1-3}$alkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; and $R^{11}$ is cyano or halo$C_{1-3}$ alkyl. In certain embodiments, provided herein are compounds of Formula (IId), (IVg), (IVh) or (IVi), or a pharmaceutically acceptable salt thereof, wherein $R^1$ is hydrogen, fluoro, chloro or methyl; X is N or CH; $R^4$ is hydrogen, halo, cyano, $C_{1-3}$alkyl or halo$C_{1-3}$alkyl; $R^5$ is halo, $C_{1-3}$alkyl, $C_{3-5}$cycloalkyl, halo$C_{1-3}$alkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; and $R^{11}$ is cyano or fluoro$C_{1-3}$alkyl. In certain embodiments, provided herein are compounds of Formula (IId), (IVg), (IVh) or (IVi), or a pharmaceutically acceptable salt thereof, wherein $R^1$ is hydrogen, fluoro, chloro or methyl; X is N or CH; $R^4$ is hydrogen, halo, cyano, $C_{1-3}$alkyl or halo$C_{1-3}$alkyl; $R^5$ is halo, $C_{1-3}$alkyl, $C_{3-5}$cycloalkyl, halo$C_{1-3}$alkyl, halo$C_{1-3}$ alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; and $R^{11}$ is cyano, $-CHF_2$ or $-CF_3$.

In certain embodiments, provided herein are compounds of Formula (IId), (IVg), (IVh) or (IVi), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is cyano or halo$C_{1-3}$alkyl. In certain embodiments, provided herein are compounds of Formula (IId), (IVg), (IVh) or (IVi), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is cyano or fluoro$C_{1-3}$alkyl. In certain embodiments, provided herein are compounds of Formula (IId), (IVg), (IVh) or (IVi), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is cyano, $-CHF_2$ or $-CF_3$.

In certain embodiments, provided herein are compounds of Formula (IId), (IVg), (IVh) or (IVi), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is cyano or halo$C_{1-3}$alkyl.

In certain embodiments, provided herein are compounds of Formula (IId), (IVg), (IVh) or (IVi), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is cyano or fluoro$C_{1-3}$alkyl.

In certain embodiments, provided herein are compounds of Formula (IId), (IVg), (IVh) or (IVi), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is cyano, $-CHF_2$ or $-CF_3$.

In certain embodiments, provided herein are compounds of Formula (I), (IVb) or (IVf) having the Formula (IVj):

(IVj)

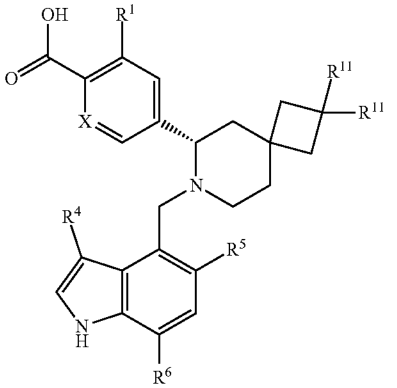

or a pharmaceutically acceptable salt thereof. In certain embodiments, provided herein are compounds of Formula (IIe) or (IVj), or a pharmaceutically acceptable salt thereof, wherein $R^{11}$ is each independently halo; and the remaining variables are as described elsewhere herein for Formulae (IIe) and (IVj).

In certain embodiments, provided herein are compounds of Formula (IIe) or (IVj), or a pharmaceutically acceptable salt thereof, wherein $R^1$ is hydrogen, fluoro, chloro or methyl; X is N or CH; $R^4$ is hydrogen, halo, cyano, $C_{1-3}$alkyl or halo$C_{1-3}$alkyl; $R^5$ is halo, $C_{1-3}$alkyl, $C_{3-5}$cycloalkyl, halo$C_{1-3}$alkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; and $R^{11}$ is each independently halo.

In certain embodiments, provided herein are compounds of Formula (IIe) or (IVj), or a pharmaceutically acceptable salt thereof, wherein $R^1$ is hydrogen, fluoro, chloro or methyl; X is N or CH; $R^4$ is hydrogen, halo, cyano, $C_{1-3}$alkyl or halo$C_{1-3}$alkyl; $R^5$ is halo, $C_{1-3}$alkyl, $C_{3-5}$cycloalkyl, halo$C_{1-3}$alkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; and $R^{11}$ is fluoro.

In certain embodiments, provided herein are compounds of Formula (IIe) or (IVj), or a pharmaceutically acceptable salt thereof, wherein $R^{11}$ is fluoro; and the remaining variables are as described elsewhere herein for Formula (IIe) and (IVj), respectively. In certain embodiments, provided herein are compounds of Formula (IIe) or (IVj), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is fluoro. In certain embodiments, provided herein are compounds of Formula (IIe) or (IVj), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is fluoro.

In certain embodiments, provided herein are compounds of Formula (I) having the Formula (IVk):

(IVk)

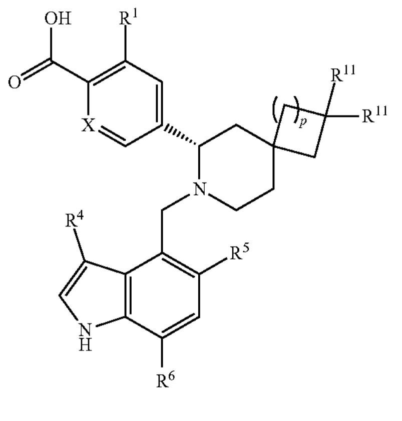

or a pharmaceutically acceptable salt thereof, where p is 1 or 2. In certain embodiments, provided herein are compounds of Formula (IIf) or (IVk), or a pharmaceutically acceptable salt thereof, wherein $R^{11}$ is each independently halo and the remaining variables are as described for Formulae (IIf) and (IVk), respectively. In certain embodiments, provided herein are compounds of Formula (IIf) or (IVk), or a pharmaceutically acceptable salt thereof, wherein $R^{11}$ is fluoros and the remaining variables are as described for Formulae (IIf) and (IVk), respectively. In certain embodiments, provided herein are compounds of Formula (IIf) or (IVk), or a pharmaceutically acceptable salt thereof, wherein: $R^1$ is hydrogen, fluoro, chloro or methyl;

X is N or CH;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is each independently halo;

and p is 1 or 2. In yet certain embodiments, provided herein are compounds of Formula (IIf) or (IVk) wherein:

$R^1$ is hydrogen, fluoro, chloro or methyl;

X is N or CH;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy;

$R^{11}$ is fluoro;

and p is 1 or 2.

In certain embodiments, provided herein are compounds of Formula (IIf) or (IVk), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl and $R^{11}$ is fluoro. In certain embodiments, provided herein are compounds of Formula (IIf) or (IVk), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and $R^{11}$ is fluoro.

In certain embodiments, provided herein are compounds of Formula (I), (IVa), (IVb), (IVf) or (IVj) having the Formula (IVl):

(IVl)

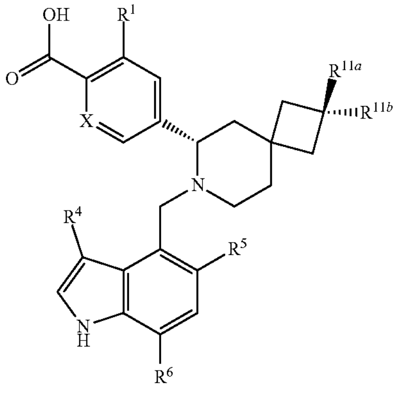

or a pharmaceutically acceptable salt thereof, wherein $R^{11a}$ and $R^{11b}$ are each independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo; and the remaining variables are as described elsewhere herein for Formulae (I) (IVa), (IVb), (IVf) and (IVj), respectively.

In certain embodiments, provided herein are compounds of Formula (IVl) wherein $R^{11a}$ is halo, cyano, $C_{1-3}$alkyl, deutero$C_{1-3}$alkyl, halo$C_{1-3}$alkyl or cyano$C_{1-3}$alkyl; $R^{11b}$ is halo, hydroxy$C_{1-3}$alkyl, $C_{1-3}$alkoxy$C_{1-3}$alkyl, halo$C_{1-3}$ alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; and the remaining variables are as described elsewhere herein for Formula (IVl).

In certain embodiments, provided herein are compounds of Formula (IVl) wherein $R^{11a}$ is halo, $C_{1-3}$alkyl or halo$C_{1-3}$ alkyl and $R^{11b}$ is halo or hydroxyl, and the other variables are as described elsewhere herein for Formula (IVl). In certain embodiments, provided herein are compounds of Formula (IVl), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11a}$ is halo, $C_{1-3}$alkyl or halo$C_{1-3}$alkyl and $R^{11b}$ is halo or hydroxyl. In certain embodiments, provided herein are compounds of Formula (IVl), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11a}$ is halo, $C_{1-3}$alkyl or halo$C_{1-3}$alkyl and $R^{11b}$ is halo or hydroxyl.

In certain embodiments, provided herein are compounds of Formula (IVl), or a pharmaceutically acceptable salt thereof, wherein $R^{11a}$ is $C_{1-3}$alkyl or halo$C_{1-3}$alkyl; $R^{11b}$ is hydroxyl, and the remaining variables are as described elsewhere herein for Formula (IVl). In certain embodiments, provided herein are compounds of Formula (IVl), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11a}$ is $C_{1-3}$alkyl or halo$C_{1-3}$alkyl and $R^{11b}$ is hydroxyl, and the remaining variables are as described elsewhere herein for Formula (IVl). In certain embodiments, provided herein are compounds of Formula (IVl), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11a}$ is $C_{1-3}$alkyl or halo$C_{1-3}$alkyl and $R^{11b}$ is hydroxyl.

In certain embodiments, provided herein are compounds of Formula (IVl), or a pharmaceutically acceptable salt thereof, wherein $R^{11a}$ is methyl or trifluoromethyl and $R^{11b}$ is hydroxyl, and the remaining variables are as described elsewhere herein for Formulae (IVl). In certain embodiments, provided herein are compounds of Formula (IVl), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11a}$ is methyl or trifluoromethyl and $R^{11b}$ is hydroxyl. In certain embodiments, provided herein are compounds of Formula (IVl), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11a}$ is methyl or trifluoromethyl and $R^{11b}$ is hydroxyl.

In certain embodiments, provided herein are compounds of Formula (IVl) wherein $R^{11a}$ is fluoro and $R^{11b}$ is fluoro, and the other variables are as described elsewhere herein for Formula (IVl). In certain embodiments, provided herein are compounds of Formula (I), (II), (IIa), (IIc), (IIe), (IV), (IVa), (IVb), (IVf), (IVj), (IVk) or (IVl), wherein each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl, or two $R^{11}$ groups, together with the carbon atom to which they are attached, form $C_{3-5}$cycloalkyl, 3- to 6-membered heterocyclyl or oxo; and the other variables are as described elsewhere herein for Formulae (I), (II), (IIa), (IIc), (IIe), (IV), (IVa), (IVb), (IVf), (IVj), (IVk) and (IVl), respectively. In certain embodiments, provided herein are compounds of Formula (I), (II), (IIa), (IIc), (IIe), (IV), (IVa), (IVb), (IVf), (IVj), (IVk) or (IVl), wherein each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, hydroxyl, $C_{1-3}$alkoxy, halo$C_{1-3}$alkoxy; or two $R^{11}$ groups, together with the carbon atom to which they are attached, form $C_{3-5}$cycloalkyl, 3- to 6-membered heterocyclyl or oxo; and the other variables are as described elsewhere herein for Formulae (I), (II), (IIa), (IIc), (IIe), (IIf), (IV), (IVa), (IVb), (IVf), (IVj), (IVk) or (IVl), respectively. In certain embodiments, provided herein are compounds of Formula (I), (II), (IIa), (IIc), (IIe), (IIf), (IV), (IVa), (IVb), (IVf), (IVj), (IVk) or (IVl), wherein each $R^{11}$ is independently halo, cyano, oxo, $C_{1-3}$alkyl, halo$C_{1-3}$alkyl, hydroxyl, halo$C_{1-3}$alkoxy; or two $R^{11}$ groups, together with the carbon atom to which they are attached, form $C_{3-5}$cycloalkyl; and the other variables are as described elsewhere herein for Formulae (I), (II), (IIa), (IIc), (IIe), (IIf), (IV), (IVa), (IVb), (IVf), (IVj), (IVk) or (IVi), respectively. In certain embodiments, provided herein are compounds of Formula (I), (II), (IIa), (IIc), (IIe), (IIf), (IV), (IVa), (IVb), (IVf), (IVj), (IVk) or (IVl), wherein each $R^{11}$ is independently fluoro, cyano, oxo, hydroxyl, methyl, —$CHF_2$, —$CF_3$ or —$OCHF_2$, or two $R^{11}$ groups, together with the carbon atom to which they are attached, form cyclobutyl or oxo; and the other variables are as described elsewhere herein for Formulae (I), (II), (IIa), (IIc), (IIe), (IIf), (IV), (IVa), (IVb), (IVf), (IVj), (IVk) and (IVl), respectively. In certain embodiments, provided herein are compounds of Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) or (IVl), wherein each $R^{11}$ is independently halo, cyano, oxo, $C_{1-3}$alkyl, halo$C_{1-3}$alkyl, hydroxyl or halo$C_{1-3}$alkoxy; and the other variables are as described elsewhere herein for Formulae (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) or (IVl), respectively. In certain embodiments, provided herein are compounds of Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) or (IVl), wherein each $R^{11}$ is independently fluoro, cyano, oxo, hydroxyl, methyl, —$CHF_2$, —$CF_3$ or —$OCHF_2$; and the other variables are as described elsewhere herein for Formulae (I), (II), (IIa), (IIb), (IIc), (IId), (IIe), (IIf), (IV), (IVa), (IVb), (IVc), (IV), (IVe), (IVf), (IVg), (IVh), (IV), (IVj), (IVk) and (IVl), respectively. In certain embodiments, provided herein are compounds of Formula (I), (II), (IIa), (IIb), (IIc), (IId), (IIe), (IIf), (IV), (IVa), (IVb), (IVc), (IV), (IVe), (IVf), (IVg), (IVh), (IVi), (IVj), (IVk) or (IVl), wherein $R^{11}$ is halo, cyano, $C_{1-3}$alkyl, deutero$C_{1-3}$ alkyl or halo$C_{1-3}$alkyl; and the other variables are as described elsewhere herein for Formulae (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), respectively. In certain embodiments, provided herein are compounds of Formula (I), (II), (IIa), (IIb), (IIc), (IId), (IIe), (IV), (IVa), (IVb), (IVc), (IVd), (IVe), (IVf), (IVg), (IVh), (IVi), (IVj), (IVk) or (IVl), wherein $R^{11}$ is halo, cyano, or halo$C_{1-3}$alkyl; and the other variables are as described elsewhere herein for Formulae (I), (II), (IIa), (IIb), (IIc), (IId), (IIe), (IIf), (IV), (IVa), (IVb), (IVc), (IV), (IVe), (IVf), (IVg), (IVh), (IV), (IVj), (IVk) and (IVl), respectively. In certain embodiments, provided herein are compounds Formula (I), (II), (IIa), (IIb), (IIc), (IId), (IIe), (IIf), (IV), (IVa), (IVb), (IVc), (IV), (IVe), (IVf), (IVg), (IVh), (IVi), (IVj), (IVk) or (IVl), wherein $R^{11}$ is fluoro, cyano, or fluoro$C_{1-3}$alkyl; and the other variables are as described elsewhere herein for Formulae (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), respectively. In certain embodiments, provided herein are compounds Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) or (IVl), wherein $R^{11}$ is fluoro, cyano, —$CHF_2$ or —$CF_3$; and the other variables are as described elsewhere herein for Formulae (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), respectively. In certain embodiments, provided herein are compounds of Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), wherein $R^{11}$ is halo; and the other variables are as described elsewhere herein for Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), respectively. In certain embodiments, provided herein are compounds of Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) or (IVl), wherein $R^{11}$ is fluoro; and the other variables are as described elsewhere herein for Formula (I), (II), (IIa), (IIb), (IIc), (IId), (IIe), (IIf), (IV), (IVa), (IVb), (IVc), (IVd), (IVe), (IVf), (IVg), (IVh), (IVi), (IVj), (IVk) and (IVl), respectively.

In certain embodiments, provided herein are compounds of Formula (I) having the Formula (V):

(V)

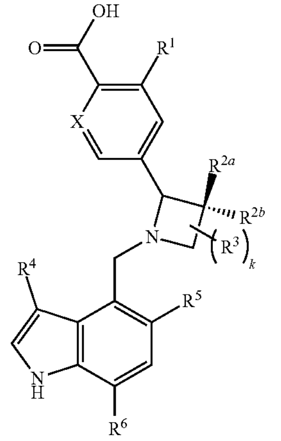

or a pharmaceutically acceptable salt thereof.

In certain embodiments, provided herein are compounds of Formula (I), (II) or (IV) having the Formula (VI):

(VI)

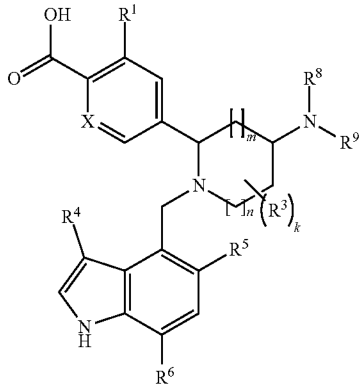

or a pharmaceutically acceptable salt thereof. In certain embodiments, provided herein are compounds of Formula (VI) wherein $R^3$ is halo, cyano, alkyl, or haloalkyl; $R^4$ is hydrogen, halo, $C_{1-3}$alkyl or halo$C_{1-3}$alkyl; $R^5$ is halo, $C_{1-3}$alkyl, $C_{3-5}$cycloalkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; $R^8$ is hydrogen, alkyl or haloalkyl; $R^9$ is cycloalkyl or heterocyclyl wherein the cycloalkyl or heterocyclyl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted by one two or three independently selected $R^{11}$; each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$ alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; k is 0, 1 or 2; m is 0 or 1; and n is 0, 1 or 2. In certain embodiments, provided herein are compounds of Formula (I) or (VI) wherein $R^8$ is hydrogen, alkyl or haloalkyl; $R^9$ is haloalkyl —$R_u$-cycloalkyl or cycloalkyl wherein the —$R_u$-cycloalkyl or cycloalkyl is optionally substituted with one, two or three $R^{11}$; each $R^{11}$ is independently halo or halo$C_{1-3}$alkyl and the other variables are as described elsewhere herein for Formula (I) and (VI), respectively. In certain embodiments, provided herein are compounds of Formula (I) or (VI) wherein $R^8$ is hydrogen, $C_{1-3}$alkyl or halo$C_{1-3}$alkyl; $R^9$ is halo $C_{1-3}$alkyl —$R_u$—$C_{3-5}$cycloalkyl or $C_{3-5}$cycloalkyl wherein the —$R_u$—$C_{3-5}$cycloalkyl or $C_{3-5}$cycloalkyl is optionally substituted with one, two or three $R^{11}$; each $R^{11}$ is independently halo or halo$C_{1-3}$alkyl and the remaining variables are as described elsewhere herein for Formulae (I) and (VI), respectively.

In certain embodiments, provided herein are compounds of Formula (I) or (VI) wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^8$ is hydrogen, $C_{1-3}$alkyl or halo$C_{1-3}$alkyl; $R^9$ is halo$C_{1-3}$alkyl —$R_u$—$C_{3-5}$ cycloalkyl or $C_{3-5}$cycloalkyl wherein the —$R_u$—$C_{3-5}$cycloalkyl or $C_{3-5}$cycloalkyl is optionally substituted with one, two or three $R^{11}$; each $R^{11}$ is independently halo or halo$C_{1-3}$alkyl; and the remaining variables are as described elsewhere herein for Formulae (I) and (VI), respectively. In certain embodiments, provided herein are compounds of Formula (I) or (VI) wherein $R^1$ is hydrogen or fluoro; X is CH; $R^4$ is hydrogen, fluoro, chloro or methyl; $R^5$ is methoxy or cyclopropyl; $R^6$ is methyl; $R^8$ is hydrogen, $C_{1-3}$alkyl or halo$C_{1-3}$alkyl; $R^9$ is halo$C_{1-3}$alkyl —$R_u$—$C_{3-5}$cycloalkyl or $C_{3-5}$cycloalkyl wherein the —$R_u$—$C_{3-5}$cycloalkyl or $C_{3-5}$cycloalkyl is optionally substituted with one, two or three $R^{11}$; each $R^{11}$ is independently halo or halo$C_{1-3}$alkyl; and the remaining variables are as described elsewhere herein for Formulae (I) and (VI), respectively.

In certain embodiments, provided herein are compounds of Formula (I) or (VI) wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^8$ is hydrogen, $C_{1-3}$alkyl or halo$C_{1-3}$alkyl; $R^9$ is halo$C_{1-3}$alkyl —$R_u$—$C_{3-5}$ cycloalkyl or $C_{3-5}$cycloalkyl wherein the —$R_u$—$C_{3-5}$cycloalkyl or $C_{3-5}$cycloalkyl is optionally substituted with one, two or three $R^{11}$; each $R^{11}$ is independently halo or halo$C_{1-3}$alkyl; m and n are both 1 and k is 0. In certain embodiments, provided herein are compounds of Formula (I) or (VI) wherein $R^1$ is hydrogen or fluoro; X is CH; $R^4$ is hydrogen, fluoro, chloro or methyl; $R^5$ is methoxy or cyclopropyl; $R^6$ is methyl; $R^8$ is hydrogen, $C_{1-3}$alkyl or halo$C_{1-3}$ alkyl; $R^9$ is halo$C_{1-3}$alkyl —$R_u$—$C_{3-5}$cycloalkyl or $C_{3-5}$cycloalkyl wherein the —$R_u$—$C_{3-5}$cycloalkyl or $C_{3-5}$cycloalkyl is optionally substituted with one, two or three $R^{11}$; each $R^{11}$ is independently halo or halo$C_{1-3}$alkyl; m and n are both 1 and k is 0. In certain embodiments, provided herein are compounds of Formula (I) or (VI), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; and the remaining variables are as described elsewhere herein for Formulae (I) and (VI), respectively.

In certain embodiments, provided herein are compounds of Formula (I) or (VI) wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^8$ is hydrogen; $R^9$ is —$CH_2CHF_2$, cyclopropylmethyl, cyclobutyl, or bicyclo [1.1.1]pentan-1-yl or wherein the cyclopropylmethyl, cyclobutyl, or bicyclo[1.1.1]pentan-1-yl is optionally substituted with one, two or three $R^{11}$; each $R^{11}$ is independently fluoro or trifluoromethyl; m and n are both 1 and k is 0. In certain embodiments, provided herein are compounds of Formula (I) or (VI) wherein $R^1$ is hydrogen or fluoro; X is CH; $R^4$ is hydrogen, fluoro, chloro or methyl; $R^5$ is methoxy or cyclopropyl; $R^6$ is methyl; $R^8$ is hydrogen; $R^9$ is $—CH_2CHF_2$, cyclopropylmethyl, cyclobutyl, or bicyclo[1.1.1]pentan-1-yl or wherein the cyclopropylmethyl, cyclobutyl, or bicyclo[1.1.1]pentan-1-yl is optionally substituted with one, two or three $R^{11}$; each $R^{11}$ is independently fluoro or trifluoromethyl; m and n are both 1 and k is 0.

In certain embodiments, provided herein are compounds of Formula (I) or (VI) wherein $R^8$ is hydrogen, alkyl or haloalkyl; $R^9$ is $—R_u$-cycloalkyl or cycloalkyl wherein the $—R_u$-cycloalkyl or cycloalkyl is optionally substituted with one, two or three $R^{11}$; each $R^{11}$ is independently halo or halo$C_{1-3}$alkyl and the other variables are as described elsewhere herein for Formula (I) and (VI), respectively. In certain embodiments, provided herein are compounds of Formula (I) or (VI) wherein $R^8$ is hydrogen, alkyl or haloalkyl; $R^9$ is $—R_u$-cycloalkyl or cycloalkyl wherein the $—R_u$-cycloalkyl or cycloalkyl is optionally substituted with one, two or three $R^{11}$; each $R^{11}$ is independently halo or halo$C_{1-3}$ alkyl and the other variables are as described elsewhere herein for Formula (I) and (VI), respectively. In certain embodiments, provided herein are compounds of Formula (I) or (VI) wherein $R^8$ is hydrogen, alkyl or haloalkyl; $R^9$ is cyclopropylmethyl or cyclobutyl wherein the cyclopropylmethyl or cyclobutyl is optionally substituted with one, two or three fluoro or trifluoromethyl and the other variables are as described elsewhere herein for Formula (I) and (VI), respectively. In certain embodiments, provided herein are compounds of Formula (I) or (VI) wherein k is 0; m is 1; n is 1 and the other variables are as described elsewhere herein for Formula (I) and (VI), respectively. In certain embodiments, provided herein are compounds of Formula (I) or (VI) wherein $R^{11}$ is fluoro and the other variables are as described elsewhere herein for Formula (I) and (VI), respectively. In certain embodiments, provided herein are compounds of provided herein are compounds of Formula (I), (II), (IV), (IVa) or (VI) having the Formula (VIa):

(VIa)

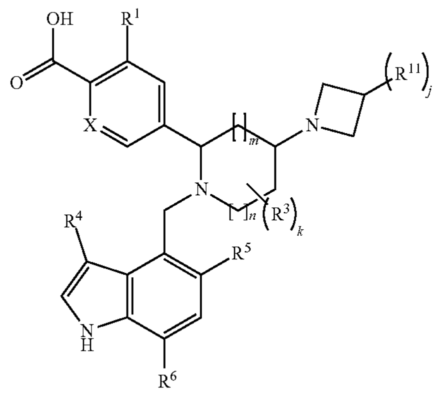

or a pharmaceutically acceptable salt thereof, wherein j is 1 or 2. In certain embodiments, provided herein are compounds of Formula (VIa), or a pharmaceutically acceptable salt thereof, wherein $R^{11}$ is each independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; or two $R^{11}$ groups, together with the carbon atom to which they are attached, form $C_{3-5}$cycloalkyl; j is 1 or 2 and the remaining variables are as described elsewhere herein for Formula (VIa). In certain embodiments, provided herein are compounds of Formula (VIa), or a pharmaceutically acceptable salt thereof, wherein $R^{11}$ is each independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; or two $R^{11}$ groups, together with the carbon atom to which they are attached, form $C_{3-5}$cycloalkyl; j is 1; and the remaining variables are as described elsewhere herein for Formula (VIa). In certain embodiments, provided herein are compounds of Formula (VIa), or a pharmaceutically acceptable salt thereof, wherein $R^{11}$ is halo$C_{1-3}$alkyl; j is 1; and the remaining variables are as described elsewhere herein for Formula (VIa). In certain embodiments, provided herein are compounds of Formula (VIa), or a pharmaceutically acceptable salt thereof, wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; $R^{11}$ is halo$C_{1-3}$alkyl; j is 1; k is 0; m is 1; and n is 1. In certain embodiments, provided herein are compounds of Formula (VIa), or a pharmaceutically acceptable salt thereof, wherein $R^1$ is hydrogen, fluoro, chloro or methyl;

X is N or CH;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; $R^{11}$ is trifluoromethyl; j is 1; k is 0; m is 1; and n is 1.

In certain embodiments, provided herein are compounds of Formula (VIa), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is halo$C_{1-3}$alkyl; j is 1; k is 0; m is 1; and n is 1. In certain embodiments, provided herein are compounds of Formula (VIa), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is trifluoromethyl; j is 1; k is 0; m is 1; and n is 1.

In certain embodiments, provided herein are compounds of Formula (VIa), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl; j is 1 or 2; k is 0; m is 1; and n is 1.

In certain embodiments, provided herein are compounds of Formula (VIa), or a pharmaceutically acceptable salt thereof, wherein $R^{11}$ is each independently fluoro, cyano, $—CF_3$, $—CHF_2$, $—OCF_3$ or $—S(O)_2CH_3$ or two $R^{11}$ groups, together with the carbon atom to which they are attached, form cyclopropyl; j is 1 or 2; and the remaining variables are as described elsewhere herein for Formula (VIa).

In certain embodiments, provided herein are compounds of Formula (VIa), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently fluoro, cyano, —$CF_3$, —$CHF_2$—$OCF_3$ or —$S(O)_2CH_3$; or two $R^{11}$ groups, together with the carbon atom to which they are attached, form cyclopropyl; j is 1 or 2 and k is 0; m is 1 and n is 1.

In certain embodiments, provided herein are compounds of Formula (VIa), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently fluoro, cyano, —$CF_3$, —$CHF_2$—$OCF_3$ or —$S(O)_2CH_3$; or two $R^{11}$ groups, together with the carbon atom to which they are attached, form cyclopropyl; j is 1 or 2 and k is 0; m is 1 and n is 1.

In certain embodiments, provided herein are compounds of Formula (I), (II), (IV), (IVa) or (VI) having the Formula (VIb):

(VIb)

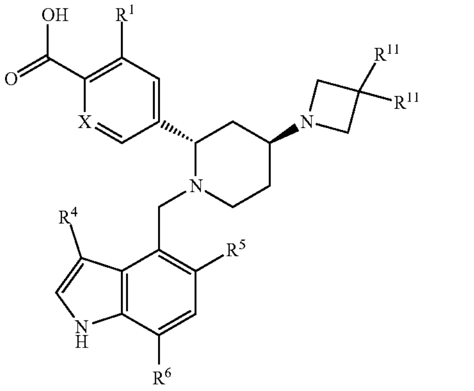

or a pharmaceutically acceptable salt thereof.

In certain embodiments, provided herein are compounds of Formula (I), (II), (IV), (IVa) or (VI) having the Formula (VIc):

(VIc)

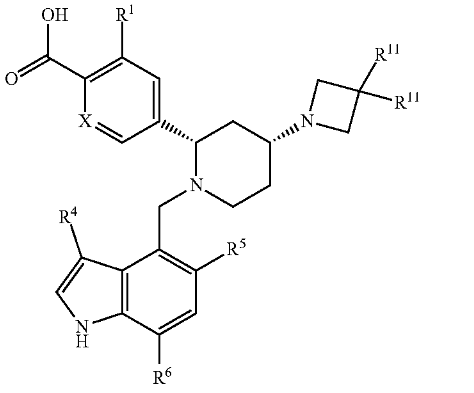

or a pharmaceutically acceptable salt thereof.

In certain embodiments, provided herein are compounds of Formula (VIb) or (VIc), or a pharmaceutically acceptable salt thereof, wherein $R^{11}$ is each independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; or two $R^{11}$ groups, together with the carbon atom to which they are attached, form $C_{3-5}$cycloalkyl, and the remaining variables are as described elsewhere herein for Formulae (VIb) and (VIc), respectively.

In certain embodiments, provided herein are compounds of Formula (VIb) or (VIc), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl; and the remaining variables are as described elsewhere herein for Formula (VIb) and (VIc), respectively.

In certain embodiments, provided herein are compounds of Formula (VIb) or (VIc), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; and $R^{11}$ is each independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl.

In certain embodiments, provided herein are compounds of Formula (VIb) or (VIc), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl; and the remaining variables are as described elsewhere herein for Formula (VIb) or (VIc).

In certain embodiments, provided herein are compounds of Formula (VIb) or (VIc), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl; m is 1; n is 1; j is 1 or 2 and k is 0.

In certain embodiments, provided herein are compounds of Formula (VIb) or (VIc), or a pharmaceutically acceptable salt thereof, wherein $R^{11}$ is each independently fluoro, cyano, —$CF_3$, —$CHF_2$, —$OCF_3$ or —$S(O)_2CH_3$ or two $R^{11}$ groups, together with the carbon atom to which they are attached, form cyclopropyl; j is 1 or 2; and the remaining variables are as described elsewhere herein for Formulae (VIb) and (VIc), respectively.

In certain embodiments, provided herein are compounds of Formula (VIb) or (VIc), or a pharmaceutically acceptable salt thereof, wherein $R^1$ is hydrogen, fluoro or chloro; X is CH; $R^4$ is hydrogen, fluoro, chloro or methyl; $R^5$ is methoxy or cyclopropyl; $R^6$ is methyl; $R^{11}$ is each independently fluoro, cyano, —$CF_3$, —$CHF_2$—$OCF_3$ or —$S(O)_2CH_3$; or two $R^{11}$ groups, together with the carbon atom to which they are attached, form cyclopropyl; m is 1; n is 1; j is 1 or 2 and k is 0.

In certain embodiments, provided herein are compounds of Formula (VIb) or (VIc), or a pharmaceutically acceptable salt thereof, wherein $R^1$ is hydrogen or fluoro; X is CH; $R^4$ is hydrogen, fluoro, chloro or methyl; $R^5$ is methoxy or cyclopropyl; $R^6$ is methyl; $R^{11}$ is each independently fluoro, cyano, —$CF_3$, —$CHF_2$—$OCF_3$ or —$S(O)_2CH_3$; or two $R^{11}$ groups, together with the carbon atom to which they are attached, form cyclopropyl; m is 1; n is 1; j is 1 or 2 and k is 0.

In certain embodiments, provided herein are compounds of Formula (I), (II), (IV), (IVa), (VI), (VIa), (VIb) or (VIc), wherein each $R^{11}$ is independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; or two $R^{11}$ groups, together with the carbon atom to which they are attached, form $C_{3-5}$cycloalkyl or oxo; and the other variables are as described elsewhere herein for Formulae (I), (II), (IV), (IVa), (VI), (VIa), (VIb) and (VIc), respectively.

In certain embodiments, provided herein are compounds of Formula (I), (II), (IV), (IVa), (VI), (VIa), (VIb) or (VIc), wherein each $R^{11}$ is independently halo, cyano$C_{1-3}$alkyl, halo$C_{1-3}$alkyl, hydroxyl, halo$C_{1-3}$alkoxy, $C_{1-3}$alkylsulfonyl or halo$C_{1-3}$alkylsulfonyl; or two $R^{11}$ groups, together with the carbon atom to which they are attached, form $C_{3-5}$cycloalkyl or oxo; and the other variables are as described elsewhere herein for Formulae (I), (II), (IV), (IVa), (VI), (VIa), (VIb) and (VIc), respectively.

In certain embodiments, provided herein are compounds of Formula (I), (II), (IV), (IVa), (VI), (VIa), (VIb) or (VIc), wherein each $R^{11}$ is independently halo, cyano$C_{1-3}$alkyl, halo$C_{1-3}$alkyl, hydroxyl, halo$C_{1-3}$alkoxy or $C_{1-3}$alkylsulfonyl; or two $R^{11}$ groups, together with the carbon atom to which they are attached, form $C_{3-5}$cycloalkyl or oxo; and the other variables are as described elsewhere herein for Formulae (I), (II), (IV), (IVa), (VI), (VIa), (VIb) and (VIc), respectively.

In certain embodiments, provided herein are compounds of Formula (I), (II), (IV), (IVa), (VI), (VIa), (VIb) or (VIc), wherein each $R^{11}$ is independently halo, cyano, $C_{1-3}$alkyl, halo$C_{1-3}$alkyl, halo$C_{1-3}$alkoxy or $C_{1-3}$alkylsulfonyl; and the other variables are as described elsewhere herein for Formulae (I), (II), (IV), (IVa), (VI), (VIa), (VIb) and (VIc), respectively. In certain embodiments, provided herein are compounds of Formulae (I), (II), (IV), (IVa), (VI), (VIa), (VIb) or (VIc), wherein each $R^{11}$ is independently fluoro, cyano, —$CHF_2$, —$CF_3$, —$OCF_3$, —$OCHF_2$ or —$S(O)_2CH_3$; or two $R^{11}$ groups, together with the carbon atom to which they are attached, form cyclopropyl; and the other variables are as described elsewhere herein for Formulae (I), (II), (IV), (IVa), (VI), (VIa), (VIb) and (VIc), respectively. In certain embodiments, provided herein are compounds of Formula (I), (II), (IV), (IVa), (VI), (VIa), (VIb) or (VIc), wherein each $R^{11}$ is independently fluoro, cyano, —$CHF_2$, —$CF_3$, —$OCF_3$ or —$S(O)_2CH_3$; or two $R^{11}$ groups, together with the carbon atom to which they are attached, form cyclopropyl and the other variables are as described elsewhere herein for Formula (I), (II), (IV), (IVa), (VI), (VIa), (VIb) and (VIc), respectively. In certain embodiments, provided herein are compounds of Formula (I), (II), (IV), (IVa), (VI), (VIa), (VIb) or (VIc), wherein each $R^{11}$ is independently fluoro, cyano, —$CHF_2$, —$CF_3$, —$OCF_3$ or —$S(O)_2CH_3$; and the other variables are as described elsewhere herein for Formulae (I), (II), (IV), (IVa), (VI), (VIa), (VIb) and (VIc), respectively.

In certain embodiments, provided herein are compounds of Formula (I), (II), (IV), (VI) or (X) having the Formula (VII):

(VII)

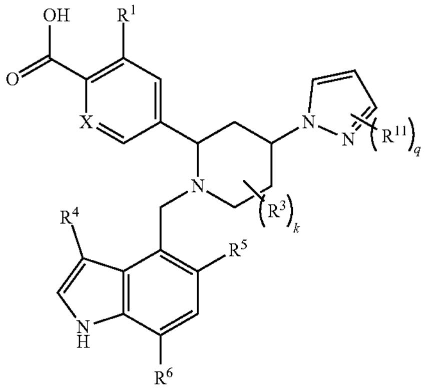

or a pharmaceutically acceptable salt thereof, wherein q is 0, 1, 2 or 3. In certain embodiments, provided herein are compounds of Formula (I), (II), (IV), (VI) or (X) having the Formula (VIIa):

(VIIa)

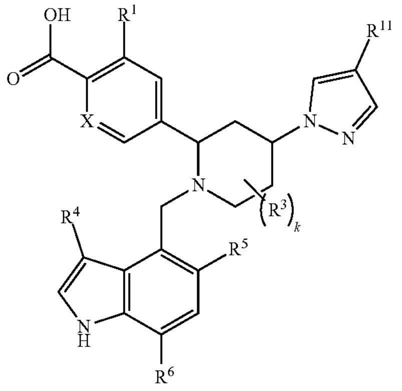

or a pharmaceutically acceptable salt thereof. In certain embodiments, provided herein are compounds of Formula (VII) or (VIIa) wherein each $R^{11}$ is independently halo, cyano, halo$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy or halo$C_{1-3}$alkoxy; k is 0; X is CH; $R^1$ is hydrogen; and the other variables are as described for Formula (I), (II), (IV), (VI) and (X), respectively. In certain embodiments, provided herein are compounds of Formula (VII) or (VIIa) wherein each $R^{11}$ is independently halo, cyano, haloalkyl or hydroxyl; k is 0; X is CH; $R^1$ is hydrogen; and the other variables are as described for Formula (I), (II), (IV), (VI) and (X), respectively. In yet certain embodiments, provided herein are compounds of Formula (VII) or (VIIa) wherein each $R^{11}$ is independently halo, cyano or halo$C_{1-3}$alkyl; k is 0; X is CH; $R^1$ is hydrogen; and the other variables are as described for Formula (I), (II), (IV), (VI) and (X), respectively. In yet certain embodiments, provided herein are compounds of Formula (VII) or (VIIa) wherein $R^4$ is hydrogen; $R^5$ is methoxy; $R^6$ is methyl and X, $R^1$ $R^{11}$ and k are as described above.

In certain embodiments, provided herein are compounds of Formula (I), (II) or (IV) having the Formula (VIII):

(VIII)

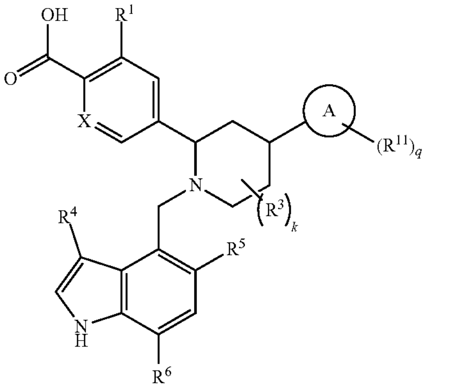

or a pharmaceutically acceptable salt thereof, wherein Ring A is cycloalkyl, heterocyclyl, aryl or heteroaryl; q is 0, 1, 2 or 3; and the other variables are as described for Formulae (I), (II) and (IV), respectively. In certain embodiments, provided herein are compounds of Formula (VIII) wherein Ring A is heterocyclyl or heteroaryl. In certain embodiments, provided herein are compounds of Formula (VIII) wherein Ring A is heterocyclyl. In certain embodiments, provided herein are compounds of Formula (VIII) wherein Ring A is heteroaryl. In certain embodiments, provided herein are compounds of Formula (VIII) wherein Ring A is pyridinyl, pyrimidinyl, pyridazinyl, pyrazinyl, triazolyl, imidazolyl, thiazolyl, or pyrazolyl. In certain embodiments, provided herein are compounds of Formula (VIII) wherein Ring A is pyridinyl or pyrazolyl. In certain embodiments, provided herein are compounds of Formula (VIII) wherein Ring A is pyridinyl. In certain embodiments, provided herein are compounds of Formula (VIII) wherein Ring A is pyrazolyl. In certain embodiments, provided herein are compounds of Formula (VIII) wherein Ring A is azolyl. In certain embodiments, provided herein are compounds of Formula (VIII) wherein X is CH, $R^1$ is hydrogen; $R^4$ is hydrogen; $R^5$ is methoxy; $R^6$ is methyl; each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; k is 0; q is 0, 1, 2 or 3 and Ring A is as described above.

In certain embodiments, provided herein are compounds of Formula (I) having the Formula (X):

(X)

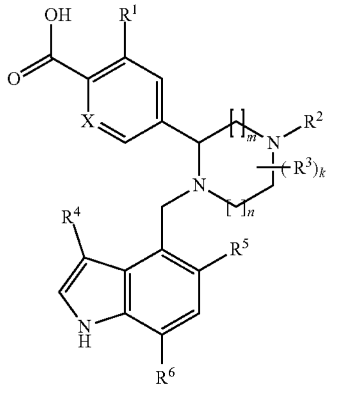

or a pharmaceutically acceptable salt thereof. In certain embodiments, provided herein are compounds of Formula (I) or (X), wherein $R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl, wherein the alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl is optionally substituted with one, two or three independently selected $R^{11}$; and $R_u$ and $R^{11}$ are as described elsewhere herein for Formula (I) and (X), respectively. In certain embodiments, provided herein are compounds of Formula (I) or (X), wherein $R^2$ is $C_{1-6}$alkyl, halo$C_{1-6}$alkyl, deutero$C_{1-6}$alkyl, hydroxy$C_{1-6}$alkyl, $C_{1-6}$alkoxy$C_{1-6}$alkyl, cyano$C_{1-6}$alkyl, —$R_u$—$C_{3-6}$cycloalkyl, —$R_u$-3- to 7-membered heterocyclyl, $C_{3-6}$cycloalkyl, 3- to 7-membered heterocyclyl or 5- to 10-membered heteroaryl, wherein the $C_{1-6}$alkyl, halo$C_{1-6}$ alkyl, deutero$C_{1-6}$alkyl, hydroxy$C_{1-6}$alkyl, C1-6alkoxy$C_{1-6}$ alkyl, cyano$C_{1-6}$alkyl, —$R_u$—$C_{3-6}$cycloalkyl, —$R_u$-3- to 7-membered heterocyclyl, $C_{3-6}$cycloalkyl, 3- to 7-membered heterocyclyl or 5- to 10-membered heteroaryl is optionally substituted with one, two or three independently selected $R^{11}$; and $R_u$ and $R^{11}$ are as described elsewhere herein for Formula (I) and (X), respectively. In certain embodiments, provided herein are compounds of Formula (I) or (X), wherein $R^2$ is $C_{1-3}$alkyl, halo$C_{1-3}$alkyl, deutero$C_{1-3}$ alkyl, hydroxy$C_{1-3}$alkyl, $C_{1-3}$alkoxy$C_{1-3}$alkyl, cyano$C_{1-3}$alkyl, —$R_u$—$C_{3-6}$cycloalkyl, —$R_u$-3- to 6-membered heterocyclyl, $C_{3-6}$cycloalkyl, 3- to 6-membered heterocyclyl or 5- to 6-membered heteroaryl, wherein the $C_{1-3}$alkyl, halo$C_{1-3}$alkyl, deutero$C_{1-3}$alkyl, hydroxy$C_{1-3}$alkyl, $C_{1-3}$alkoxy$C_{1-3}$alkyl, cyano$C_{1-3}$alkyl, —$R_u$—$C_{3-6}$cycloalkyl, —$R_u$-3- to 6-membered heterocyclyl, $C_{3-6}$cycloalkyl, 3- to 6-membered heterocyclyl or 5- to 6-membered heteroaryl is optionally substituted with one, two or three independently selected $R^{11}$ groups; and $R_u$ and $R^{11}$ are as described elsewhere herein for Formula (I) and (X), respectively. In certain embodiments, provided herein are compounds of Formula (I) or (X), wherein $R^2$ is alkyl, haloalkyl, deuteroalkyl, hydroxyalkyl, cyanoalkyl, —$R_u$-cycloalkyl or —$R_u$-heterocyclyl, wherein the alkyl, haloalkyl, deuteroalkyl, hydroxyalkyl, cyanoalkyl-$R_u$-cycloalkyl or —$R_u$-heterocyclyl is optionally substituted with $R^{11}$ and $R^{11}$ and the other variables are as described elsewhere herein for Formulae (I) and (X), respectively. In certain embodiments, provided herein are compounds of Formula (I) or (X), wherein $R^2$ is $C_{1-3}$alkyl, halo$C_{1-3}$alkyl, deutero$C_{1-3}$alkyl, hydroxy$C_{1-3}$alkyl, cyano$C_{1-3}$alkyl, —$R_u$—$C_{3-5}$cycloalkyl, —$R_u$-3- to 5-membered heterocyclyl, wherein the $C_{1-3}$alkyl, halo$C_{1-3}$ alkyl, deutero$C_{1-3}$alkyl, hydroxy$C_{1-3}$alkyl, cyano$C_{1-3}$alkyl, —$R_u$—$C_{3-5}$cycloalkyl, —$R_u$-3- to 5-membered heterocyclyl is optionally substituted with independently selected $R^{11}$ groups and $R^{11}$ and the other variables are as described elsewhere herein for Formulae (I) and (X), respectively. In certain embodiments, provided herein are compounds of Formula (I) or (X), wherein $R^2$ is haloalkyl, deuteroalkyl, —$R_u$— cycloalkyl or —$R_u$-heterocyclyl, wherein the haloalkyl, deuteroalkyl, —$R_u$-cycloalkyl or —$R_u$— heterocyclyl is optionally substituted with independently selected $R^{11}$ groups and $R^{11}$ and the other variables are as described elsewhere herein for Formulae (I) and (X), respectively. In certain embodiments, provided herein are compounds of Formula (I) or (X), wherein $R^2$ is halo$C_{1-3}$alkyl, deutero$C_{1-3}$ alkyl, —$R_u$—$C_{3-5}$cycloalkyl or —$R_u$-3- to 5-membered heterocyclyl, wherein the halo$C_{1-3}$alkyl, deutero$C_{1-3}$alkyl, —$R_u$—$C_{3-5}$cycloalkyl or —$R_u$-3- to 5-membered heterocyclyl is optionally substituted with independently selected $R^{11}$ groups and $R^{11}$ and the other variables are as described elsewhere herein for Formulae (I) and (X), respectively. In certain embodiments, provided herein are compounds of Formula (I) or (X), wherein $R^2$ is haloalkyl or —$R_u$-heterocyclyl, wherein the —$R_u$-heterocyclyl is optionally substituted with independently selected halo; and the other variables are as described elsewhere herein for Formula (I) and (X), respectively. In certain embodiments, provided herein are compounds of Formula (I) or (X), wherein $R^2$ is halo$C_{1-3}$ alkyl or —$R_u$-3- to 5-membered heterocyclyl, wherein the —$R_u$-3- to 5-membered heterocyclyl is optionally substituted with independently selected halo; and the other variables are as described elsewhere herein for Formula (I) and (X), respectively. In certain embodiments, provided herein are compounds of Formula (I) or (X), wherein $R^2$ is fluoroethyl or 3-fluorooxetan-3-yl)methyl; and the other variables are as described elsewhere herein for Formula (I) and (X), respectively. In certain embodiments, provided herein are compounds of Formula (I) or (X), wherein $R^2$ is fluoroethyl; and the other variables are as described elsewhere herein for Formula (I) and (X), respectively. In certain embodiments, provided herein are compounds of Formula (I) or (X) wherein $R^2$ is 3-fluorooxetan-3-yl)methyl; and the other variables are as described elsewhere herein for Formula (I) and (X), respectively. In certain embodiments, provided herein are compounds of Formula (I) or (X), wherein $R^2$ is alkyl, haloalkyl, deuteroalkyl, hydroxyalkyl or cyanoalkyl wherein the alkyl, haloalkyl, deuteroalkyl, hydroxyalkyl or cyanoalkyl is optionally substituted with one $R^{11}$ and $R^{11}$ is as described elsewhere herein for Formulae (I) and (X), respectively. In yet certain embodiments, provided herein are compounds of Formula (X) wherein X is CH, $R^1$ is hydrogen, $R^4$ is hydrogen; $R^5$ is methoxy; $R^6$ is methyl; each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; k is 0; and $R^2$ is as described above.

In certain embodiments, provided herein are compounds of Formula (III), (IIIa) or Formula (V) wherein $R^{2a}$ and $R^{2b}$, together with the carbon atom to which they are attached, form cycloalkyl optionally substituted with one, two or three independently selected $R^{11}$; and each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl and the other variables are as described elsewhere herein for Formula (III), (IIIa) and (V), respectively. In certain embodiments, provided herein are compounds of Formula (III), (IIIa) or Formula (V), wherein $R^{2a}$ and $R^{2b}$, together with the carbon atom to which they are attached, form $C_{3-6}$cycloalkyl optionally substituted with one, two or three independently selected $R^{11}$ and $R^{11}$ is as described for Formula (I).

In certain embodiments, provided herein are compounds of Formula (I), (II), (IV), (IVa), (VI) or (X) wherein m is 0 or 1; n is 0, 1 or 2 and the other variables are as described elsewhere herein for Formulae (I), (II), (IV), (IVa), (VI) and (X), respectively. In certain embodiments, provided herein are compounds of Formula (I), (II), (IV), (IVa), (VI) or (X) wherein m is 0 or 1; n is 0 or 1 and the other variables are as described elsewhere herein for Formulae (I), (II), (IV), (IVa), (VI) and (X), respectively. In certain embodiments, provided herein are compounds of Formula (I), (II), (IIa), (IIb), (IIc), (IV), (IVa), (IVb), (IVc), (IVd), (IVe), (IVf), (VI), (VIa) or (X) wherein m is 1; n is 1 and the other variables are as described elsewhere herein for Formulae (I), (II), (IIa), (IIb), (IIc), (IV), (IVa), (IVb), (IVc), (IVd), (IVe), (IVf), (VI), (VIa) and (X), respectively. In certain embodiments, provided herein are compounds of Formula (I), (II), (IIa), (IIb), (IIc), (IV), (IVa), (IVb), (IVc), (IVd), (IVe), (IVf), (VI), (VIa) or (X) wherein k is 0; m is 1; n is 1 and the other variables are as described elsewhere herein for Formulae (I), (II), (IIa), (IIb), (IIc), (IV), (IVa), (IVb), (IVc), (IVd), (IVe), (IVf), (VI), (VIa) and (X), respectively.

In certain embodiments, provided herein are compounds of Formula (I), (II), (III), (IIIa), (IV), (IVa), or (V) wherein $R^{2a}$ and $R^{2b}$, together with the carbon atom to which they are attached, form cycloalkyl substituted with one, two or three independently selected $R^{11}$ or form heterocyclyl optionally substituted with one, two or three independently selected $R^{11}$; and each $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ and $R^{2b}$, together with the carbon atom to which they are attached, form cycloalkyl substituted with one, two or three independently selected $R^{11}$; and each $R^{11}$ is as described elsewhere herein for Formulae (I), (II), (III), (IIIa), (IV), (IVa), and (V), respectively.

In certain embodiments, provided herein are compounds of Formula (I), (III), (IIIa), or (V) wherein $R^{2a}$ and $R^{2b}$, together with the carbon atom to which they are attached, form $C_{3-6}$cycloalkyl optionally substituted with one, two or three independently selected $R^{11}$; and each $R^{11}$ is as described elsewhere herein for Formulae (III), (IIIa), and (V), respectively.

In certain embodiments, provided herein are compounds of Formula (I), (II), (III), (IIIa), (IV), (IVa), or (V) wherein $R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form cycloalkyl substituted with one, two or three independently selected $R^{11}$, or form heterocyclyl optionally substituted with one, two or three independently selected $R^{11}$; and $R_u$, $R^7$, $R^1$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form cycloalkyl substituted with one, two or three independently selected $R^{11}$ or form heterocyclyl optionally substituted with one, two or three independently selected $R^{11}$; and $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form $C_{3-6}$cycloalkyl substituted with one, two or three independently selected $R^{11}$, or form 4-6-membered heterocyclyl optionally substituted with one, two or three independently selected $R^{11}$; and $R^u$, $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, —$OR^7$, —$SR^7$ or —$NR^8R^9$, wherein the cycloalkyl or heterocyclyl is optionally substituted with one, two or three independently selected $R^{11}$ and $R^{2b}$ is hydrogen, deuterium, halogen, $C_{1-3}$alkyl, deutero$C_{1-3}$ alkyl or halo$C_{1-3}$alkyl; or $R^{2a}$ and $R^{2b}$, together with the carbon atom to which they are attached, form $C_{3-6}$cycloalkyl substituted with one, two or three independently selected $R^{11}$, or form 4-6-membered heterocyclyl optionally substituted with one, two or three independently selected $R^{11}$; and $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form $C_{3-5}$cycloalkyl substituted with one, two or three independently selected $R^{11}$, or form 4-5-membered heterocyclyl optionally substituted with one, two or three independently selected $R^{11}$; and $R^u$, $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$; and $R^u$, $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$; and $R^u$, $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is —$R_u$-cycloalkyl or cycloalkyl, wherein the —$R_u$-cycloalkyl or cycloalkyl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$ alkyl; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is —$R_u$-cycloalkyl, —$R_u$-heterocyclyl, cycloalkyl or heterocyclyl wherein the —$R_u$-cycloalkyl, —$R_u$-heterocyclyl, cycloalkyl or heterocyclyl is optionally substituted with one, two or three independently selected $R^{11}$; $R^{2b}$ is hydrogen, deuterium, halogen, $C_{1-3}$alkyl, deutero$C_{1-3}$alkyl or halo$C_{1-3}$alkyl; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl or heteroaryl, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl or heteroaryl, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is heterocyclyl or heteroaryl, wherein the heterocyclyl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is heteroaryl, wherein the heteroaryl is optionally substituted with one, two or three independently selected $R^{11}$ and $R^{2b}$ is hydrogen, deuterium, halogen, $C_{1-3}$alkyl, deuteroC$_{1-3}$alkyl or haloC$_{1-3}$alkyl; and $R^{11}$ is as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deuteroC$_{1-3}$alkyl or haloC$_{1-3}$alkyl; or $R^{2a}$ and $R^{2b}$, together with the carbon atom to which they are attached, form 4-5-membered heterocyclyl optionally substituted with one, two or three independently selected $R^{11}$; and $R^7$, $R^1$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (IV) or (IVa) wherein $R^{2a}$ and $R^{2b}$, together with the carbon atom to which they are attached, form cyclobutyl substituted with one, two or three independently selected $R^{11}$, or form oxetanyl; and $R^{11}$ are as described elsewhere herein for Formulae (I), (II), (IV) and (IVa), respectively. In certain embodiments, provided herein are compounds of Formula (I), (II), (IV) or (IVa) wherein $R^{2a}$ and $R^{2b}$, together with the carbon atom to which they are attached, form cyclobutyl substituted with one or two $R^{11}$, or form oxetanyl; each $R^{11}$ is independently fluoro, cyano, —$CHF_2$, —$CF_3$, —$OCF_3$ or —$S(O)_2CH_3$; or two $R^{11}$ groups, together with the carbon atom to which they are attached, form cyclopropyl; m is 1; n is 1; and the other variables are as described elsewhere herein for Formulae (I), (II), (IV) and (IVa), respectively.

In certain embodiments, provided herein are compounds of Formula (I), (II), (III), (IIIa), (IV), (IVa), or (V) wherein $R^{2a}$ is —$OR^7$, —$SR^7$ or —$NR^8R^9$; $R^{2b}$ is hydrogen, deuterium, halogen, $C_{1-3}$alkyl, deuteroC$_{1-3}$alkyl or haloC$_{1-3}$alkyl; and $R^7$, $R^8$, $R^9$ and $R^{11}$ are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is —$R_u$-cycloalkyl, —$OR^7$, —$SR^7$ or —$NR^8R^9$; $R^{2b}$ is hydrogen, deuterium, halogen, $C_{1-3}$alkyl, deuteroC$_{1-3}$alkyl or haloC$_{1-3}$alkyl; $R^7$ is haloalkyl or cycloalkyl; $R^8$ is hydrogen; $R^9$ is —$R_u$-cycloalkyl or cycloalkyl wherein the —$R_u$-cycloalkyl or cycloalkyl is optionally substituted with one, two or three independently selected $R^{11}$ and the remaining variables are as described elsewhere herein for Formulae (I), (II), (III), (IIIa), (IV), (IVa), and (V), respectively. In certain embodiments, provided herein are compounds of Formula (I), (II), (III), (IIIa), (IV), (IVa), or (V) wherein $R^{2a}$ is —$R_u$-cycloalkyl, —$OR^7$, —$SR^7$ or —$NR^8R^9$; $R^{2b}$ is hydrogen, deuterium, halogen, $C_{1-3}$alkyl, deuteroC$_{1-3}$alkyl or haloC$_{1-3}$alkyl; $R^7$ is haloalkyl or cycloalkyl; $R^8$ is hydrogen; $R^9$ is —$R_u$-cycloalkyl or cycloalkyl wherein the —$R_u$-cycloalkyl or cycloalkyl is optionally substituted with one, two or three independently selected $R^{11}$; $R^{11}$ is each independently halo or haloC$_{1-3}$alkyl; and the remaining variables are as described elsewhere herein for Formulae (I), (II), (III), (IIIa), (IV), (IVa), and (V), respectively. In certain embodiments, provided herein are compounds of Formula (I), (II), (III), (IIIa), (IV), (IVa), or (V) wherein $R^{2a}$ is cyclopropylmethyl, —$OR^7$, —$SR^7$ or —$NR^8R^9$; $R^{2b}$ is hydrogen, deuterium, halogen, $C_{1-3}$alkyl, deuteroC$_{1-3}$alkyl or haloC$_{1-3}$alkyl; $R^7$ is —$CH_2CF_3$ or cyclobutyl; $R^8$ is hydrogen; $R^9$ is cyclopropylmethyl or cyclobutyl wherein the cyclopropylmethyl or cyclobutyl is optionally substituted with one, two or three $R^{11}$; each $R^{11}$ is independently fluoro or trifluoromethyl and the remaining variables are as described elsewhere herein for Formulae (I), (II), (III), (IIIa), (IV), (IVa), and (V), respectively. In certain embodiments, $R^{2b}$ is hydrogen.

In certain embodiments, provided herein are compounds of Formula (I), (II), (III), (IIIa), (IV), (IVa), or (V) wherein $R^{2a}$ is —$OR^7$, —$SR^7$ or —$NR^8R^9$; $R^{2b}$ is hydrogen, deuterium, halogen, $C_{1-3}$alkyl, deuteroC$_{1-3}$alkyl or haloC$_{1-3}$alkyl; and $R^7$ is —$CH_2CF_3$ or cyclobutyl; $R^9$ is cyclopropylmethyl or cyclobutyl wherein the cyclopropylmethyl or cyclobutyl is optionally substituted with one, two or three $R^{11}$; each $R^{11}$ is independently fluoro or trifluoromethyl and the remaining variables are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^7$ is —$R_u$-cycloalkyl, —$R_u$-heterocyclyl, cycloalkyl, heterocyclyl, or heteroaryl wherein the —$R_u$-cycloalkyl, —$R_u$-heterocyclyl, cycloalkyl, heterocyclyl or heteroaryl is optionally substituted with one, two or three independently selected $R^{11}$; $R^8$ is hydrogen, deuterium, alkyl, deuteroalkyl or haloalkyl; $R^9$ is —$R_u$-cycloalkyl, —$R_u$-heterocyclyl, cycloalkyl, heterocyclyl or heteroaryl wherein the —$R_u$-cycloalkyl, —$R_u$-heterocyclyl, cycloalkyl, heterocyclyl or heteroaryl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$; each $R^{11}$ is independently halo, cyano, oxo, $C_{1-3}$alkyl, deuteroC$_{1-3}$alkyl, haloC$_{1-3}$alkyl, cyanoC$_{1-3}$alkyl, hydroxyC$_{1-3}$alkyl, $C_{1-3}$alkoxyC$_{1-3}$alkyl, haloC$_{1-3}$alkoxyC$_{1-3}$ alkyl, hydroxyl, $C_{1-3}$alkoxy, haloC$_{1-3}$alkoxy, $C_{1-3}$alkylthio, haloC$_{1-3}$alkylthio, $C_{1-3}$alkylsulfonyl, haloC$_{1-3}$alkylsulfonyl, $C_{1-3}$alkylsulfinyl or haloC$_{1-3}$alkylsulfinyl; and $R^u$ is methylene, ethylene or propylene linker optionally substituted with one to six independently selected halo.

In certain embodiments, provided herein are compounds of Formula (I), (II), (III), (IIIa), (IV), (IVa), or (V) wherein $R^7$ is cycloalkyl, heterocyclyl or heteroaryl wherein the cycloalkyl, heterocyclyl or heteroaryl is optionally substituted with one, two or three independently selected $R^{11}$; $R^8$ is hydrogen, deuterium, alkyl, deuteroalkyl or haloalkyl; $R^9$ is cycloalkyl, heterocyclyl or heteroaryl wherein the cycloalkyl, heterocyclyl or heteroaryl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$ and wherein the heterocyclyl is further optionally substituted with oxo and each $R^{11}$ is independently halo, cyano, oxo, $C_{1-3}$alkyl, deuteroC$_{1-3}$alkyl, haloC$_{1-3}$alkyl, cyanoC$_{1-3}$alkyl, hydroxyC$_{1-3}$alkyl, $C_{1-3}$alkoxyC$_{1-3}$alkyl, haloC$_{1-3}$alkoxyC$_{1-3}$alkyl, hydroxyl, $C_{1-3}$alkoxy, haloC$_{1-3}$alkoxy, $C_{1-3}$alkylthio, haloC$_{1-3}$alkylthio, $C_{1-3}$alkylsulfonyl, haloC$_{1-3}$alkylsulfonyl, $C_{1-3}$alkylsulfinyl or haloC$_{1-3}$alkylsulfinyl; and $R^u$ is methylene, ethylene or propylene linker optionally substituted with one to six independently selected halo.

In certain embodiments, provided herein are compounds of Formula (I), (II), (III), (IIIa), (IV), (IVa), or (V) wherein $R^7$ is cycloalkyl or heterocyclyl optionally substituted with one, two or three independently selected $R^{11}$; $R^8$ is hydrogen, deuterium, alkyl, deuteroalkyl or haloalkyl; $R^9$ is cycloalkyl or heterocyclyl wherein the cycloalkyl or heterocyclyl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$; $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl.

In certain embodiments, provided herein are compounds of Formula (I), (II), (III), (IIIa), (IV), (IVa), or (V) wherein $R^7$ is —$R_u$-heterocyclyl or heterocyclyl wherein the —$R_u$-heterocyclyl or heterocyclyl is optionally substituted with one, two or three independently selected $R^{11}$; and each $R^{11}$ is independently halo, cyano, oxo, $C_{1-3}$alkyl, deutero$C_{1-3}$ alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl.

In certain embodiments, provided herein are compounds of Formula (I), (II), (III), (IIIa), (IV), (IVa), or (V) wherein $R^7$ is haloalkyl; $R^8$ is hydrogen, deuterium, alkyl, deuteroalkyl or haloalkyl; and $R^9$ is haloalkyl.

In certain embodiments, provided herein are compounds of Formula (I), (II), (III), (IIIa), (IV), (IVa), or (V) wherein $R^{2a}$ is —$NR^8R^9$; $R^{2b}$ is hydrogen, deuterium, halogen, $C_{1-3}$alkyl, deutero$C_{1-3}$alkyl or halo$C_{1-3}$alkyl; and $R^8$, $R^9$ and $R^{11}$ are as described for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^{2a}$ is —$NR^8R^9$; $R^{2b}$ is hydrogen, deuterium, halogen, $C_{1-3}$alkyl, deutero$C_{1-3}$alkyl or halo$C_{1-3}$alkyl; and $R^9$ is —$R_u$-cycloalkyl optionally substituted with one, two or three $R^{11}$ and $R^{11}$ are as described elsewhere herein for Formulae (I), (II), (III), (IIIa), (IV), (IVa), and (V), respectively. In certain embodiments, provided herein are compounds of Formula (I), (II), (III), (IIIa), (IV), (IVa), or (V) wherein $R^{2a}$ is —$NR^8R^9$; $R^{2b}$ is hydrogen, deuterium, halogen, $C_{1-3}$alkyl, deutero$C_{1-3}$alkyl or halo$C_{1-3}$alkyl; and $R^9$ is cycloalkyl optionally substituted with one, two or three independently selected $R^{11}$ and $R^{11}$ are as described elsewhere herein for Formulae (I), (II), (III), (IIIa), (IV), (IVa), and (V), respectively. In certain embodiments, provided herein are compounds of Formula (I), (II), (III), (IIIa), (IV), (IVa), or (V) wherein $R^{2a}$ is —$NR^8R^9$; $R^{2b}$ is hydrogen, deuterium, halogen, $C_{1-3}$alkyl, deutero$C_{1-3}$alkyl or halo$C_{1-3}$ alkyl; and $R^9$ is cyclopropyl optionally substituted with one, two or three fluoro and the remaining variables are as described elsewhere herein for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^8$ is hydrogen, deuterium, alkyl, deuteroalkyl or haloalkyl; $R^9$ is haloalkyl, —$R_u$-cycloalkyl, —$R_u$-heterocyclyl, cycloalkyl or heterocyclyl, wherein the haloalkyl, —$R_u$-cycloalkyl, —$R_u$-heterocyclyl, cycloalkyl or heterocyclyl is optionally substituted with one, two or three independently selected $R^{11}$ and each $R^{11}$ is independently halo, cyano, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl for Formulae (I), (II), (III), (IIIa), (IV), (IVa), and (V), respectively.

In certain embodiments, provided herein are compounds of Formula (I), (II), (III), (IIIa), (IV), (IVa), or (V) wherein $R^8$ is hydrogen, deuterium, alkyl, deuteroalkyl or haloalkyl; $R^9$ is haloalkyl, —$R_u$-heterocyclyl or heterocyclyl, wherein the haloalkyl, —$R_u$-heterocyclyl or heterocyclyl is optionally substituted with one, two or three independently selected $R^{11}$; and $R^{11}$ is as described for Formulae (I), (II), (III), (IIIa), (IV), (IVa), and (V), respectively.

In certain embodiments, provided herein are compounds of Formula (I), (II), (III), (IIIa), (IV), (IVa) or (V) wherein $R^{2a}$ is —$OR^7$; $R^7$ is haloalkyl, —$R_u$-cycloalkyl, —$R_u$-heterocyclyl, cycloalkyl or heterocyclyl, wherein the haloalkyl, —$R_u$-cycloalkyl, —$R_u$-heterocyclyl, cycloalkyl or heterocyclyl is optionally substituted with one, two or three independently selected $R^{11}$; and $R^{11}$ is as described for Formulae (I), (II), (III), (IIIa), (IV), (IVa), and (V), respectively.

In certain embodiments, provided herein are compounds of Formula (I), (II), (III), (IIIa), (IV), (IVa) or (V) wherein $R^{2b}$ is hydrogen or methyl. In certain embodiments, provided herein are compounds of Formula (I), (II), (III), (IIIa), (IV), (IVa) or (V) wherein $R^{2b}$ is hydrogen. In certain embodiments, provided herein are compounds of Formula (I), (II), (III), (IIIa), (IV), (IVa) or (V) wherein $R^{2b}$ is hydrogen and the other variables are as described elsewhere herein for Formulae (I), (II), (III), (IIIa), (IV), (IVa) and (V), respectively.

In certain embodiments, provided herein are compounds of Formula (I), (II), (IV), (IVa), (VI) or (X) wherein m is 0 and the other variables are as described elsewhere herein for Formula (I), (II), (IV), (IVa), (VI) and (X), respectively. In certain embodiments, provided herein are compounds of Formula (I), (II), (IV), (IVa), (VI) or (X) wherein m is 0, n is 0 or 1 and the other variables are as described elsewhere herein for Formula (I), (II), (IV), (VI) and (X) respectively.

In certain embodiments, provided herein are compounds of Formula (I), (II), (III), (IIIa), (IV), (IVa), (V), (VI), (VII), (VIIa), (VIII), (IX) or (X) wherein each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl or halo$C_{1-3}$alkylsulfinyl, and the other variables are as described herein for Formulae (I), (II), (III), (IIIa), (IV), (IVa), (V), (VI), (VII), (VIIa), (VIII), (IX) and (X) respectively. In certain embodiments, provided herein are compounds of Formula (I), (II), (III), (IIIa), (IV), (IVa), (V), (VI), (VII), (VIIa), (VIII), (IX) or (X) wherein each $R^{11}$ is independently halo, cyano, $C_{1-3}$alkyl or halo$C_{1-3}$alkyl, and the other variables are as described herein for Formulae (I), (II), (III), (IIIa), (IV), (IVa), (V), (VI), (VII), (VIIa), (VIII), (IX) and (X) respectively. In certain embodiments, provided herein are compounds of Formula (I), (II), (III), (IIIa), (IV), (IVa), (V), (VI), (VII), (VIIa), (VIII), (IX) or (X) wherein each $R^{11}$ is independently halo, cyano or halo$C_{1-3}$alkyl, and the other variables are as described herein for Formulae (I), (II), (III), (IIIa), (IV), (IVa), (V), (VI), (VII), (VIIa), (VIII), (IX) and (X) respectively. In certain embodiments, provided herein are compounds of Formula (I), (II), (III), (IIIa), (IV), (IVa), (V), (VI), (VII), (VIIa), (VIII), (IX) or (X) wherein each $R^{11}$ is independently halo, cyano, halo$C_{1-3}$alkyl, hydroxy$C_{1-3}$alkyl, $C_{1-3}$alkoxy$C_{1-3}$alkyl, halo$C_{1-3}$alkoxy$C_{1-3}$ alkyl, hydroxyl, $C_{1-3}$alkoxy or halo$C_{1-3}$alkoxy, and the other variables are as described herein for Formulae (I), (II), (III), (IIIa), (IV), (IVa), (V), (VI), (VII), (VIIa), (VIII), (IX) and (X) respectively. In certain embodiments, each $R^{11}$ is independently halo, cyano, halo$C_{1-3}$alkyl or hydroxyl.

In certain embodiments, provided herein are compounds of Formula (I), (II), (III), (IIIa), (IV), (IVa), (V), (VI), (VII), (VIIa), (VIII), (IX) or (X) wherein each $R^{11}$ is independently halo, cyano or halo$C_{1-3}$alkyl, and the other variables are as described herein for Formulae (I), (II), (III), (IIIa), (IV), (IVa), (V), (VI), (VII), (VIIa), (VIII), (IX) and (X) respectively. In certain embodiments, each $R^{11}$ is independently halo or cyano.

In certain embodiments, provided herein are compounds of Formula (I), (II), (III), (IIIa), (IV), (IVa), (V), (VI), (VII), (VIIa), (VIII), (IX) or (X) wherein each $R^{11}$ is independently fluoro, chloro, bromo, cyano, —$CHF_2$ or —$CF_3$, and the other variables are as described elsewhere herein for Formulae (I), (II), (III), (IIIa), (IV), (IVa), (V), (VI), (VII), (VIIa), (VIII), (IX) and (X), respectively. In certain embodiments, each $R^{11}$ is independently Cl or cyano.

In certain embodiments, provided herein are compounds of Formula (I), (II), (III), (IIIa), (IV), (IVa), (V), (VI), (VII), (VIIa), (VIII), (IX) or (X) wherein the nitrogen of the indole is protected by a protecting group and the other variables are as described elsewhere herein for Formulae (I), (II), (III), (IIIa), (IV), (IVa), (V), (VI), (VII), (VIIa), (VIII), (IX) and (X) respectively. In certain embodiments, provided herein are compounds of Formula (I), (II), (III), (IIIa), (IV), (IVa), (V), (VI), (VII), (VIIa), (VIII), (IX) or (X) wherein the nitrogen of the indole is protected by Boc or p-toluene sulfonamide and the other variables are as described elsewhere herein for Formulae (I), (II), (III), (IIIa), (IV), (IVa), (V), (VI), (VII), (VIIa), (VIII), (IX) and (X) respectively.

In certain embodiments, provided herein are compounds of Formula (I), (II), (III), (IIIa), (IV), (IVa), (V), (VI), (VII), (VIIa), (VIII), (IX) or (X) wherein k is 0 and the other variables are as described elsewhere herein for Formulae (I), (II), (III), (IIIa), (IV), (IVa), (V), (VI), (VII), (VIIa), (VIII), (IX) and (X), respectively. In certain embodiments, provided herein are compounds of Formula (I), (II), (IIa), (IIb), (IIc), (III), (IIIa), (IV), (IVa), (IVb), (IVc), (IVd), (IVe), (IVf), (V), (VI), (VII), (VIIa), (VIII), (IX) or (X) wherein k is 0 and the other variables are as described elsewhere herein for Formulae (I), (II), (IIa), (IIb), (IIc), (III), (IIIa), (IV), (IVa), (IVb), (IVc), (IVd), (IVe), (IVf), (V), (VI), (VII), (VIIa), (VIII), (IX) and (X), respectively.

In certain embodiments, provided herein are compounds of Formula (I), (II), (III), (IIIa), (IV), (IVa), (V), (VI), (VII), (VIIa), (VIII), (IX) or (X) wherein $R^3$ is halo, methyl or —$CF_3$ and the other variables are as described elsewhere herein for Formulae (I), (II), (III), (IIIa), (IV), (IVa), (V), (VI), (VII), (VIIa), (VIII), (IX) and (X), respectively. In certain embodiments, provided herein are compounds of Formula (I), (II), (III), (IIIa), (IV), (IVa), (V), (VI), (VII), (VIIa), (VIII), (IX) or (X) wherein $R^3$ is methyl and the other variables are as described elsewhere herein for Formulae (I), (II), (III), (IIIa), (IV), (IVa), (V), (VI), (VII), (VIIa), (VIII), (IX) and (X), respectively.

In certain embodiments, provided herein are compounds of Formula (I), (II), (III), (IIIa), (IV), (IVa), (V), (VI), (VII), (VIIa), (VIII), (IX) or (X) wherein $R^4$ is hydrogen, halo, $C_{1-3}$alkyl or halo$C_{1-3}$alkyl and the other variables are as described elsewhere herein for Formulae (I), (II), (III), (IIIa), (IV), (IVa), (V), (VI), (VII), (VIIa), (VIII), (IX) and (X), respectively. In yet certain embodiments, $R^4$ is hydrogen, fluoro, chloro, methyl or —$CF_3$. In yet certain embodiments, $R^4$ is hydrogen, fluoro, chloro or methyl. In yet certain embodiments, $R^4$ is hydrogen.

In certain embodiments, provided herein are compounds of Formula (I), (II), (III), (IIIa), (IV), (IVa), (V), (VI), (VII), (VIIa), (VIII), (IX) or (X) wherein $R^5$ is halo, $C_{1-3}$alkyl, $C_{3-5}$cycloalkyl or $C_{1-3}$alkoxy; and the other variables are as described elsewhere herein for Formulae (I), (II), (III), (IIIa), (IV), (IVa), (V), (VI), (VII), (VIIa), (VIII), (IX) and (X), respectively. In certain embodiments, $R^5$ is chloro, bromo, methyl, cyclopropyl or methoxy.

In certain embodiments, provided herein are compounds of Formula (I), (II), (III), (IIIa), (IV), (IVa), (V), (VI), (VII), (VIIa), (VIII), (IX) or (X) wherein $R^6$ is halo, cyano, $C_{1-3}$alkyl, $C_{3-5}$cycloalkyl or $C_{1-3}$alkoxy; and the other variables are as described elsewhere herein for Formulae (I), (II), (III), (IIIa), (IV), (IVa), (V), (VI), (VII), (VIIa), (VIII), (IX) and (X), respectively. In certain embodiments, $R^6$ is chloro, bromo, cyano, methyl, cyclopropyl or methoxy.

In certain embodiments, provided herein are compounds of Formula (I), (II), (III), (IIIa), (IV), (IVa), (V), (VI), (VII), (VIIa), (VIII), (IX) or (X) wherein $R^4$ is hydrogen or methyl; $R^5$ is methoxy; $R^6$ is methyl and the other variables are as described elsewhere herein for Formulae (I), (II), (III), (IIIa), (IV), (IVa), (V), (VI), (VII), (VIIa), (VIII), (IX) and (X), respectively. In yet certain embodiments, $R^4$ is hydrogen; $R^5$ is methoxy and $R^6$ is methyl. In certain embodiments, provided herein are compounds of Formula (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) or (X) wherein $R^4$ is hydrogen, fluoro, chloro or methyl; $R^5$ is methoxy or cyclopropyl; $R^6$ is methyl and the other variables are as described elsewhere herein for Formulae (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) and (X), respectively. In certain embodiments, provided herein are compounds of Formula (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) or (X) wherein $R^1$ is hydrogen, fluoro or chloro; X is CH; $R^4$ is hydrogen, fluoro, chloro or methyl; $R^5$ is methoxy or cyclopropyl; $R^6$ is methyl and the other variables are as described elsewhere herein for Formulae (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) and (X), respectively. In certain embodiments, provided herein are compounds of Formula (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) or (X) wherein $R^1$ is hydrogen or fluoro; X is CH; $R^4$ is hydrogen, fluoro, chloro or methyl; $R^5$ is methoxy or cyclopropyl; $R^6$ is methyl and the other variables are as described elsewhere herein for Formulae (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVi), (V), (VI), (VIa), (VIb), (IVc), (VII), (VIIa), (VIII), (IX) and (X), respectively. In certain embodiments, provided herein are compounds of Formula (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVi), (V), (VI), (VIa), (VIb), (IVc), (VII), (VIIa), (VIII), (IX) or (X) wherein $R^1$ is hydrogen or fluoro; X is CH; $R^4$ is hydrogen, fluoro or chloro; $R^5$ is methoxy; $R^6$ is methyl and the other variables are as described elsewhere herein for Formulae (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVl), (V), (VI), (VIa), (VIb), (IVc), (VII), (VIIa), (VIII), (IX) and (X), respectively.

In certain embodiments, provided herein are compounds of Formula (I), (II), (III), (IIIa), (IV), (IVa), (IVb), (IVc), (IVd), (IVe), (IVf), (IVg), (IVh), (IVi), (IVj), (IVk), (IVl), (V), (VI), (VII), (VIIa), (VIII), (IX) or (X) wherein $R^1$ is hydrogen; X is CH and the other variables are as described elsewhere herein for Formulae (I), (II), (III), (IIIa), (IV), (IVa), (IVb), (IVc), (IVd), (IVe), (IVf), (IVg), (IVh), (IVi), (IVj), (IVk), (IVi), (V), (VI), (VII), (VIIa), (VIII), (IX) and (X), respectively.

In certain embodiments, provided herein are compounds of Formula (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (IVk), (IVi), (V), (VI), (VIa), (VIb), (IVc), (VII), (VIIa), (VIII), (IX) or (X) wherein $R^1$ is hydrogen; X is CH and the other variables are as described elsewhere herein for Formulae (I), (II), (IIa), (IIb), (IIc), (IId), (IIe), (IIf), (III), (IIIa), (IV), (IVa), (IVb), (IVc), (IVd), (IVe), (IVf), (IVg), (IVh), (IVi), (IVj), (V), (VI), (VIa), (VIb), (IVc), (VII), (VIIa), (VIII), (IX) and (X), respectively.

In certain embodiments, provided herein are pharmaceutical compositions comprising any of the compounds described herein (e.g., a compound of Formula (I), (I), (II), (IIa), (IIb), (IIc), (III), (IIIa), (IV), (IVa), (IVa), (IVb), (IVc), (IVd), (IVe), (IVf), (IVg), (IVh), (IVi), (IVj), (IVk), (IVl), (IVm), (V), (VI), (VIa), (VIb), (IVc), (VII), (VIIa), (VIII), (IX), or (X)), or a pharmaceutically acceptable salt thereof; and a pharmaceutically acceptable carrier.

In certain embodiments, provided herein is a compound of Formula (I) wherein the compound is selected from:

4-((2S,4S)-4-(4-fluoro-1H-pyrazol-1-yl)-1-((5-methoxy-7-methyl-1H-indol-4-yl)methyl)piperidin-2-yl)benzoic acid; (Example 1)

4-((2R,4R)-4-(4-fluoro-1H-pyrazol-1-yl)-1-((5-methoxy-7-methyl-1H-indol-4-yl)methyl)piperidin-2-yl)benzoic acid;

4-((2S,4R)-4-(4-fluoro-1H-pyrazol-1-yl)-1-((5-methoxy-7-methyl-1H-indol-4-yl)methyl)piperidin-2-yl)benzoic acid;

4-((2R,4S)-4-(4-fluoro-1H-pyrazol-1-yl)-1-((5-methoxy-7-methyl-1H-indol-4-yl)methyl)piperidin-2-yl)benzoic acid;

4-(4-(4-fluoro-1H-pyrazol-1-yl)-1-((5-methoxy-7-methyl-1H-indol-4-yl)methyl)piperidin-2-yl)benzoic acid;

(±)-trans-4-(4-(4-bromo-1H-pyrazol-1-yl)-1-((5-methoxy-7-methyl-1H-indol-4-yl)methyl)piperidin-2-yl)benzoic acid; (Example 2)

4-((2S,4S)-(4-(4-bromo-1H-pyrazol-1-yl)-1-((5-methoxy-7-methyl-1H-indol-4-yl)methyl)piperidin-2-yl)benzoic acid;

4-((2R,4R)-(4-(4-bromo-1H-pyrazol-1-yl)-1-((5-methoxy-7-methyl-1H-indol-4-yl)methyl)piperidin-2-yl)benzoic acid;

4-((2S,4R)-(4-(4-bromo-1H-pyrazol-1-yl)-1-((5-methoxy-7-methyl-1H-indol-4-yl)methyl)piperidin-2-yl)benzoic acid;

4-((2R,4S)-(4-(4-bromo-1H-pyrazol-1-yl)-1-((5-methoxy-7-methyl-1H-indol-4-yl)methyl)piperidin-2-yl)benzoic acid;

4-(4-(4-bromo-1H-pyrazol-1-yl)-1-((5-methoxy-7-methyl-1H-indol-4-yl)methyl)piperidin-2-yl)benzoic acid;

(±)-trans-4-(1-((5-methoxy-7-methyl-1H-indol-4-yl)methyl)-4-(1H-1,2,4-triazol-1-yl)piperidin-2-yl)benzoic acid; (Example 3)

4-((2S,4S)-(1-((5-methoxy-7-methyl-1H-indol-4-yl)methyl)-4-(1H-1,2,4-triazol-1-yl)piperidin-2-yl)benzoic acid;

4-((2R,4R)-(1-((5-methoxy-7-methyl-1H-indol-4-yl)methyl)-4-(1H-1,2,4-triazol-1-yl)piperidin-2-yl)benzoic acid;

4-((2S,4R)-(1-((5-methoxy-7-methyl-1H-indol-4-yl)methyl)-4-(1H-1,2,4-triazol-1-yl)piperidin-2-yl)benzoic acid;

4-((2R,4S)-(1-((5-methoxy-7-methyl-1H-indol-4-yl)methyl)-4-(1H-1,2,4-triazol-1-yl)piperidin-2-yl)benzoic acid;

4-(1-((5-methoxy-7-methyl-1H-indol-4-yl)methyl)-4-(1H-1,2,4-triazol-1-yl)piperidin-2-yl)benzoic acid;

4-((2S,4S)-1-((5-methoxy-7-methyl-1H-indol-4-yl)methyl)-4-(4-(trifluoromethyl)-1H-pyrazol-1-yl)piperidin-2-yl)benzoic acid; (Example 4)

4-((2R,4R)-1-((5-methoxy-7-methyl-1H-indol-4-yl)methyl)-4-(4-(trifluoromethyl)-1H-pyrazol-1-yl)piperidin-2-yl)benzoic acid;

4-((2S,4R)-1-((5-methoxy-7-methyl-1H-indol-4-yl)methyl)-4-(4-(trifluoromethyl)-1H-pyrazol-1-yl)piperidin-2-yl)benzoic acid;

4-((2R,4S)-1-((5-methoxy-7-methyl-1H-indol-4-yl)methyl)-4-(4-(trifluoromethyl)-1H-pyrazol-1-yl)piperidin-2-yl)benzoic acid;

4-1-((5-methoxy-7-methyl-1H-indol-4-yl)methyl)-4-(4-(trifluoromethyl)-1H-pyrazol-1-yl)piperidin-2-yl)benzoic acid;

(±)-trans-4-(1-((5-methoxy-7-methyl-1H-indol-4-yl)methyl)-4-(3-(trifluoromethyl)-1H-1,2,4-triazol-1-yl)piperidin-2-yl)benzoic acid; (Example 5)

4-((2S,4S)-1-((5-methoxy-7-methyl-1H-indol-4-yl)methyl)-4-(3-(trifluoromethyl)-1H-1,2,4-triazol-1-yl)piperidin-2-yl)benzoic acid;

4-((2R,4R)-(1-((5-methoxy-7-methyl-1H-indol-4-yl)methyl)-4-(3-(trifluoromethyl)-1H-1,2,4-triazol-1-yl)piperidin-2-yl)benzoic acid;

4-((2S,4R)-(1-((5-methoxy-7-methyl-1H-indol-4-yl)methyl)-4-(3-(trifluoromethyl)-1H-1,2,4-triazol-1-yl)piperidin-2-yl)benzoic acid;

4-((2R,4S)-(1-((5-methoxy-7-methyl-1H-indol-4-yl)methyl)-4-(3-(trifluoromethyl)-1H-1,2,4-triazol-1-yl)piperidin-2-yl)benzoic acid;

4-(1-((5-methoxy-7-methyl-1H-indol-4-yl)methyl)-4-(3-(trifluoromethyl)-1H-1,2,4-triazol-1-yl)piperidin-2-yl)benzoic acid;

(±)-trans-4-(4-(2H-indazol-2-yl)-1-((5-methoxy-7-methyl-1H-indol-4-yl)methyl)piperidin-2-yl)benzoic acid; (Example 6)

4-((2S,4S)-(4-(2H-indazol-2-yl)-1-((5-methoxy-7-methyl-1H-indol-4-yl)methyl)piperidin-2-yl)benzoic acid;

4-((2R,4R)-4-(2H-indazol-2-yl)-1-((5-methoxy-7-methyl-1H-indol-4-yl)methyl)piperidin-2-yl)benzoic acid;

4-((2S,4R)-(4-(2H-indazol-2-yl)-1-((5-methoxy-7-methyl-1H-indol-4-yl)methyl)piperidin-2-yl)benzoic acid;

4-((2R,4S)-(4-(2H-indazol-2-yl)-1-((5-methoxy-7-methyl-1H-indol-4-yl)methyl)piperidin-2-yl)benzoic acid;

4-(4-(2H-indazol-2-yl)-1-((5-methoxy-7-methyl-1H-indol-4-yl)methyl)piperidin-2-yl)benzoic acid;

(±)-trans-4-(4-(4-(difluoromethyl)-1H-pyrazol-1-yl)-1-((5-methoxy-7-methyl-1H-indol-4-yl)methyl)piperidin-2-yl)benzoic acid; (Example 7)

4-((2S,4S)-(4-(4-(difluoromethyl)-1H-pyrazol-1-yl)-1-((5-methoxy-7-methyl-1H-indol-4-yl)methyl)piperidin-2-yl)benzoic acid;

4-((2R,4R)-(4-(4-(difluoromethyl)-1H-pyrazol-1-yl)-1-((5-methoxy-7-methyl-1H-indol-4-yl)methyl)piperidin-2-yl)benzoic acid;

4-((2S,4R)-(4-(4-(difluoromethyl)-1H-pyrazol-1-yl)-1-((5-methoxy-7-methyl-1H-indol-4-yl)methyl)piperidin-2-yl)benzoic acid;

4-((2R,4S)-(4-(4-(difluoromethyl)-1H-pyrazol-1-yl)-1-((5-methoxy-7-methyl-1H-indol-4-yl)methyl)piperidin-2-yl)benzoic acid;

4-(4-(4-(difluoromethyl)-1H-pyrazol-1-yl)-1-((5-methoxy-7-methyl-1H-indol-4-yl)methyl)piperidin-2-yl)benzoic acid;

4-((2S,4S)-4-chloro-1H-pyrazol-1-yl)-1-((5-methoxy-7-methyl-1H-indol-4-yl)methyl)piperidin-2-yl)benzoic acid; (Example 8)

4-((2R,4R)-4-chloro-1H-pyrazol-1-yl)-1-((5-methoxy-7-methyl-1H-indol-4-yl)methyl)piperidin-2-yl)benzoic acid;

4-((2S,4R)-4-chloro-1H-pyrazol-1-yl)-1-((5-methoxy-7-methyl-1H-indol-4-yl)methyl)piperidin-2-yl)benzoic acid;

4-((2R,4S)-4-chloro-1H-pyrazol-1-yl)-1-((5-methoxy-7-methyl-1H-indol-4-yl)methyl)piperidin-2-yl)benzoic acid;

4-(4-chloro-1H-pyrazol-1-yl)-1-((5-methoxy-7-methyl-1H-indol-4-yl)methyl)piperidin-2-yl)benzoic acid;

(±)-trans-4-(1-((5-methoxy-7-methyl-1H-indol-4-yl)methyl)-4-(1H-pyrazol-1-yl)piperidin-2-yl)benzoic acid; (Example 9)

4-((2S,4S)-(1-((5-methoxy-7-methyl-1H-indol-4-yl)methyl)-4-(1H-pyrazol-1-yl)piperidin-2-yl)benzoic acid;

4-((2R,4R)-(1-((5-methoxy-7-methyl-1H-indol-4-yl)methyl)-4-(1H-pyrazol-1-yl)piperidin-2-yl)benzoic acid;

4-((2S,4R)-(1-((5-methoxy-7-methyl-1H-indol-4-yl)methyl)-4-(1H-pyrazol-1-yl)piperidin-2-yl)benzoic acid;

4-((2R,4S)-(1-((5-methoxy-7-methyl-1H-indol-4-yl)methyl)-4-(1H-pyrazol-1-yl)piperidin-2-yl)benzoic acid;

4-(1-((5-methoxy-7-methyl-1H-indol-4-yl)methyl)-4-(1H-pyrazol-1-yl)piperidin-2-yl)benzoic acid;

4-((2S,4S)-4-(4-cyano-1H-pyrazol-1-yl)-1-((5-methoxy-7-methyl-1H-indol-4-yl)methyl)piperidin-2-yl)benzoic acid (Example 10)

4-((2R,4R)-4-(4-cyano-1H-pyrazol-1-yl)-1-((5-methoxy-7-methyl-1H-indol-4-yl)methyl)piperidin-2-yl)benzoic acid;

4-((2S,4R)-4-(4-cyano-1H-pyrazol-1-yl)-1-((5-methoxy-7-methyl-1H-indol-4-yl)methyl)piperidin-2-yl)benzoic acid;

4-((2R,4S)-4-(4-cyano-1H-pyrazol-1-yl)-1-((5-methoxy-7-methyl-1H-indol-4-yl)methyl)piperidin-2-yl)benzoic acid;

4-(4-(4-cyano-1H-pyrazol-1-yl)-1-((5-methoxy-7-methyl-1H-indol-4-yl)methyl)piperidin-2-yl)benzoic acid;

(±)-trans-4-(1-((5-methoxy-7-methyl-1H-indol-4-yl)methyl)-4-(4-(methylsulfonyl)-1H-pyrazol-1-yl)piperidin-2-yl)benzoic acid; (Example 11)

4-((2S,4S)-(1-((5-methoxy-7-methyl-1H-indol-4-yl)methyl)-4-(4-(methylsulfonyl)-1H-pyrazol-1-yl)piperidin-2-yl)benzoic acid;

4-((2R,4R)-(1-((5-methoxy-7-methyl-1H-indol-4-yl)methyl)-4-(4-(methylsulfonyl)-1H-pyrazol-1-yl)piperidin-2-yl)benzoic acid;

4-((2S,4R)-(1-((5-methoxy-7-methyl-1H-indol-4-yl)methyl)-4-(4-(methylsulfonyl)-1H-pyrazol-1-yl)piperidin-2-yl)benzoic acid;

4-((2R,4S)-(1-((5-methoxy-7-methyl-1H-indol-4-yl)methyl)-4-(4-(methylsulfonyl)-1H-pyrazol-1-yl)piperidin-2-yl)benzoic acid;

4-(1-((5-methoxy-7-methyl-1H-indol-4-yl)methyl)-4-(4-(methylsulfonyl)-1H-pyrazol-1-yl)piperidin-2-yl)benzoic acid;

(±)-trans-4-(1-((5-methoxy-7-methyl-1H-indol-4-yl)methyl)-4-(2-oxopyrrolidin-1-yl)piperidin-2-yl)benzoic acid; (Example 12)

4-((2S,4S)-(1-((5-methoxy-7-methyl-1H-indol-4-yl)methyl)-4-(2-oxopyrrolidin-1-yl)piperidin-2-yl)benzoic acid; (Example 13)

4-((2R,4R)-(1-((5-methoxy-7-methyl-1H-indol-4-yl)methyl)-4-(2-oxopyrrolidin-1-yl)piperidin-2-yl)benzoic acid;

4-((2S,4R)-(1-((5-methoxy-7-methyl-1H-indol-4-yl)methyl)-4-(2-oxopyrrolidin-1-yl)piperidin-2-yl)benzoic acid;

4-((2R,4S)-(1-((5-methoxy-7-methyl-1H-indol-4-yl)methyl)-4-(2-oxopyrrolidin-1-yl)piperidin-2-yl)benzoic acid;

4-(1-((5-methoxy-7-methyl-1H-indol-4-yl)methyl)-4-(2-oxopyrrolidin-1-yl)piperidin-2-yl)benzoic acid;

(±)-trans-4-(1-((5-methoxy-7-methyl-1H-indol-4-yl)methyl)-4-((2,2,2-trifluoroethyl)amino)piperidin-2-yl)benzoic acid; (Example 14)

4-((2S,4S)-(1-((5-methoxy-7-methyl-1H-indol-4-yl)methyl)-4-((2,2,2-trifluoroethyl)amino)piperidin-2-yl)benzoic acid; (Example 15)

4-((2R,4R)-(1-((5-methoxy-7-methyl-1H-indol-4-yl)methyl)-4-((2,2,2-trifluoroethyl)amino)piperidin-2-yl)benzoic acid;

4-((2S,4R)-(1-((5-methoxy-7-methyl-1H-indol-4-yl)methyl)-4-((2,2,2-trifluoroethyl)amino)piperidin-2-yl)benzoic acid;

4-((2R,4S)-(1-((5-methoxy-7-methyl-1H-indol-4-yl)methyl)-4-((2,2,2-trifluoroethyl)amino)piperidin-2-yl)benzoic acid;

4-(1-((5-methoxy-7-methyl-1H-indol-4-yl)methyl)-4-((2,2,2-trifluoroethyl)amino)piperidin-2-yl)benzoic acid;

(±)-trans-4-(1-((5-methoxy-7-methyl-1H-indol-4-yl)methyl)-4-(sulfamoylamino)piperidin-2-yl)benzoic acid; (Example 16)

4-((2S,4S)-(1-((5-methoxy-7-methyl-1H-indol-4-yl)methyl)-4-(sulfamoylamino)piperidin-2-yl)benzoic acid;

4-((2R,4R)-(1-((5-methoxy-7-methyl-1H-indol-4-yl)methyl)-4-(sulfamoylamino)piperidin-2-yl)benzoic acid;

4-((2S,4R)-(1-((5-methoxy-7-methyl-1H-indol-4-yl)methyl)-4-(sulfamoylamino)piperidin-2-yl)benzoic acid;

4-((2R,4S)-(1-((5-methoxy-7-methyl-1H-indol-4-yl)methyl)-4-(sulfamoylamino)piperidin-2-yl)benzoic acid;

4-(−1-((5-methoxy-7-methyl-1H-indol-4-yl)methyl)-4-(sulfamoylamino)piperidin-2-yl)benzoic acid;

(±)-trans-4-(1-((5-methoxy-7-methyl-1H-indol-4-yl)methyl)-4-(oxetan-3-ylamino)piperidin-2-yl)benzoic acid; (Example 17)

4-((2S,4S)-(1-((5-methoxy-7-methyl-1H-indol-4-yl)methyl)-4-(oxetan-3-ylamino)piperidin-2-yl)benzoic acid; (Example 18)

4-((2R,4R)-(1-((5-methoxy-7-methyl-1H-indol-4-yl)methyl)-4-(oxetan-3-ylamino)piperidin-2-yl)benzoic acid;

4-((2S,4R)-(1-((5-methoxy-7-methyl-1H-indol-4-yl)methyl)-4-(oxetan-3-ylamino)piperidin-2-yl)benzoic acid;

4-((2R,4S)-(1-((5-methoxy-7-methyl-1H-indol-4-yl)methyl)-4-(oxetan-3-ylamino)piperidin-2-yl)benzoic acid;

4-(1-((5-methoxy-7-methyl-1H-indol-4-yl)methyl)-4-(oxetan-3-ylamino)piperidin-2-yl)benzoic acid;

4-((2S,4S)-4-((3,3-difluorocyclobutyl)amino)-1-((5-methoxy-7-methyl-1H-indol-4-yl)methyl)piperidin-2-yl)benzoic acid; (Example 19)

4-((2R,4R)-4-((3,3-difluorocyclobutyl)amino)-1-((5-methoxy-7-methyl-1H-indol-4-yl)methyl)piperidin-2-yl)benzoic acid;

4-((2S,4R)-4-((3,3-difluorocyclobutyl)amino)-1-((5-methoxy-7-methyl-1H-indol-4-yl)methyl)piperidin-2-yl)benzoic acid;

4-((2R,4S)-4-((3,3-difluorocyclobutyl)amino)-1-((5-methoxy-7-methyl-1H-indol-4-yl)methyl)piperidin-2-yl)benzoic acid;

4-((3,3-difluorocyclobutyl)amino)-1-((5-methoxy-7-methyl-1H-indol-4-yl)methyl)piperidin-2-yl)benzoic acid;

4-((2S,4S)-4-(cyclobutylamino)-1-((5-methoxy-7-methyl-1H-indol-4-yl)methyl)piperidin-2-yl)benzoic acid; (Example 20)

4-((2R,4R)-4-(cyclobutylamino)-1-((5-methoxy-7-methyl-1H-indol-4-yl)methyl)piperidin-2-yl)benzoic acid;

4-((2S,4R)-4-(cyclobutylamino)-1-((5-methoxy-7-methyl-1H-indol-4-yl)methyl)piperidin-2-yl)benzoic acid;

4-((2R,4S)-4-(cyclobutylamino)-1-((5-methoxy-7-methyl-1H-indol-4-yl)methyl)piperidin-2-yl)benzoic acid;

4-(4-(cyclobutylamino)-1-((5-methoxy-7-methyl-1H-indol-4-yl)methyl)piperidin-2-yl)benzoic acid;

4-((2S,4S)-4-(bicyclo[1.1.1]pentan-1-ylamino)-1-((5-methoxy-7-methyl-1H-indol-4-yl)methyl)piperidin-2-yl)benzoic acid; (Example 21)

4-((2R,4R)-4-(bicyclo[1.1.1]pentan-1-ylamino)-1-((5-methoxy-7-methyl-1H-indol-4-yl)methyl)piperidin-2-yl)benzoic acid;

4-((2S,4R)-4-(bicyclo[1.1.1]pentan-1-ylamino)-1-((5-methoxy-7-methyl-1H-indol-4-yl)methyl)piperidin-2-yl)benzoic acid;

4-((2R,4S)-4-(bicyclo[1.1.1]pentan-1-ylamino)-1-((5-methoxy-7-methyl-1H-indol-4-yl)methyl)piperidin-2-yl)benzoic acid;

4-(4-(bicyclo[1.1.1]pentan-1-ylamino)-1-((5-methoxy-7-methyl-1H-indol-4-yl)methyl)piperidin-2-yl)benzoic acid;

4-((2S,4S)-4-((2,2-difluoroethyl)amino)-1-((5-methoxy-7-methyl-1H-indol-4-yl)methyl)piperidin-2-yl)benzoic acid; (Example 22)

4-((2R,4R)-4-((2,2-difluoroethyl)amino)-1-((5-methoxy-7-methyl-1H-indol-4-yl)methyl)piperidin-2-yl)benzoic acid;

4-((2S,4R)-4-((2,2-difluoroethyl)amino)-1-((5-methoxy-7-methyl-1H-indol-4-yl)methyl)piperidin-2-yl)benzoic acid;

4-((2R,4S)-4-((2,2-difluoroethyl)amino)-1-((5-methoxy-7-methyl-1H-indol-4-yl)methyl)piperidin-2-yl)benzoic acid;

4-(4-((2,2-difluoroethyl)amino)-1-((5-methoxy-7-methyl-1H-indol-4-yl)methyl)piperidin-2-yl)benzoic acid;

4-((2S,4S)-4-(((1-fluorocyclopropyl)methyl)amino)-1-((5-methoxy-7-methyl-1H-indol-4-yl)methyl)piperidin-2-yl)benzoic acid; (Example 23)

4-((2R,4R)-4-(((1-fluorocyclopropyl)methyl)amino)-1-((5-methoxy-7-methyl-1H-indol-4-yl)methyl)piperidin-2-yl)benzoic acid;

4-((2S,4R)-4-(((1-fluorocyclopropyl)methyl)amino)-1-((5-methoxy-7-methyl-1H-indol-4-yl)methyl)piperidin-2-yl)benzoic acid;

4-((2R,4S)-4-(((1-fluorocyclopropyl)methyl)amino)-1-((5-methoxy-7-methyl-1H-indol-4-yl)methyl)piperidin-2-yl)benzoic acid;

4-(4-(((1-fluorocyclopropyl)methyl)amino)-1-((5-methoxy-7-methyl-1H-indol-4-yl)methyl)piperidin-2-yl)benzoic acid;

4-((2S,4S)-4-((3,3-difluorocyclobutyl)amino)-1-((5-methoxy-7-methyl-1H-indol-4-yl)methyl)piperidin-2-yl)benzoic acid; (Example 24)

4-((2R,4R)-4-((3,3-difluorocyclobutyl)amino)-1-((5-methoxy-7-methyl-1H-indol-4-yl)methyl)piperidin-2-yl)benzoic acid;

4-((2S,4R)-4-((3,3-difluorocyclobutyl)amino)-1-((5-methoxy-7-methyl-1H-indol-4-yl)methyl)piperidin-2-yl)benzoic acid;

4-((2R,4S)-4-((3,3-difluorocyclobutyl)amino)-1-((5-methoxy-7-methyl-1H-indol-4-yl)methyl)piperidin-2-yl)benzoic acid;

4-(4-((3,3-difluorocyclobutyl)amino)-1-((5-methoxy-7-methyl-1H-indol-4-yl)methyl)piperidin-2-yl)benzoic acid;

4-((2S,4S)-1-((5-cyclopropyl-7-methyl-1H-indol-4-yl)methyl)-4-((3,3-difluorocyclobutyl)amino)piperidin-2-yl)benzoic acid; (Example 25)

4-((2R,4R)-1-((5-cyclopropyl-7-methyl-1H-indol-4-yl)methyl)-4-((3,3-difluorocyclobutyl)amino)piperidin-2-yl)benzoic acid;

4-((2S,4R)-1-((5-cyclopropyl-7-methyl-1H-indol-4-yl)methyl)-4-((3,3-difluorocyclobutyl)amino)piperidin-2-yl)benzoic acid;

4-((2R,4S)-1-((5-cyclopropyl-7-methyl-1H-indol-4-yl)methyl)-4-((3,3-difluorocyclobutyl)amino)piperidin-2-yl)benzoic acid;

4-(1-((5-cyclopropyl-7-methyl-1H-indol-4-yl)methyl)-4-((3,3-difluorocyclobutyl)amino)piperidin-2-yl)benzoic acid;

4-((2S,4S)-4-((cyclopropylmethyl)amino)-1-((5-methoxy-7-methyl-1H-indol-4-yl)methyl)piperidin-2-yl)benzoic acid; (Example 26)

4-((2R,4R)-4-((cyclopropylmethyl)amino)-1-((5-methoxy-7-methyl-1H-indol-4-yl)methyl)piperidin-2-yl)benzoic acid;

4-((2S,4R)-4-((cyclopropylmethyl)amino)-1-((5-methoxy-7-methyl-1H-indol-4-yl)methyl)piperidin-2-yl)benzoic acid;

4-((2R,4S)-4-((cyclopropylmethyl)amino)-1-((5-methoxy-7-methyl-1H-indol-4-yl)methyl)piperidin-2-yl)benzoic acid;

4-(4-((cyclopropylmethyl)amino)-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(((1-(trifluoromethyl)cyclopropyl)methyl)amino)piperidin-2-yl)benzoic acid; (Example 27)

4-((2R,4R)-1-((5-methoxy-7-methyl-1H-indol-4-yl)methyl)-4-(((1-(trifluoromethyl)cyclopropyl)methyl)amino)piperidin-2-yl)benzoic acid;

4-((2S,4R)-1-((5-methoxy-7-methyl-1H-indol-4-yl)methyl)-4-(((1-(trifluoromethyl)cyclopropyl)methyl)amino)piperidin-2-yl)benzoic acid;

4-((2R,4S)-1-((5-methoxy-7-methyl-1H-indol-4-yl)methyl)-4-(((1-(trifluoromethyl)cyclopropyl)methyl)amino)piperidin-2-yl)benzoic acid;

4-(1-((5-methoxy-7-methyl-1H-indol-4-yl)methyl)-4-(((1-(trifluoromethyl)cyclopropyl)methyl)amino)piperidin-2-yl)benzoic acid;

4-((2S,4S)-4-(difluoromethoxy)-1-((5-methoxy-7-methyl-1H-indol-4-yl)methyl)piperidin-2-yl)benzoic acid; (Example 28)

4-((2R,4R)-4-(difluoromethoxy)-1-((5-methoxy-7-methyl-1H-indol-4-yl)methyl)piperidin-2-yl)benzoic acid; (Example 29)

4-((2S,4R)-4-(difluoromethoxy)-1-((5-methoxy-7-methyl-1H-indol-4-yl)methyl)piperidin-2-yl)benzoic acid;

4-((2R,4S)-4-(difluoromethoxy)-1-((5-methoxy-7-methyl-1H-indol-4-yl)methyl)piperidin-2-yl)benzoic acid;

4-(4-(difluoromethoxy)-1-((5-methoxy-7-methyl-1H-indol-4-yl)methyl)piperidin-2-yl)benzoic acid;

4-((3R,5S)-1,1-difluoro-6-((5-methoxy-7-methyl-1H-indol-4-yl)methyl)-6-azaspiro[2.5]octan-5-yl)benzoic acid; (Example 30)

4-((3S,5S)-1,1-difluoro-6-((5-methoxy-7-methyl-1H-indol-4-yl)methyl)-6-azaspiro[2.5]octan-5-yl)benzoic acid (or Example 30)

4-((3S,5R)-1,1-difluoro-6-((5-methoxy-7-methyl-1H-indol-4-yl)methyl)-6-azaspiro[2.5]octan-5-yl)benzoic acid;

4-((3R,5R)-1,1-difluoro-6-((5-methoxy-7-methyl-1H-indol-4-yl)methyl)-6-azaspiro[2.5]octan-5-yl)benzoic acid;

4-(1,1-difluoro-6-((5-methoxy-7-methyl-1H-indol-4-yl)methyl)-6-azaspiro[2.5]octan-5-yl)benzoic acid;

(±)-4-(7-((5-methoxy-7-methyl-1H-indol-4-yl)methyl)-2-oxa-7-azaspiro[3.5]nonan-6-yl)benzoic acid; (Example 31)

(S)-4-(7-((5-methoxy-7-methyl-1H-indol-4-yl)methyl)-2-oxa-7-azaspiro[3.5]nonan-6-yl)benzoic acid; (Example 32)

(R)-4-(7-((5-methoxy-7-methyl-1H-indol-4-yl)methyl)-2-oxa-7-azaspiro[3.5]nonan-6-yl)benzoic acid;

4-(7-((5-methoxy-7-methyl-1H-indol-4-yl)methyl)-2-oxa-7-azaspiro[3.5]nonan-6-yl)benzoic acid;

4-((5S,7S)-8-((5-methoxy-7-methyl-1H-indol-4-yl)methyl)-1-oxa-8-azaspiro[4.5]decan-7-yl)benzoic acid; (Example 33)

4-((5R,7S)-8-((5-methoxy-7-methyl-1H-indol-4-yl)methyl)-1-oxa-8-azaspiro[4.5]decan-7-yl)benzoic acid; (or Example 33)

4-((5R,7R)-8-((5-methoxy-7-methyl-1H-indol-4-yl)methyl)-1-oxa-8-azaspiro[4.5]decan-7-yl)benzoic acid;

4-((5S,7R)-8-((5-methoxy-7-methyl-1H-indol-4-yl)methyl)-1-oxa-8-azaspiro[4.5]decan-7-yl)benzoic acid;

4-(8-((5-methoxy-7-methyl-1H-indol-4-yl)methyl)-1-oxa-8-azaspiro[4.5]decan-7-yl)benzoic acid;

4-((5S,7S)-8-((5-methoxy-7-methyl-1H-indol-4-yl)methyl)-2-oxa-8-azaspiro[4.5]decan-7-yl)benzoic acid; (Example 34)

4-((5R,7S)-8-((5-methoxy-7-methyl-1H-indol-4-yl)methyl)-2-oxa-8-azaspiro[4.5]decan-7-yl)benzoic acid; (or Example 34)

4-((5R,7R)-8-((5-methoxy-7-methyl-1H-indol-4-yl)methyl)-2-oxa-8-azaspiro[4.5]decan-7-yl)benzoic acid;

4-((5S,7R)-8-((5-methoxy-7-methyl-1H-indol-4-yl)methyl)-2-oxa-8-azaspiro[4.5]decan-7-yl)benzoic acid;

4-(8-((5-methoxy-7-methyl-1H-indol-4-yl)methyl)-2-oxa-8-azaspiro[4.5]decan-7-yl)benzoic acid;

4-(5R,7S)-2,2-difluoro-8-((5-methoxy-7-methyl-1H-indol-4-yl)methyl)-8-azaspiro[4.5]decan-7-yl)benzoic acid; (Example 35 or 36)

4-(5S,7S)-(2,2-difluoro-8-((5-methoxy-7-methyl-1H-indol-4-yl)methyl)-8-azaspiro[4.5]decan-7-yl)benzoic acid; (or Example 36 or 35)

4-(5S,7R)-(2,2-difluoro-8-((5-methoxy-7-methyl-1H-indol-4-yl)methyl)-8-azaspiro[4.5]decan-7-yl)benzoic acid;

4-(5R,7R)-(2,2-difluoro-8-((5-methoxy-7-methyl-1H-indol-4-yl)methyl)-8-azaspiro[4.5]decan-7-yl)benzoic acid;

4-(2,2-difluoro-8-((5-methoxy-7-methyl-1H-indol-4-yl)methyl)-8-azaspiro[4.5]decan-7-yl)benzoic acid;

(±)-trans-4-(1-((5-methoxy-7-methyl-1H-indol-4-yl)methyl)-4-phenylpiperidin-2-yl)benzoic acid; (Example 37)

4-((2S,4S)-4-(1-((5-methoxy-7-methyl-1H-indol-4-yl)methyl)-4-phenylpiperidin-2-yl)benzoic acid;

4-((2R,4R)-4-(1-((5-methoxy-7-methyl-1H-indol-4-yl)methyl)-4-phenylpiperidin-2-yl)benzoic acid;

4-((2S,4R)-4-(1-((5-methoxy-7-methyl-1H-indol-4-yl)methyl)-4-phenylpiperidin-2-yl)benzoic acid;

4-((2R,4S)-4-(1-((5-methoxy-7-methyl-1H-indol-4-yl)methyl)-4-phenylpiperidin-2-yl)benzoic acid;

4-(4-(1-((5-methoxy-7-methyl-1H-indol-4-yl)methyl)-4-phenylpiperidin-2-yl)benzoic acid;

4-((2S,4S)-1-((5-methoxy-7-methyl-1H-indol-4-yl)methyl)-4-(pyridin-2-yl)piperidin-2-yl)benzoic acid; (Example 38)

4-((2R,4R)-1-((5-methoxy-7-methyl-1H-indol-4-yl)methyl)-4-(pyridin-2-yl)piperidin-2-yl)benzoic acid;

4-((2S,4R)-1-((5-methoxy-7-methyl-1H-indol-4-yl)methyl)-4-(pyridin-2-yl)piperidin-2-yl)benzoic acid;

4-((2R,4S)-1-((5-methoxy-7-methyl-1H-indol-4-yl)methyl)-4-(pyridin-2-yl)piperidin-2-yl)benzoic acid;

4-(1-((5-methoxy-7-methyl-1H-indol-4-yl)methyl)-4-(pyridin-2-yl)piperidin-2-yl)benzoic acid;

4-(2-((5-methoxy-7-methyl-1H-indol-4-yl)methyl)-2-azaspiro[3.4]octan-1-yl)benzoic acid; (Example 39)

(S)-4-(2-((5-methoxy-7-methyl-1H-indol-4-yl)methyl)-2-azaspiro[3.4]octan-1-yl)benzoic acid;

(R)-4-(2-((5-methoxy-7-methyl-1H-indol-4-yl)methyl)-2-azaspiro[3.4]octan-1-yl)benzoic acid;

(R)-4-(2-((5-methoxy-7-methyl-1H-indol-4-yl)methyl)-2-azaspiro[3.3]heptan-1-yl)benzoic acid; (Example 40)

(S)-4-(2-((5-methoxy-7-methyl-1H-indol-4-yl)methyl)-2-azaspiro[3.3]heptan-1-yl)benzoic acid;

4-(2-((5-methoxy-7-methyl-1H-indol-4-yl)methyl)-2-azaspiro[3.3]heptan-1-yl)benzoic acid;

4-((2S,4S)-4-cyclopropyl-1-((5-methoxy-7-methyl-1H-indol-4-yl)methyl)piperidin-2-yl)benzoic acid; (Example 41)

4-((2R,4R)-4-cyclopropyl-1-((5-methoxy-7-methyl-1H-indol-4-yl)methyl)piperidin-2-yl)benzoic acid;

4-((2S,4R)-4-cyclopropyl-1-((5-methoxy-7-methyl-1H-indol-4-yl)methyl)piperidin-2-yl)benzoic acid;

4-((2R,4S)-4-cyclopropyl-1-((5-methoxy-7-methyl-1H-indol-4-yl)methyl)piperidin-2-yl)benzoic acid;

4-(4-cyclopropyl-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(3,3,3-trifluoropropyl)piperidin-2-yl)benzoic acid; (Example 42)

4-((2R,4R)-1-((5-methoxy-7-methyl-1H-indol-4-yl)methyl)-4-(3,3,3-trifluoropropyl)piperidin-2-yl)benzoic acid;

4-((2S,4R)-1-((5-methoxy-7-methyl-1H-indol-4-yl)methyl)-4-(3,3,3-trifluoropropyl)piperidin-2-yl)benzoic acid;

4-((2R,4S)-1-((5-methoxy-7-methyl-1H-indol-4-yl)methyl)-4-(3,3,3-trifluoropropyl)piperidin-2-yl)benzoic acid;

4-(1-((5-methoxy-7-methyl-1H-indol-4-yl)methyl)-4-(3,3,3-trifluoropropyl)piperidin-2-yl)benzoic acid;

4-((2S,4S)-4-cyclobutyl-1-((5-methoxy-7-methyl-1H-indol-4-yl)methyl)piperidin-2-yl)benzoic acid;

4-((2S,4R)-4-cyclobutyl-1-((5-methoxy-7-methyl-1H-indol-4-yl)methyl)piperidin-2-yl)benzoic acid;

4-((2R,4R)-4-cyclobutyl-1-((5-methoxy-7-methyl-1H-indol-4-yl)methyl)piperidin-2-yl)benzoic acid;

4-((2R,4S)-4-cyclobutyl-1-((5-methoxy-7-methyl-1H-indol-4-yl)methyl)piperidin-2-yl)benzoic acid;

4-(4-cyclobutyl-1-((5-methoxy-7-methyl-1H-indol-4-yl)methyl)piperidin-2-yl)benzoic acid; (Example 43)

4-((2S,4S)-4-(cyclopropylmethyl)-1-((5-methoxy-7-methyl-1H-indol-4-yl)methyl)piperidin-2-yl)benzoic acid; (Example 44)

4-((2R,4R)-4-(cyclopropylmethyl)-1-((5-methoxy-7-methyl-1H-indol-4-yl)methyl)piperidin-2-yl)benzoic acid;

4-((2S,4R)-4-(cyclopropylmethyl)-1-((5-methoxy-7-methyl-1H-indol-4-yl)methyl)piperidin-2-yl)benzoic acid;

4-((2R,4S)-4-(cyclopropylmethyl)-1-((5-methoxy-7-methyl-1H-indol-4-yl)methyl)piperidin-2-yl)benzoic acid;

4-(4-(cyclopropylmethyl)-1-((5-methoxy-7-methyl-1H-indol-4-yl)methyl)piperidin-2-yl)benzoic acid;

(S)-4-(2,2-difluoro-7-((5-methoxy-7-methyl-1H-indol-4-yl)methyl)-7-azaspiro[3.5]nonan-6-yl)benzoic acid; (Example 45)

(R)-4-(2,2-difluoro-7-((5-methoxy-7-methyl-1H-indol-4-yl)methyl)-7-azaspiro[3.5]nonan-6-yl)benzoic acid;

4-(2,2-difluoro-7-((5-methoxy-7-methyl-1H-indol-4-yl)methyl)-7-azaspiro[3.5]nonan-6-yl)benzoic acid;

4-((2R,4s,6S)-2-(difluoromethyl)-7-((5-methoxy-7-methyl-1H-indol-4-yl)methyl)-7-azaspiro[3.5]nonan-6-yl)benzoic acid; (Example 46 or 47)

4-((2S,4r,6S)-2-(difluoromethyl)-7-((5-methoxy-7-methyl-1H-indol-4-yl)methyl)-7-azaspiro[3.5]nonan-6-yl)benzoic acid; (Example 47 or 46)

4-((2S,4s,6R)-2-(difluoromethyl)-7-((5-methoxy-7-methyl-1H-indol-4-yl)methyl)-7-azaspiro[3.5]nonan-6-yl)benzoic acid;

4-((2R,4r,6R)-2-(difluoromethyl)-7-((5-methoxy-7-methyl-1H-indol-4-yl)methyl)-7-azaspiro[3.5]nonan-6-yl)benzoic acid;

4-(2-(difluoromethyl)-7-((5-methoxy-7-methyl-1H-indol-4-yl)methyl)-7-azaspiro[3.5]nonan-6-yl)benzoic acid;

4-((2R,4s,6S)-7-((5-methoxy-7-methyl-1H-indol-4-yl)methyl)-2-(trifluoromethyl)-7-azaspiro[3.5]nonan-6-yl)benzoic acid; (Example 48 or 49)

4-((2S,4r,6S)-7-((5-methoxy-7-methyl-1H-indol-4-yl)methyl)-2-(trifluoromethyl)-7-azaspiro[3.5]nonan-6-yl)benzoic acid; (Example 49 or 48)

4-((2S,4s,6R)-7-((5-methoxy-7-methyl-1H-indol-4-yl)methyl)-2-(trifluoromethyl)-7-azaspiro[3.5]nonan-6-yl)benzoic acid;

4-((2R,4r,6R)-7-((5-methoxy-7-methyl-1H-indol-4-yl)methyl)-2-(trifluoromethyl)-7-azaspiro[3.5]nonan-6-yl)benzoic acid;

4-(7-((5-methoxy-7-methyl-1H-indol-4-yl)methyl)-2-(trifluoromethyl)-7-azaspiro[3.5]nonan-6-yl)benzoic acid;

(S)-4-(2,2-difluoro-7-((5-methoxy-7-methyl-1H-indol-4-yl)methyl)-7-azaspiro[3.5]nonan-6-yl)-2-fluorobenzoic acid; (Example 50)

(R)-4-(2,2-difluoro-7-((5-methoxy-7-methyl-1H-indol-4-yl)methyl)-7-azaspiro[3.5]nonan-6-yl)-2-fluorobenzoic acid;

4-(2,2-difluoro-7-((5-methoxy-7-methyl-1H-indol-4-yl)methyl)-7-azaspiro[3.5]nonan-6-yl)-2-fluorobenzoic acid;

(S)-4-(8-((5-methoxy-7-methyl-1H-indol-4-yl)methyl)-8-azadispiro[$2.1.5^5.1^3$]undecan-7-yl)benzoic acid; (Example 51)

(R)-4-(8-((5-methoxy-7-methyl-1H-indol-4-yl)methyl)-8-azadispiro[$2.1.5^5.1^3$]undecan-7-yl)benzoic acid;

4-(8-((5-methoxy-7-methyl-1H-indol-4-yl)methyl)-8-azadispiro[$2.1.5^5.1^3$]undecan-7-yl)benzoic acid;

(S)-4-(7-((3-chloro-5-methoxy-7-methyl-1H-indol-4-yl)methyl)-2,2-difluoro-7-azaspiro[3.5]nonan-6-yl)benzoic acid; (Example 53)

(R)-4-(7-((3-chloro-5-methoxy-7-methyl-1H-indol-4-yl)methyl)-2,2-difluoro-7-azaspiro[3.5]nonan-6-yl)benzoic acid;

4-(7-((3-chloro-5-methoxy-7-methyl-1H-indol-4-yl)methyl)-2,2-difluoro-7-azaspiro[3.5]nonan-6-yl)benzoic acid;

(S)-4-(2,2-difluoro-7-((3-fluoro-5-methoxy-7-methyl-1H-indol-4-yl)methyl)-7-azaspiro[3.5]nonan-6-yl)benzoic acid; (Example 54)

(R)-4-(2,2-difluoro-7-((3-fluoro-5-methoxy-7-methyl-1H-indol-4-yl)methyl)-7-azaspiro[3.5]nonan-6-yl)benzoic acid;

4-(2,2-difluoro-7-((3-fluoro-5-methoxy-7-methyl-1H-indol-4-yl)methyl)-7-azaspiro[3.5]nonan-6-yl)benzoic acid;

4-((2R,4s,6S)-2-cyano-7-((5-methoxy-7-methyl-1H-indol-4-yl)methyl)-7-azaspiro[3.5]nonan-6-yl)benzoic acid; (Example 52 or 55)

4-((2S,4r,6S)-2-cyano-7-((5-methoxy-7-methyl-1H-indol-4-yl)methyl)-7-azaspiro[3.5]nonan-6-yl)benzoic acid; (Example 55 or 52)

4-((2S,4s,6R)-2-cyano-7-((5-methoxy-7-methyl-1H-indol-4-yl)methyl)-7-azaspiro[3.5]nonan-6-yl)benzoic acid;

4-((2R,4r,6R)-2-cyano-7-((5-methoxy-7-methyl-1H-indol-4-yl)methyl)-7-azaspiro[3.5]nonan-6-yl)benzoic acid;

4-(2-cyano-7-((5-methoxy-7-methyl-1H-indol-4-yl)methyl)-7-azaspiro[3.5]nonan-6-yl)benzoic acid;

4-((2R,4s,6S)-2-(difluoromethoxy)-7-((5-methoxy-7-methyl-1H-indol-4-yl)methyl)-7-azaspiro[3.5]nonan-6-yl)benzoic acid; (Example 56 or 57)

4-((2S,4r,6S)-2-(difluoromethoxy)-7-((5-methoxy-7-methyl-1H-indol-4-yl)methyl)-7-azaspiro[3.5]nonan-6-yl)benzoic acid; (Example 57 or 56)

4-((2S,4s,6R)-2-(difluoromethoxy)-7-((5-methoxy-7-methyl-1H-indol-4-yl)methyl)-7-azaspiro[3.5]nonan-6-yl)benzoic acid;

4-((2R,4r,6R)-2-(difluoromethoxy)-7-((5-methoxy-7-methyl-1H-indol-4-yl)methyl)-7-azaspiro[3.5]nonan-6-yl)benzoic acid;

4-(2-(difluoromethoxy)-7-((5-methoxy-7-methyl-1H-indol-4-yl)methyl)-7-azaspiro[3.5]nonan-6-yl)benzoic acid;

(S)-4-(7-((5-methoxy-7-methyl-1H-indol-4-yl)methyl)-2-oxo-7-azaspiro[3.5]nonan-6-yl)benzoic acid; (Example 58)

(R)-4-(7-((5-methoxy-7-methyl-1H-indol-4-yl)methyl)-2-oxo-7-azaspiro[3.5]nonan-6-yl)benzoic acid;

4-(7-((5-methoxy-7-methyl-1H-indol-4-yl)methyl)-2-oxo-7-azaspiro[3.5]nonan-6-yl)benzoic acid;

4-((2R,4s,6S)-2-hydroxy-7-((5-methoxy-7-methyl-1H-indol-4-yl)methyl)-2-methyl-7-azaspiro[3.5]nonan-6-yl)benzoic acid; (Example 59 or 60)

4-((2S,4r,6S)-2-hydroxy-7-((5-methoxy-7-methyl-1H-indol-4-yl)methyl)-2-methyl-7-azaspiro[3.5]nonan-6-yl)benzoic acid; (Example 60 or 59)

4-((2S,4s,6R)-2-hydroxy-7-((5-methoxy-7-methyl-1H-indol-4-yl)methyl)-2-methyl-7-azaspiro[3.5]nonan-6-yl)benzoic acid;

4-((2R,4r,6R)-2-hydroxy-7-((5-methoxy-7-methyl-1H-indol-4-yl)methyl)-2-methyl-7-azaspiro[3.5]nonan-6-yl)benzoic acid;

4-(2-hydroxy-7-((5-methoxy-7-methyl-1H-indol-4-yl)methyl)-2-methyl-7-azaspiro[3.5]nonan-6-yl)benzoic acid;

4-((2S)-2-fluoro-7-((5-methoxy-7-methyl-1H-indol-4-yl)methyl)-7-azaspiro[3.5]nonan-6-yl)benzoic acid; (Example 61)
4-((2R,4s,6S)-2-fluoro-7-((5-methoxy-7-methyl-1H-indol-4-yl)methyl)-7-azaspiro[3.5]nonan-6-yl)benzoic acid; (Example 62 or 63)
4-((2S,4r,6S)-2-fluoro-7-((5-methoxy-7-methyl-1H-indol-4-yl)methyl)-7-azaspiro[3.5]nonan-6-yl)benzoic acid; (Example 62 or 63)
4-((2S,4s,6R)-2-fluoro-7-((5-methoxy-7-methyl-1H-indol-4-yl)methyl)-7-azaspiro[3.5]nonan-6-yl)benzoic acid;
4-((2R,4r,6R)-2-fluoro-7-((5-methoxy-7-methyl-1H-indol-4-yl)methyl)-7-azaspiro[3.5]nonan-6-yl)benzoic acid;
4-(2-fluoro-7-((5-methoxy-7-methyl-1H-indol-4-yl)methyl)-7-azaspiro[3.5]nonan-6-yl)benzoic acid;
4-((2R,4s,6S)-4-(2-hydroxy-7-((5-methoxy-7-methyl-1H-indol-4-yl)methyl)-7-azaspiro[3.5]nonan-6-yl)benzoic acid; (Example 64)
4-((2S,4r,6S)-2-hydroxy-7-((5-methoxy-7-methyl-1H-indol-4-yl)methyl)-7-azaspiro[3.5]nonan-6-yl)benzoic acid; (Example 64)
4-((2S,4s,6R)-2-hydroxy-7-((5-methoxy-7-methyl-1H-indol-4-yl)methyl)-7-azaspiro[3.5]nonan-6-yl)benzoic acid;
4-((2R,4r,6R)-2-hydroxy-7-((5-methoxy-7-methyl-1H-indol-4-yl)methyl)-7-azaspiro[3.5]nonan-6-yl)benzoic acid;
4-(2-hydroxy-7-((5-methoxy-7-methyl-1H-indol-4-yl)methyl)-7-azaspiro[3.5]nonan-6-yl)benzoic acid;
(R)-4-(1-((5-methoxy-7-methyl-1H-indol-4-yl)methyl)-4-(2,2,2-trifluoroethyl)piperazin-2-yl)benzoic acid; (Example 65)
(S)-4-(1-((5-methoxy-7-methyl-1H-indol-4-yl)methyl)-4-(2,2,2-trifluoroethyl)piperazin-2-yl)benzoic acid;
4-(1-((5-methoxy-7-methyl-1H-indol-4-yl)methyl)-4-(2,2,2-trifluoroethyl)piperazin-2-yl)benzoic acid;
(R)-4-(4-(2,2-difluoroethyl)-1-((5-methoxy-7-methyl-1H-indol-4-yl)methyl)piperazin-2-yl)benzoic acid; (Example 66)
(S)-4-(4-(2,2-difluoroethyl)-1-((5-methoxy-7-methyl-1H-indol-4-yl)methyl)piperazin-2-yl)benzoic acid;
4-(4-(2,2-difluoroethyl)-1-((5-methoxy-7-methyl-1H-indol-4-yl)methyl)piperazin-2-yl)benzoic acid;
(R)-4-(4-((3,3-difluorocyclobutyl)methyl)-1-((5-methoxy-7-methyl-1H-indol-4-yl)methyl)piperazin-2-yl)benzoic acid; (Example 67)
(S)-4-(4-((3,3-difluorocyclobutyl)methyl)-1-((5-methoxy-7-methyl-1H-indol-4-yl)methyl)piperazin-2-yl)benzoic acid;
4-(4-((3,3-difluorocyclobutyl)methyl)-1-((5-methoxy-7-methyl-1H-indol-4-yl)methyl)piperazin-2-yl)benzoic acid;
(R)-4-(1-((5-methoxy-7-methyl-1H-indol-4-yl)methyl)-4-(3,3,3-trifluoropropyl)piperazin-2-yl)benzoic acid; (Example 68)
(S)-4-(1-((5-methoxy-7-methyl-1H-indol-4-yl)methyl)-4-(3,3,3-trifluoropropyl)piperazin-2-yl)benzoic acid;
4-(1-((5-methoxy-7-methyl-1H-indol-4-yl)methyl)-4-(3,3,3-trifluoropropyl)piperazin-2-yl)benzoic acid;
(R)-4-(4-((3-fluorooxetan-3-yl)methyl)-1-((5-methoxy-7-methyl-1H-indol-4-yl)methyl)piperazin-2-yl)benzoic acid; (Example 69)
(S)-4-(4-((3-fluorooxetan-3-yl)methyl)-1-((5-methoxy-7-methyl-1H-indol-4-yl)methyl)piperazin-2-yl)benzoic acid;

4-(4-((3-fluorooxetan-3-yl)methyl)-1-((5-methoxy-7-methyl-1H-indol-4-yl)methyl)piperazin-2-yl)benzoic acid;
(R)-4-(4-(2-fluoroethyl)-1-((5-methoxy-7-methyl-1H-indol-4-yl)methyl)piperazin-2-yl)benzoic acid; (Example 70)
(S)-4-(4-(2-fluoroethyl)-1-((5-methoxy-7-methyl-1H-indol-4-yl)methyl)piperazin-2-yl)benzoic acid;
4-(4-(2-fluoroethyl)-1-((5-methoxy-7-methyl-1H-indol-4-yl)methyl)piperazin-2-yl)benzoic acid;
(±)-trans-4-1-((5-methoxy-7-methyl-1H-indol-4-yl)methyl)-4-(3-(trifluoromethyl)azetidin-1-yl)piperidin-2-yl)benzoic acid; (Example 71)
4-((2S,4S)-1-((5-methoxy-7-methyl-1H-indol-4-yl)methyl)-4-(3-(trifluoromethyl)azetidin-1-yl)piperidin-2-yl)benzoic acid; (Example 81)
4-((2R,4R)-1-((5-methoxy-7-methyl-1H-indol-4-yl)methyl)-4-(3-(trifluoromethyl)azetidin-1-yl)piperidin-2-yl)benzoic acid;
4-((2S,4R)-1-((5-methoxy-7-methyl-1H-indol-4-yl)methyl)-4-(3-(trifluoromethyl)azetidin-1-yl)piperidin-2-yl)benzoic acid;
4-((2R,4S)-1-((5-methoxy-7-methyl-1H-indol-4-yl)methyl)-4-(3-(trifluoromethyl)azetidin-1-yl)piperidin-2-yl)benzoic acid;
4-(1-((5-methoxy-7-methyl-1H-indol-4-yl)methyl)-4-(3-(trifluoromethyl)azetidin-1-yl)piperidin-2-yl)benzoic acid;
4-((2S,4S)-1-((5-methoxy-7-methyl-1H-indol-4-yl)methyl)-4-(3-(trifluoromethoxy)azetidin-1-yl)piperidin-2-yl)benzoic acid; (Example 72)
4-((2R,4R)-1-((5-methoxy-7-methyl-1H-indol-4-yl)methyl)-4-(3-(trifluoromethoxy)azetidin-1-yl)piperidin-2-yl)benzoic acid;
4-((2S,4R)-1-((5-methoxy-7-methyl-1H-indol-4-yl)methyl)-4-(3-(trifluoromethoxy)azetidin-1-yl)piperidin-2-yl)benzoic acid;
4-((2R,4S)-1-((5-methoxy-7-methyl-1H-indol-4-yl)methyl)-4-(3-(trifluoromethoxy)azetidin-1-yl)piperidin-2-yl)benzoic acid;
4-(1-((5-methoxy-7-methyl-1H-indol-4-yl)methyl)-4-(3-(trifluoromethoxy)azetidin-1-yl)piperidin-2-yl)benzoic acid;
4-((2S,4S)-4-(3-cyanoazetidin-1-yl)-1-((5-methoxy-7-methyl-1H-indol-4-yl)methyl)piperidin-2-yl)benzoic acid; (Example 73)
4-((2R,4R)-4-(3-cyanoazetidin-1-yl)-1-((5-methoxy-7-methyl-1H-indol-4-yl)methyl)piperidin-2-yl)benzoic acid;
4-((2S,4R)-4-(3-cyanoazetidin-1-yl)-1-((5-methoxy-7-methyl-1H-indol-4-yl)methyl)piperidin-2-yl)benzoic acid;
4-((2R,4S)-4-(3-cyanoazetidin-1-yl)-1-((5-methoxy-7-methyl-1H-indol-4-yl)methyl)piperidin-2-yl)benzoic acid;
4-(4-(3-cyanoazetidin-1-yl)-1-((5-methoxy-7-methyl-1H-indol-4-yl)methyl)piperidin-2-yl)benzoic acid;
4-((2S,4S)-4-(3-(difluoromethyl)azetidin-1-yl)-1-((5-methoxy-7-methyl-1H-indol-4-yl)methyl)piperidin-2-yl)benzoic acid; (Example 74)
4-((2R,4R)-4-(3-(difluoromethyl)azetidin-1-yl)-1-((5-methoxy-7-methyl-1H-indol-4-yl)methyl)piperidin-2-yl)benzoic acid;
4-((2S,4R)-4-(3-(difluoromethyl)azetidin-1-yl)-1-((5-methoxy-7-methyl-1H-indol-4-yl)methyl)piperidin-2-yl)benzoic acid;

4-((2R,4S)-4-(3-(difluoromethyl)azetidin-1-yl)-1-((5-methoxy-7-methyl-1H-indol-4-yl)methyl)piperidin-2-yl)benzoic acid;

4-(4-(3-(difluoromethyl)azetidin-1-yl)-1-((5-methoxy-7-methyl-1H-indol-4-yl)methyl)piperidin-2-yl)benzoic acid;

4-((2S,4S)-1-((3-chloro-5-methoxy-7-methyl-1H-indol-4-yl)methyl)-4-(3-(trifluoromethyl)azetidin-1-yl)piperidin-2-yl)benzoic acid; (Example 75)

4-((2R,4R)-1-((3-chloro-5-methoxy-7-methyl-1H-indol-4-yl)methyl)-4-(3-(trifluoromethyl)azetidin-1-yl)piperidin-2-yl)benzoic acid;

4-((2S,4R)-1-((3-chloro-5-methoxy-7-methyl-1H-indol-4-yl)methyl)-4-(3-(trifluoromethyl)azetidin-1-yl)piperidin-2-yl)benzoic acid;

4-((2R,4S)-1-((3-chloro-5-methoxy-7-methyl-1H-indol-4-yl)methyl)-4-(3-(trifluoromethyl)azetidin-1-yl)piperidin-2-yl)benzoic acid;

4-(1-((3-chloro-5-methoxy-7-methyl-1H-indol-4-yl)methyl)-4-(3-(trifluoromethyl)azetidin-1-yl)piperidin-2-yl)benzoic acid;

4-((2S,4S)-1-((5-cyclopropyl-7-methyl-1H-indol-4-yl)methyl)-4-(3-(trifluoromethyl)azetidin-1-yl)piperidin-2-yl)benzoic acid; (Example 76)

4-((2R,4R)-1-((5-cyclopropyl-7-methyl-1H-indol-4-yl)methyl)-4-(3-(trifluoromethyl)azetidin-1-yl)piperidin-2-yl)benzoic acid;

4-((2S,4R)-1-((5-cyclopropyl-7-methyl-1H-indol-4-yl)methyl)-4-(3-(trifluoromethyl)azetidin-1-yl)piperidin-2-yl)benzoic acid;

4-((2R,4S)-1-((5-cyclopropyl-7-methyl-1H-indol-4-yl)methyl)-4-(3-(trifluoromethyl)azetidin-1-yl)piperidin-2-yl)benzoic acid;

4-(1-((5-cyclopropyl-7-methyl-1H-indol-4-yl)methyl)-4-(3-(trifluoromethyl)azetidin-1-yl)piperidin-2-yl)benzoic acid;

4-((2S,4S)-4-(3-cyanoazetidin-1-yl)-1-((5-cyclopropyl-7-methyl-1H-indol-4-yl)methyl)piperidin-2-yl)benzoic acid; (Example 77)

4-((2R,4R)-4-(3-cyanoazetidin-1-yl)-1-((5-cyclopropyl-7-methyl-1H-indol-4-yl)methyl)piperidin-2-yl)benzoic acid;

4-((2S,4R)-4-(3-cyanoazetidin-1-yl)-1-((5-cyclopropyl-7-methyl-1H-indol-4-yl)methyl)piperidin-2-yl)benzoic acid;

4-((2R,4S)-4-(3-cyanoazetidin-1-yl)-1-((5-cyclopropyl-7-methyl-1H-indol-4-yl)methyl)piperidin-2-yl)benzoic acid;

4-(4-(3-cyanoazetidin-1-yl)-1-((5-cyclopropyl-7-methyl-1H-indol-4-yl)methyl)piperidin-2-yl)benzoic acid;

4-((2S,4S)-1-((5-cyclopropyl-7-methyl-1H-indol-4-yl)methyl)-4-(5-azaspiro[2.3]hexan-5-yl)piperidin-2-yl)benzoic acid; (Example 78)

4-((2R,4R)-1-((5-cyclopropyl-7-methyl-1H-indol-4-yl)methyl)-4-(5-azaspiro[2.3]hexan-5-yl)piperidin-2-yl)benzoic acid;

4-((2S,4R)-1-((5-cyclopropyl-7-methyl-1H-indol-4-yl)methyl)-4-(5-azaspiro[2.3]hexan-5-yl)piperidin-2-yl)benzoic acid;

4-((2R,4S)-1-((5-cyclopropyl-7-methyl-1H-indol-4-yl)methyl)-4-(5-azaspiro[2.3]hexan-5-yl)piperidin-2-yl)benzoic acid;

4-(1-((5-cyclopropyl-7-methyl-1H-indol-4-yl)methyl)-4-(5-azaspiro[2.3]hexan-5-yl)piperidin-2-yl)benzoic acid;

4-((2S,4S)-1-((5-methoxy-7-methyl-1H-indol-4-yl)methyl)-4-(3-(methylsulfonyl)azetidin-1-yl)piperidin-2-yl)benzoic acid; (Example 79)

4-((2R,4R)-1-((5-methoxy-7-methyl-1H-indol-4-yl)methyl)-4-(3-(methylsulfonyl)azetidin-1-yl)piperidin-2-yl)benzoic acid;

4-((2S,4R)-1-((5-methoxy-7-methyl-1H-indol-4-yl)methyl)-4-(3-(methylsulfonyl)azetidin-1-yl)piperidin-2-yl)benzoic acid;

4-((2R,4S)-1-((5-methoxy-7-methyl-1H-indol-4-yl)methyl)-4-(3-(methylsulfonyl)azetidin-1-yl)piperidin-2-yl)benzoic acid;

4-(1-((5-methoxy-7-methyl-1H-indol-4-yl)methyl)-4-(3-(methylsulfonyl)azetidin-1-yl)piperidin-2-yl)benzoic acid;

4-((2S,4S)-4-(3-fluoroazetidin-1-yl)-1-((5-methoxy-7-methyl-1H-indol-4-yl)methyl)piperidin-2-yl)benzoic acid; (Example 80)

4-((2R,4R)-4-(3-fluoroazetidin-1-yl)-1-((5-methoxy-7-methyl-1H-indol-4-yl)methyl)piperidin-2-yl)benzoic acid;

4-((2S,4R)-4-(3-fluoroazetidin-1-yl)-1-((5-methoxy-7-methyl-1H-indol-4-yl)methyl)piperidin-2-yl)benzoic acid;

4-((2R,4S)-4-(3-fluoroazetidin-1-yl)-1-((5-methoxy-7-methyl-1H-indol-4-yl)methyl)piperidin-2-yl)benzoic acid;

4-(4-(3-fluoroazetidin-1-yl)-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(oxetan-3-yloxy)piperidin-2-yl)benzoic acid; (Example 82)

4-((2R,4R)-1-((5-methoxy-7-methyl-1H-indol-4-yl)methyl)-4-(oxetan-3-yloxy)piperidin-2-yl)benzoic acid;

4-((2S,4R)-1-((5-methoxy-7-methyl-1H-indol-4-yl)methyl)-4-(oxetan-3-yloxy)piperidin-2-yl)benzoic acid;

4-((2R,4S)-1-((5-methoxy-7-methyl-1H-indol-4-yl)methyl)-4-(oxetan-3-yloxy)piperidin-2-yl)benzoic acid;

4-(1-((5-methoxy-7-methyl-1H-indol-4-yl)methyl)-4-(oxetan-3-yloxy)piperidin-2-yl)benzoic acid;

4-((2S,4S)-4-(2,2-difluoroethoxy)-1-((5-methoxy-7-methyl-1H-indol-4-yl)methyl)piperidin-2-yl)benzoic acid; (Example 83)

4-((2R,4R)-4-(2,2-difluoroethoxy)-1-((5-methoxy-7-methyl-1H-indol-4-yl)methyl)piperidin-2-yl)benzoic acid;

4-((2S,4R)-4-(2,2-difluoroethoxy)-1-((5-methoxy-7-methyl-1H-indol-4-yl)methyl)piperidin-2-yl)benzoic acid;

4-((2R,4S)-4-(2,2-difluoroethoxy)-1-((5-methoxy-7-methyl-1H-indol-4-yl)methyl)piperidin-2-yl)benzoic acid;

4-(4-(2,2-difluoroethoxy)-1-((5-methoxy-7-methyl-1H-indol-4-yl)methyl)piperidin-2-yl)benzoic acid;

4-((2S,4S)-4-cyclobutoxy-1-((5-methoxy-7-methyl-1H-indol-4-yl)methyl)piperidin-2-yl)benzoic acid; (Example 84)

4-((2R,4R)-4-cyclobutoxy-1-((5-methoxy-7-methyl-1H-indol-4-yl)methyl)piperidin-2-yl)benzoic acid;

4-((2S,4R)-4-cyclobutoxy-1-((5-methoxy-7-methyl-1H-indol-4-yl)methyl)piperidin-2-yl)benzoic acid;

4-((2R,4S)-4-cyclobutoxy-1-((5-methoxy-7-methyl-1H-indol-4-yl)methyl)piperidin-2-yl)benzoic acid;

4-(4-cyclobutoxy-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(2,2,2-trifluoroethoxy)piperidin-2-yl)benzoic acid; (Example 85)

4-((2R,4R)-1-((5-methoxy-7-methyl-1H-indol-4-yl)methyl)-4-(2,2,2-trifluoroethoxy)piperidin-2-yl)benzoic acid;
4-((2S,4R)-1-((5-methoxy-7-methyl-1H-indol-4-yl)methyl)-4-(2,2,2-trifluoroethoxy)piperidin-2-yl)benzoic acid;
4-((2R,4S)-1-((5-methoxy-7-methyl-1H-indol-4-yl)methyl)-4-(2,2,2-trifluoroethoxy)piperidin-2-yl)benzoic acid; and
4-(1-((5-methoxy-7-methyl-1H-indol-4-yl)methyl)-4-(2,2,2-trifluoroethoxy)piperidin-2-yl)benzoic acid.

In certain embodiments, provided herein is a compound of Formula (I) wherein the compound is selected from the group consisting of the compounds in Table A below and pharmaceutically acceptable salts thereof:

| Example | Structure |
|---|---|
| 1 | 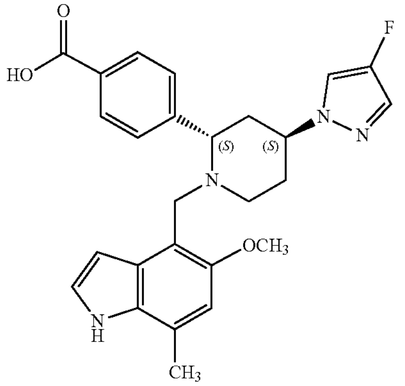 |
| 2 | 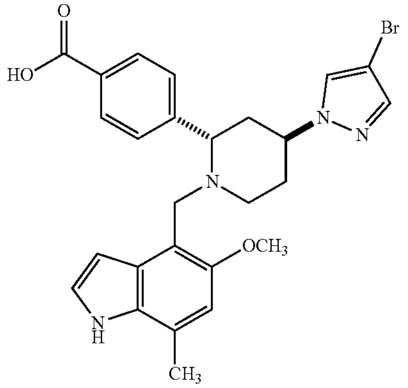<br>(+/-)-trans |
| 3 | 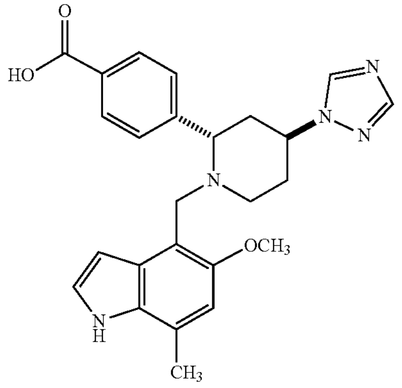 [SMILES: COc1cc(C)c2[nH]ccc2c1CN1CC[C@H](n2cccn2)C[C@H]1c1ccc(C(=O)O)cc1]<br>(+/-)-trans |

-continued

| Example | Structure |
|---|---|
| 4 | 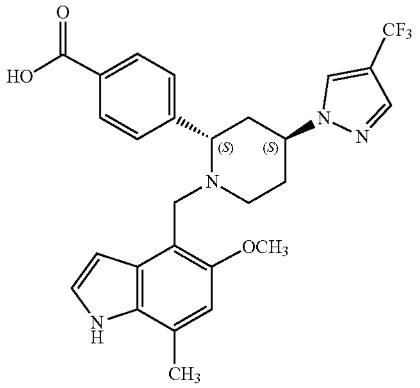 |
| 5 | 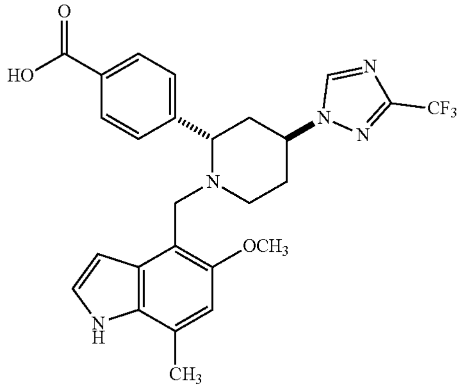<br>(+/-)-trans |
| 6 | 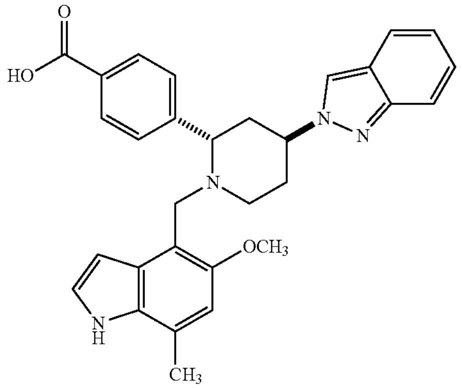<br>(+/-)-trans |

-continued
| Example | Structure |
|---|---|
| 7 | 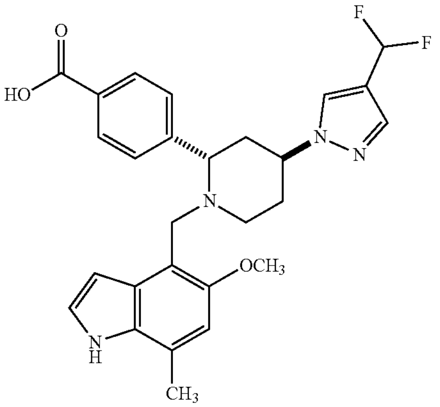 (+/-)-trans |
| 8 | 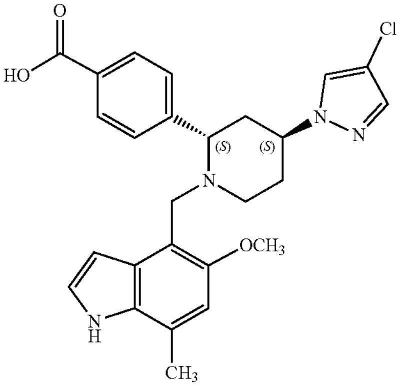 |
| 9 | 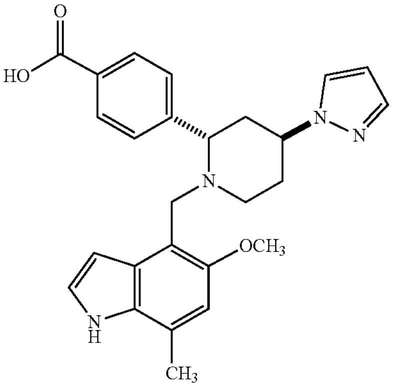 |
| 10 | 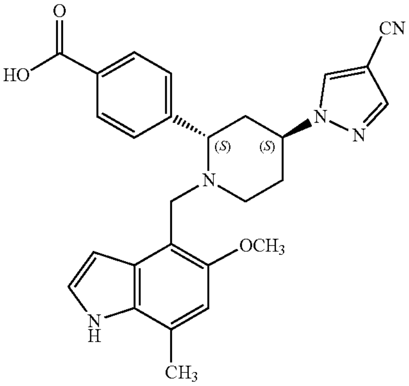 |
-continued
| Example | Structure |
|---|---|
| 11 | 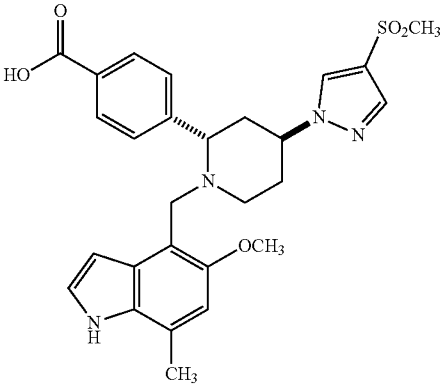 (+/-)-trans |
| 12 | 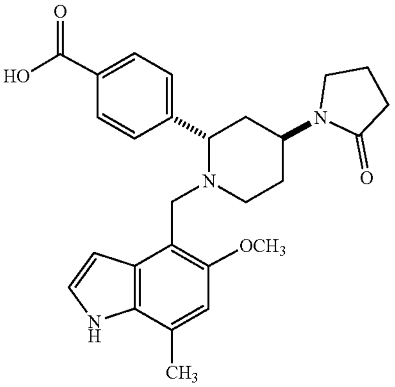 (+/-)-trans |
| 13 | 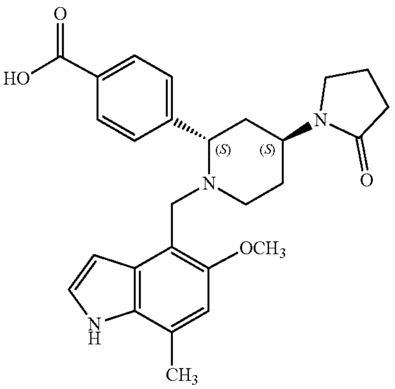 |

-continued
| Example | Structure |
|---|---|
| 14 | 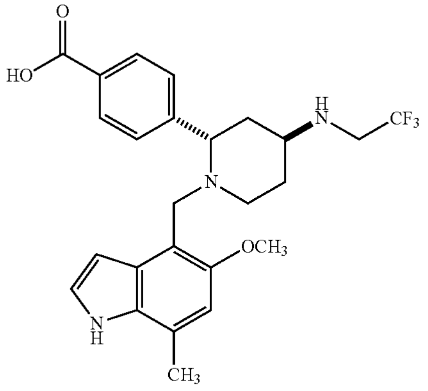 (+/-)-trans |
| 15 | 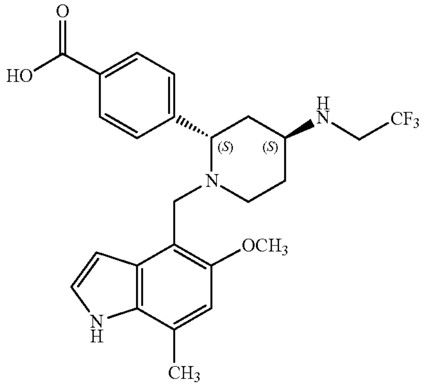 |
| 16 | 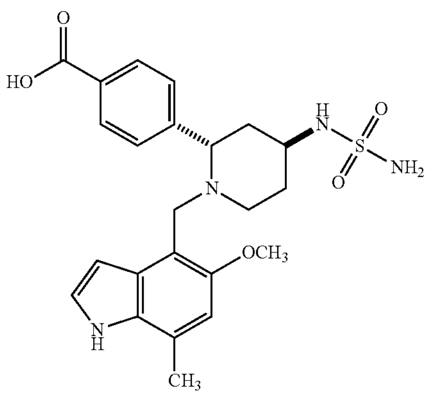 (+/-)-trans |
-continued
| Example | Structure |
|---|---|
| 17 | 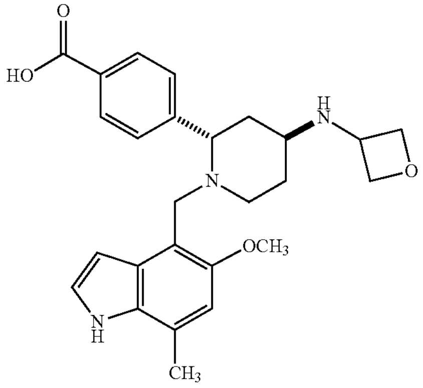 (+/-)-trans |
| 18 | 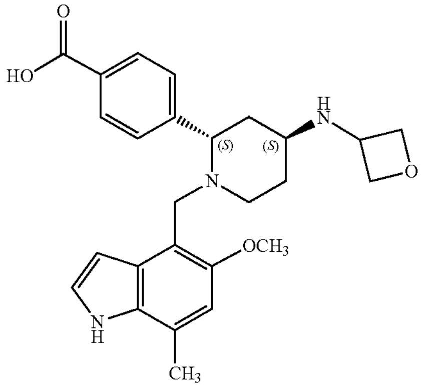 |
| 19 | 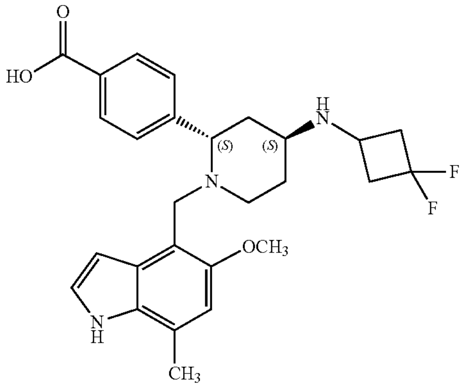 |
| 20 | 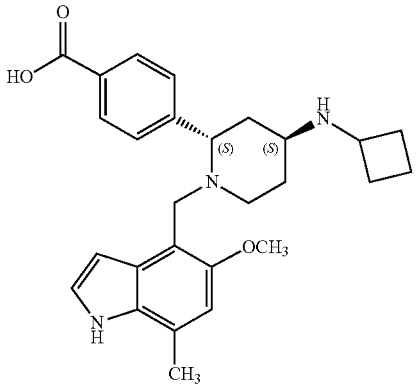 |

-continued
| Example | Structure |
| --- | --- |
| 21 | 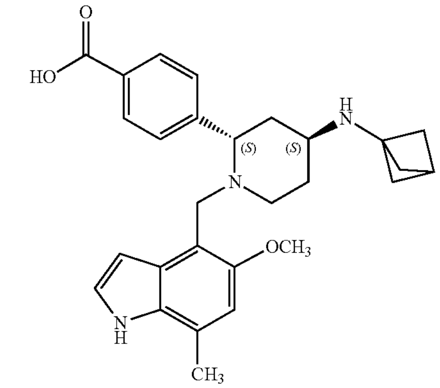 |
| 22 | 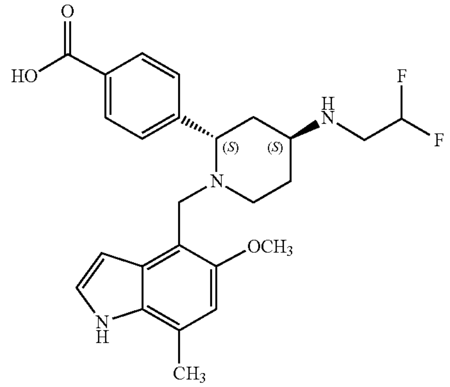 |
| 23 | 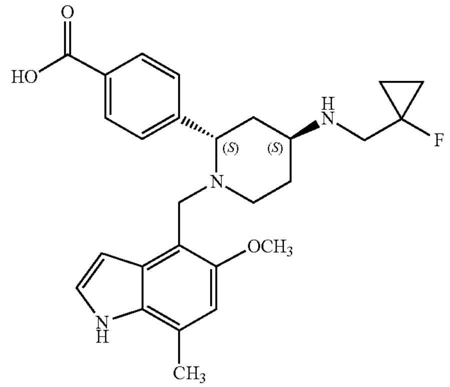 |
| 24 | 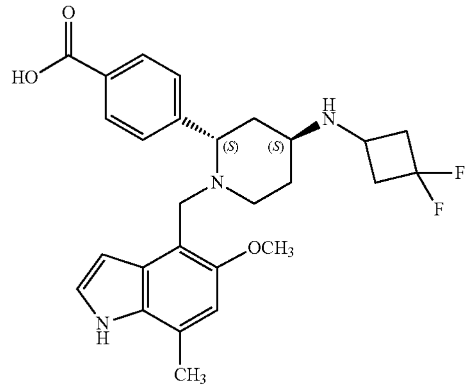 |
-continued
| Example | Structure |
| --- | --- |
| 25 | 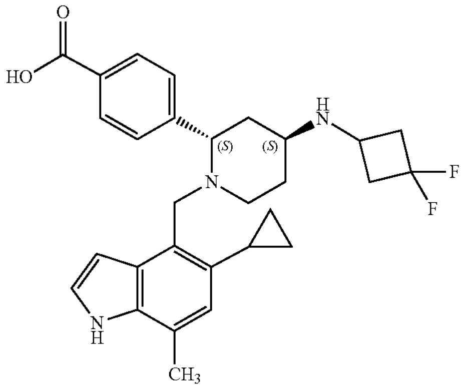 |
| 26 | 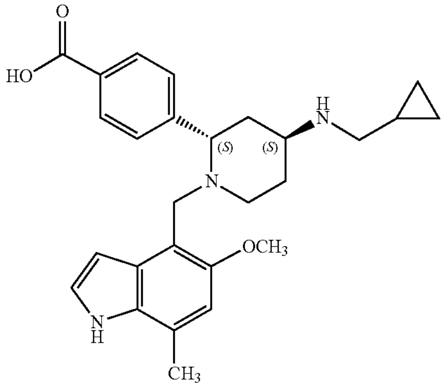 |
| 27 | 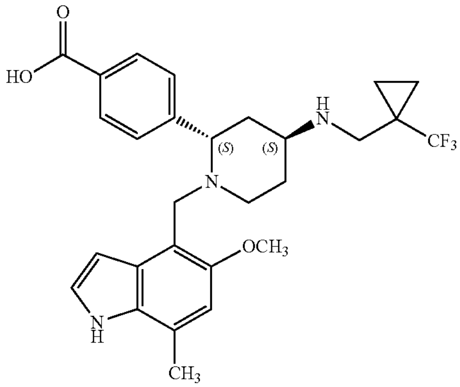 |
| 28 | 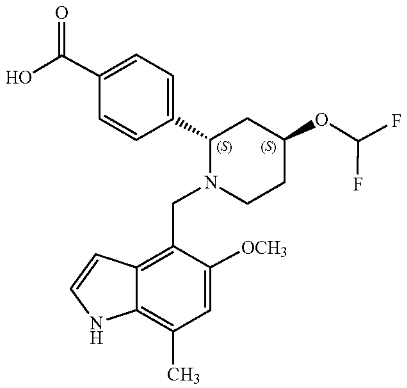 |

-continued
| Example | Structure |
| --- | --- |
| 29 | 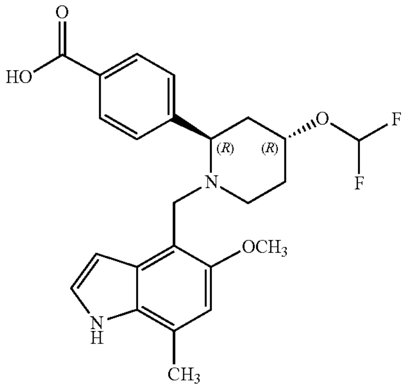 |
| 30 | 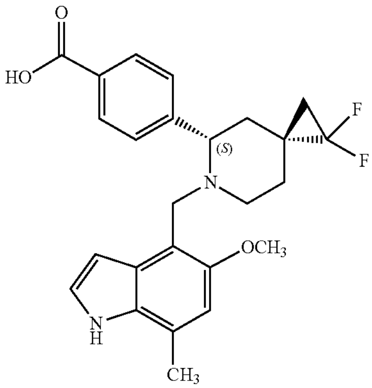 or 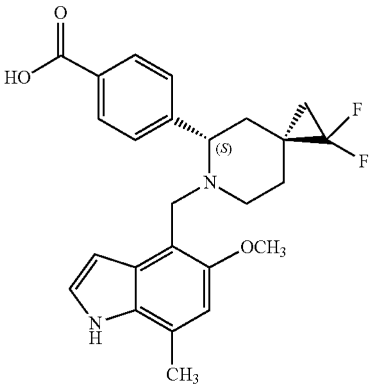 |
| 31 | 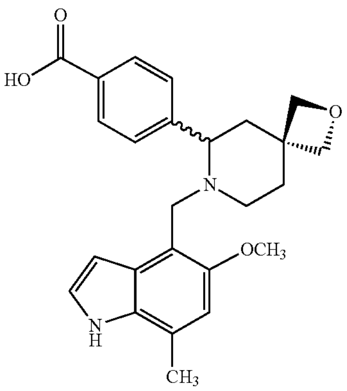 |
| 32 | 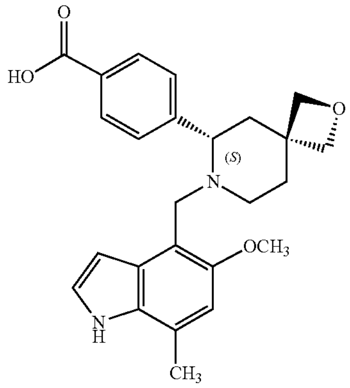 |
| 33 | 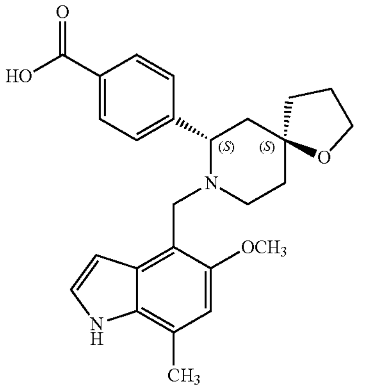 or 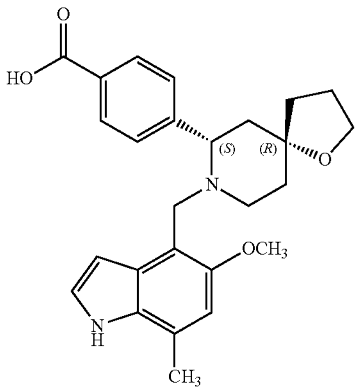 |

-continued
| Example | Structure |
|---|---|
| 34 | 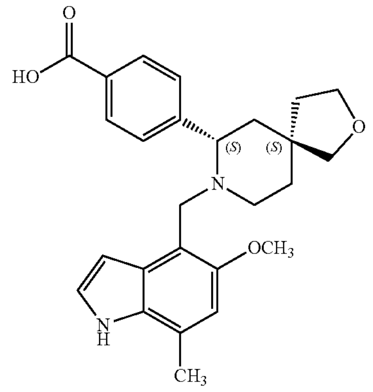 or |
| | 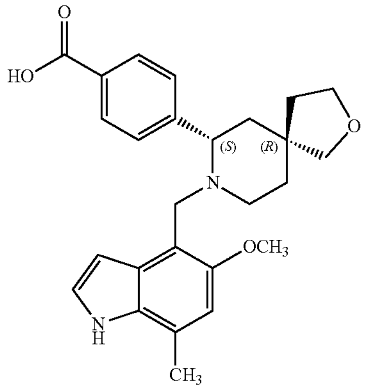 |
| 35 | 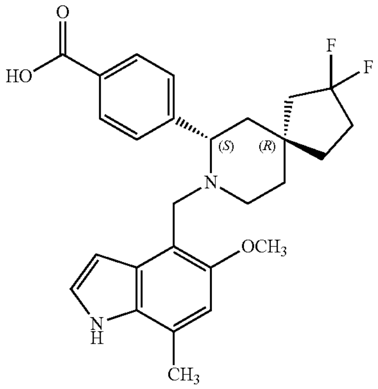 or |
| | 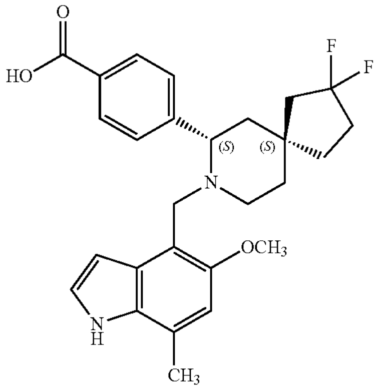 |
-continued
| Example | Structure |
|---|---|
| 36 | 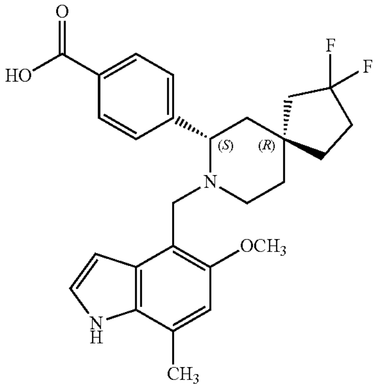 or |
| | 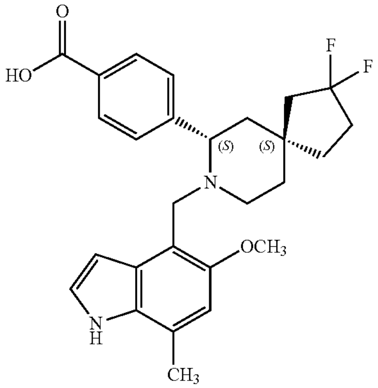 |
| 37 | 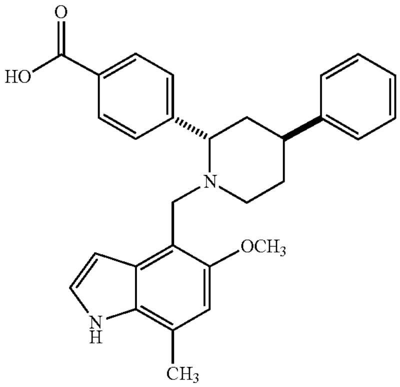 [SMILES: COc1cc(C)c2[nH]ccc2c1CN1CC[C@H](c2ccccc2)C[C@H]1c1ccc(C(=O)O)cc1] |
| 38 | 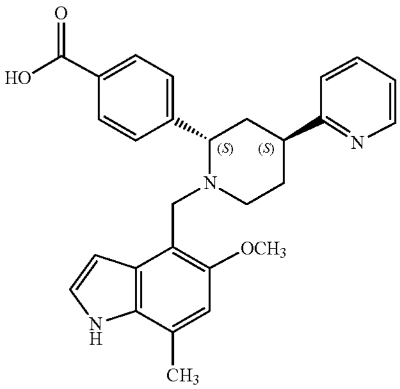 |

-continued
| Example | Structure |
|---|---|
| 39 | 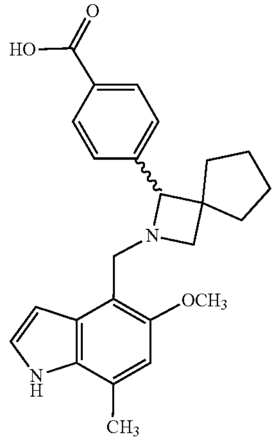 [SMILES: COc1cc(C)c2[nH]ccc2c1CN1CC2(CCCC2)C1c1ccc(C(=O)O)cc1] |
| 40 | 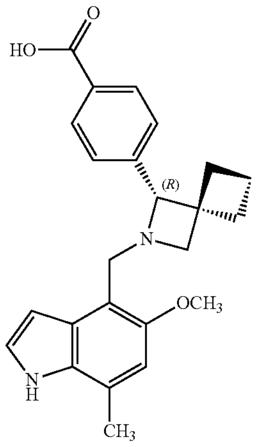 |
| 41 | 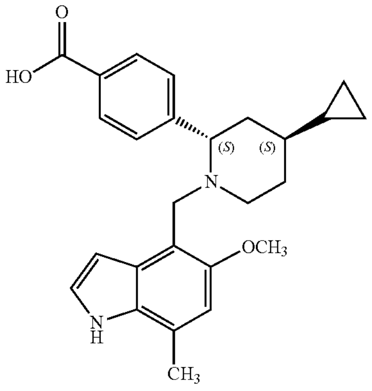 |
-continued
| Example | Structure |
|---|---|
| 42 | 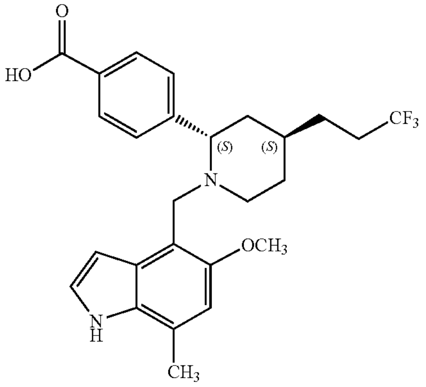 |
| 43 | 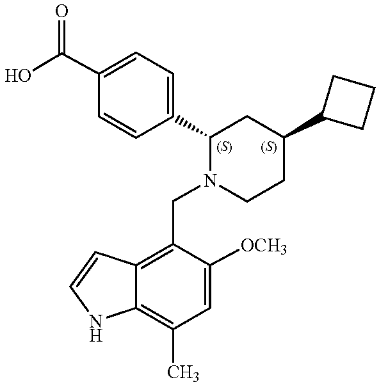 and 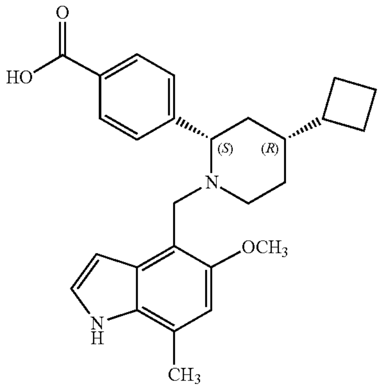 mixture of diastereomers |
| 44 | 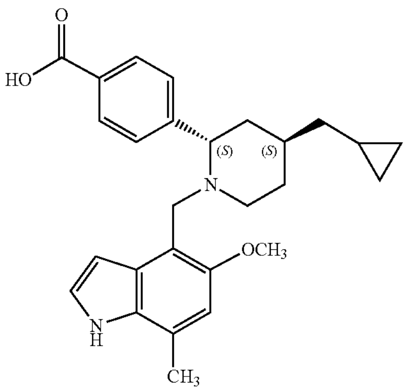 |

-continued
| Example | Structure |
|---|---|
| 45 | 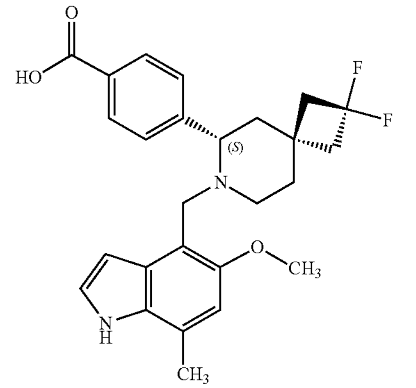 |
| 46 | 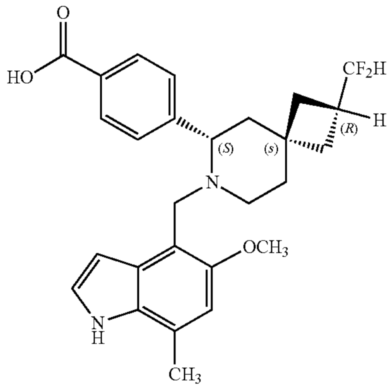 or 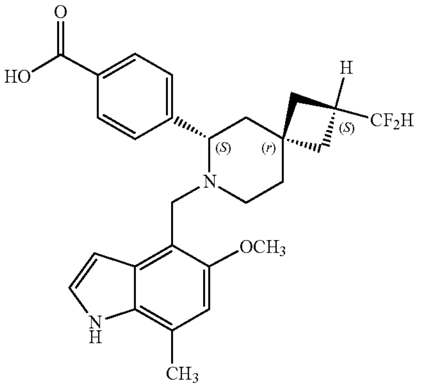 |
-continued
| Example | Structure |
|---|---|
| 47 | 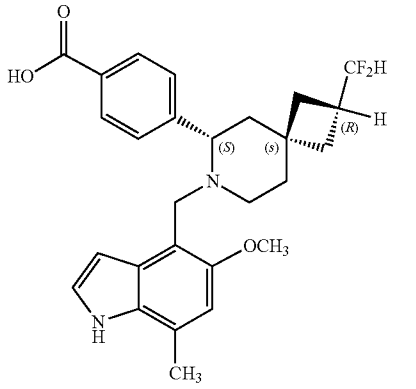 or 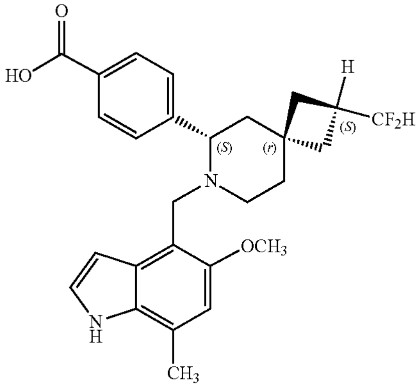 |
| 48 | 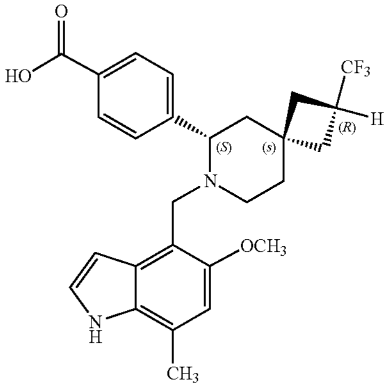 or 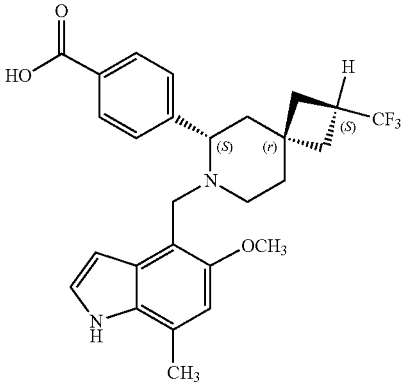 |

-continued
| Example | Structure |
| --- | --- |
| 49 | 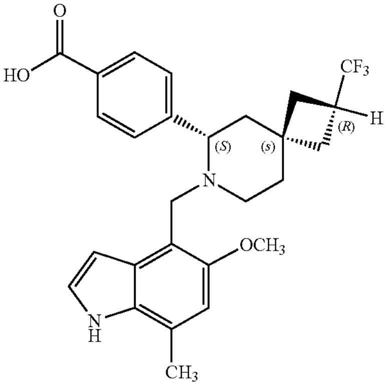 or 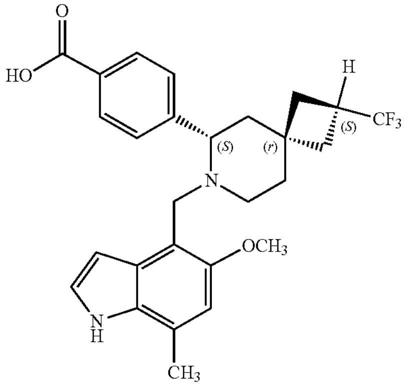 |
| 50 | 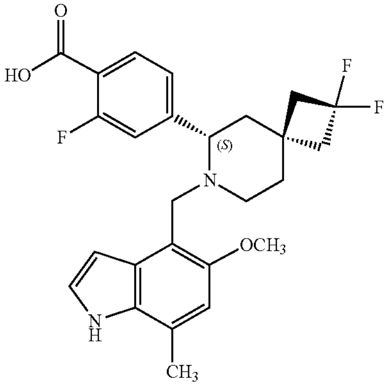 |
| 51 | 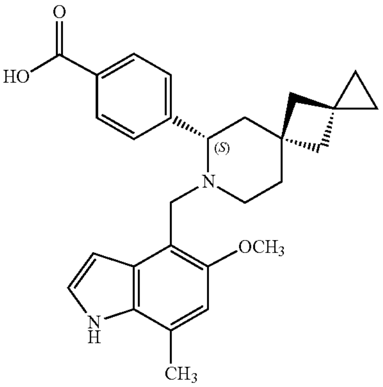 |
-continued
| Example | Structure |
| --- | --- |
| 52 | 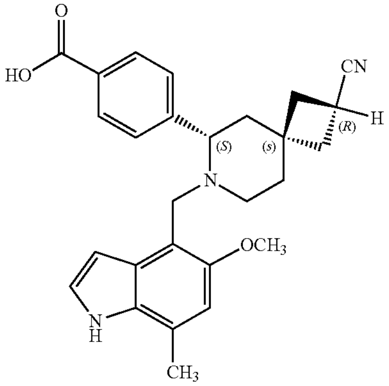 or 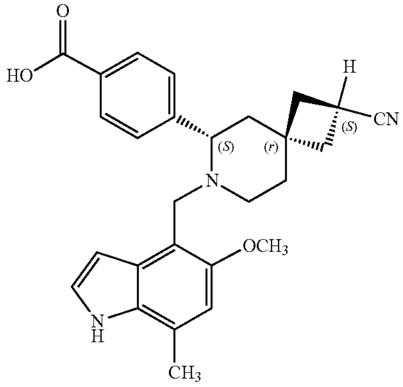 |
| 53 | 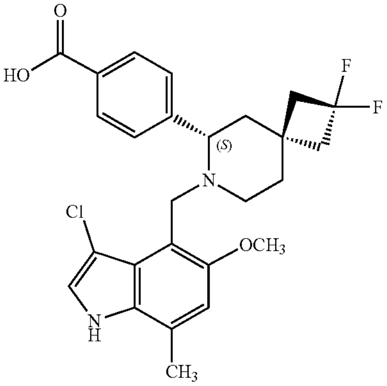 |
| 54 | 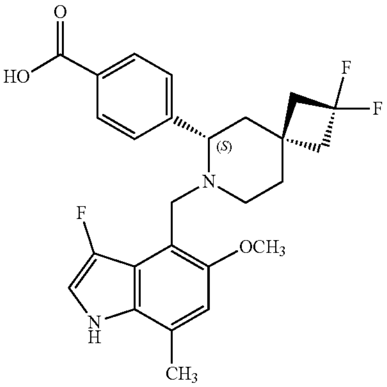 |

-continued
| Example | Structure |
|---|---|
| 55 | 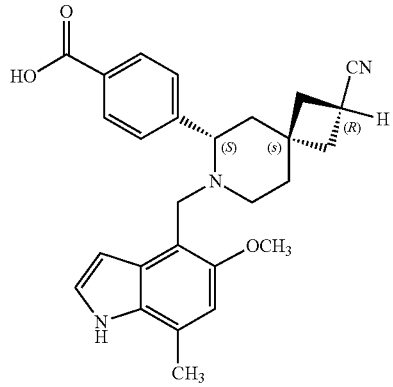 or 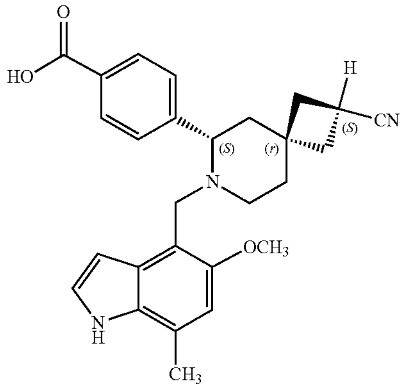 |
| 56 | 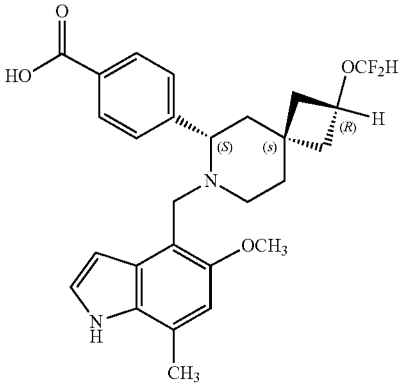 or 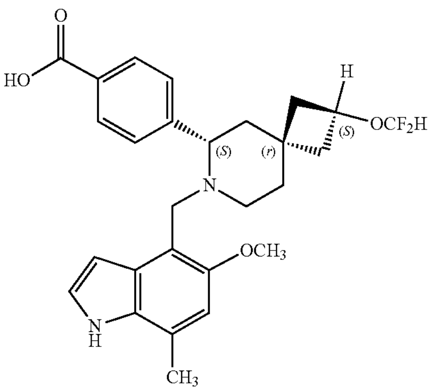 |
-continued
| Example | Structure |
|---|---|
| 57 | 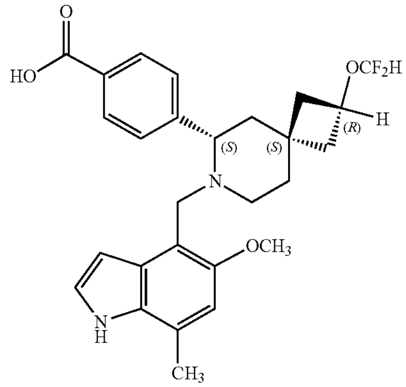 or 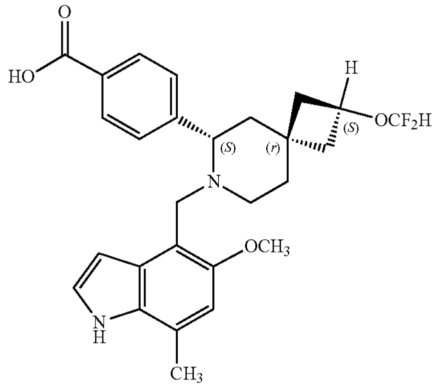 |
| 58 | 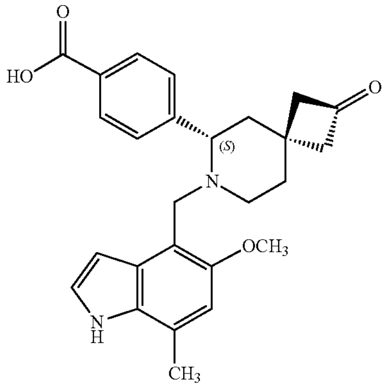 |

-continued
| Example | Structure |
|---|---|
| 59 | 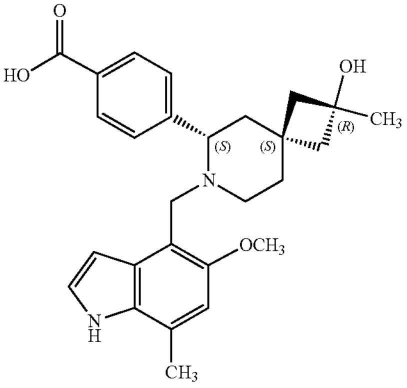 or |
| | 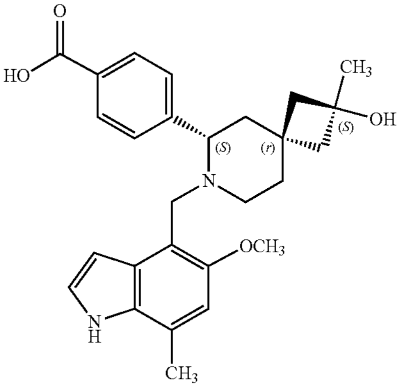 |
| 60 | 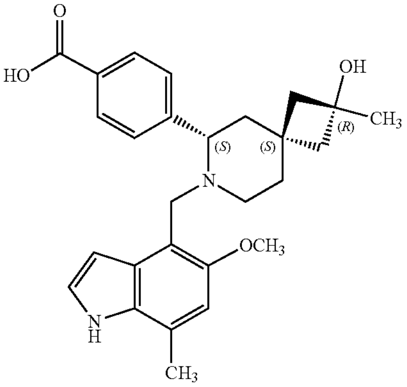 or |
| | 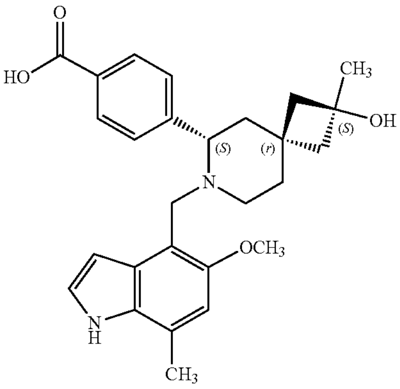 |
-continued
| Example | Structure |
|---|---|
| 61 | 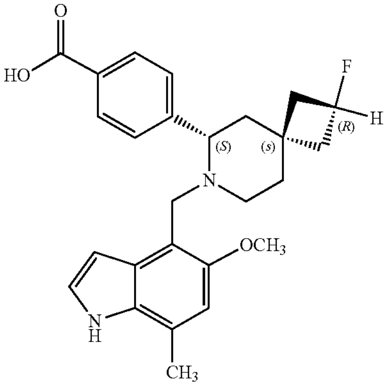 and |
| | 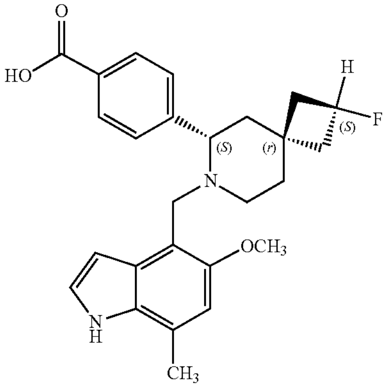 |
| 62 | 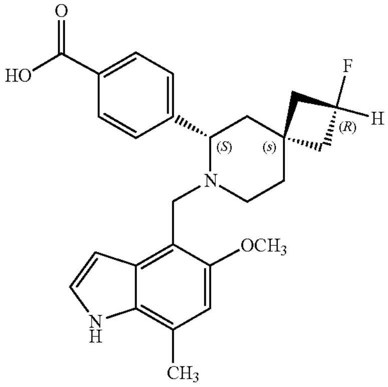 or |
| | 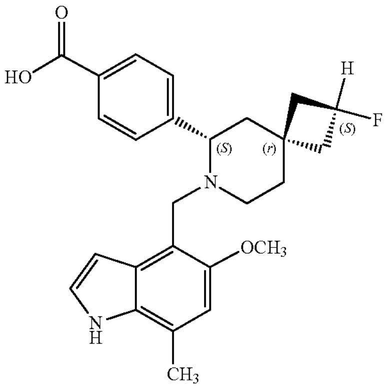 |

-continued
| Example | Structure |
|---|---|
| 63 | 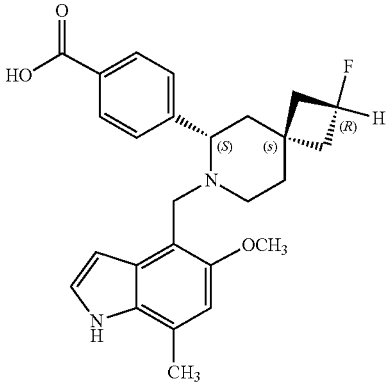 or |
| | 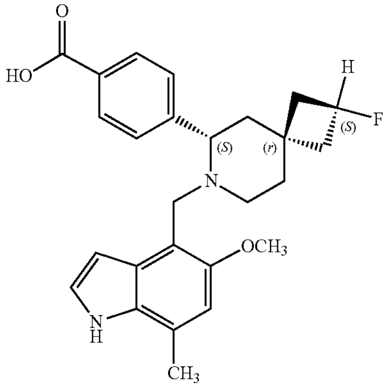 |
| 64 | 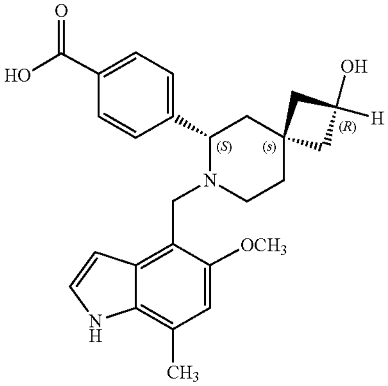 and |
| | 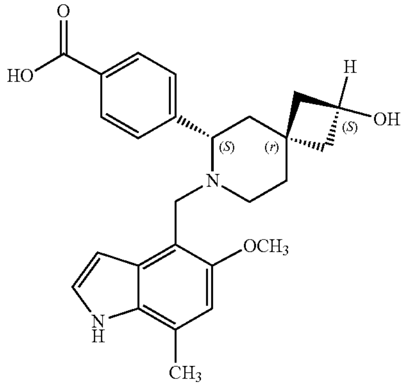 |
-continued
| Example | Structure |
|---|---|
| 65 | 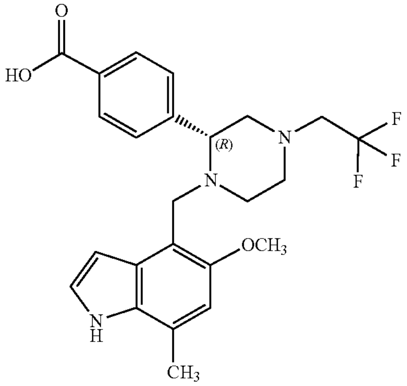 |
| 66 | 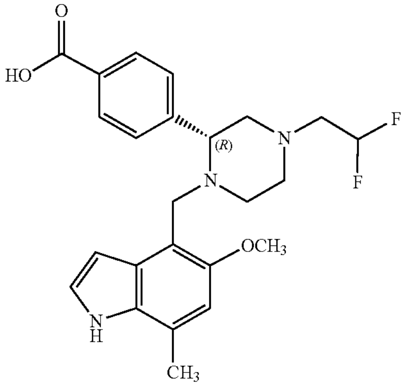 |
| 67 | 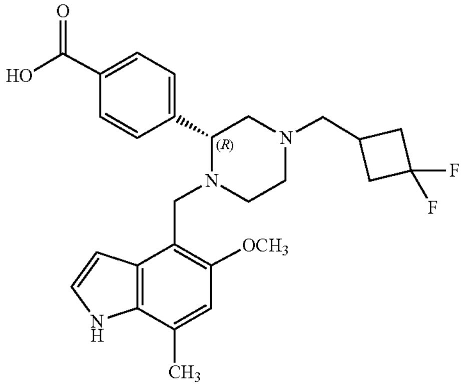 |
| 68 | 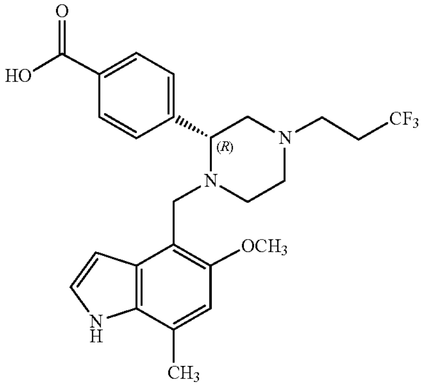 |

-continued
| Example | Structure |
|---|---|
| 69 | 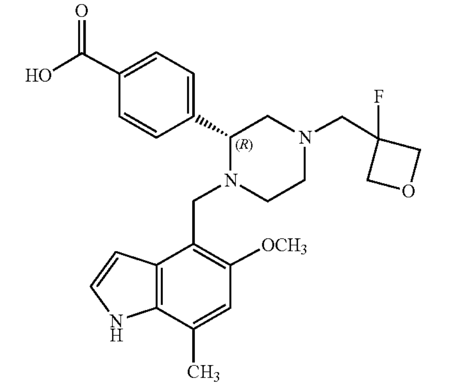 |
| 70 | 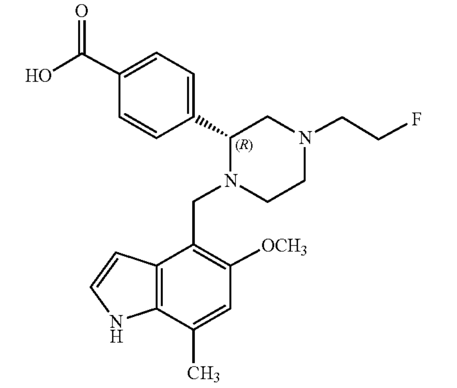 |
| 71 | 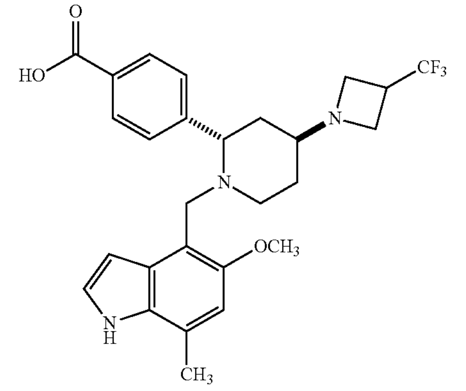 (+/-)-trans |
| 72 | 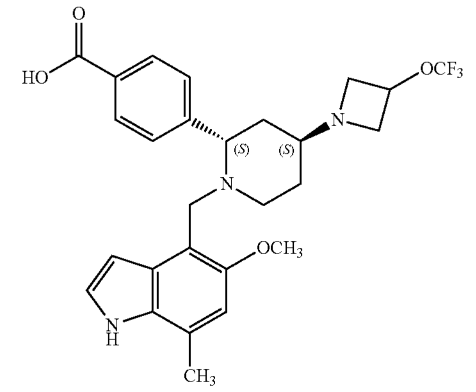 |
-continued
| Example | Structure |
|---|---|
| 73 | 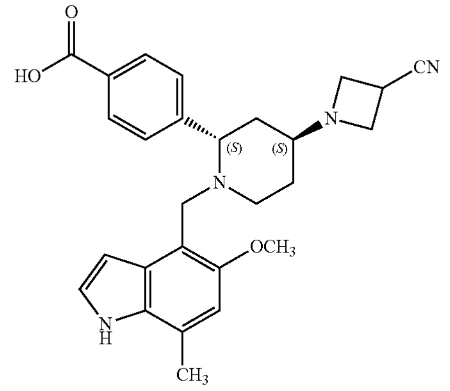 |
| 74 | 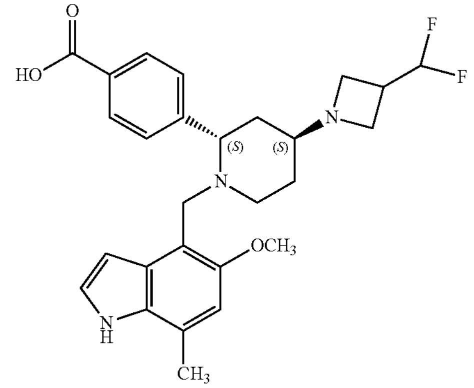 |
| 75 | 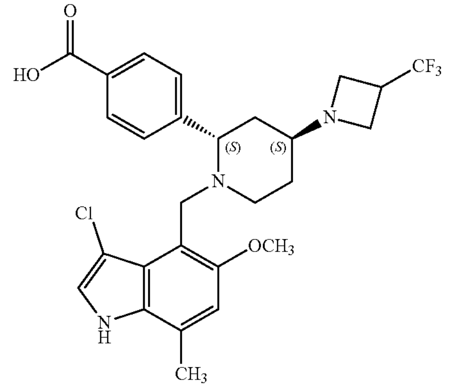 |
| 76 | 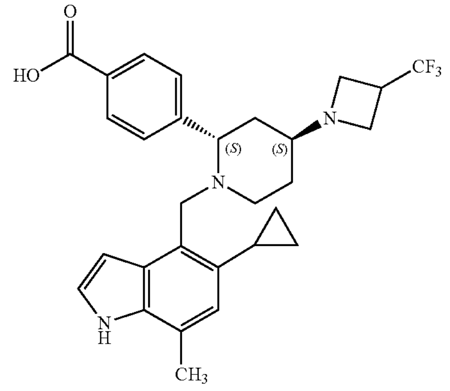 |

-continued
| Example | Structure |
| --- | --- |
| 77 | 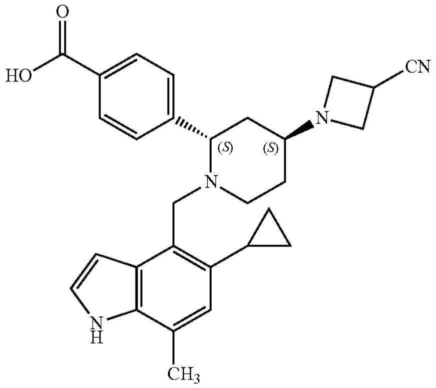 |
| 78 | 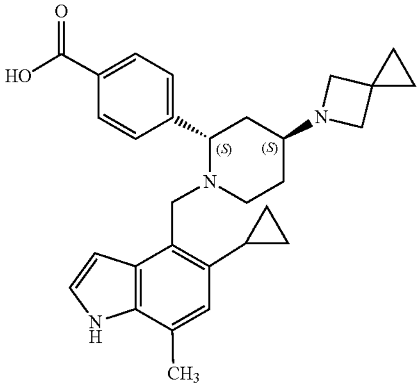 |
| 79 | 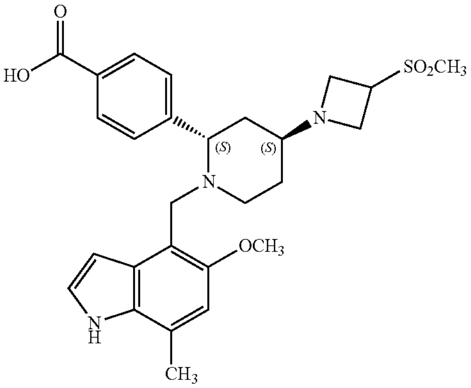 |
| 80 | 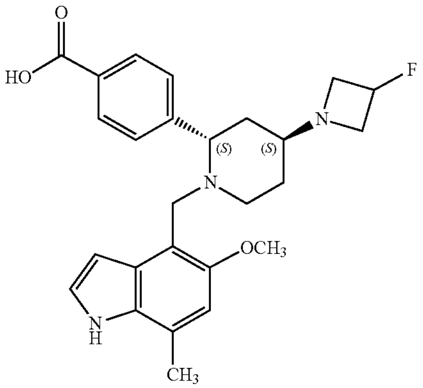 |
-continued
| Example | Structure |
| --- | --- |
| 81 | 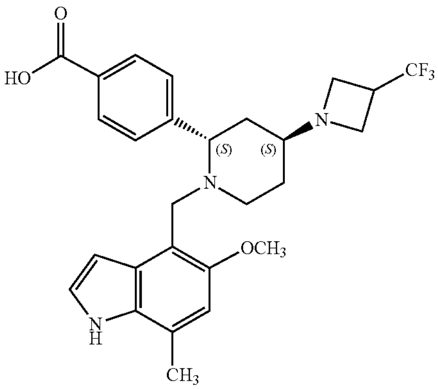 |
| 82 | 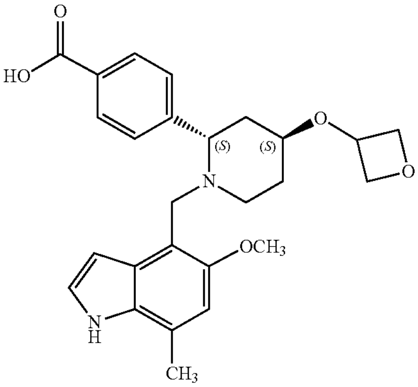 |
| 83 | 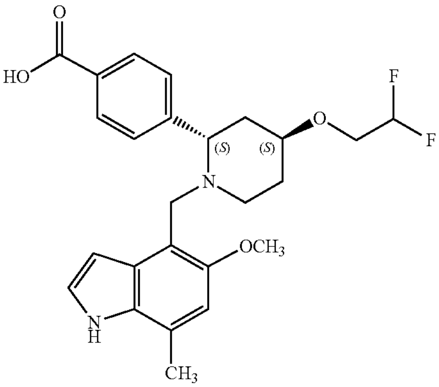 |
| 84 | 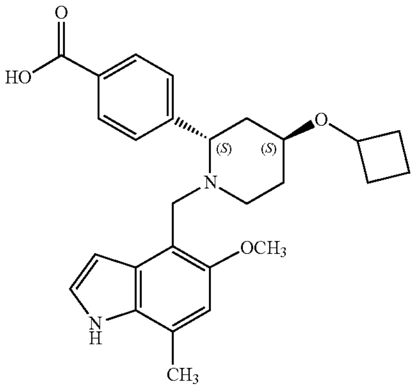 |

-continued
| Example | Structure |
|---|---|
| 85 | 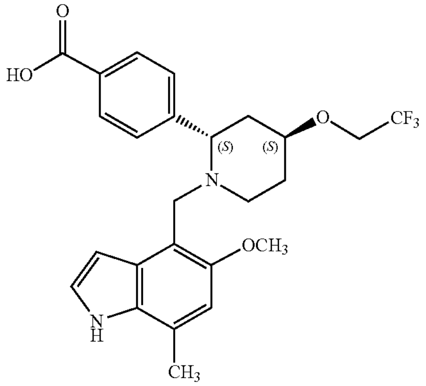 |
In certain embodiments, provided herein is a compound of Formula (I) wherein the compound is selected from the group consisting of the compounds in Table B below and pharmaceutically acceptable salts thereof:
| Example | Structure |
|---|---|
| 1 | 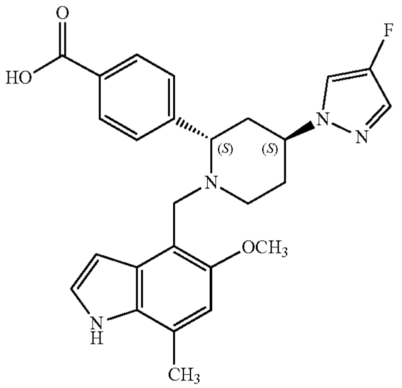 |
| 2 | 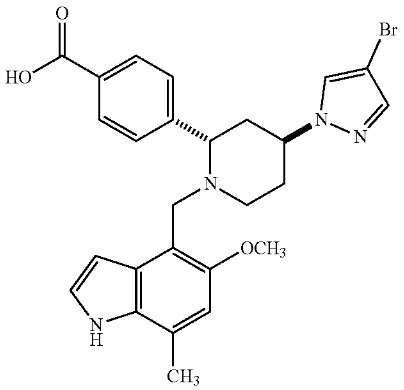<br>(+/-)-trans |

-continued
| Example | Structure |
|---|---|
| 3 | 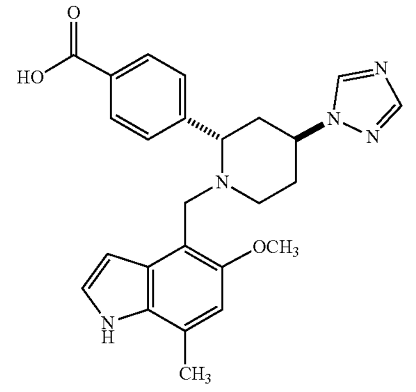<br>(+/-)-trans |
| 4 | 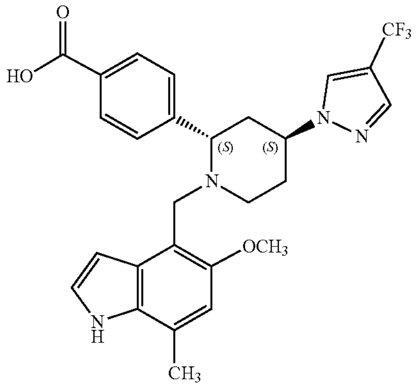 |
| 5 | 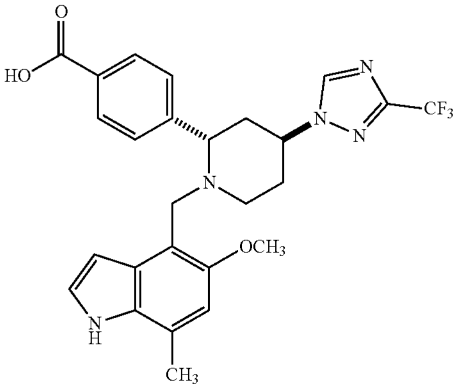<br>(+/-)-trans |

-continued
| Example | Structure |
|---|---|
| 6 | 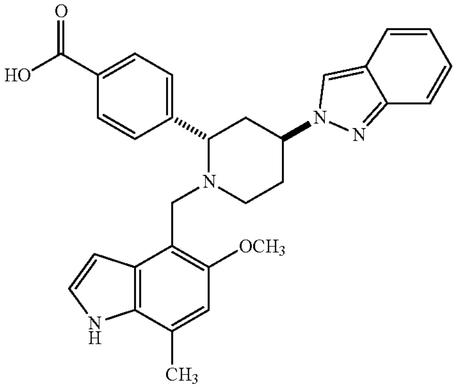 (+/-)-trans |
| 7 | 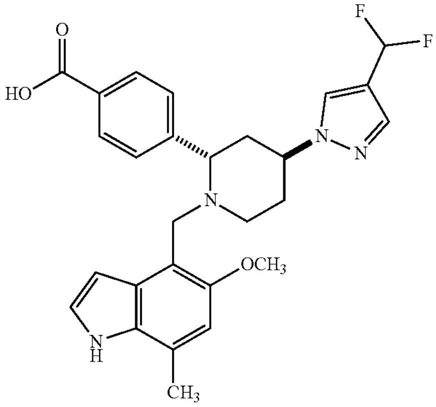 (+/-)-trans |
| 8 | 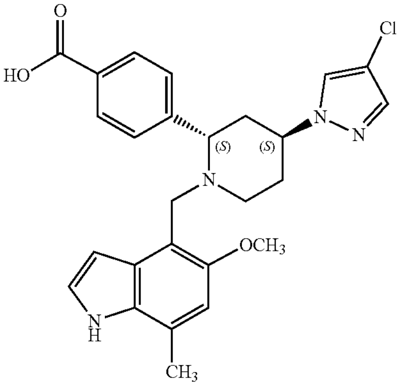 |

-continued
| Example | Structure |
|---|---|
| 9 | 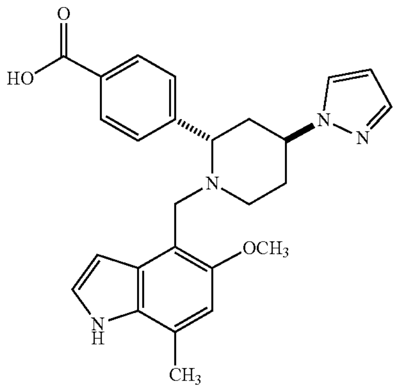 [SMILES: COc1cc(C)c2[nH]ccc2c1CN1CC[C@H](n2cccn2)C[C@H]1c1ccc(C(=O)O)cc1] |
| 10 | 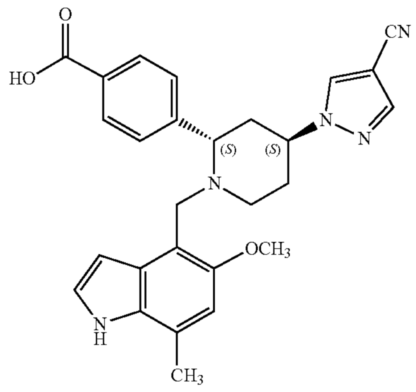 |
| 11 | 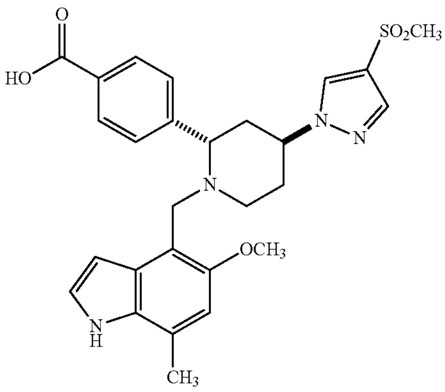<br>(+/-)-trans |

-continued
| Example | Structure |
| --- | --- |
| 12 | 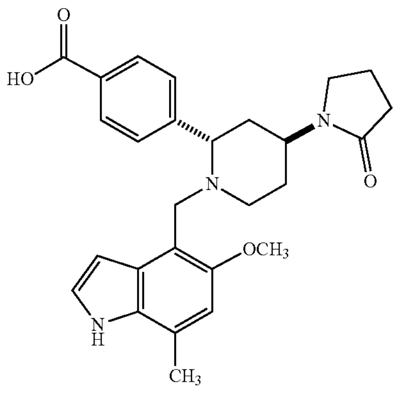 (+/-)-trans |
| 13 | 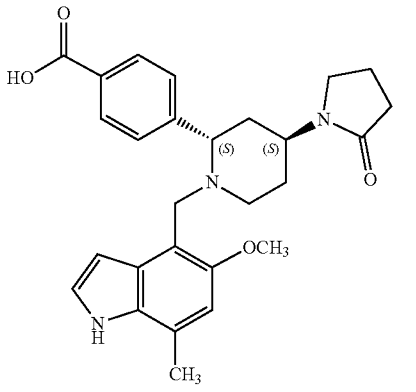 |
| 16 | 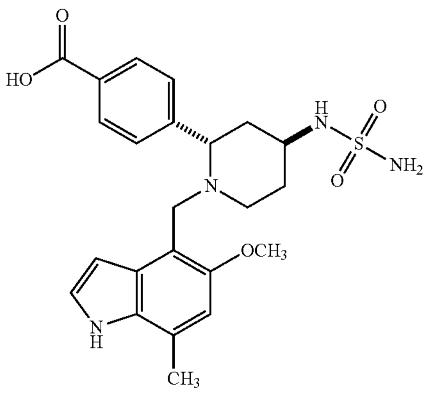 (+/-)-trans |

-continued
| Example | Structure |
|---|---|
| 17 | 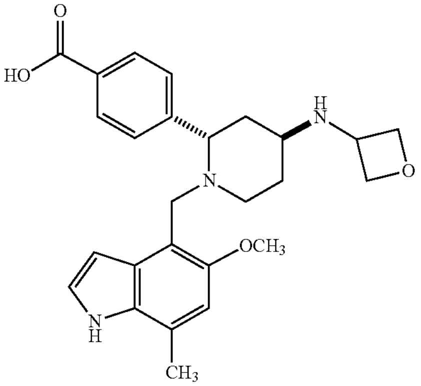<br>(+/-)-trans |
| 18 | 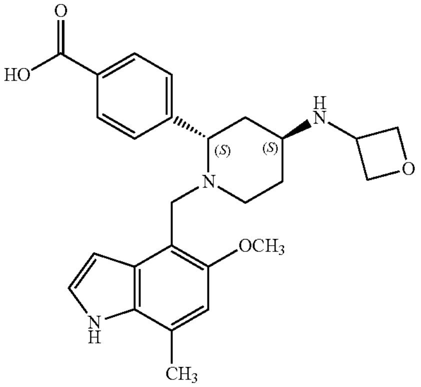 |
| 19 | 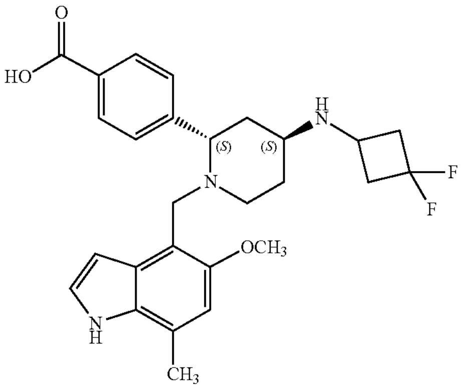 |
| 20 | 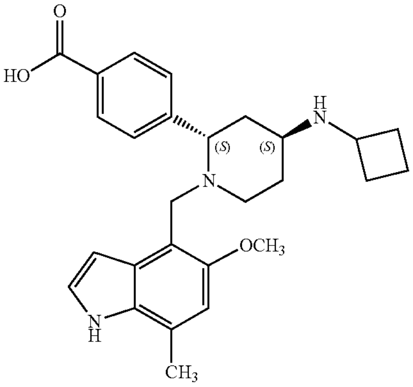 |

-continued
| Example | Structure |
| --- | --- |
| 21 | 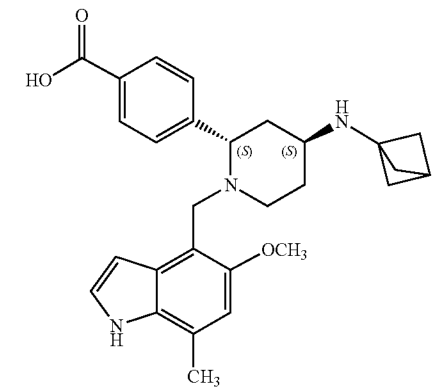 |
| 24 | 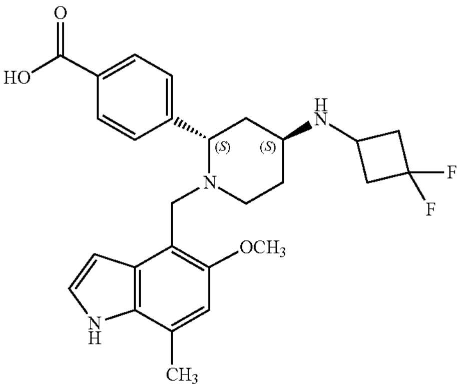 |
| 25 | 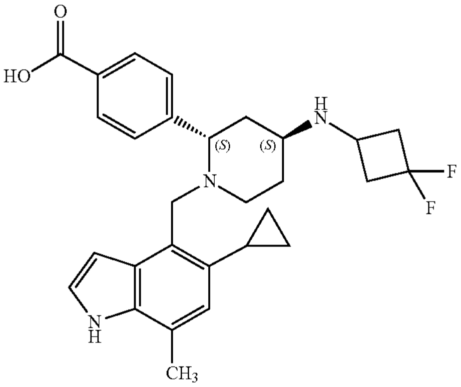 |
| 26 | 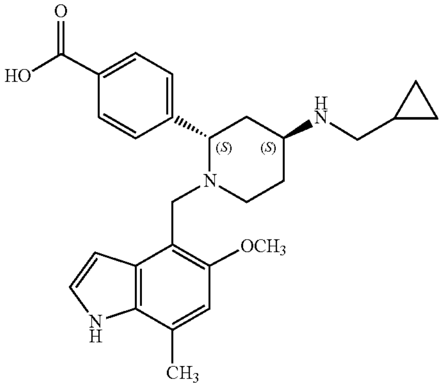 |

-continued
| Example | Structure |
|---|---|
| 27 | 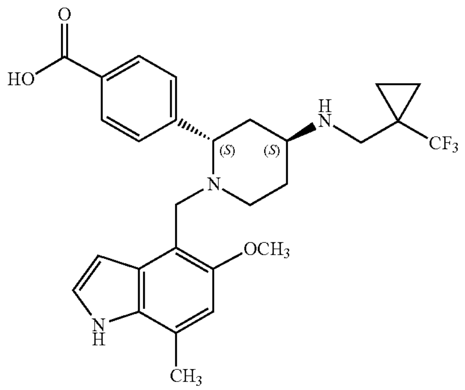 |
| 37 | 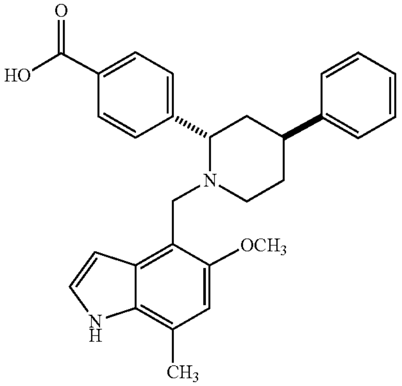 [SMILES: COc1cc(C)c2[nH]ccc2c1CN1CC[C@H](c2ccccc2)C[C@H]1c1ccc(C(=O)O)cc1] |
| 38 | 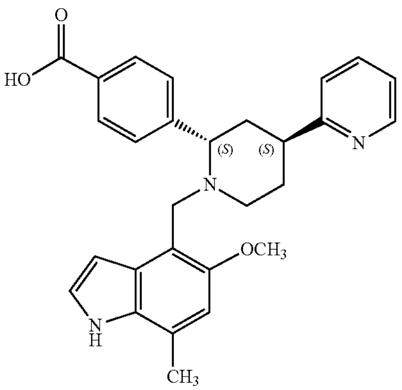 |

-continued
| Example | Structure |
|---|---|
| 39 | 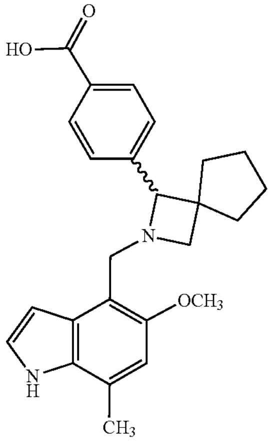 [SMILES: COc1cc(C)c2[nH]ccc2c1CN1CC2(CCCC2)C1c1ccc(C(=O)O)cc1] |
| 40 | 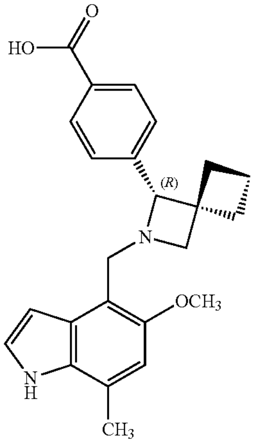 |
| 41 | 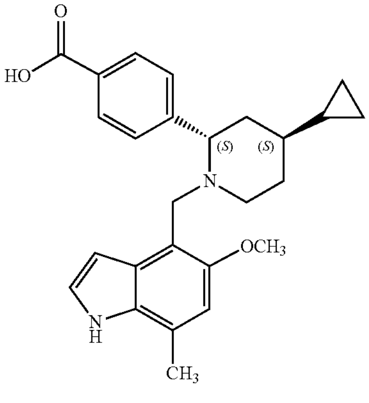 |

-continued
| Example | Structure |
|---|---|
| 43 | 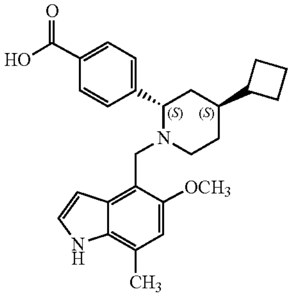 and 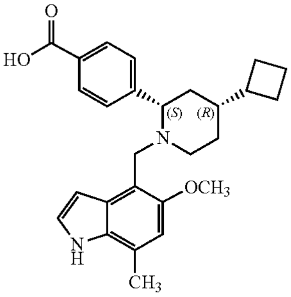 mixture of diastereomers |
| 44 | 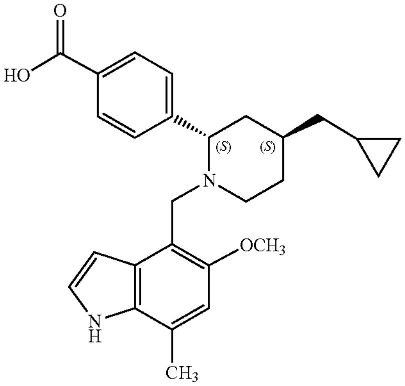 |
| 51 | 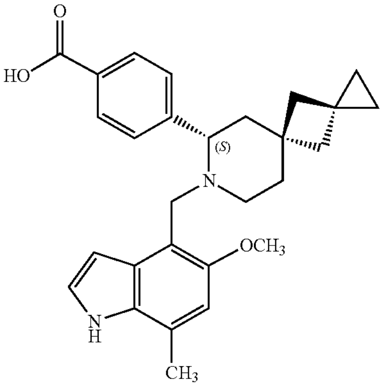 |
| 58 | 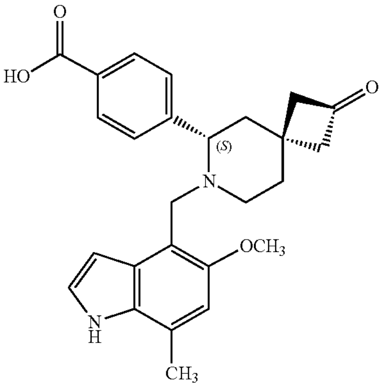 |

-continued
| Example | Structure |
| --- | --- |
| 59 | 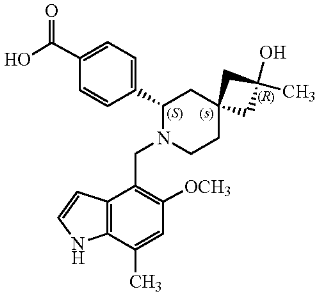 or 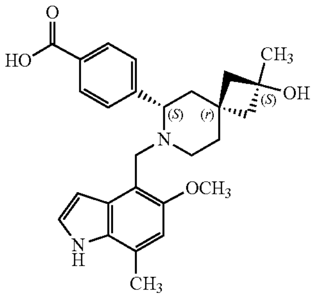 |
| 65 | 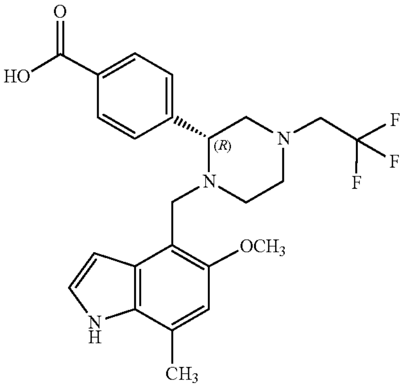 |
| 67 | 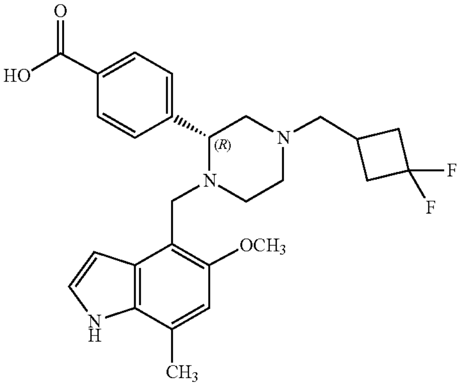 |
| 69 | 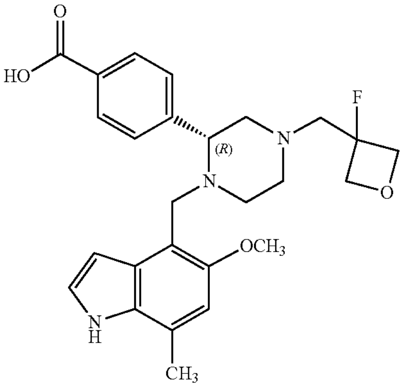 |

-continued
| Example | Structure |
| --- | --- |
| 71 | 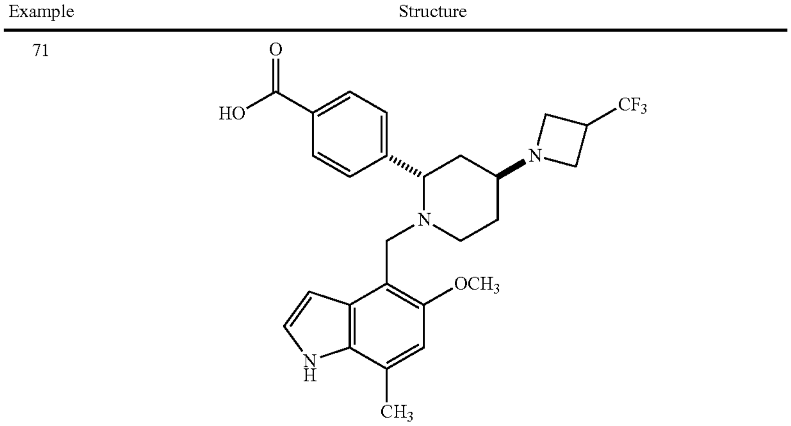 (+/-)-trans |
| 72 | 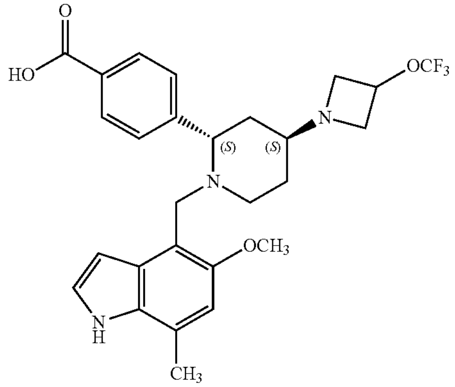 |
| 73 | 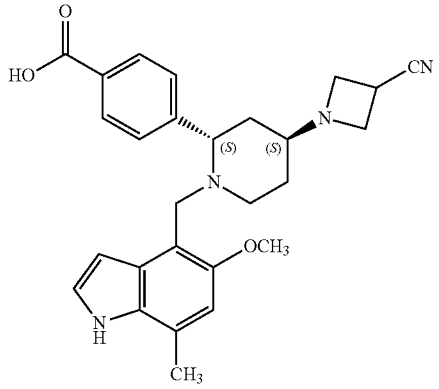 |
| 74 | 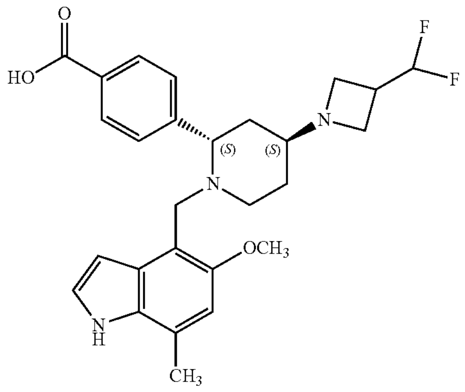 |

-continued
| Example | Structure |
|---|---|
| 75 | 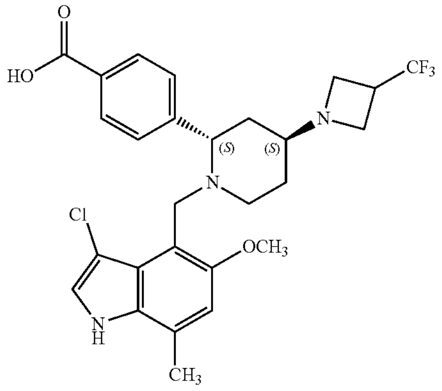 |
| 76 | 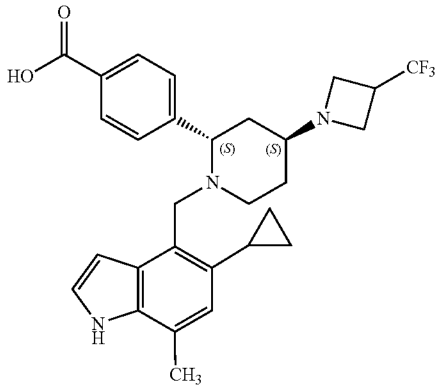 |
| 77 | 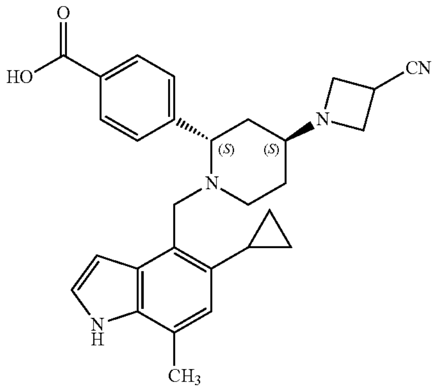 |
| 78 | 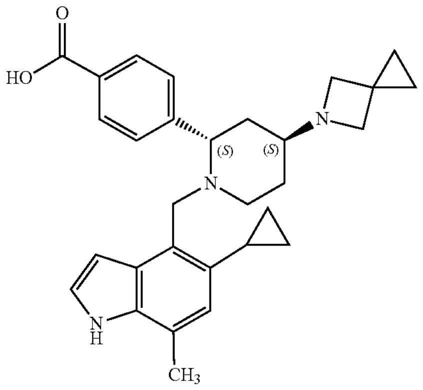 |

-continued
| Example | Structure |
| --- | --- |
| 79 | 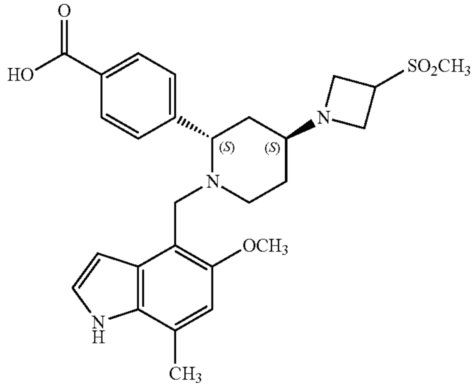 |
| 80 | 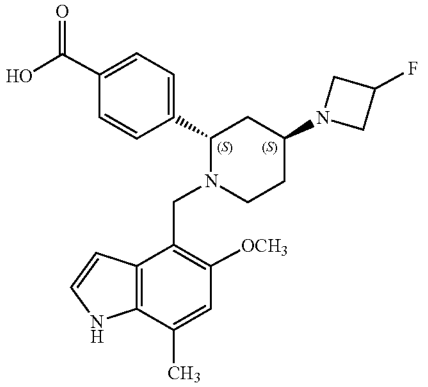 |
| 81 | 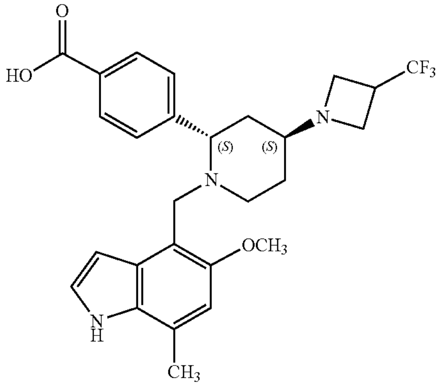 |

In certain embodiments, provided herein is a compound of Formula (I) wherein the compound is selected from the group consisting of the compounds in Table C below and pharmaceutically acceptable salts thereof:
| Example | Structure |
|---|---|
| 1 | 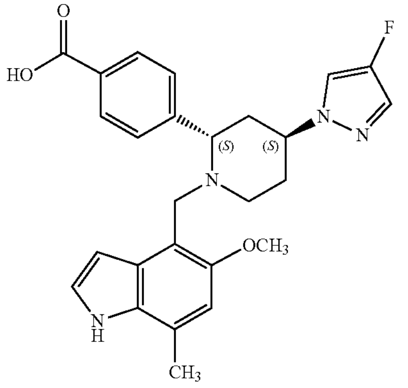 |
| 2 | 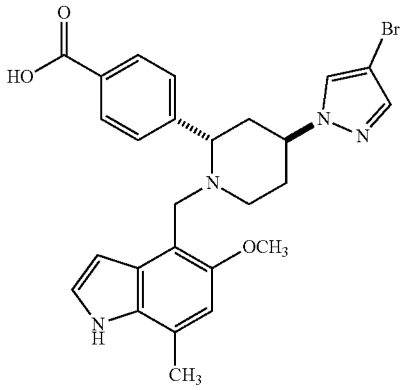 (+/-)-trans |
| 3 | 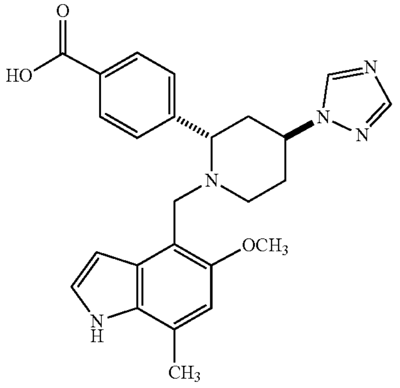 (+/-)-trans |
-continued
| Example | Structure |
|---|---|
| 4 | 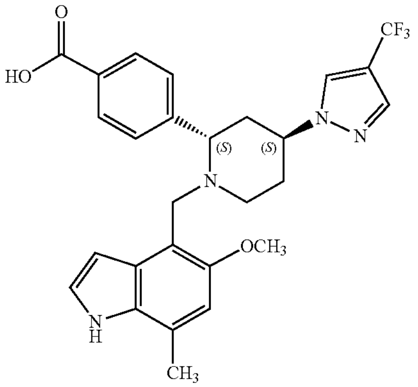 |
| 5 | 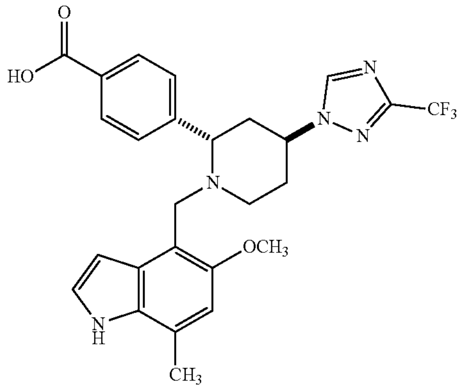 (+/-)-trans |
| 6 | 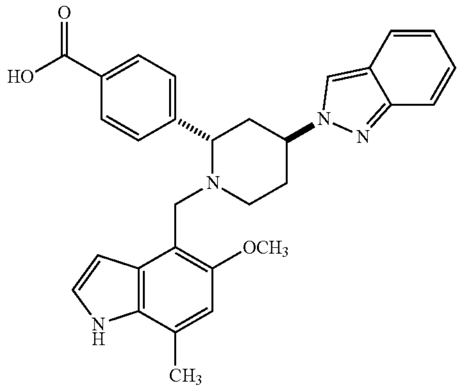 (+/-)-trans |

-continued
| Example | Structure |
|---|---|
| 7 | 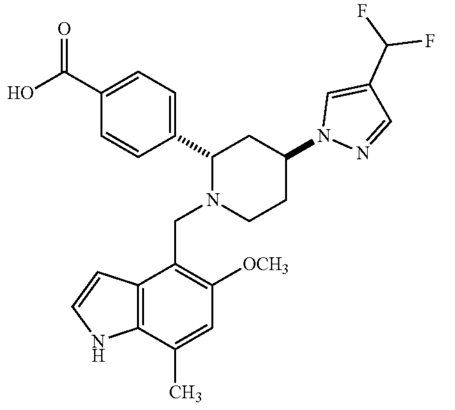<br>(+/-)-trans |
| 8 | 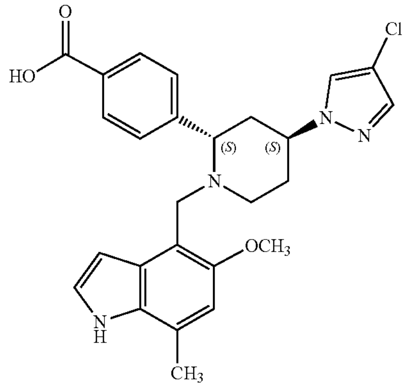 |
| 9 | 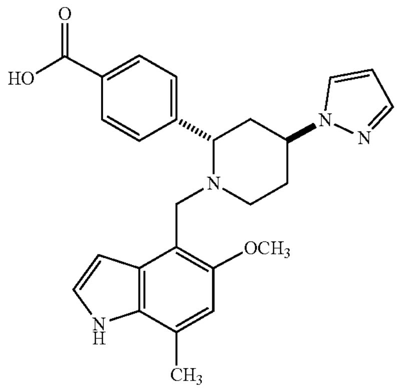 [SMILES: COc1cc(C)c2[nH]ccc2c1CN1CC[C@H](n2cccn2)C[C@H]1c1ccc(C(=O)O)cc1] |
| 10 | 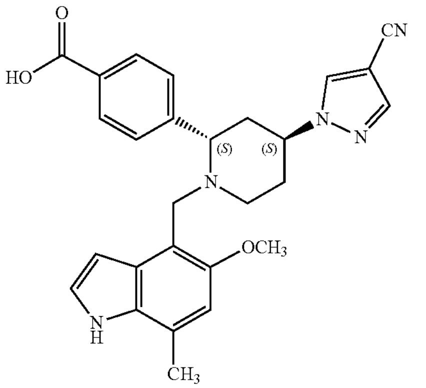 |
| 11 | 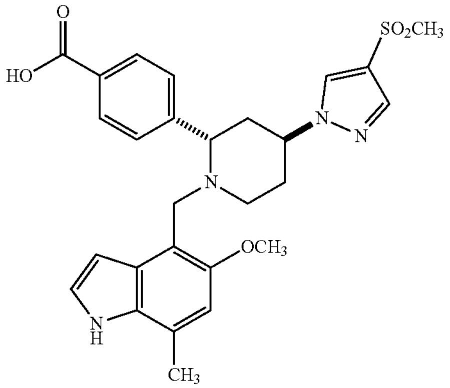<br>(+/-)-trans |
| 12 | 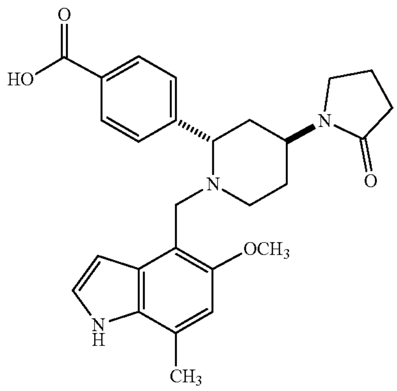<br>(+/-)-trans |

-continued
| Example | Structure |
|---|---|
| 13 | 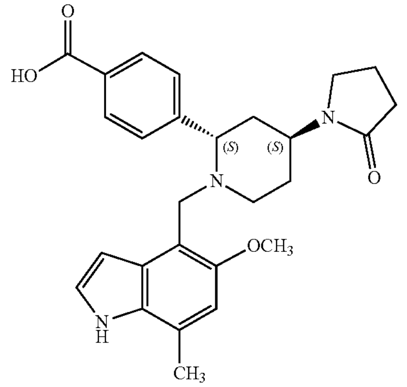 |
| 16 | 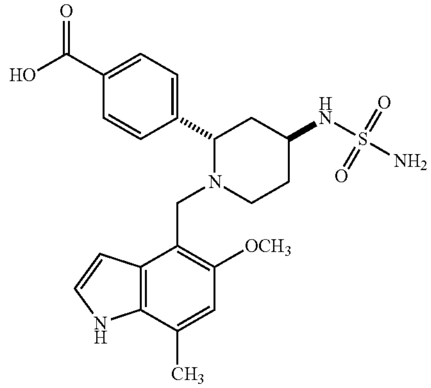 (+/-)-trans |
| 17 | 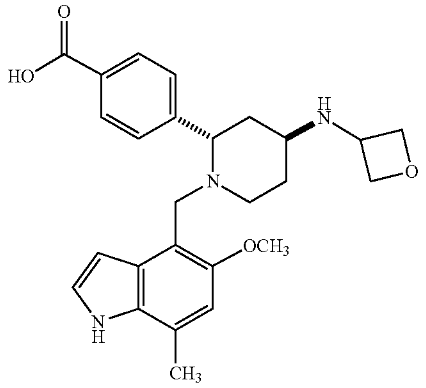 (+/-)-trans |
-continued
| Example | Structure |
|---|---|
| 18 | 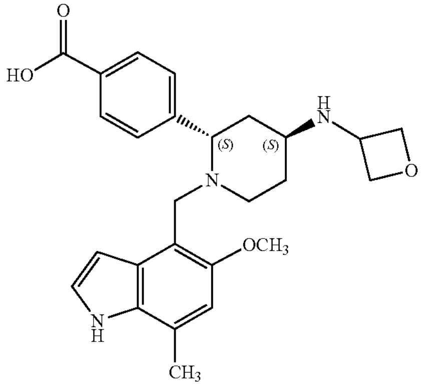 |
| 19 | 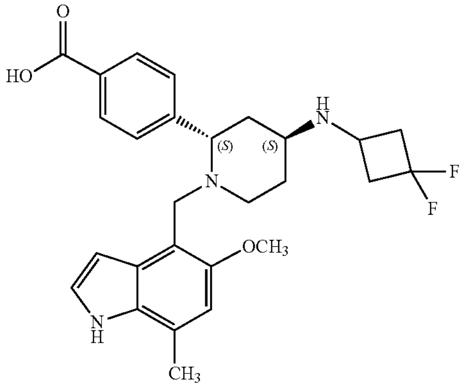 |
| 20 | 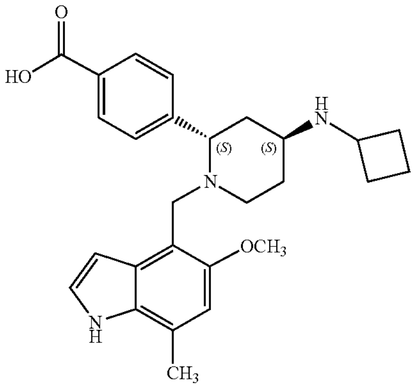 |
| 21 | 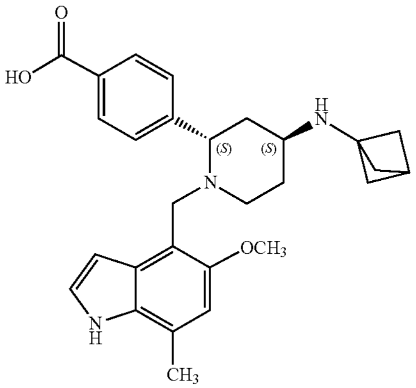 |

-continued
| Example | Structure |
|---|---|
| 24 | 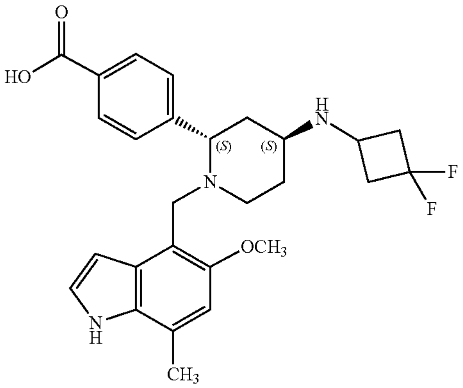 |
| 25 | 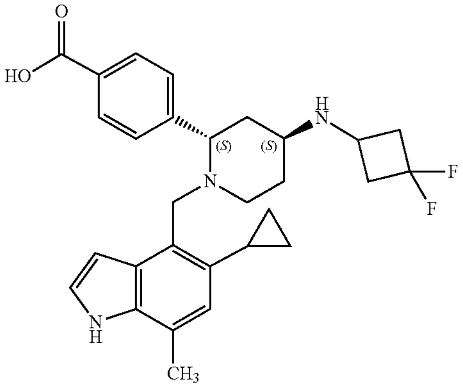 |
| 26 | 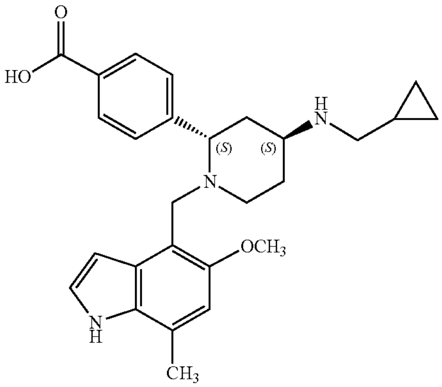 |
| 27 | 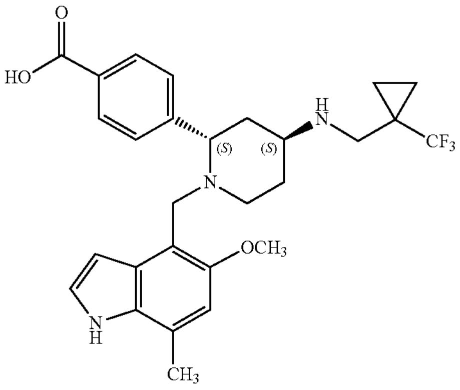 |
-continued
| Example | Structure |
|---|---|
| 37 | 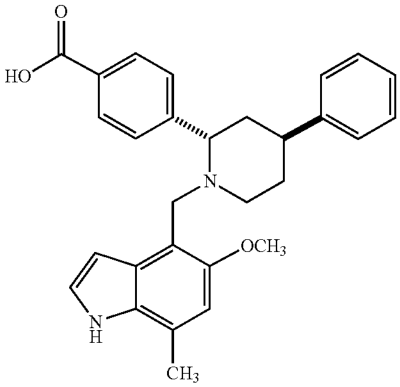 [SMILES: COc1cc(C)c2[nH]ccc2c1CN1CC[C@H](c2ccccc2)C[C@H]1c1ccc(C(=O)O)cc1] |
| 38 | 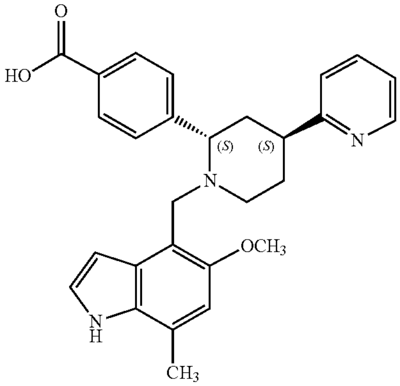 |
| 39 | 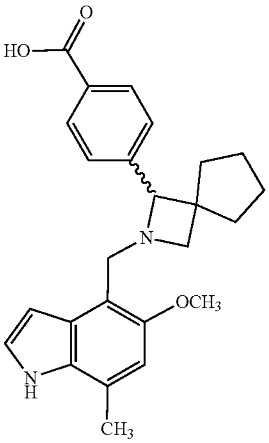 [SMILES: COc1cc(C)c2[nH]ccc2c1CN1CC2(CCCC2)C1c1ccc(C(=O)O)cc1] |

-continued
| Example | Structure |
|---|---|
| 40 | 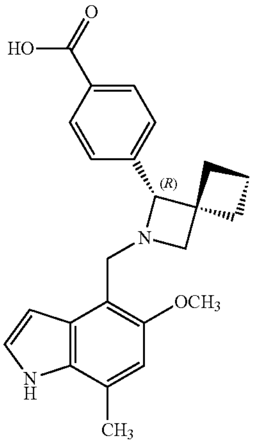 |
| 51 | 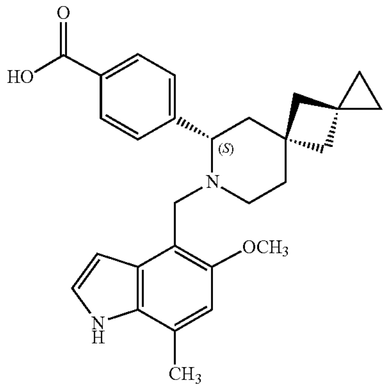 |
| 65 | 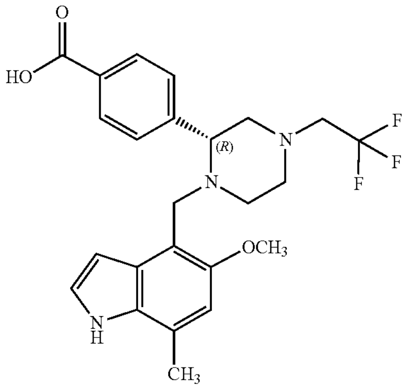 |
-continued
| Example | Structure |
|---|---|
| 67 | 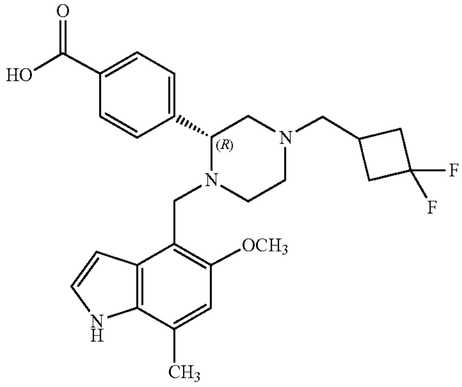 |
| 69 | 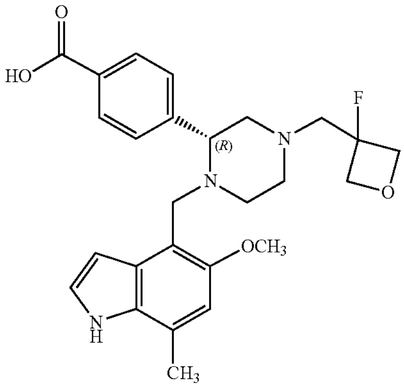 |
| 71 | 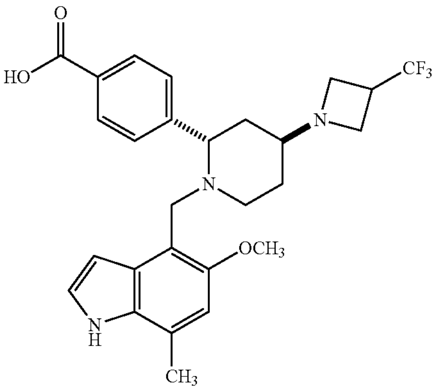 (+/-)-trans |
| 72 | 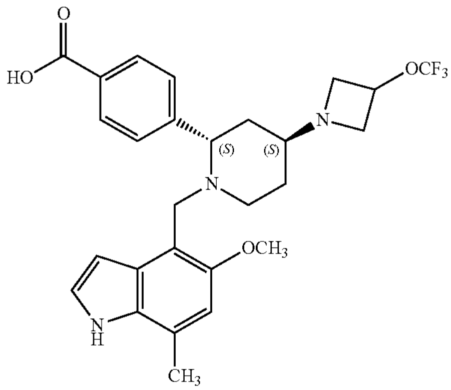 |

-continued
| Example | Structure |
|---|---|
| 73 | 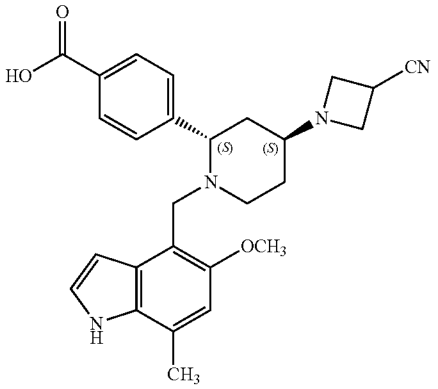 |
| 74 | 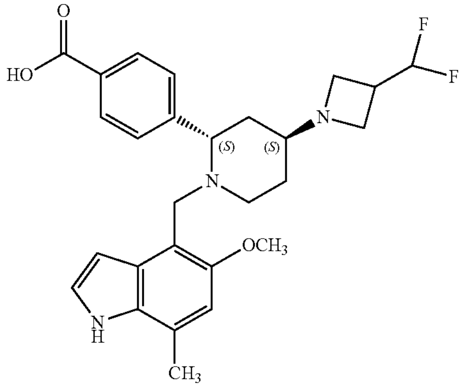 |
| 75 | 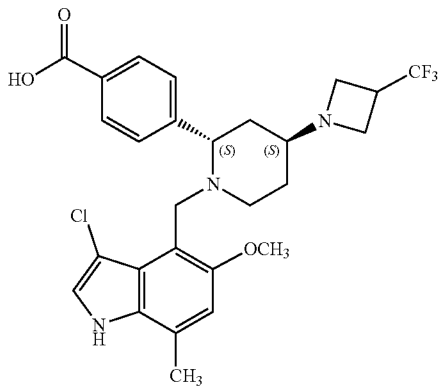 |
| 76 | 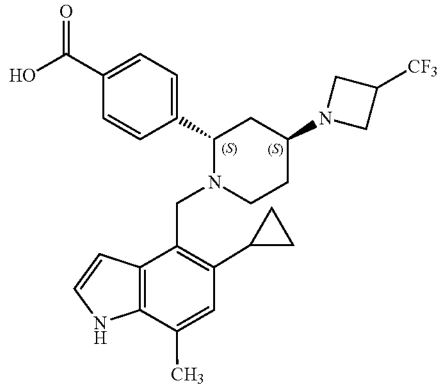 |
-continued
| Example | Structure |
|---|---|
| 77 | 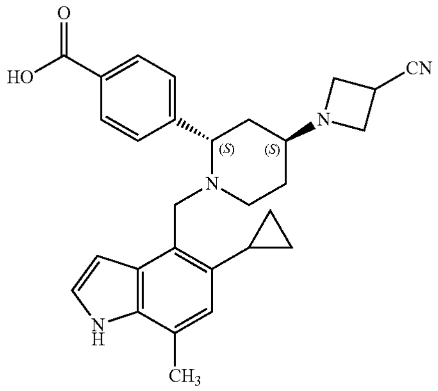 |
| 78 | 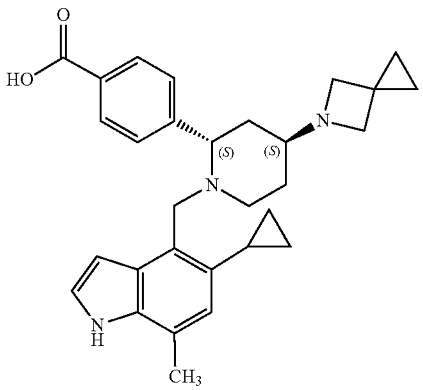 |
| 79 | 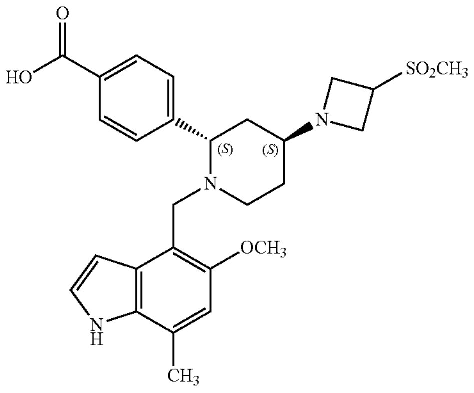 |
| 80 | 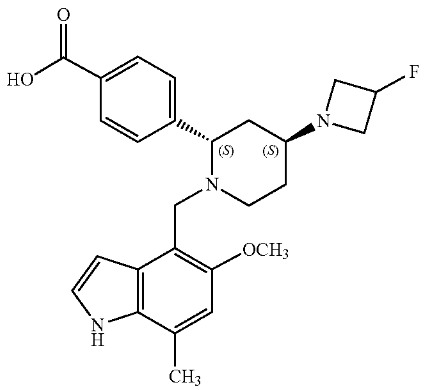 |

-continued
| Example | Structure |
|---|---|
| 81 | 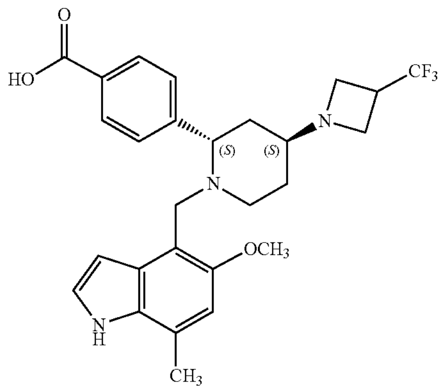 |
In certain embodiments, provided herein is a compound of Formula (I) wherein the compound is selected from the group consisting of the compounds in Table D below and pharmaceutically acceptable salts thereof:
| Example | Structure |
|---|---|
| 1 | 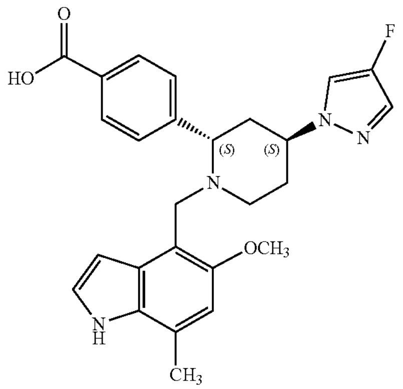 |
| 2 | 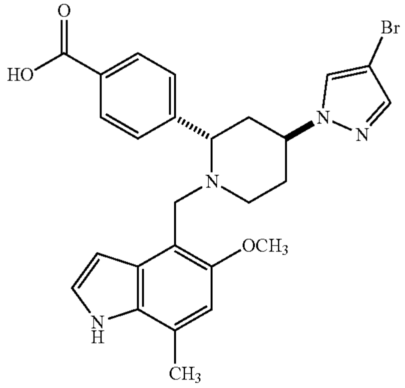 (+/-)-trans |
-continued
| Example | Structure |
|---|---|
| 3 | 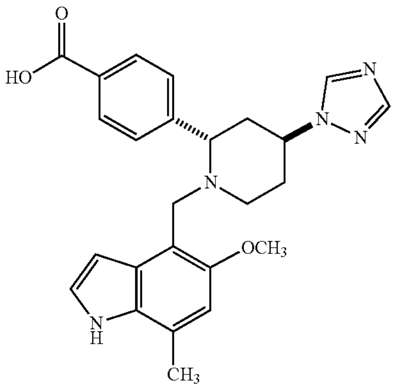 [SMILES: COc1cc(C)c2[nH]ccc2c1CN1CC[C@H](n2cccn2)C[C@H]1c1ccc(C(=O)O)cc1] (+/-)-trans |
| 4 | 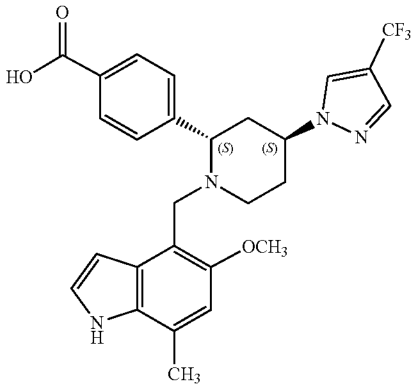 |
| 5 | 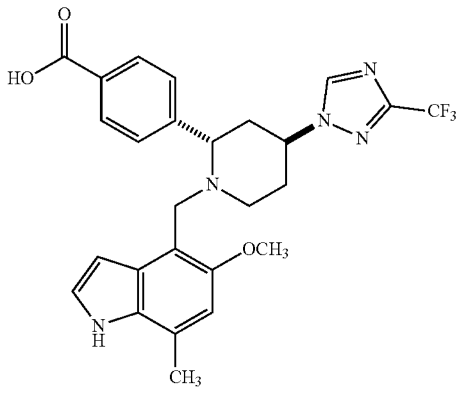 (+/-)-trans |

-continued
| Example | Structure |
|---|---|
| 6 | 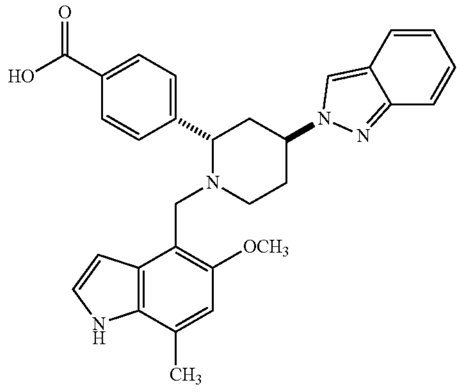 (+/-)-trans |
| 7 | 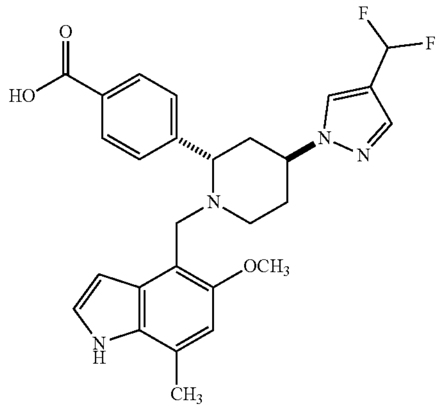 (+/-)-trans |
| 8 | 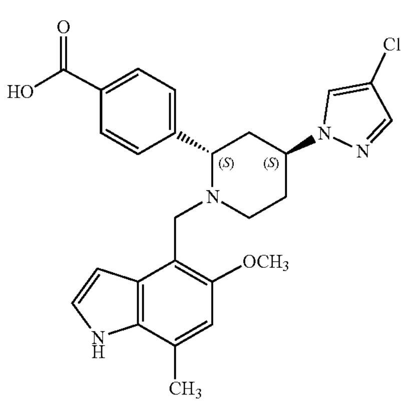 |
-continued
| Example | Structure |
|---|---|
| 9 | 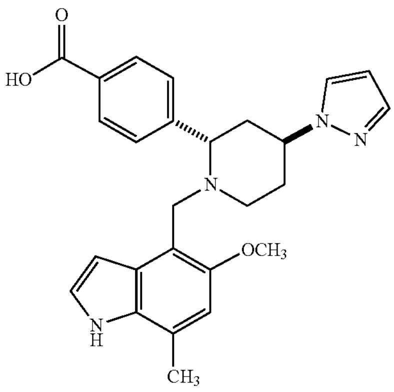 |
| 10 | 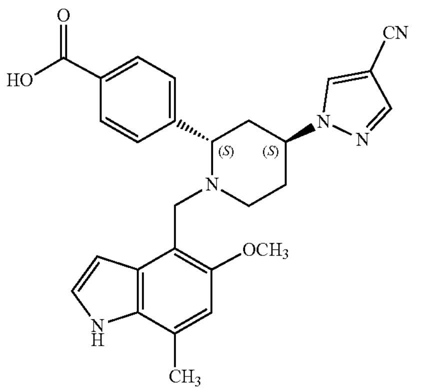 |
| 11 | 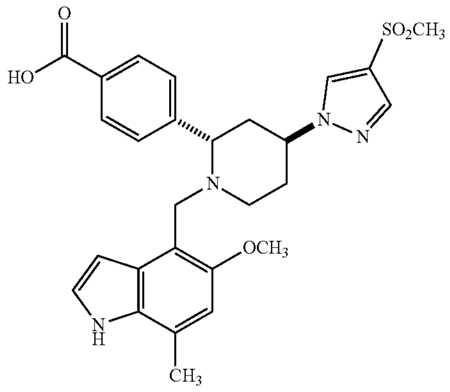 (+/-)-trans |

-continued
| Example | Structure |
|---|---|
| 12 | 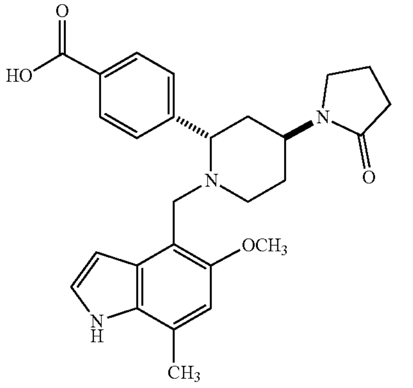 (+/-)-trans |
| 13 | 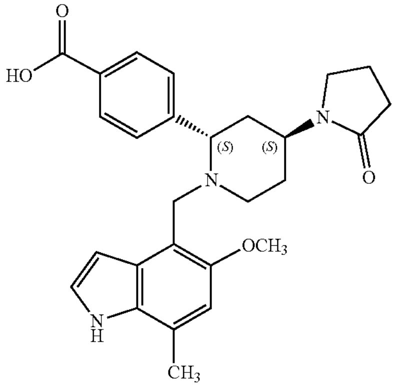 |
| 16 | 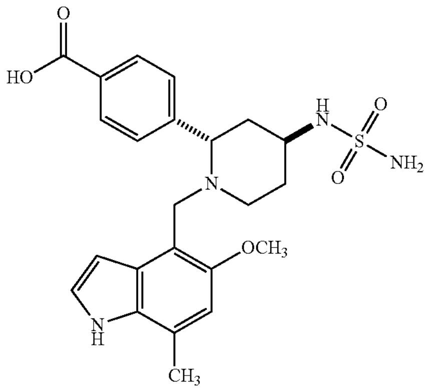 (+/-)-trans |
-continued
| Example | Structure |
|---|---|
| 17 | 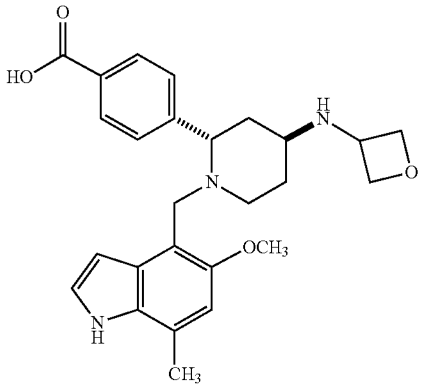 (+/-)-trans |
| 18 | 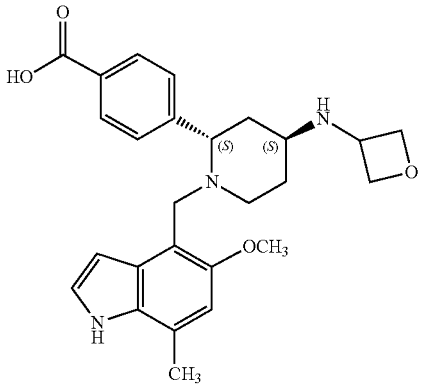 |
| 19 | 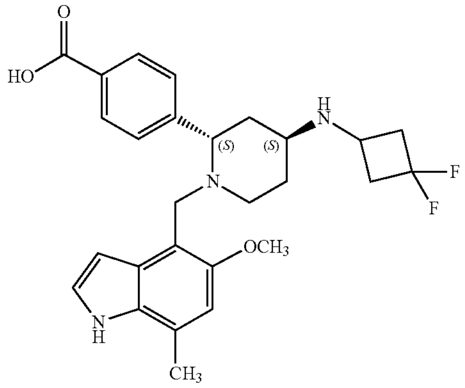 |
| 37 | 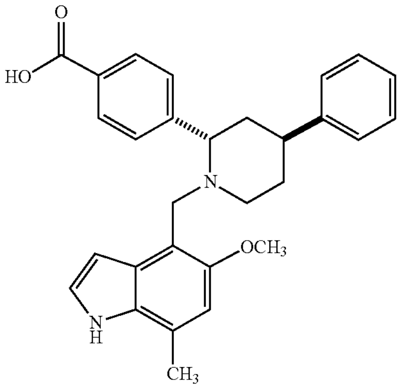 [SMILES: COc1cc(C)c2[nH]ccc2c1CN1CC[C@H](c2ccccc2)C[C@H]1c1ccc(C(=O)O)cc1] |

-continued
| Example | Structure |
|---|---|
| 38 | 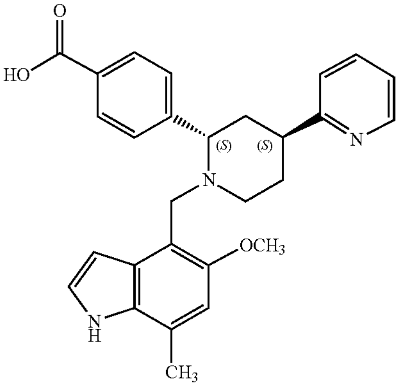 |
| 39 | 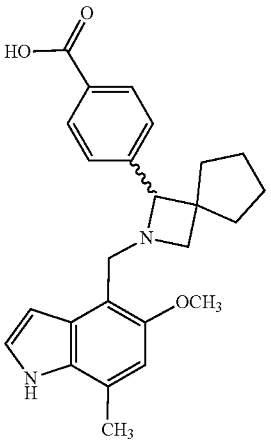 [SMILES: COc1cc(C)c2[nH]ccc2c1CN1CC2(CCCC2)C1c1ccc(C(=O)O)cc1] |
| 40 | 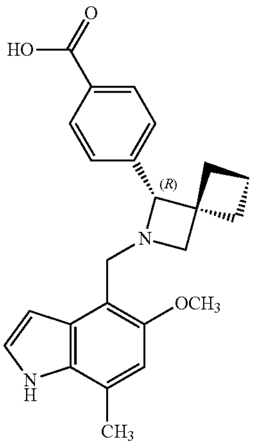 |
-continued
| Example | Structure |
|---|---|
| 51 | 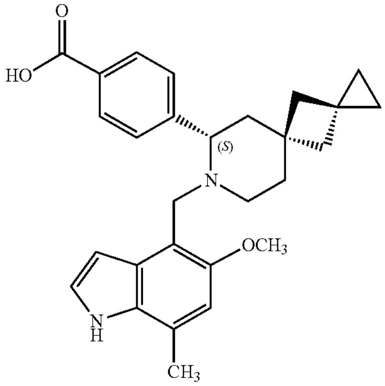 |
| 67 | 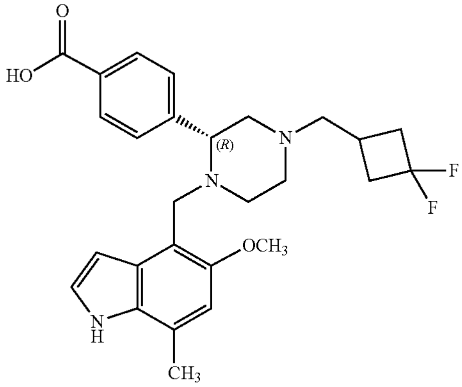 |
| 69 | 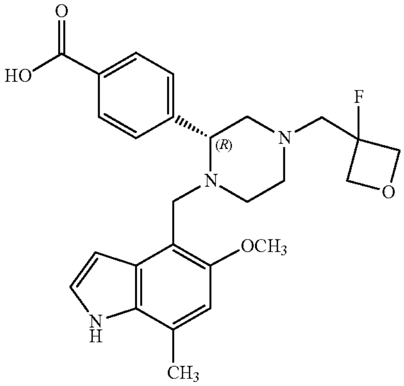 |
| 71 | 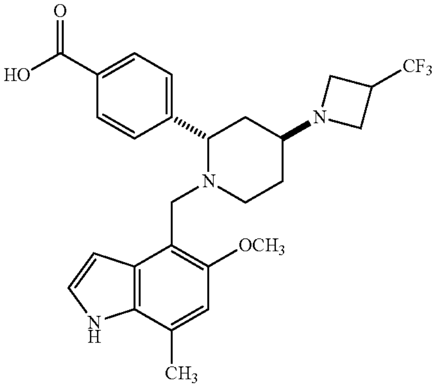<br>(+/-)-trans |

-continued
| Example | Structure |
|---|---|
| 72 | 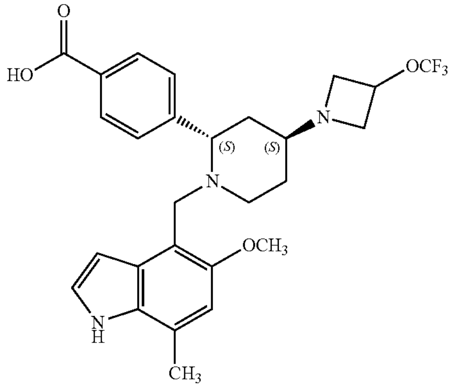 |
| 73 | 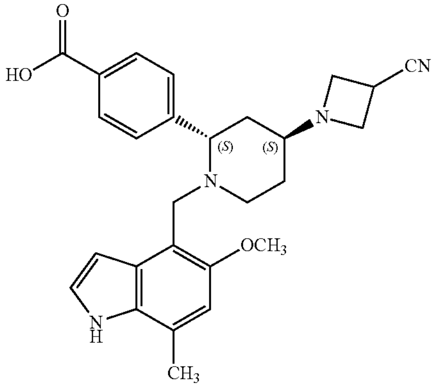 |
| 74 | 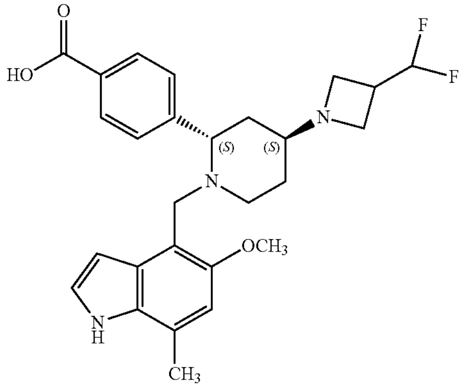 |
| 75 | 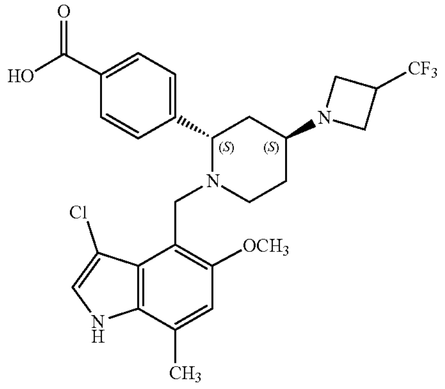 |
-continued
| Example | Structure |
|---|---|
| 76 | 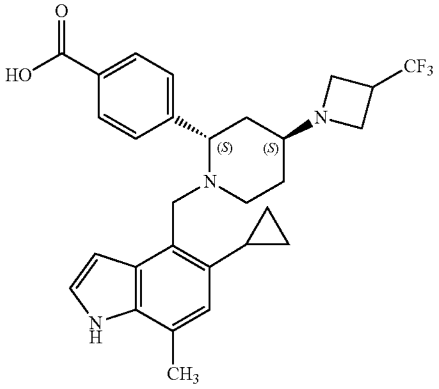 |
| 77 | 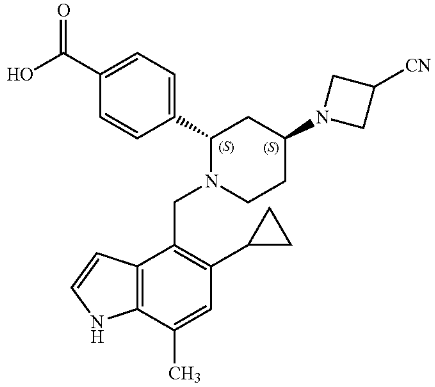 |
| 78 | 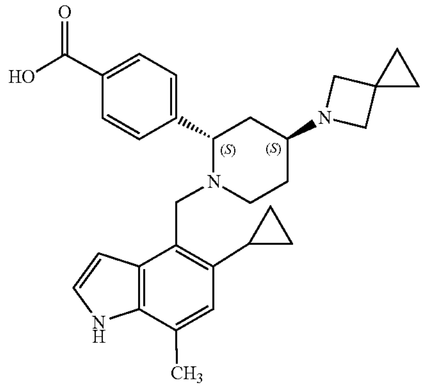 |
| 79 | 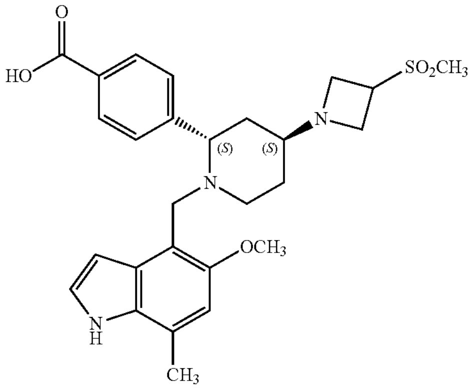 |

-continued

| Example | Structure |
|---|---|
| 80 | 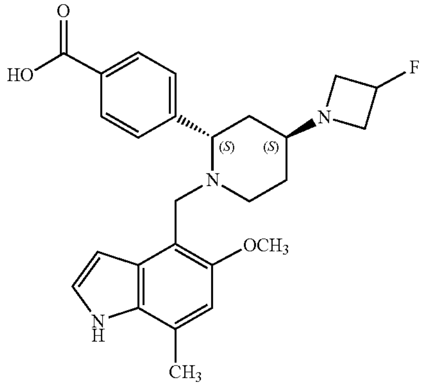 |
| 81 | 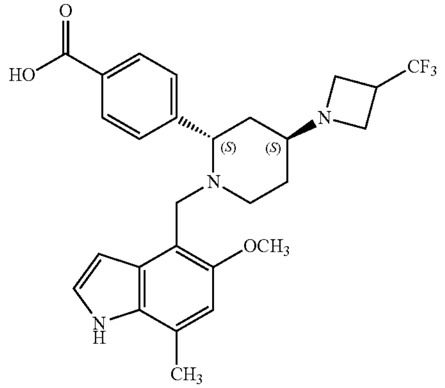 |

In some embodiments, the compound of Formula (I) is not a compound selected from the following list of compounds:
4-(7-((5-methoxy-7-methyl-1H-indol-4-yl)methyl)-2-oxa-7-azaspiro[3.5]nonan-6-yl)benzoic acid;
4-(7-((5-methoxy-7-methyl-1H-indol-4-yl)methyl)-1-oxa-7-azaspiro[3.5]nonan-6-yl)benzoic acid;
4-(8-((5-methoxy-7-methyl-1H-indol-4-yl)methyl)-1-oxa-8-azaspiro[4.5]decan-7-yl)benzoic acid;
4-(9-((5-methoxy-7-methyl-1H-indol-4-yl)methyl)-1-oxa-9-azaspiro[5.5]undecan-8-yl)benzoic acid;
4-(1,1-difluoro-6-((5-methoxy-7-methyl-1H-indol-4-yl)methyl)-6-azaspiro[2.5]octan-5-yl)benzoic acid;
4-(1-methoxy-6-((5-methoxy-7-methyl-1H-indol-4-yl)methyl)-6-azaspiro[2.5]octan-5-yl)benzoic acid;
4-(1,1-difluoro-7-((5-methoxy-7-methyl-1H-indol-4-yl)methyl)-7-azaspiro[3.5]nonan-6-yl)benzoic acid;
4-(2,2-difluoro-7-((5-methoxy-7-methyl-1H-indol-4-yl)methyl)-7-azaspiro[3.5]nonan-6-yl)benzoic acid;
4-(1-methoxy-7-((5-methoxy-7-methyl-1H-indol-4-yl)methyl)-7-azaspiro[3.5]nonan-6-yl)benzoic acid;
4-(2-methoxy-7-((5-methoxy-7-methyl-1H-indol-4-yl)methyl)-7-azaspiro[3.5]nonan-6-yl)benzoic acid;
4-(2-ethoxy-7-((5-methoxy-7-methyl-1H-indol-4-yl)methyl)-7-azaspiro[3.5]nonan-6-yl)benzoic acid;
4-(1-((5-methoxy-7-methyl-1H-indol-4-yl)methyl)-4-(trifluoromethyl)piperidin-2-yl)benzoic acid;
4-(4-(difluoromethyl)-1-((5-methoxy-7-methyl-1H-indol-4-yl)methyl)piperidin-2-yl)benzoic acid;
4-(4-fluoro-1-((5-methoxy-7-methyl-1H-indol-4-yl)methyl)-4-methylpiperidin-2-yl)benzoic acid;
4-(4-ethyl-4-fluoro-1-((5-methoxy-7-methyl-1H-indol-4-yl)methyl)piperidin-2-yl)benzoic acid;

4-(4-fluoro-1-((5-methoxy-7-methyl-1H-indol-4-yl)methyl)-4-propylpiperidin-2-yl)benzoic acid;
4-((1R,3S,5S)-3-ethoxy-8-((5-methoxy-7-methyl-1H-indol-4-yl)methyl)-8-azabicyclo[3.2.1]octan-1-yl)benzoic acid;
4-((2R,8R)-8-ethoxy-3-((5-methoxy-7-methyl-1H-indol-4-yl)methyl)-3-azabicyclo[3.2.1]octan-2-yl)benzoic acid;
4-((1R,4R,5R)-5-ethoxy-2-((5-methoxy-7-methyl-1H-indol-4-yl)methyl)-2-azabicyclo[2.2.2]octan-1-yl)benzoic acid;
4-((3R,5R)-5-ethoxy-2-((5-methoxy-7-methyl-1H-indol-4-yl)methyl)-2-azabicyclo[2.2.2]octan-3-yl)benzoic acid;
4-((2R,4R)-4-cyclopropoxy-1-((5-methoxy-7-methyl-1H-indol-4-yl)methyl)piperidin-2-yl)benzoic acid;
4-((2R,4R)-4-cyclobutoxy-1-((5-methoxy-7-methyl-1H-indol-4-yl)methyl)piperidin-2-yl)benzoic acid;
4-((2R,4R)-4-(cyclopentyloxy)-1-((5-methoxy-7-methyl-1H-indol-4-yl)methyl)piperidin-2-yl)benzoic acid;
4-((2R,4R)-4-(cyclopropylmethoxy)-1-((5-methoxy-7-methyl-1H-indol-4-yl)methyl)piperidin-2-yl)benzoic acid;
4-((2R,4R)-4-(cyclobutylmethoxy)-1-((5-methoxy-7-methyl-1H-indol-4-yl)methyl)piperidin-2-yl)benzoic acid;
4-((2R,4R)-4-(cyclopentylmethoxy)-1-((5-methoxy-7-methyl-1H-indol-4-yl)methyl)piperidin-2-yl)benzoic acid;
4-((2R,4R)-4-(cyclohexylmethoxy)-1-((5-methoxy-7-methyl-1H-indol-4-yl)methyl)piperidin-2-yl)benzoic acid;
4-((2R,4R)-1-((5-methoxy-7-methyl-1H-indol-4-yl)methyl)-4-(oxetan-3-ylmethoxy)piperidin-2-yl)benzoic acid;
4-((2R,4R)-1-((5-methoxy-7-methyl-1H-indol-4-yl)methyl)-4-((tetrahydrofuran-3-yl)methoxy)piperidin-2-yl)benzoic acid;
4-((2R,4R)-1-((5-methoxy-7-methyl-1H-indol-4-yl)methyl)-4-(oxetan-2-ylmethoxy)piperidin-2-yl)benzoic acid;
4-((2R,4R)-1-((5-methoxy-7-methyl-1H-indol-4-yl)methyl)-4-((tetrahydrofuran-2-yl)methoxy)piperidin-2-yl)benzoic acid;
4-((2R,4R)-1-((5-methoxy-7-methyl-1H-indol-4-yl)methyl)-4-((tetrahydro-2H-pyran-2-yl)methoxy)piperidin-2-yl)benzoic acid;
4-((2R,4R)-1-((5-methoxy-7-methyl-1H-indol-4-yl)methyl)-4-((tetrahydro-2H-pyran-3-yl)methoxy)piperidin-2-yl)benzoic acid;
4-((2R,4R)-1-((5-methoxy-7-methyl-1H-indol-4-yl)methyl)-4-((tetrahydro-2H-pyran-4-yl)methoxy)piperidin-2-yl)benzoic acid;
4-((2R,4R)-1-((5-methoxy-7-methyl-1H-indol-4-yl)methyl)-4-(trifluoromethoxy)piperidin-2-yl)benzoic acid;
4-((2R,4R)-4-(difluoromethoxy)-1-((5-methoxy-7-methyl-1H-indol-4-yl)methyl)piperidin-2-yl)benzoic acid;
4-(3-((5-methoxy-7-methyl-1H-indol-4-yl)methyl)-3-azabicyclo[4.1.0]heptan-2-yl)benzoic acid;
4-(3-((5-methoxy-7-methyl-1H-indol-4-yl)methyl)-3-azabicyclo[4.1.0]heptan-4-yl)benzoic acid;
4-(6-ethoxy-3-((5-methoxy-7-methyl-1H-indol-4-yl)methyl)-3-azabicyclo[4.1.0]heptan-2-yl)benzoic acid;
4-(6-ethoxy-3-((5-methoxy-7-methyl-1H-indol-4-yl)methyl)-3-azabicyclo[4.1.0]heptan-4-yl)benzoic acid;
4-((2R,4R)-4-(2,2-difluorocyclopropoxy)-1-((5-methoxy-7-methyl-1H-indol-4-yl)methyl)piperidin-2-yl)benzoic acid;

4-((2R,4R)-4-(2-fluoro-2-methylcyclopropoxy)-1-((5-methoxy-7-methyl-1H-indol-4-yl)methyl)piperidin-2-yl)benzoic acid;
4-((2R,4R)-4-(2,2-dimethylcyclopropoxy)-1-((5-methoxy-7-methyl-1H-indol-4-yl)methyl)piperidin-2-yl)benzoic acid;
4-((2R,4R)-4-(3,3-difluorocyclobutoxy)-1-((5-methoxy-7-methyl-1H-indol-4-yl)methyl)piperidin-2-yl)benzoic acid;
4-(4-acetamido-1-((5-methoxy-7-methyl-1H-indol-4-yl)methyl)piperidin-2-yl)benzoic acid;
4-((2R,4R)-4-((2,2-difluorocyclopropyl)methoxy)-1-((5-methoxy-7-methyl-1H-indol-4-yl)methyl)piperidin-2-yl)benzoic acid;
4-((2R,4R)-4-((2-fluoro-2-methylcyclopropyl)methoxy)-1-((5-methoxy-7-methyl-1H-indol-4-yl)methyl)piperidin-2-yl)benzoic acid;
4-((2R,4R)-1-((5-methoxy-7-methyl-1H-indol-4-yl)methyl)-4-((2-methylcyclopropyl)methoxy)piperidin-2-yl)benzoic acid;
4-((2R,4R)-4-((2,2-dimethylcyclopropyl)methoxy)-1-((5-methoxy-7-methyl-1H-indol-4-yl)methyl)piperidin-2-yl)benzoic acid;
4-((2R,4R)-1-((5-methoxy-7-methyl-1H-indol-4-yl)methyl)-4-(1-methylcyclopropoxy)piperidin-2-yl)benzoic acid;
4-(5-((5-methoxy-7-methyl-1H-indol-4-yl)methyl)octahydrofuro[3,2-c]pyridin-4-yl)benzoic acid;
4-((6S)-5-((5-methoxy-7-methyl-1H-indol-4-yl)methyl)octahydrofuro[3,2-c]pyridin-6-yl)benzoic acid;
4-(6-(((5S)-5-methoxy-7-methyloctahydro-1H-indol-4-yl)methyl)-2H-6l4-pyrano[3,2-c]pyridin-5-yl)benzoic acid;
4-(6-(((7S)-5-methoxy-7-methyloctahydro-1H-indol-4-yl)methyl)-2H-6l4-pyrano[3,2-c]pyridin-7-yl)benzoic acid;
4-((1R)-2-((5-methoxy-7-methyl-1H-indol-4-yl)methyl)-1,2,3,4-tetrahydro-2l4-isoquinolin-1-yl)benzoic acid;
(S)-4-(5-((5-methoxy-7-methyl-1H-indol-4-yl)methyl)-5-azaspiro[2.5]octan-4-yl)benzoic acid;
4-((2R,4R)-4-ethoxy-1-((6-fluoro-5-methoxy-7-methyl-1H-indol-4-yl)methyl)piperidin-2-yl)benzoic acid;
4-((2R,4R)-1-((6-chloro-5-methoxy-7-methyl-1H-indol-4-yl)methyl)-4-ethoxypiperidin-2-yl)benzoic acid;
4-((2R,4R)-4-ethoxy-1-((5-methoxy-6,7-dimethyl-1H-indol-4-yl)methyl)piperidin-2-yl)benzoic acid;
4-((2R,4R)-1-((7-cyclopropyl-5-methoxy-1H-indol-4-yl)methyl)-4-ethoxypiperidin-2-yl)benzoic acid;
4-((2R,4R)-1-((7-cyano-5-methoxy-1H-indol-4-yl)methyl)-4-ethoxypiperidin-2-yl)benzoic acid;
4-((2R,4R)-4-ethoxy-1-((5-methoxy-7-(trifluoromethyl)-1H-indol-4-yl)methyl)piperidin-2-yl)benzoic acid;
4-((2R,4R)-1-((7-(difluoromethyl)-5-methoxy-1H-indol-4-yl)methyl)-4-ethoxypiperidin-2-yl)benzoic acid;
rac-4-((2R,4S)-4-(cyclopropylmethoxy)-1-((5-methoxy-7-(methyl-d3)-1H-indol-4-yl)methyl)piperidin-2-yl)benzoic acid;
4-((2R,4R)-4-(cyclopropylmethoxy)-1-((3-fluoro-5-methoxy-7-methyl-1H-indol-4-yl)methyl)piperidin-2-yl)benzoic acid;
4-((2R,4R)-4-ethoxy-1-(4-methyl-3,7,8,9-tetrahydropyrano[3,2-e]indol-9-yl)piperidin-2-yl)benzoic acid;
4-((2R,4R)-4-ethoxy-1-(4-methyl-6,7,8,9-tetrahydro-3H-benzo[e]indol-9-yl)piperidin-2-yl)benzoic acid;
4-((2R,4R)-4-ethoxy-1-(5-methyl-1,6-dihydro-2H-furo[3,2-e]indol-1-yl)piperidin-2-yl)benzoic acid;
4-((2R,4R)-4-ethoxy-1-(4-methyl-3,6,7,8-tetrahydrocyclopenta[e]indol-8-yl)piperidin-2-yl)benzoic acid;
4-((2R,4R)-4-ethoxy-1-(4-methyl-3,7,8,9-tetrahydrothiopyrano[3,2-e]indol-9-yl)piperidin-2-yl)benzoic acid;
4-((2R,4R)-4-ethoxy-1-(4-methyl-6,6-dioxido-3,7,8,9-tetrahydrothiopyrano[3,2-e]indol-9-yl)piperidin-2-yl)benzoic acid;
4-((2R,4R)-4-ethoxy-1-(6-methoxy-8-methyl-1,3,4,5-tetrahydrobenzo[cd]indol-5-yl)piperidin-2-yl)benzoic acid;
4-((2R,4R)-4-ethoxy-1-(6-methoxy-8-methyl-4,5-dihydro-1H-pyrano[2,3,4-cd]indol-5-yl)piperidin-2-yl)benzoic acid;
4-((2R,4R)-4-(cyclopropylmethoxy)-1-(4-methyl-3,7,8,9-tetrahydropyrano[3,2-e]indol-9-yl)piperidin-2-yl)benzoic acid;
4-((2R,4R)-4-(cyclopropylmethoxy)-1-(4-methyl-6,7,8,9-tetrahydro-3H-benzo[e]indol-9-yl)piperidin-2-yl)benzoic acid;
4-((2R,4R)-4-(cyclopropylmethoxy)-1-(5-methyl-1,6-dihydro-2H-furo[3,2-e]indol-1-yl)piperidin-2-yl)benzoic acid;
4-((2R,4R)-4-(cyclopropylmethoxy)-1-(4-methyl-3,6,7,8-tetrahydrocyclopenta[e]indol-8-yl)piperidin-2-yl)benzoic acid;
4-((2R,4R)-4-(cyclopropylmethoxy)-1-(4-methyl-3,7,8,9-tetrahydrothiopyrano[3,2-e]indol-9-yl)piperidin-2-yl)benzoic acid;
4-((2R,4R)-4-(cyclopropylmethoxy)-1-(4-methyl-6,6-dioxido-3,7,8,9-tetrahydrothiopyrano[3,2-e]indol-9-yl)piperidin-2-yl)benzoic acid;
4-((2R,4R)-4-(cyclopropylmethoxy)-1-(6-methoxy-8-methyl-1,3,4,5-tetrahydrobenzo[cd]indol-5-yl)piperidin-2-yl)benzoic acid;
4-((2R,4R)-4-(cyclopropylmethoxy)-1-(6-methoxy-8-methyl-4,5-dihydro-1H-pyrano[2,3,4-cd]indol-5-yl)piperidin-2-yl)benzoic acid;
4-((2R,4R)-4-(cyclopropylmethoxy)-1-((5-methoxy-7-methyl-1H-indol-4-yl)methyl)piperidin-2-yl)-1-naphthoic acid;
5-((2R,4R)-4-(cyclopropylmethoxy)-1-((5-methoxy-7-methyl-1H-indol-4-yl)methyl)piperidin-2-yl)quinoline-8-carboxylic acid;
8-((2R,4R)-4-(cyclopropylmethoxy)-1-((5-methoxy-7-methyl-1H-indol-4-yl)methyl)piperidin-2-yl)quinoline-5-carboxylic acid;
8-((2R,4R)-4-(cyclopropylmethoxy)-1-((5-methoxy-7-methyl-1H-indol-4-yl)methyl)piperidin-2-yl)imidazo[1,2-a]pyridine-5-carboxylic acid;
5-((2R,4R)-4-(cyclopropylmethoxy)-1-((5-methoxy-7-methyl-1H-indol-4-yl)methyl)piperidin-2-yl)-6-oxo-1,6-dihydropyridine-2-carboxylic acid;
6-((2R,4R)-4-(cyclopropylmethoxy)-1-((5-methoxy-7-methyl-1H-indol-4-yl)methyl)piperidin-2-yl)-2-oxo-1,2-dihydropyridine-3-carboxylic acid;
4-((2R,4R)-4-(cyclopropylmethoxy)-1-((5-methoxy-7-methyl-1H-indol-4-yl)methyl)piperidin-2-yl)-5,6,7,8-tetrahydronaphthalene-1-carboxylic acid;
rac-7-((2R,4S)-4-(cyclopropylmethoxy)-1-((5-methoxy-7-methyl-1H-indol-4-yl)methyl)piperidin-2-yl)-2,3-dihydro-1H-indene-4-carboxylic acid;
7-((2R,4R)-4-(cyclopropylmethoxy)-1-((5-methoxy-7-methyl-1H-indol-4-yl)methyl)piperidin-2-yl)-2,3-dihydrobenzofuran-4-carboxylic acid;
(S)-3-(4-(cyclopropylmethoxy)-1-((5-methoxy-7-methyl-1H-indol-4-yl)methyl)-1,2,3,4-tetrahydroquinolin-7-yl)propanoic acid;
(S)-2-((4-(cyclopropylmethoxy)-1-((5-methoxy-7-methyl-1H-indol-4-yl)methyl)-1,2,3,4-tetrahydroquinolin-7-yl)oxy)acetic acid;

4-(9-((5-methoxy-7-(methyl-d3)-1H-indol-4-yl)methyl)-1-oxa-9-azaspiro[5.5]undecan-8-yl)benzoic acid;
4-(7-((5-methoxy-7-(methyl-d3)-1H-indol-4-yl)methyl)-1-oxa-7-azaspiro[3.5]nonan-6-yl)benzoic acid;
4-(8-((5-methoxy-7-(methyl-d3)-1H-indol-4-yl)methyl)-1-oxa-8-azaspiro[4.5]decan-7-yl)benzoic acid;
(4-(1-((5-methoxy-7-methyl-1H-indol-4-yl)methyl)piperidin-2-yl)phenyl)phosphonic acid;
rac-4-((2R,4S)-4-ethoxy-1-((5-methoxy-7-(methyl-d3)-1H-indol-4-yl)methyl)piperidin-2-yl)benzoic acid;
4-((2R,4R)-4-ethoxy-1-((5-ethyl-7-methyl-1H-indol-4-yl)methyl)piperidin-2-yl)benzoic acid;
N-hydroxy-4-(1-((5-methoxy-7-methyl-1H-indol-4-yl)methyl)piperidin-2-yl)benzamide;
(4-(1-((5-methoxy-7-methyl-1H-indol-4-yl)methyl)piperidin-2-yl)phenyl)boronic acid;
imino(4-(1-((5-methoxy-7-methyl-1H-indol-4-yl)methyl)piperidin-2-yl)phenyl)(methyl)-16-sulfanone;
(S)-4-(4,4-difluoro-1-((5-methoxy-7-methyl-1H-indol-4-yl)methyl)piperidin-2-yl)benzoic acid;
4-(5-ethoxy-2-((5-methoxy-7-methyl-1H-indol-4-yl)methyl)-2-azabicyclo[4.1.0]heptan-1-yl)benzoic acid;
4-(5-ethoxy-2-((5-methoxy-7-methyl-1H-indol-4-yl)methyl)-2-azabicyclo[4.1.0]heptan-3-yl)benzoic acid;
4-(1-ethoxy-6-((5-methoxy-7-methyl-1H-indol-4-yl)methyl)-6-azaspiro[2.5]octan-5-yl)benzoic acid;
4-(1-ethoxy-7-((5-methoxy-7-methyl-1H-indol-4-yl)methyl)-7-azaspiro[3.5]nonan-6-yl)benzoic acid;
methyl 4-(4-(ethylamino)-1-((5-methoxy-7-methyl-1H-indol-4-yl)methyl)piperidin-2-yl)benzoate;
7-(1-((5-methoxy-7-methyl-1H-indol-4-yl)methyl)piperidin-2-yl)-2,3-dihydrobenzofuran-4-carboxylic acid;
8-(1-((5-methoxy-7-methyl-1H-indol-4-yl)methyl)piperidin-2-yl)imidazo[1,2-a]pyridine-5-carboxylic acid;
4-((2S)-3-((5-methoxy-7-methyl-1H-indol-4-yl)methyl)-3-azabicyclo[4.1.0]heptan-2-yl)benzoic acid;
4-(((2R,4R)-2-(4-(2H-tetrazol-5-yl)phenyl)-4-(cyclopropylmethoxy)piperidin-1-yl)methyl)-5-methoxy-7-methyl-1H-indole;
5-(1-((5-methoxy-7-methyl-1H-indol-4-yl)methyl)piperidin-2-yl)-6-oxo-1,6-dihydropyridine-2-carboxylic acid;
4-(8-((5-methoxy-7-methyl-1H-indol-4-yl)methyl)-2,2-dimethyl-1-oxa-8-azaspiro[4.5]decan-7-yl)benzoic acid;
4-((2S)-4-(cyclopropylmethoxy)-1-((5-methoxy-7-methyl-1H-indol-4-yl)methyl)piperidin-2-yl)-2-fluorobenzoic acid; and
4-[4-(ethylamino)-1-[(5-methoxy-7-methyl-1H-indol-4-yl)methyl]-2-piperidinyl]-2-fluoro-benzoic acid; or stereoisomers and pharmaceutically acceptable salts thereof.

In some embodiments, the compound of Formula (I) is not a compound disclosed in PCT Publication No. WO2022/028527, which is incorporated by reference herein for purposes of excluding the compounds disclosed therein.

Any combination of the groups described above for the various variables is contemplated herein. Throughout the specification, groups and substituents thereof are chosen by one skilled in the field to provide stable moieties and compounds.

The compounds of the present disclosure include the compounds themselves, as well as their salts. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to acid or base addition salts, including but not limited to, base addition salts formed by the compound of Formula (I) having an acidic moiety with pharmaceutically acceptable cations, for example, sodium, potassium, magnesium, calcium, aluminum, lithium, and ammonium. Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature.

Examples of isotopes which can be incorporated into a compound according to the present disclosure are those of hydrogen, carbon, nitrogen, oxygen, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{18}F$, $^{36}Cl$, $^{82}Br$, $^{123}I$, $^{124}I$, $^{125}I$, $^{129}I$ and $^{131}I$. Particular isotopic variants of a compound according to the present disclosure, especially those in which one or more radioactive isotopes have been incorporated, may be beneficial, for example, for the examination of the mechanism of action or of the active compound distribution in the body. Compounds labelled with $^{3}H$, $^{14}C$ and/or $^{18}F$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required.

Accordingly, certain embodiments provide isotopically enriched analogs of the compounds disclosed herein, for example, deuterated analogs, to improve pharmacokinetics (PK), pharmacodynamics (PD) and toxicity profiles of the compounds.

In some embodiments, hydrogen atoms of the compounds described herein may be replaced with deuterium atoms. In certain embodiments, "deuterated" as applied to a chemical group and unless otherwise indicated, refers to a chemical group that is isotopically enriched with deuterium in an amount substantially greater than its natural abundance, for example, at least 90% deuterium in the specified position(s).

Isotopic variants of the compounds according to the present disclosure can be prepared by various, including, for example, the methods described below and in the working examples, by using corresponding isotopic modifications of the particular reagents and/or starting compounds therein.

C. Formulation

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt thereof, and which does not destroy the pharmacological activity thereof and is nontoxic when administered in doses sufficient to deliver a therapeutic amount of the compound.

The amount administered depends on the compound formulation, route of administration, etc. and is generally empirically determined, and variations will necessarily occur depending on the target, the host, and the route of administration, etc. Generally, the quantity of active compound in a unit dose of preparation may be varied or adjusted from about 1 milligram (mg) to about 100 mg or from about 1 mg to about 1000 mg, according to the particular application. For convenience, the total daily dosage may be divided and administered in portions during the day.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragées, capsules, pills, and granules can be prepared with coatings and shells such as enteric coatings and other pharmaceutical coatings. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Pharmaceutical compositions of the present disclosure for injection comprise pharmaceutically acceptable sterile aqueous or non-aqueous solutions, dispersions, suspensions, or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

Besides inert diluents, these pharmaceutical compositions may also contain adjuvants such as preservative, wetting agents, emulsifying agents, dispersing agents, sweetening, flavoring, and perfuming agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminum monostearate and gelatin. The compounds can be incorporated into slow release or targeted delivery systems such as polymer matrices, liposomes, and microspheres. Such formulations may provide more effective distribution of the compounds.

The pharmaceutical compositions that are injectable formulations can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

Dosage forms for topical administration of a compound or pharmaceutical composition of the present disclosure include powders, patches, sprays, ointments, and inhalants. The active compound is mixed under sterile conditions with a pharmaceutically acceptable carrier and any preservatives, buffers, or propellants which may be required.

The compounds and compositions described herein can, for example, be administered orally, parenterally (e.g., subcutaneously, intracutaneously, intravenously or intramuscularly), topically, rectally, nasally sublingually or buccally, with a dosage ranging from about 0.01 milligrams per kilogram (mg/kg) to about 1000 mg/kg, (e.g., from about 0.01 to about 100 mg/kg, from about 0.1 to about 100 mg/kg) every 4 to 120 hours, or according to the requirements of the particular drug, dosage form, and/or route of administration. Other routes of administration include enteric, intraarterial, intraperitoneal and intrathecal administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of a therapeutically effective amount of compound or compound composition to achieve a desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 mg to about 2,000 mg (including, from about 0.001 mg to about 1,000 mg, from about 0.001 mg to about 500 mg, from about 0.01 mg to about 250 mg) of a compound of Formula (I) or a salt (e.g., a pharmaceutically acceptable salt) thereof as defined anywhere herein. The dosage forms can further include a pharmaceutically acceptable carrier and/or an additional therapeutic agent.

Appropriate dosage levels may be determined by any suitable method. Preferably, the active substance is administered at a frequency of 1 to 4 times per day for topical administration, or less often if a drug delivery system is used. Nevertheless, actual dosage levels and time course of administration of the active ingredients in the pharmaceutical compositions of the present disclosure may be varied so as to obtain an amount of the active ingredient which is effective to achieve a desired therapeutic response for a particular patient, composition and mode of administration, without being intolerably toxic to the patient. In certain cases, dosages may deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit may be exceeded. It may in the event of administration of larger amounts be advisable to divide these into multiple individual doses spread over the day.

D. Methods of Use

Provided herein are methods of using the compounds disclosed herein, or pharmaceutically acceptable salts thereof, or pharmaceutical compositions thereof, for the treatment, prevention or amelioration of a disease or disorder that is mediated by or otherwise affected via complement alternative pathway. In yet certain embodiments, provided herein are methods of using the compounds disclosed herein, or pharmaceutically acceptable salts thereof, or pharmaceutical compositions thereof, for the treatment, prevention or amelioration of a disease or disorder that is mediated by or otherwise affected via complement factor B (CFB). In yet certain embodiments, provided herein are methods of using the compounds disclosed herein, or pharmaceutically acceptable salts thereof, or pharmaceutical compositions thereof, for the treatment, prevention or amelioration of a disease or disorder that is mediated by or otherwise affected via inhibition of the complement alternative pathway. In yet certain embodiments, provided herein are methods of using the compounds disclosed herein, or pharmaceutically acceptable salts thereof, or pharmaceutical compositions thereof, for the treatment, prevention or amelioration of a disease or disorder that is mediated by or otherwise affected via inhibition of complement factor B.

Examples of known complement related diseases or disorders include: neurological disorders, multiple sclerosis, stroke, Guillain Barre Syndrome, traumatic brain injury, Parkinson's disease, disorders of inappropriate or undesirable complement activation, hemodialysis complications, hyperacute allograft rejection, xenograft rejection, interleukin-2 induced toxicity during I L-2 therapy, inflammatory disorders, inflammation of autoimmune diseases, Crohn's disease, adult respiratory distress syndrome, thermal injury including burns or frostbite, myocarditis, post-ischemic reperfusion conditions, myocardial infarction, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration and neural regeneration. In addition, other known complement related disease are lung disease and disorders such as dyspnea, hemoptysis, ARDS, asthma, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), asthma, allergy, bronchoconstriction, hypersensitivity pneumonitis, parasitic diseases, Goodpasture's Syndrome, pulmonary vasculitis, Pauci-immune vasculitis, immune complex-associated inflammation; eye diseases including age related macular degeneration, diabetic retinopathy, retinitis pigmentosa, macular edema, Behcet's uveitis, multifocal choroiditis, Vogt-Koyangi-Harada syndrome, intermediate uveitis, birdshot retino-choroiditis, sympathetic ophthalmia, ocular cicatricial pemphigoid, ocular pemphigus, nonarteritic ischemic optic neuropathy, postoperative inflammation, and retinal vein occlusion uveitis (including Behcet's disease and other sub-types of uveitis), antiphospholipid syndrome.

In certain embodiments, provided herein are methods of treating kidney disease, chronic kidney disease, diabetic nephropathy, glomerular kidney disease, complement $C_3$ glomerulopathy (C3G), IgA nephropathy (IgAN), membranous nephropathy (MN), focal segmental glomerulosclerosis (FSGS), atypical hemolytic uremic syndrome (aHUS), dense-deposit disease (DDD), minimal change disease (MCD), paroxysmal nocturnal hemoglobinuria (PNH), ANCA-associated vasculitis, lupus nephritis or polycystic kidney disease (PKD).

E. Embodiments

Embodiment 1: The compound of Formula (I):

(I)

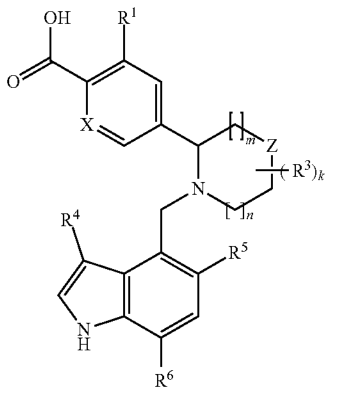

or a pharmaceutically acceptable salt thereof, wherein:

$R^8$ is hydrogen, fluoro, chloro or methyl;

X is N or CH;

Z is $NR^2$ or $CR^{2a}R^{2b}$;

$R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl, heteroaryl, —$C(O)R^{12}$, —$C(O)NR^{13}R^{14}$ or —$S(O)_tR^{12}$ wherein the alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl is optionally substituted with one, two or three independently selected $R^{11}$;

$R^{2a}$ is haloalkyl, —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$;

and $R^{2b}$ is hydrogen, deuterium, halogen, $C_{1-3}$alkyl, deutero$C_{1-3}$alkyl, or halo$C_{1-3}$alkyl;

or $R^{2a}$ and $R^{2b}$, together with the carbon atom to which they are attached, form cycloalkyl or heterocyclyl, wherein the cycloalkyl or heterocyclyl is optionally substituted with one, two or three independently selected $R^{11}$;

$R^3$ is halo, cyano, $C_{1-3}$alkyl, or halo$C_{1-3}$alkyl;

$R^4$ is hydrogen, halo, cyano, $C_{1-3}$alkyl or halo$C_{1-3}$alkyl;

$R^5$ is halo, $C_{1-3}$alkyl, $C_{3-5}$cycloalkyl, halo$C_{1-3}$alkyl, halo$C_{1-3}$alkoxy or $C_{1-3}$alkoxy;

$R^6$ is halo, cyano, $C_{1-3}$alkyl, $C_{3-5}$cycloalkyl, halo$C_{1-3}$ alkyl, $C_{1-3}$alkoxy or halo$C_{1-3}$alkoxy;

$R^7$ is haloalkyl, —$R_u$-cycloalkyl, —$R_u$-heterocyclyl, cycloalkyl, heterocyclyl, or heteroaryl wherein the haloalkyl, deuteroalkyl, —$R_u$-cycloalkyl, —$R_u$-heterocyclyl, cycloalkyl, heterocyclyl or heteroaryl is optionally substituted with one, two or three independently selected $R^{11}$;

$R^8$ is hydrogen, deuterium, alkyl, deuteroalkyl or haloalkyl;

$R^9$ is haloalkyl, —$R_u$-cycloalkyl, —$R_u$-heterocyclyl, cycloalkyl, heterocyclyl, heteroaryl, —$C(O)R^{12}$, —$C(O)NR^{13}R^{14}$, —$S(O)_tR^{12}$, or —$S(O)_tNR^{13}R^{14}$, wherein the —$R_u$-cycloalkyl, —$R_u$-heterocyclyl, cycloalkyl, heterocyclyl or heteroaryl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted with one two or three independently selected $R^{11}$;

each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, $C_{1-3}$alkoxy$C_{1-3}$alkyl, halo$C_{1-3}$ alkoxy$C_{1-3}$alkyl, hydroxyl, $C_{1-3}$alkoxy, halo$C_{1-3}$ alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl; or two $R^{11}$ groups, together with the carbon atom to which they are attached, form $C_{3-5}$cycloalkyl, 3- to 6-membered heterocyclyl or oxo where the $C_{3-5}$cycloalkyl or 3- to 6-membered heterocyclyl is optionally substituted with 1 or 2 independently selected halo;

$R^{12}$ is alkyl, deuteroalkyl or haloalkyl;

$R^{13}$ and $R^{14}$ are each independently hydrogen, alkyl, deuteroalkyl or haloalkyl or $R^{13}$ and $R^{14}$, together with the nitrogen atom to which they are attached, form heterocyclyl optionally substituted with one, two or three independently selected $R^{11}$;

$R^u$ is methylene, ethylene or propylene linker optionally substituted with one to six independently selected halo;

k is 0, 1, 2 or 3;

t is 1 or 2;

m is 0, 1 or 2; and n is 0, 1, or 2 provided that:

when Z is $NR^2$, m is 1 and n is 1 or 2; and when Z is $CR^{2a}R^{2b}$ and $R^{2a}$ and $R^{2b}$, together with the carbon atom to which they are attached, form cycloalkyl, and m is 1, then the cycloalkyl is substituted with at least one $R^{11}$.

Embodiment 2: The compound of embodiment 1, wherein m is 0 or 1; n is 0, 1 or 2, provided that when Z is $NR^2$, m is 1 and n is 1 or 2.

Embodiment 3: The compound of embodiment 1, wherein m is 0 or 1; and n is 0 or 1, provided that when Z is $NR^2$, m is 1 and n is 1.

Embodiment 4: The compound of any one of embodiments 1 to 3 having the Formula (II):

(II)

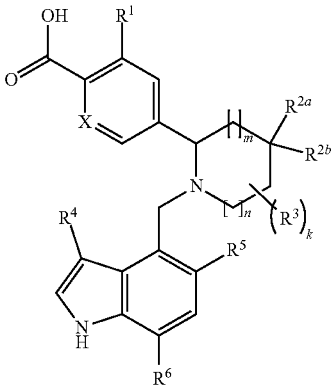

or a pharmaceutically acceptable salt thereof, wherein m is 0 or 1; n is 0 or 1; and X, $R^1$, $R^{2a}$, $R^{2b}$, $R^3$, $R^4$, $R^5$, $R^6$ and k are as described for embodiment 1.

Embodiment 5: The compound of any one of embodiments 1 to 4 having the Formula (III):

(III)

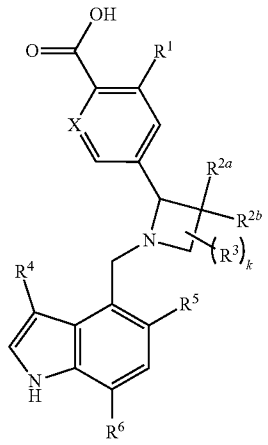

or a pharmaceutically acceptable salt thereof, wherein X, $R^1$, $R^{2a}$, $R^{2b}$, $R^3$, $R^4$, $R^5$, $R^6$ and k are as described for embodiment 1.

Embodiment 6: The compound of any one of embodiments 1 to 4 having the Formula (IV):

(IV)

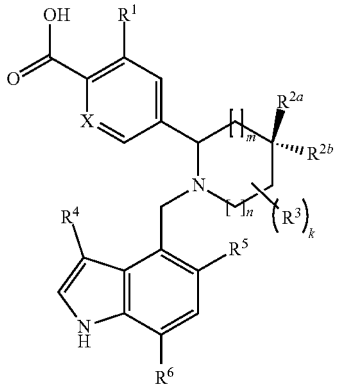

or a pharmaceutically acceptable salt thereof, wherein m is 0 or 1; n is 0 or 1; and X, $R^1$, $R^{2a}$, $R^{2b}$, $R^3$, $R^4$, $R^5$, $R^6$, k, m and n are as described for embodiment 1.

Embodiment 7: The compound of any one of embodiments 1 to 4 having the Formula (IVa):

(IVa)

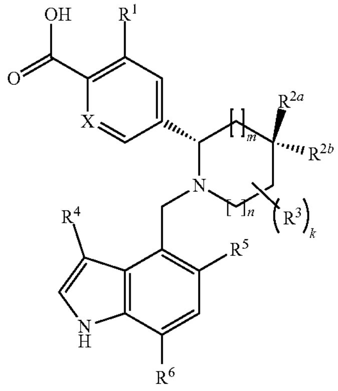

or a pharmaceutically acceptable salt thereof.

Embodiment 8: The compound of any one of embodiments 1 to 4 having the Formula (V):

(V)

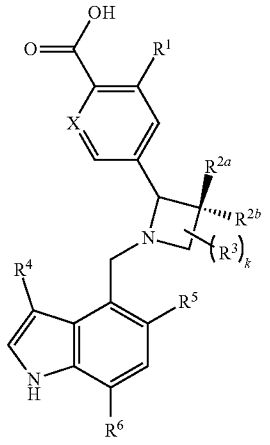

or a pharmaceutically acceptable salt thereof, wherein X, $R^1$, $R^{2a}$, $R^{2b}$, $R^3$, $R^4$, $R^5$, $R^6$ and k are as described for embodiment 1.

Embodiment 9: The compound of any one of embodiments 1 to 8, wherein $R^{2a}$ and $R^{2b}$, together with the carbon atom to which they are attached, form cycloalkyl substituted with one, two or three independently selected $R^{11}$ or form heterocyclyl optionally substituted with one, two or three independently selected $R^{11}$.

Embodiment 10: The compound of any one of embodiments 1 to 8, wherein $R^{2a}$ and $R^{2b}$, together with the carbon atom to which they are attached, form cycloalkyl substituted with one, two or three independently selected $R^{11}$.

Embodiment 11: The compound of embodiment 5 or 8, wherein $R^{2a}$ and $R^{2b}$, together with the carbon atom to which they are attached, form $C_{3-6}$cycloalkyl optionally substituted with one, two or three independently selected $R^{11}$.

Embodiment 12: The compound of any one of embodiments 1 to 8, wherein $R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form cycloalkyl substituted with one, two or three independently selected $R^{11}$, or form heterocyclyl optionally substituted with one, two or three independently selected $R^{11}$.

Embodiment 13: The compound of any one of embodiments 1 to 8, wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form cycloalkyl substituted with one, two or three independently selected $R^{11}$ or form heterocyclyl optionally substituted with one, two or three independently selected $R^{11}$.

Embodiment 14: The compound of any one of embodiments 1 to 8, wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form $C_{3-6}$cycloalkyl substituted with one, two or three independently selected $R^{11}$, or form 4-6-membered heterocyclyl optionally substituted with one, two or three independently selected $R^{11}$.

Embodiment 15: The compound of any one of embodiments 1 to 8, wherein $R^{2a}$ is cycloalkyl, heterocyclyl, —$OR^7$, —$SR^7$ or —$NR^8R^9$, wherein the cycloalkyl or heterocyclyl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form $C_{3-6}$cycloalkyl substituted with one, two or three independently selected $R^{11}$, or form 4-6-membered heterocyclyl optionally substituted with one, two or three independently selected $R^{11}$.

Embodiment 16: The compound of any one of embodiments 1 to 8, wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form $C_{3-5}$cycloalkyl substituted with one, two or three independently selected $R^{11}$, or form 4-5-membered heterocyclyl optionally substituted with one, two or three independently selected $R^{11}$.

Embodiment 17: The compound of any one of embodiments 1 to 8, wherein $R^{2a}$ is —$R_u$-cycloalkyl, —$R_u$-heterocyclyl, cycloalkyl, heterocyclyl, aryl, heteroaryl, —$OR^7$, —$SR^7$ or —$NR^8R^9$, wherein the —$R_u$-cycloalkyl, —$R_u$-heterocyclyl, cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$.

Embodiment 18: The compound of any one of embodiments 1 to 8, wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$.

Embodiment 19: The compound of any one of embodiments 1 to 8, wherein $R^{2a}$ is —$R_u$-cycloalkyl or cycloalkyl, wherein the —$R_u$-cycloalkyl or cycloalkyl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl.

Embodiment 20: The compound of any one of embodiments 1 to 8, wherein $R^{2a}$ is —$R_u$-cycloalkyl, —$R_u$-heterocyclyl, cycloalkyl or heterocyclyl wherein the —$R_u$-cycloalkyl, —$R_u$-heterocyclyl, cycloalkyl or heterocyclyl is optionally substituted with one, two or three independently selected $R^{11}$; $R^{2b}$ is hydrogen, deuterium, halogen, $C_{1-3}$alkyl, deutero$C_{1-3}$alkyl or halo$C_{1-3}$alkyl.

Embodiment 21: The compound of any one of embodiments 1 to 8, wherein $R^{2a}$ is cycloalkyl, heterocyclyl, aryl or heteroaryl, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form heterocyclyl optionally substituted with one, two or three independently selected $R^{11}$.

Embodiment 22: The compound of any one of embodiments 1 to 8, wherein $R^{2a}$ is cycloalkyl, heterocyclyl, aryl or heteroaryl, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl.

Embodiment 23: The compound of any one of embodiments 1 to 8, wherein $R^{2a}$ is heterocyclyl or heteroaryl, wherein the heterocyclyl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl.

Embodiment 24: The compound of any one of embodiments 1 to 8, wherein $R^{2a}$ is heteroaryl, wherein the heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl.

Embodiment 25: The compound of any one of embodiments 1 to 8, wherein $R^{2a}$ is cycloalkyl, heterocyclyl, aryl, heteroaryl, —$OR^7$, —$SR^7$ or —$NR^8R^9$, wherein the cycloalkyl, heterocyclyl, aryl or heteroaryl is optionally substituted with one, two or three independently selected $R^{11}$ and $R^{2b}$ is hydrogen, deuterium, halogen, $C_{1-3}$alkyl, deutero$C_{1-3}$alkyl or halo$C_{1-3}$alkyl; or $R^{2a}$ and $R^{2b}$, together with the carbon atom to which they are attached, form 4-5-membered heterocyclyl optionally substituted with one, two or three independently selected $R^{11}$; and $R^7$, $R^8$, $R^9$ and $R^{11}$ are as described for embodiment 1.

Embodiment 26: The compound of any one of embodiments 1 to 8, wherein $R^{2a}$ is —$OR^7$, —$SR^7$ or —$NR^8R^9$; $R^{2b}$ is hydrogen, deuterium, halogen, $C_{1-3}$alkyl, deutero$C_{1-3}$alkyl or halo$C_{1-3}$alkyl; and $R^7$, $R^8$, $R^9$ and $R^{11}$ are as described for embodiment 1.

Embodiment 27: The compound of any one of embodiments 1 to 8, wherein $R^{2a}$ is —$R_u$-cycloalkyl, —$OR^7$, —$SR^7$ or —$NR^8R^9$; $R^{2b}$ is hydrogen, deuterium, halogen, $C_{1-3}$alkyl, deutero$C_{1-3}$alkyl or halo$C_{1-3}$alkyl; $R^7$ is haloalkyl or cycloalkyl; $R^8$ is hydrogen; $R^9$ is —$R_u$-cycloalkyl or cycloalkyl wherein the —$R_u$-cycloalkyl or cycloalkyl is optionally substituted with one, two or three independently selected $R^{11}$; and $R^{11}$ is each independently halo or halo$C_{1-3}$ alkyl.

Embodiment 28: The compound of any one of embodiments 1 to 8, 12 to 18, 25 and 26, wherein $R^7$ is —$R_u$-cycloalkyl, —$R_u$-heterocyclyl, cycloalkyl, heterocyclyl, or heteroaryl wherein the —$R_u$-cycloalkyl, —$R_u$-heterocyclyl, cycloalkyl, heterocyclyl or heteroaryl is optionally substituted with one, two or three independently selected $R^{11}$, cycloalkyl or heterocyclyl optionally substituted with one, two or three independently selected $R^{11}$; $R^8$ is hydrogen, deuterium, alkyl, deuteroalkyl or haloalkyl; $R^9$ is —$R_u$-cycloalkyl, —$R_u$-heterocyclyl, cycloalkyl, heterocyclyl or heteroaryl wherein the —$R_u$-cycloalkyl, —$R_u$-heterocyclyl, cycloalkyl, heterocyclyl or heteroaryl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$; each $R^{11}$ is independently halo, cyano, oxo, $C_{1-3}$alkyl, deutero$C_{1-3}$alkyl, halo$C_{1-3}$ alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; and $R^u$ is methylene, ethylene or propylene linker optionally substituted with one to six independently selected halo.

Embodiment 29: The compound of any one of embodiments 1 to 8, 12 to 18, 25 and 26, wherein $R^7$ is cycloalkyl, heterocyclyl or heteroaryl wherein the cycloalkyl, heterocyclyl or heteroaryl is optionally substituted with one, two or three independently selected $R^{11}$; $R^8$ is hydrogen, deuterium, alkyl, deuteroalkyl or haloalkyl; $R^9$ is cycloalkyl, heterocyclyl or heteroaryl wherein the cycloalkyl, heterocyclyl or heteroaryl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$ and wherein the heterocyclyl is further optionally substituted with oxo and each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; and $R^u$ is methylene, ethylene or propylene linker optionally substituted with one to six independently selected halo.

Embodiment 30: The compound of any one of embodiments 1 to 8, 12 to 18, 25 and 26, wherein $R^7$ is cycloalkyl or heterocyclyl optionally substituted with one, two or three independently selected $R^{11}$; $R^8$ is hydrogen, deuterium, alkyl, deuteroalkyl or haloalkyl; $R^9$ is cycloalkyl or heterocyclyl wherein the cycloalkyl or heterocyclyl is optionally substituted with one, two or three independently selected $R^{11}$, or $R^8$ and $R^9$, together with the nitrogen atom to which they are attached, form heterocyclyl or heteroaryl wherein the heterocyclyl or heteroaryl is optionally substituted by one two or three independently selected $R^{11}$; each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl.

Embodiment 31: The compound of any one of embodiments 1 to 8, 12 to 18, 25, and 26 wherein $R^7$ is —$R_u$-heterocyclyl or heterocyclyl wherein the —$R_u$-heterocyclyl or heterocyclyl is optionally substituted with one, two or three independently selected $R^{11}$; and each $R^{11}$ is independently halo, cyano, oxo, $C_{1-3}$alkyl, deutero$C_{1-3}$alkyl, halo$C_{1-3}$ alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl.

Embodiment 32: The compound of any one of embodiments 1 to 8, 12 to 18, 25 and 26, wherein $R^7$ is haloalkyl; $R^8$ is hydrogen, deuterium, alkyl, deuteroalkyl or haloalkyl; and $R^9$ is haloalkyl.

Embodiment 33: The compound of any one of embodiments 1 to 8, 12 to 18, 25 and 26, wherein $R^{2a}$ is —$NR^8R^9$; $R^{2b}$ is hydrogen, deuterium, halogen, $C_{1-3}$alkyl, deutero$C_{1-3}$ alkyl or halo$C_{1-3}$alkyl.

Embodiment 34: The compound of embodiment 33, wherein $R^8$ is hydrogen, deuterium, alkyl, deuteroalkyl or haloalkyl; $R^9$ is haloalkyl, —$R_u$-cycloalkyl, —$R_u$-heterocyclyl, cycloalkyl or heterocyclyl, wherein the haloalkyl, —$R_u$-cycloalkyl, —$R_u$-heterocyclyl, cycloalkyl or heterocyclyl is optionally substituted with one, two or three independently selected $R^{11}$ and each $R^{11}$ is independently halo, cyano, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl.

Embodiment 35: The compound of embodiment 33, wherein $R^8$ is hydrogen, deuterium, alkyl, deuteroalkyl or haloalkyl; $R^9$ is haloalkyl, —$R_u$-heterocyclyl or heterocyclyl, wherein the haloalkyl, —$R_u$-heterocyclyl or heterocyclyl is optionally substituted with one, two or three independently selected $R^{11}$.

Embodiment 36: The compound of any one of embodiments 1 to 8, 12 to 18, 25, and 26 wherein $R^{2a}$ is —$OR^7$; $R^7$ is haloalkyl, —$R_u$-cycloalkyl, —$R_u$-heterocyclyl, cycloalkyl or heterocyclyl, wherein the haloalkyl, —$R_u$-cycloalkyl, —$R_u$-heterocyclyl, cycloalkyl or heterocyclyl is optionally substituted with one, two or three independently selected $R^{11}$; and $R^{11}$ is as described for embodiment 1.

Embodiment 37: The compound of any one of embodiments 1 to 8, 12 to 36, wherein $R^{2b}$ is hydrogen or methyl.

Embodiment 38: The compound of any one of embodiments 1 to 8, 12 to 37, wherein $R^{2b}$ is hydrogen.

Embodiment 39: The compound of embodiment 1, 4, or 6 having the Formula (VI):

(VI)

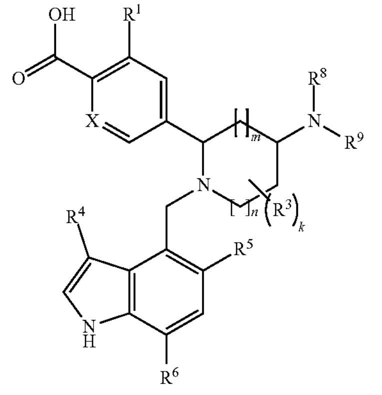

or a pharmaceutically acceptable salt thereof, wherein X, $R^1$, $R^3$, $R^4$, $R^5$, $R^6$, $R^8$, $R^9$ and k are as described for embodiment 1, 4 and 6, respectively.

Embodiment 40: The compound of embodiment 39, wherein $R^3$ is halo, cyano, alkyl, or haloalkyl; $R^4$ is hydrogen, halo, $C_{1-3}$alkyl or halo$C_{1-3}$alkyl; $R^5$ is halo, $C_{1-3}$alkyl, $C_{3-5}$cycloalkyl, halo$C_{1-3}$alkoxy or $C_{1-3}$alkoxy; $R^6$ is halo, cyano, $C_{1-3}$alkyl, $C_{3-5}$cycloalkyl, halo$C_{1-3}$alkyl, $C_{1-3}$alkoxy or halo$C_{1-3}$alkoxy; $R^8$ is hydrogen, deuterium, alkyl or haloalkyl; $R^9$ is cycloalkyl or heterocyclyl wherein the cycloalkyl or heterocyclyl is optionally substituted with one, two or three independently selected $R^{11}$; or $R^8$ and $R^9$, together with the nitrogen atom to which they are attached, form heterocyclyl or heteroaryl wherein the heterocyclyl or heteroaryl is optionally substituted by one two or three independently selected $R^{11}$; each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, halo$C_{1-3}$alkylsulfonyl, $C_{1-3}$alkylsulfinyl or halo$C_{1-3}$alkylsulfinyl; k is 0, 1 or 2; m is 0 or 1; and n is 0, 1 or 2.

Embodiment 41: The compound of embodiment 1, 4, 6, or 39 having the Formula (VIa):

(VIa)

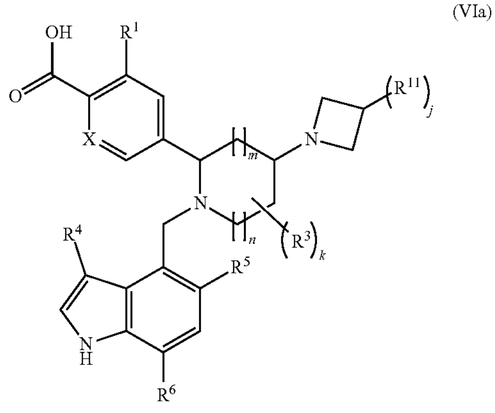

or a pharmaceutically acceptable salt thereof, wherein j is 1 or 2 and X, $R^1$, $R^3$, $R^4$, $R^5$, $R^6$, $R^{11}$, k, m and n are as described for embodiments 1, 4, 6 and 39, respectively.

Embodiment 42: The compound of embodiment 1 or 4 having the Formula (VII):

(VII)

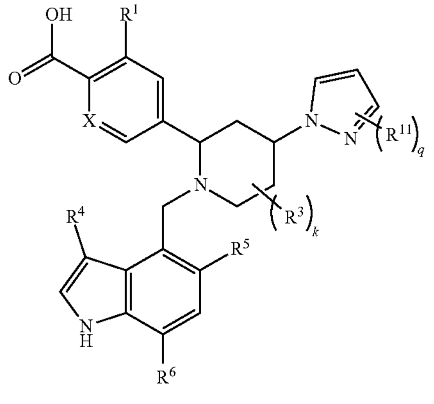

or a pharmaceutically acceptable salt thereof, wherein q is 0, 1, 2 or 3 and X, $R^1$, $R^3$, $R^4$, $R^5$, $R^6$ and k are as described for embodiment 1 or 4 respectively.

Embodiment 43: The compound of embodiment 42 having the Formula (VIIa):

(VIIa)

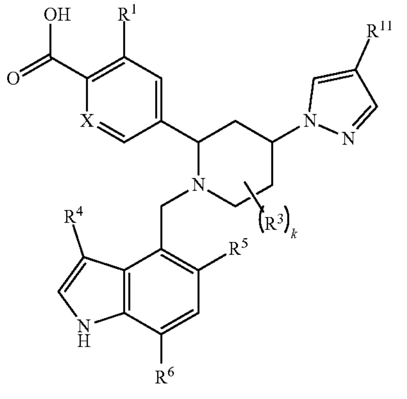

or a pharmaceutically acceptable salt thereof.

Embodiment 44: The compound of embodiment 1, 4 or 6 having the Formula (VIII):

(VIII)

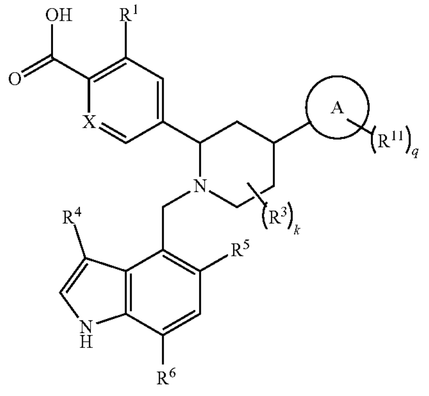

or a pharmaceutically acceptable salt thereof, wherein Ring A is cycloalkyl, heterocyclyl, aryl or heteroaryl; q is 0, 1, 2 or 3 and X, $R^1$, $R^3$, $R^4$, $R^5$, $R^6$, $R^{11}$ and k are as described for embodiment 1, 4 and 6, respectively.

Embodiment 45: The compound of embodiment 44, wherein Ring A is heterocyclyl or heteroaryl.

Embodiment 46: The compound of embodiment 44, wherein Ring A is heteroaryl.

Embodiment 47: The compound of embodiment 44, wherein Ring A is pyridinyl, pyrimidinyl, pyridazinyl, pyrazinyl, triazolyl, imidazolyl, thiazolyl, or pyrazolyl.

Embodiment 48: The compound of embodiment 44, wherein Ring A is pyridinyl or pyrazolyl; q is 0, 1, 2 or 3 and X, $R^1$, $R^3$, $R^4$, $R^5$, $R^6$, $R^{11}$ and k are as described for embodiment 44.

Embodiment 49: The compound of embodiment 44, wherein Ring A is pyridinyl; q is 0, 1, 2 or 3 and X, $R^1$, $R^3$, $R^4$, $R^5$, $R^6$, $R^{11}$ and k are as described for embodiment 44.

Embodiment 50: The compound of embodiment 44, wherein Ring A is pyrazolyl; q is 0, 1, 2 or 3 and X, $R^1$, $R^3$, $R^4$, $R^5$, $R^6$, $R^{11}$ and k are as described for embodiment 44.

Embodiment 51: The compound of embodiment 44, wherein Ring A is azolyl; q is 0, 1, 2 or 3 and X, $R^1$, $R^3$, $R^4$, $R^5$, $R^6$, $R^{11}$ and k are as described for embodiment 44.

Embodiment 52: The compound of embodiment 1, 4, or 6 having the Formula (IX):

(IX)

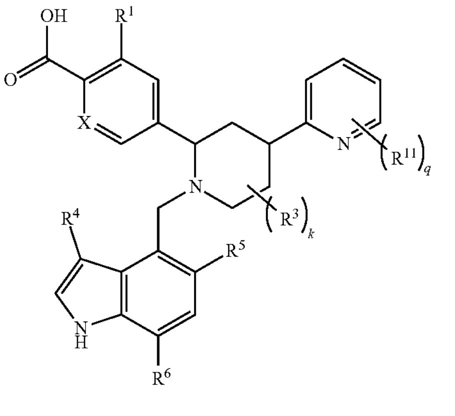

or a pharmaceutically acceptable salt thereof, wherein q is 0, 1, 2 or 3 and $R^1$, $R^3$, $R^4$, $R^5$, $R^6$ and k are as described for embodiment 1, 4 and 6, respectively.

Embodiment 53: The compound of embodiment 1 having the Formula (X):

(X)

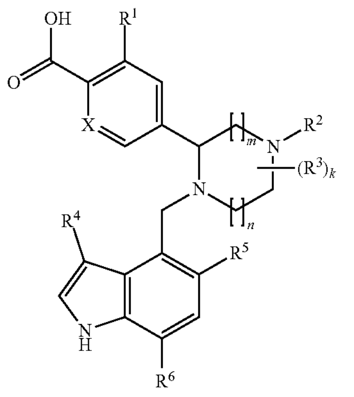

or a pharmaceutically acceptable salt thereof, wherein m is 1; n is 1 or 2, and X, $R^1$, $R^2$, $R^3$, $R^4$, $R^5$, $R^6$ k, m and n are as described for embodiment 1.

Embodiment 54: The compound of embodiment 53, wherein $R^2$ is alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl, wherein the alkyl, haloalkyl, deuteroalkyl, hydroxyalkyl, alkoxyalkyl, cyanoalkyl, —$R_u$-cycloalkyl, —$R_u$-heterocyclyl, cycloalkyl, heterocyclyl or heteroaryl is optionally substituted with one, two or three independently selected $R^{11}$; and $R_u$ and $R^{11}$ are as described for embodiment 1.

Embodiment 55: The compound of embodiment 53, wherein $R^2$ is alkyl, haloalkyl, deuteroalkyl, hydroxyalkyl or cyanoalkyl wherein the alkyl, haloalkyl, deuteroalkyl, hydroxyalkyl or cyanoalkyl is optionally substituted with $R^{11}$; $R^1$, $R^3$, $R^4$, $R^5$, $R^6$, $R^{11}$, $R^{11}$, k, m and n are as described for embodiment 1.

Embodiment 56: The compound of embodiment 53, wherein $R^2$ is $C_{1-6}$alkyl, halo$C_{1-6}$alkyl, deutero$C_{1-6}$alkyl, hydroxy$C_{1-6}$alkyl, C1-6alkoxy$C_{1-6}$alkyl, cyano$C_{1-6}$alkyl, —$R_u$—$C_{3-6}$cycloalkyl, —$R_u$-3- to 7-membered heterocyclyl, $C_{3-6}$cycloalkyl, 3- to 7-membered heterocyclyl or 5- to 10-membered heteroaryl, wherein the $C_{1-6}$alkyl, halo$C_{1-6}$ alkyl, deutero$C_{1-6}$alkyl, hydroxy$C_{1-6}$alkyl, C1-6alkoxy$C_{1-6}$ alkyl, cyano$C_{1-6}$alkyl, —$R_u$—$C_{3-6}$cycloalkyl, —$R_u$-3- to 7-membered heterocyclyl, $C_{3-6}$cycloalkyl, 3- to 7-membered heterocyclyl or 5- to 10-membered heteroaryl is optionally substituted with one, two or three independently selected $R^{11}$; $R^1$, $R^3$, $R^4$, $R^5$, $R^6$, $R^{11}$, k, m and n are as described for embodiment 1.

Embodiment 57: The compound of embodiment 53, wherein $R^2$ is halo$C_{1-3}$alkyl or —$R_u$-3- to 5-membered heterocyclyl, wherein the —$R_u$-3- to 5-membered heterocyclyl is optionally substituted with independently selected halo; and $R^1$, $R^3$, $R^4$, $R^5$, $R^6$, k, m and n are as described for embodiment 1.

Embodiment 58: The compound of embodiment 53, wherein $R^2$ is fluoroethyl or 3-fluorooxetan-3-yl)methyl and $R^1$, $R^3$, $R^4$, $R^5$, $R^6$, k, m and n are as described for embodiment 1.

Embodiment 59: The compound of embodiment 1, 4, or 6 having the Formula (IIa):

(IIa)

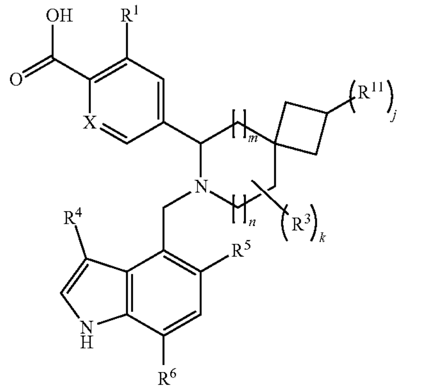

or a pharmaceutically acceptable salt thereof, wherein j is 1 or 2; X, $R^1$, $R^3$, $R^4$, $R^5$, $R^6$, $R^{11}$, k, m and n are as described for embodiment 1, 4 and 6, respectively.

Embodiment 60: The compound of embodiment 1, 4, or 6 having the Formula (IIc):

(IIc)

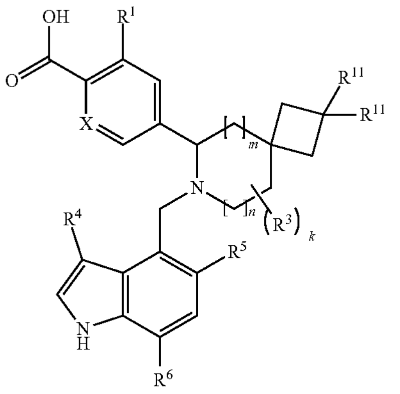

or a pharmaceutically acceptable salt thereof, wherein X, $R^1$, $R^3$, $R^4$, $R^5$, $R^6$, $R^{11}$, k, m and n are as described for embodiment 1, 4 and 6, respectively.

Embodiment 61: The compound of embodiment 1, 4, 6, or 59 having the Formula (IVb):

(IVb)

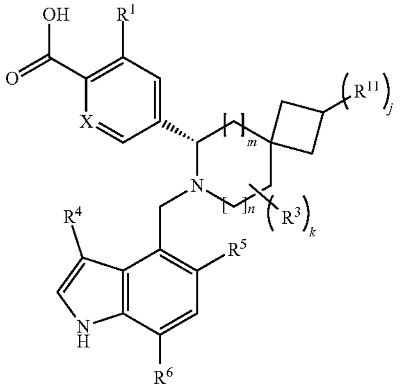

or a pharmaceutically acceptable salt thereof, wherein j is 1 or 2; X, $R^1$, $R^3$, $R^4$, $R^5$, $R^6$, $R^{11}$ and k are as described for embodiment 1, 4, 6 and 59, respectively.

Embodiment 62: The compound of embodiment 1, 4, 6 or 59 having the Formula (IIe):

(IIe)

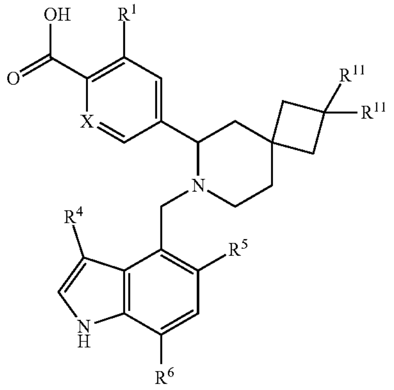

or a pharmaceutically acceptable salt thereof, wherein X, $R^1$, $R^4$, $R^5$, $R^6$ and $R^{11}$ are as described for embodiments 1, 4, 6 and 59, respectively.

Embodiment 63: The compound of embodiment 1, 4, or 6 having the Formula (IIf):

(IIf)

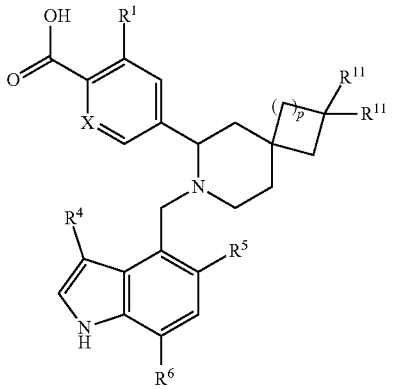

or a pharmaceutically acceptable salt thereof, wherein p is 1 or 2; and X, $R^1$, $R^4$, $R^5$, $R^6$ and $R^{11}$ are as described for embodiments 1, 4 and 6, respectively.

Embodiment 64: The compound of embodiment 1, 4, or 6 having the Formula (IVk):

(IVk)

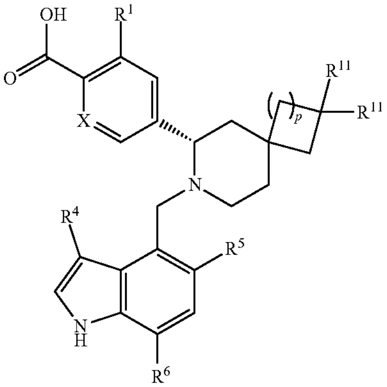

or a pharmaceutically acceptable salt thereof, wherein p is 1 or 2; and X, $R^1$, $R^4$, $R^5$, $R^6$ and $R^{11}$ are as described for embodiments 1, 4 and 6, respectively.

Embodiment 65: The compound of embodiment 1, 4, 6, 59, or 60 having the Formula (IVf):

(IVf)

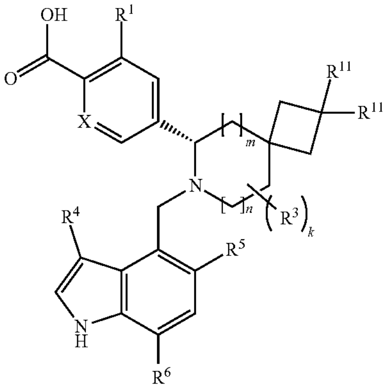

or a pharmaceutically acceptable salt thereof, wherein X, $R^1$, $R^3$, $R^4$, $R^5$, $R^6$, $R^{11}$ and k are as described for embodiment 1, 4, 6, 59 and 60, respectively.

Embodiment 66: The compound of embodiment 1, 4, 6, 59 or 60 having the Formula (IVj):

(IVj)

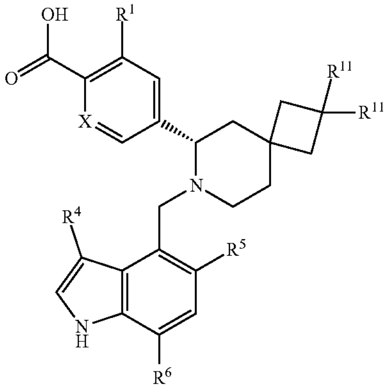

or a pharmaceutically acceptable salt thereof, wherein X, $R^1$, $R^4$, $R^5$, $R^6$ and $R^{11}$ are as described for embodiment 1, 4, 6, 59 and 60, respectively.

Embodiment 67: The compound of embodiment 1, 4, 6, or 59 having the Formula (IIb):

(IIb)

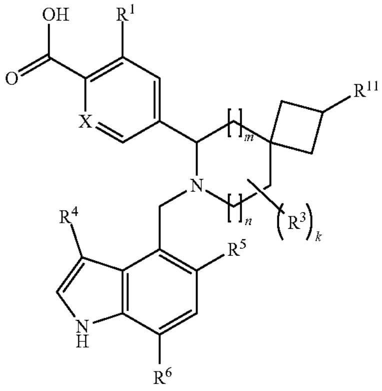

or a pharmaceutically acceptable salt thereof.

Embodiment 68: The compound of embodiment 67, wherein m is 1; n is 1; and wherein X, $R^1$, $R^4$, $R^5$, $R^6$ and $R^{11}$ are as described for embodiment 1, 4, 6 and 59, respectively, or a pharmaceutically acceptable salt thereof.

Embodiment 69: The compound of embodiment 1, 4, 6, or 59 having the Formula (IId):

(IId)

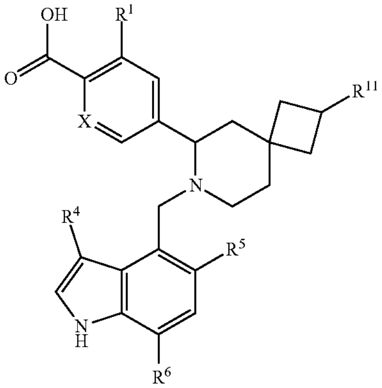

or a pharmaceutically acceptable salt thereof, wherein X, $R^1$, $R^4$, $R^5$, $R^6$ and $R^{11}$ are as described for embodiment 1, 4, 6 and 59, respectively.

Embodiment 70: The compound of embodiment 1, 4, 6, or 59 having the Formula (IVc):

(IVc)

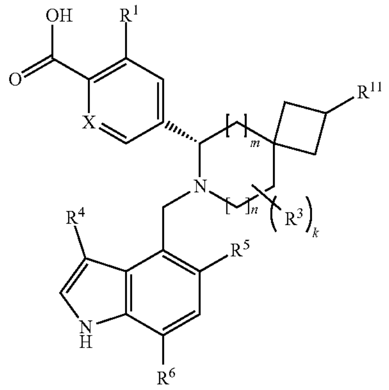

or a pharmaceutically acceptable salt thereof, wherein X, $R^1$, $R^3$, $R^4$, $R^5$, $R^6$, $R^{11}$, k, m and n are as described for embodiment 1, 4, 6 and 59, respectively.

Embodiment 71: The compound of embodiment 1, 4, 6 or 59 having the Formula (IVg):

(IVg)

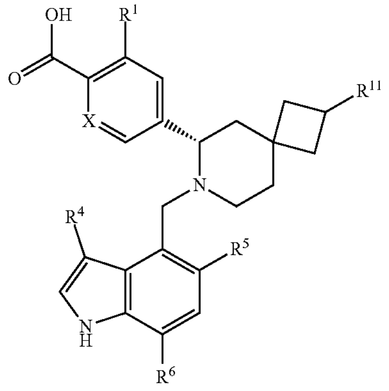

or a pharmaceutically acceptable salt thereof, wherein X, $R^1$, $R^4$, $R^5$, $R^6$ and $R^{11}$ are as described for embodiment 1, 4, 6, and 59, respectively.

Embodiment 72: The compound of embodiment 1, 4, 6 or 59 having the Formula (IVd):

(IVd)

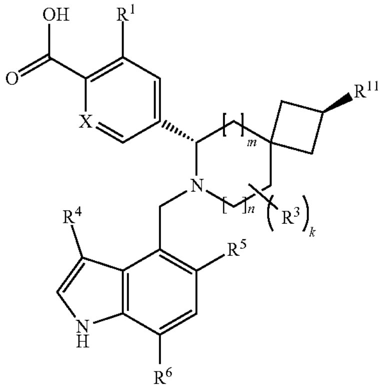

or a pharmaceutically acceptable salt thereof, wherein X, $R^1$, $R^3$, $R^4$, $R^5$, $R^6$, $R^{11}$, k, m and n as described for embodiment 1, 4, 6 and 59, respectively.

Embodiment 73: The compound of embodiment 1, 4, 6 or 59 having the Formula (IVe):

(IVe)

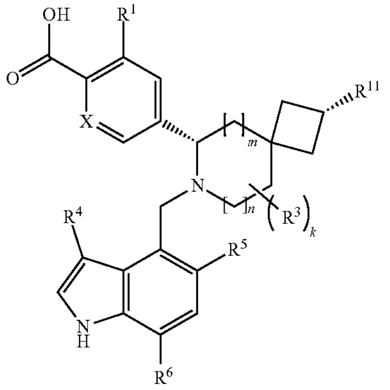

or a pharmaceutically acceptable salt thereof, wherein X, $R^1$, $R^3$, $R^4$, $R^5$, $R^6$, $R^{11}$, k, m and n are as described for embodiment 1, 4, 6, and 59, respectively.

Embodiment 74: The compound of embodiment 1, 4, 6, or 59 having the Formula (IVh)

(IVh)

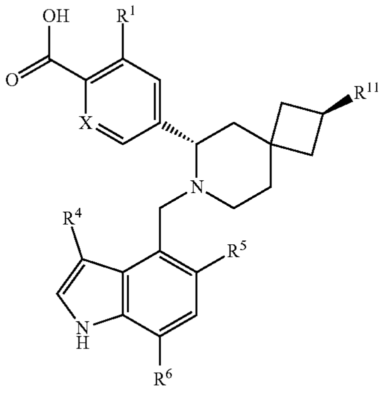

or a pharmaceutically acceptable salt thereof, wherein X, $R^1$, $R^4$, $R^5$, $R^6$ and $R^{11}$ are as described for embodiment 1, 4, 6, and 59, respectively.

Embodiment 75: The compound of embodiment 1, 4, 6, or 59, having the Formula (IVi):

(IVi)

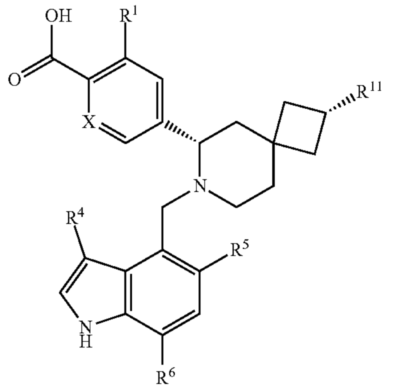

or a pharmaceutically acceptable salt thereof, wherein X, $R^1$, $R^4$, $R^5$, $R^6$ and $R^{11}$ are as described for embodiment 1, 4, 6, and 59, respectively.

Embodiment 76: The compound of any one of embodiments 1 to 75, wherein each $R^{11}$ is independently halo, cyano, oxo, $C_{1-3}$alkyl, deutero$C_{1-3}$alkyl, halo$C_{1-3}$alkyl, cyano$C_{1-3}$alkyl, hydroxy$C_{1-3}$alkyl, hydroxyl, $C_{1-3}$alkoxy, halo$C_{1-3}$alkoxy; or two $R^{11}$ groups, together with the carbon atom to which they are attached, form $C_{3-5}$cycloalkyl or oxo.

Embodiment 77: The compound of any one of embodiments 1 to 75, wherein each $R^{11}$ is independently fluoro, cyano, oxo, hydroxyl, methyl, —$CHF_2$, —$CF_3$ or —$OCHF_2$, or two $R^{11}$ groups, together with the carbon atom to which they are attached, form cyclobutyl or oxo.

Embodiment 78: The compound of any one of embodiments 1 to 75, wherein each $R^{11}$ is independently halo, cyano, halo$C_{1-3}$alkyl, halo$C_{1-3}$alkoxy or $C_{1-3}$alkylsulfonyl; or two $R^{11}$ groups, together with the carbon atom to which they are attached, form $C_{3-5}$cycloalkyl.

Embodiment 79: The compound of any one of embodiments 1 to 75, wherein each $R^{11}$ is independently fluoro, cyano, —$CF_3$, —$CHF_2$, —$OCF_3$ or —$S(O)_2CH_3$ or two $R^{11}$ groups, together with the carbon atom to which they are attached, form cyclopropyl;

Embodiment 80: The compound of any one of embodiments 1 to 75, wherein each $R^{11}$ is independently halo, cyano, oxo, $C_{1-3}$alkyl, halo$C_{1-3}$alkyl, cyano$C_{1-3}$alkyl, hydroxyl, $C_{1-3}$alkoxy, halo$C_{1-3}$alkoxy, $C_{1-3}$alkylthio, halo$C_{1-3}$alkylthio, $C_{1-3}$alkylsulfonyl, $C_{1-3}$alkylsulfinyl, or halo$C_{1-3}$alkylsulfinyl.

Embodiment 81: The compound of any one of embodiments 1 to 75, wherein each $R^{11}$ is independently halo, cyano, halo$C_{1-3}$alkyl, hydroxy$C_{1-3}$alkyl, $C_{1-3}$alkoxy$C_{1-3}$alkyl, halo$C_{1-3}$alkoxy$C_{1-3}$alkyl, hydroxyl, $C_{1-3}$alkoxy or halo$C_{1-3}$alkoxy.

Embodiment 82: The compound of any one of embodiments 1 to 75, wherein each $R^{11}$ is independently halo, cyano, or halo$C_{1-3}$alkyl or hydroxyl.

Embodiment 83: The compound of any one of embodiments 1 to 75, wherein each $R^{11}$ is independently halo, cyano or halo$C_{1-3}$alkyl.

Embodiment 84: The compound of any one of embodiments 1 to 75, wherein each $R^{11}$ is independently F, Cl, Br, cyano, —$CHF_2$ or —$CF_3$.

Embodiment 85: The compound of any one of embodiments 1 to 75, wherein each $R^{11}$ is independently halo or cyano.

Embodiment 86: The compound of any one of embodiments 1 to 75, wherein each $R^{11}$ is independently chloro or cyano.

Embodiment 87: The compound of any one of embodiments 1 to 76, 78, 80 to 83, or 85, wherein $R^{11}$ is halo.

Embodiment 88: The compound of any one of embodiments 1 to 76, 78, 80 to 83, or 85, wherein $R^{11}$ is fluoro.

Embodiment 89: The compound of any one of embodiments 1-76, 78, or 80 to 83, wherein $R^{11}$ is cyano or halo$C_{1-3}$alkyl.

Embodiment 90: The compound of any one of embodiments 1-76, 78, 80, or 89, wherein $R^{11}$ is halo$C_{1-3}$alkyl.

Embodiment 91: The compound of any one of embodiments 1-76, 78, 80, or 89, wherein $R^{11}$ is fluoro$C_{1-3}$alkyl.

Embodiment 92: The compound of any one of embodiments 1-76, 78, or 80 to 83, wherein $R^{11}$ is cyano, —$CHF_2$ or —$CF_3$.

Embodiment 93: The compound of any one of embodiments 1-76, 78, 80, or 89, wherein $R^{11}$ is —$CF_3$.

Embodiment 94: The compound of any one of embodiments 1 to 53, 59, 60, 61, 65, 67, 69, 70 72, or 73, wherein k is 0.

Embodiment 95 The compound of any one of embodiments 1 to 53, 59, 60, 61, 65, 67, 69, 70 72, or 73, wherein k is 1.

Embodiment 96: The compound of any one of embodiments 1, 4, 6, 7, 39, 41, 53, 59, 60, 61, 65, 67, 70, 72 or 73, wherein m is 1 and n is 1.

Embodiment 97: The compound of embodiment 96, wherein $R^3$ is halo, methyl or —$CF_3$.

Embodiment 98: The compound of embodiment 97, wherein $R^3$ is methyl.

Embodiment 99: The compound of any one of embodiments 1 to 98, wherein $R^4$ is hydrogen, halo, $C_{1-3}$alkyl or halo$C_{1-3}$alkyl.

Embodiment 100: The compound of any one of embodiments 1 to 99, wherein $R^4$ is hydrogen, fluoro, chloro, methyl or —$CF_3$.

Embodiment 101: The compound of any one of embodiments 1 to 100, wherein $R^4$ is hydrogen, fluoro, chloro or methyl.

Embodiment 102: The compound of any one of embodiments 1 to 101, wherein $R^4$ is hydrogen.

Embodiment 103: The compound of any one of embodiments 1 to 102, wherein $R^5$ is halo, $C_{1-3}$alkyl, $C_{3-5}$cycloalkyl or $C_{1-3}$alkoxy.

Embodiment 104: The compound any one of embodiments 1 to 103, wherein $R^5$ is chloro, bromo, methyl, cyclopropyl or methoxy.

Embodiment 105: The compound of any one of embodiments 1 to 104, wherein $R^6$ is halo, cyano, $C_{1-3}$alkyl, $C_{3-5}$cycloalkyl or $C_{1-3}$alkoxy.

Embodiment 106: The compound of any one of embodiments 1 to 105, wherein $R^6$ is chloro, bromo, cyano, methyl, cyclopropyl or methoxy.

Embodiment 107: The compound of any one of embodiments 1 to 106, wherein $R^4$ is hydrogen or methyl; $R^5$ is methoxy and $R^6$ is methyl.

Embodiment 108: The compound of any one of embodiments 1 to 107, wherein $R^4$ is hydrogen; $R^5$ is methoxy and $R^6$ is methyl.

Embodiment 109: The compound of any one of embodiments 1 to 108, wherein $R^1$ is hydrogen and X is CH.

Embodiment 110: The compound of embodiment 1, wherein the compound is selected from the group consisting of:

4-((2S,4S)-4-(4-fluoro-1H-pyrazol-1-yl)-1-((5-methoxy-7-methyl-1H-indol-4-yl)methyl)piperidin-2-yl)benzoic acid; (Example 1)

4-((2R,4R)-4-(4-fluoro-1H-pyrazol-1-yl)-1-((5-methoxy-7-methyl-1H-indol-4-yl)methyl)piperidin-2-yl)benzoic acid;

4-((2S,4R)-4-(4-fluoro-1H-pyrazol-1-yl)-1-((5-methoxy-7-methyl-1H-indol-4-yl)methyl)piperidin-2-yl)benzoic acid;

4-((2R,4S)-4-(4-fluoro-1H-pyrazol-1-yl)-1-((5-methoxy-7-methyl-1H-indol-4-yl)methyl)piperidin-2-yl)benzoic acid;

4-(4-(4-fluoro-1H-pyrazol-1-yl)-1-((5-methoxy-7-methyl-1H-indol-4-yl)methyl)piperidin-2-yl)benzoic acid;

( )-trans-4-(4-(4-bromo-1H-pyrazol-1-yl)-1-((5-methoxy-7-methyl-1H-indol-4-yl)methyl)piperidin-2-yl)benzoic acid; (Example 2)

4-((2S,4S)-(4-(4-bromo-1H-pyrazol-1-yl)-1-((5-methoxy-7-methyl-1H-indol-4-yl)methyl)piperidin-2-yl)benzoic acid;

4-((2R,4R)-(4-(4-bromo-1H-pyrazol-1-yl)-1-((5-methoxy-7-methyl-1H-indol-4-yl)methyl)piperidin-2-yl)benzoic acid;

4-((2S,4R)-(4-(4-bromo-1H-pyrazol-1-yl)-1-((5-methoxy-7-methyl-1H-indol-4-yl)methyl)piperidin-2-yl)benzoic acid;

4-((2R,4S)-(4-(4-bromo-1H-pyrazol-1-yl)-1-((5-methoxy-7-methyl-1H-indol-4-yl)methyl)piperidin-2-yl)benzoic acid;

4-(4-(4-bromo-1H-pyrazol-1-yl)-1-((5-methoxy-7-methyl-1H-indol-4-yl)methyl)piperidin-2-yl)benzoic acid;

( )-trans-4-(1-((5-methoxy-7-methyl-1H-indol-4-yl)methyl)-4-(1H-1,2,4-triazol-1-yl)piperidin-2-yl)benzoic acid; (Example 3)

4-((2S,4S)-(1-((5-methoxy-7-methyl-1H-indol-4-yl)methyl)-4-(1H-1,2,4-triazol-1-yl)piperidin-2-yl)benzoic acid;

4-((2R,4R)-(1-((5-methoxy-7-methyl-1H-indol-4-yl)methyl)-4-(1H-1,2,4-triazol-1-yl)piperidin-2-yl)benzoic acid;

4-((2S,4R)-(1-((5-methoxy-7-methyl-1H-indol-4-yl)methyl)-4-(1H-1,2,4-triazol-1-yl)piperidin-2-yl)benzoic acid;

4-((2R,4S)-(1-((5-methoxy-7-methyl-1H-indol-4-yl)methyl)-4-(1H-1,2,4-triazol-1-yl)piperidin-2-yl)benzoic acid;

4-(1-((5-methoxy-7-methyl-1H-indol-4-yl)methyl)-4-(1H-1,2,4-triazol-1-yl)piperidin-2-yl)benzoic acid;

4-((2S,4S)-1-((5-methoxy-7-methyl-1H-indol-4-yl)methyl)-4-(4-(trifluoromethyl)-1H-pyrazol-1-yl)piperidin-2-yl)benzoic acid; (Example 4)

4-((2R,4R)-1-((5-methoxy-7-methyl-1H-indol-4-yl)methyl)-4-(4-(trifluoromethyl)-1H-pyrazol-1-yl)piperidin-2-yl)benzoic acid;

4-((2S,4R)-1-((5-methoxy-7-methyl-1H-indol-4-yl)methyl)-4-(4-(trifluoromethyl)-1H-pyrazol-1-yl)piperidin-2-yl)benzoic acid;

4-((2R,4S)-1-((5-methoxy-7-methyl-1H-indol-4-yl)methyl)-4-(4-(trifluoromethyl)-1H-pyrazol-1-yl)piperidin-2-yl)benzoic acid;

4-1-((5-methoxy-7-methyl-1H-indol-4-yl)methyl)-4-(4-(trifluoromethyl)-1H-pyrazol-1-yl)piperidin-2-yl)benzoic acid;

( )-trans-4-(1-((5-methoxy-7-methyl-1H-indol-4-yl)methyl)-4-(3-(trifluoromethyl)-1H-1,2,4-triazol-1-yl)piperidin-2-yl)benzoic acid; (Example 5)

4-((2S,4S)-1-((5-methoxy-7-methyl-1H-indol-4-yl)methyl)-4-(3-(trifluoromethyl)-1H-1,2,4-triazol-1-yl)piperidin-2-yl)benzoic acid;

4-((2R,4R)-(1-((5-methoxy-7-methyl-1H-indol-4-yl)methyl)-4-(3-(trifluoromethyl)-1H-1,2,4-triazol-1-yl)piperidin-2-yl)benzoic acid;

4-((2S,4R)-(1-((5-methoxy-7-methyl-1H-indol-4-yl)methyl)-4-(3-(trifluoromethyl)-1H-1,2,4-triazol-1-yl)piperidin-2-yl)benzoic acid;

4-((2R,4S)-(1-((5-methoxy-7-methyl-1H-indol-4-yl)methyl)-4-(3-(trifluoromethyl)-1H-1,2,4-triazol-1-yl)piperidin-2-yl)benzoic acid;

4-(1-((5-methoxy-7-methyl-1H-indol-4-yl)methyl)-4-(3-(trifluoromethyl)-1H-1,2,4-triazol-1-yl)piperidin-2-yl)benzoic acid;

( )-trans-4-(4-(2H-indazol-2-yl)-1-((5-methoxy-7-methyl-1H-indol-4-yl)methyl)piperidin-2-yl)benzoic acid; (Example 6)

4-((2S,4S)-(4-(2H-indazol-2-yl)-1-((5-methoxy-7-methyl-1H-indol-4-yl)methyl)piperidin-2-yl)benzoic acid;

4-((2R,4R)-4-(2H-indazol-2-yl)-1-((5-methoxy-7-methyl-1H-indol-4-yl)methyl)piperidin-2-yl)benzoic acid;

4-((2S,4R)-(4-(2H-indazol-2-yl)-1-((5-methoxy-7-methyl-1H-indol-4-yl)methyl)piperidin-2-yl)benzoic acid;

4-((2R,4S)-(4-(2H-indazol-2-yl)-1-((5-methoxy-7-methyl-1H-indol-4-yl)methyl)piperidin-2-yl)benzoic acid;

4-(4-(2H-indazol-2-yl)-1-((5-methoxy-7-methyl-1H-indol-4-yl)methyl)piperidin-2-yl)benzoic acid;

( )-trans-4-(4-(4-(difluoromethyl)-1H-pyrazol-1-yl)-1-((5-methoxy-7-methyl-1H-indol-4-yl)methyl)piperidin-2-yl)benzoic acid; (Example 7)

4-((2S,4S)-(4-(4-(difluoromethyl)-1H-pyrazol-1-yl)-1-((5-methoxy-7-methyl-1H-indol-4-yl)methyl)piperidin-2-yl)benzoic acid;

4-((2R,4R)-(4-(4-(difluoromethyl)-1H-pyrazol-1-yl)-1-((5-methoxy-7-methyl-1H-indol-4-yl)methyl)piperidin-2-yl)benzoic acid;

4-((2S,4R)-(4-(4-(difluoromethyl)-1H-pyrazol-1-yl)-1-((5-methoxy-7-methyl-1H-indol-4-yl)methyl)piperidin-2-yl)benzoic acid;

4-((2R,4S)-(4-(4-(difluoromethyl)-1H-pyrazol-1-yl)-1-((5-methoxy-7-methyl-1H-indol-4-yl)methyl)piperidin-2-yl)benzoic acid;

4-(4-(4-(difluoromethyl)-1H-pyrazol-1-yl)-1-((5-methoxy-7-methyl-1H-indol-4-yl)methyl)piperidin-2-yl)benzoic acid;

4-((2S,4S)-4-chloro-1H-pyrazol-1-yl)-1-((5-methoxy-7-methyl-1H-indol-4-yl)methyl)piperidin-2-yl)benzoic acid; (Example 8)

4-((2R,4R)-4-chloro-1H-pyrazol-1-yl)-1-((5-methoxy-7-methyl-1H-indol-4-yl)methyl)piperidin-2-yl)benzoic acid;

4-((2S,4R)-4-chloro-1H-pyrazol-1-yl)-1-((5-methoxy-7-methyl-1H-indol-4-yl)methyl)piperidin-2-yl)benzoic acid;

4-((2R,4S)-4-chloro-1H-pyrazol-1-yl)-1-((5-methoxy-7-methyl-1H-indol-4-yl)methyl)piperidin-2-yl)benzoic acid;

4-(4-chloro-1H-pyrazol-1-yl)-1-((5-methoxy-7-methyl-1H-indol-4-yl)methyl)piperidin-2-yl)benzoic acid;

(±)-trans-4-(1-((5-methoxy-7-methyl-1H-indol-4-yl)methyl)-4-(1H-pyrazol-1-yl)piperidin-2-yl)benzoic acid; (Example 9)

4-((2S,4S)-(1-((5-methoxy-7-methyl-1H-indol-4-yl)methyl)-4-(1H-pyrazol-1-yl)piperidin-2-yl)benzoic acid;

4-((2R,4R)-(1-((5-methoxy-7-methyl-1H-indol-4-yl)methyl)-4-(1H-pyrazol-1-yl)piperidin-2-yl)benzoic acid;

4-((2S,4R)-(1-((5-methoxy-7-methyl-1H-indol-4-yl)methyl)-4-(1H-pyrazol-1-yl)piperidin-2-yl)benzoic acid;

4-((2R,4S)-(1-((5-methoxy-7-methyl-1H-indol-4-yl)methyl)-4-(1H-pyrazol-1-yl)piperidin-2-yl)benzoic acid;

4-(1-((5-methoxy-7-methyl-1H-indol-4-yl)methyl)-4-(1H-pyrazol-1-yl)piperidin-2-yl)benzoic acid;

4-((2S,4S)-4-(4-cyano-1H-pyrazol-1-yl)-1-((5-methoxy-7-methyl-1H-indol-4-yl)methyl)piperidin-2-yl)benzoic acid (Example 10)

4-((2R,4R)-4-(4-cyano-1H-pyrazol-1-yl)-1-((5-methoxy-7-methyl-1H-indol-4-yl)methyl)piperidin-2-yl)benzoic acid;

4-((2S,4R)-4-(4-cyano-1H-pyrazol-1-yl)-1-((5-methoxy-7-methyl-1H-indol-4-yl)methyl)piperidin-2-yl)benzoic acid;

4-((2R,4S)-4-(4-cyano-1H-pyrazol-1-yl)-1-((5-methoxy-7-methyl-1H-indol-4-yl)methyl)piperidin-2-yl)benzoic acid;

4-(4-(4-cyano-1H-pyrazol-1-yl)-1-((5-methoxy-7-methyl-1H-indol-4-yl)methyl)piperidin-2-yl)benzoic acid;

( )-trans-4-(1-((5-methoxy-7-methyl-1H-indol-4-yl)methyl)-4-(4-(methylsulfonyl)-1H-pyrazol-1-yl)piperidin-2-yl)benzoic acid; (Example 11)

4-((2S,4S)-(1-((5-methoxy-7-methyl-1H-indol-4-yl)methyl)-4-(4-(methylsulfonyl)-1H-pyrazol-1-yl)piperidin-2-yl)benzoic acid;

4-((2R,4R)-(1-((5-methoxy-7-methyl-1H-indol-4-yl)methyl)-4-(4-(methylsulfonyl)-1H-pyrazol-1-yl)piperidin-2-yl)benzoic acid;

4-((2S,4R)-(1-((5-methoxy-7-methyl-1H-indol-4-yl)methyl)-4-(4-(methylsulfonyl)-1H-pyrazol-1-yl)piperidin-2-yl)benzoic acid;

4-((2R,4S)-(1-((5-methoxy-7-methyl-1H-indol-4-yl)methyl)-4-(4-(methylsulfonyl)-1H-pyrazol-1-yl)piperidin-2-yl)benzoic acid;

4-(1-((5-methoxy-7-methyl-1H-indol-4-yl)methyl)-4-(4-(methylsulfonyl)-1H-pyrazol-1-yl)piperidin-2-yl)benzoic acid;

(+)-trans-4-(1-((5-methoxy-7-methyl-1H-indol-4-yl)methyl)-4-(2-oxopyrrolidin-1-yl)piperidin-2-yl)benzoic acid; (Example 12)

4-((2S,4S)-(1-((5-methoxy-7-methyl-1H-indol-4-yl)methyl)-4-(2-oxopyrrolidin-1-yl)piperidin-2-yl)benzoic acid; (Example 13)

4-((2R,4R)-(1-((5-methoxy-7-methyl-1H-indol-4-yl)methyl)-4-(2-oxopyrrolidin-1-yl)piperidin-2-yl)benzoic acid;

4-((2S,4R)-(1-((5-methoxy-7-methyl-1H-indol-4-yl)methyl)-4-(2-oxopyrrolidin-1-yl)piperidin-2-yl)benzoic acid;

4-((2R,4S)-(1-((5-methoxy-7-methyl-1H-indol-4-yl)methyl)-4-(2-oxopyrrolidin-1-yl)piperidin-2-yl)benzoic acid;

4-(1-((5-methoxy-7-methyl-1H-indol-4-yl)methyl)-4-(2-oxopyrrolidin-1-yl)piperidin-2-yl)benzoic acid;

(±)-trans-4-(1-((5-methoxy-7-methyl-1H-indol-4-yl)methyl)-4-((2,2,2-trifluoroethyl)amino)piperidin-2-yl)benzoic acid; (Example 14)

4-((2S,4S)-(1-((5-methoxy-7-methyl-1H-indol-4-yl)methyl)-4-((2,2,2-trifluoroethyl)amino)piperidin-2-yl)benzoic acid; (Example 15)

4-((2R,4R)-(1-((5-methoxy-7-methyl-1H-indol-4-yl)methyl)-4-((2,2,2-trifluoroethyl)amino)piperidin-2-yl)benzoic acid;

4-((2S,4R)-(1-((5-methoxy-7-methyl-1H-indol-4-yl)methyl)-4-((2,2,2-trifluoroethyl)amino)piperidin-2-yl)benzoic acid;

4-((2R,4S)-(1-((5-methoxy-7-methyl-1H-indol-4-yl)methyl)-4-((2,2,2-trifluoroethyl)amino)piperidin-2-yl)benzoic acid;

4-(1-((5-methoxy-7-methyl-1H-indol-4-yl)methyl)-4-((2,2,2-trifluoroethyl)amino)piperidin-2-yl)benzoic acid;

(±)-trans-4-(1-((5-methoxy-7-methyl-1H-indol-4-yl)methyl)-4-(sulfamoylamino)piperidin-2-yl)benzoic acid; (Example 16)

4-((2S,4S)-(1-((5-methoxy-7-methyl-1H-indol-4-yl)methyl)-4-(sulfamoylamino)piperidin-2-yl)benzoic acid;

4-((2R,4R)-(1-((5-methoxy-7-methyl-1H-indol-4-yl)methyl)-4-(sulfamoylamino)piperidin-2-yl)benzoic acid;

4-((2S,4R)-(1-((5-methoxy-7-methyl-1H-indol-4-yl)methyl)-4-(sulfamoylamino)piperidin-2-yl)benzoic acid;

4-((2R,4S)-(1-((5-methoxy-7-methyl-1H-indol-4-yl)methyl)-4-(sulfamoylamino)piperidin-2-yl)benzoic acid;

4-(−1-((5-methoxy-7-methyl-1H-indol-4-yl)methyl)-4-(sulfamoylamino)piperidin-2-yl)benzoic acid;

(±)-trans-4-(1-((5-methoxy-7-methyl-1H-indol-4-yl)methyl)-4-(oxetan-3-ylamino)piperidin-2-yl)benzoic acid; (Example 17)

4-((2S,4S)-(1-((5-methoxy-7-methyl-1H-indol-4-yl)methyl)-4-(oxetan-3-ylamino)piperidin-2-yl)benzoic acid; (Example 18)

4-((2R,4R)-(1-((5-methoxy-7-methyl-1H-indol-4-yl)methyl)-4-(oxetan-3-ylamino)piperidin-2-yl)benzoic acid;

4-((2S,4R)-(1-((5-methoxy-7-methyl-1H-indol-4-yl)methyl)-4-(oxetan-3-ylamino)piperidin-2-yl)benzoic acid;

4-((2R,4S)-(1-((5-methoxy-7-methyl-1H-indol-4-yl)methyl)-4-(oxetan-3-ylamino)piperidin-2-yl)benzoic acid;

4-(1-((5-methoxy-7-methyl-1H-indol-4-yl)methyl)-4-(oxetan-3-ylamino)piperidin-2-yl)benzoic acid;

4-((2S,4S)-4-((3,3-difluorocyclobutyl)amino)-1-((5-methoxy-7-methyl-1H-indol-4-yl)methyl)piperidin-2-yl)benzoic acid; (Example 19)

4-((2R,4R)-4-((3,3-difluorocyclobutyl)amino)-1-((5-methoxy-7-methyl-1H-indol-4-yl)methyl)piperidin-2-yl)benzoic acid;

4-((2S,4R)-4-((3,3-difluorocyclobutyl)amino)-1-((5-methoxy-7-methyl-1H-indol-4-yl)methyl)piperidin-2-yl)benzoic acid;

4-((2R,4S)-4-((3,3-difluorocyclobutyl)amino)-1-((5-methoxy-7-methyl-1H-indol-4-yl)methyl)piperidin-2-yl)benzoic acid;

4-((3,3-difluorocyclobutyl)amino)-1-((5-methoxy-7-methyl-1H-indol-4-yl)methyl)piperidin-2-yl)benzoic acid;

4-((2S,4S)-4-(cyclobutylamino)-1-((5-methoxy-7-methyl-1H-indol-4-yl)methyl)piperidin-2-yl)benzoic acid; (Example 20)

4-((2R,4R)-4-(cyclobutylamino)-1-((5-methoxy-7-methyl-1H-indol-4-yl)methyl)piperidin-2-yl)benzoic acid;

4-((2S,4R)-4-(cyclobutylamino)-1-((5-methoxy-7-methyl-1H-indol-4-yl)methyl)piperidin-2-yl)benzoic acid;

4-((2R,4S)-4-(cyclobutylamino)-1-((5-methoxy-7-methyl-1H-indol-4-yl)methyl)piperidin-2-yl)benzoic acid;

4-(4-(cyclobutylamino)-1-((5-methoxy-7-methyl-1H-indol-4-yl)methyl)piperidin-2-yl)benzoic acid;

4-((2S,4S)-4-(bicyclo[1.1.1]pentan-1-ylamino)-1-((5-methoxy-7-methyl-1H-indol-4-yl)methyl)piperidin-2-yl)benzoic acid; (Example 21)
4-((2R,4R)-4-(bicyclo[1.1.1]pentan-1-ylamino)-1-((5-methoxy-7-methyl-1H-indol-4-yl)methyl)piperidin-2-yl)benzoic acid;
4-((2S,4R)-4-(bicyclo[1.1.1]pentan-1-ylamino)-1-((5-methoxy-7-methyl-1H-indol-4-yl)methyl)piperidin-2-yl)benzoic acid;
4-((2R,4S)-4-(bicyclo[1.1.1]pentan-1-ylamino)-1-((5-methoxy-7-methyl-1H-indol-4-yl)methyl)piperidin-2-yl)benzoic acid;
4-(4-(bicyclo[1.1.1]pentan-1-ylamino)-1-((5-methoxy-7-methyl-1H-indol-4-yl)methyl)piperidin-2-yl)benzoic acid;
4-((2S,4S)-4-((2,2-difluoroethyl)amino)-1-((5-methoxy-7-methyl-1H-indol-4-yl)methyl)piperidin-2-yl)benzoic acid; (Example 22)
4-((2R,4R)-4-((2,2-difluoroethyl)amino)-1-((5-methoxy-7-methyl-1H-indol-4-yl)methyl)piperidin-2-yl)benzoic acid;
4-((2S,4R)-4-((2,2-difluoroethyl)amino)-1-((5-methoxy-7-methyl-1H-indol-4-yl)methyl)piperidin-2-yl)benzoic acid;
4-((2R,4S)-4-((2,2-difluoroethyl)amino)-1-((5-methoxy-7-methyl-1H-indol-4-yl)methyl)piperidin-2-yl)benzoic acid;
4-(4-((2,2-difluoroethyl)amino)-1-((5-methoxy-7-methyl-1H-indol-4-yl)methyl)piperidin-2-yl)benzoic acid;
4-((2S,4S)-4-(((1-fluorocyclopropyl)methyl)amino)-1-((5-methoxy-7-methyl-1H-indol-4-yl)methyl)piperidin-2-yl)benzoic acid; (Example 23)
4-((2R,4R)-4-(((1-fluorocyclopropyl)methyl)amino)-1-((5-methoxy-7-methyl-1H-indol-4-yl)methyl)piperidin-2-yl)benzoic acid;
4-((2S,4R)-4-(((1-fluorocyclopropyl)methyl)amino)-1-((5-methoxy-7-methyl-1H-indol-4-yl)methyl)piperidin-2-yl)benzoic acid;
4-((2R,4S)-4-(((1-fluorocyclopropyl)methyl)amino)-1-((5-methoxy-7-methyl-1H-indol-4-yl)methyl)piperidin-2-yl)benzoic acid;
4-(4-(((1-fluorocyclopropyl)methyl)amino)-1-((5-methoxy-7-methyl-1H-indol-4-yl)methyl)piperidin-2-yl)benzoic acid;
4-((2S,4S)-4-((3,3-difluorocyclobutyl)amino)-1-((5-methoxy-7-methyl-1H-indol-4-yl)methyl)piperidin-2-yl)benzoic acid; (Example 24)
4-((2R,4R)-4-((3,3-difluorocyclobutyl)amino)-1-((5-methoxy-7-methyl-1H-indol-4-yl)methyl)piperidin-2-yl)benzoic acid;
4-((2S,4R)-4-((3,3-difluorocyclobutyl)amino)-1-((5-methoxy-7-methyl-1H-indol-4-yl)methyl)piperidin-2-yl)benzoic acid;
4-((2R,4S)-4-((3,3-difluorocyclobutyl)amino)-1-((5-methoxy-7-methyl-1H-indol-4-yl)methyl)piperidin-2-yl)benzoic acid;
4-(4-((3,3-difluorocyclobutyl)amino)-1-((5-methoxy-7-methyl-1H-indol-4-yl)methyl)piperidin-2-yl)benzoic acid;
4-((2S,4S)-1-((5-cyclopropyl-7-methyl-1H-indol-4-yl)methyl)-4-((3,3-difluorocyclobutyl)amino)piperidin-2-yl)benzoic acid; (Example 25)
4-((2R,4R)-1-((5-cyclopropyl-7-methyl-1H-indol-4-yl)methyl)-4-((3,3-difluorocyclobutyl)amino)piperidin-2-yl)benzoic acid;
4-((2S,4R)-1-((5-cyclopropyl-7-methyl-1H-indol-4-yl)methyl)-4-((3,3-difluorocyclobutyl)amino)piperidin-2-yl)benzoic acid;
4-((2R,4S)-1-((5-cyclopropyl-7-methyl-1H-indol-4-yl)methyl)-4-((3,3-difluorocyclobutyl)amino)piperidin-2-yl)benzoic acid;
4-(1-((5-cyclopropyl-7-methyl-1H-indol-4-yl)methyl)-4-((3,3-difluorocyclobutyl)amino)piperidin-2-yl)benzoic acid;
4-((2S,4S)-4-((cyclopropylmethyl)amino)-1-((5-methoxy-7-methyl-1H-indol-4-yl)methyl)piperidin-2-yl)benzoic acid; (Example 26)
4-((2R,4R)-4-((cyclopropylmethyl)amino)-1-((5-methoxy-7-methyl-1H-indol-4-yl)methyl)piperidin-2-yl)benzoic acid;
4-((2S,4R)-4-((cyclopropylmethyl)amino)-1-((5-methoxy-7-methyl-1H-indol-4-yl)methyl)piperidin-2-yl)benzoic acid;
4-((2R,4S)-4-((cyclopropylmethyl)amino)-1-((5-methoxy-7-methyl-1H-indol-4-yl)methyl)piperidin-2-yl)benzoic acid;
4-(4-((cyclopropylmethyl)amino)-1-((5-methoxy-7-methyl-1H-indol-4-yl)methyl)piperidin-2-yl)benzoic acid;
4-((2S,4S)-1-((5-methoxy-7-methyl-1H-indol-4-yl)methyl)-4-(((1-(trifluoromethyl)cyclopropyl)methyl)amino)piperidin-2-yl)benzoic acid; (Example 27)
4-((2R,4R)-1-((5-methoxy-7-methyl-1H-indol-4-yl)methyl)-4-(((1-(trifluoromethyl)cyclopropyl)methyl)amino)piperidin-2-yl)benzoic acid;
4-((2S,4R)-1-((5-methoxy-7-methyl-1H-indol-4-yl)methyl)-4-(((1-(trifluoromethyl)cyclopropyl)methyl)amino)piperidin-2-yl)benzoic acid;
4-((2R,4S)-1-((5-methoxy-7-methyl-1H-indol-4-yl)methyl)-4-(((1-(trifluoromethyl)cyclopropyl)methyl)amino)piperidin-2-yl)benzoic acid;
4-(1-((5-methoxy-7-methyl-1H-indol-4-yl)methyl)-4-(((1-(trifluoromethyl)cyclopropyl)methyl)amino)piperidin-2-yl)benzoic acid;
4-((2S,4S)-4-(difluoromethoxy)-1-((5-methoxy-7-methyl-1H-indol-4-yl)methyl)piperidin-2-yl)benzoic acid; (Example 28)
4-((2R,4R)-4-(difluoromethoxy)-1-((5-methoxy-7-methyl-1H-indol-4-yl)methyl)piperidin-2-yl)benzoic acid; (Example 29)
4-((2S,4R)-4-(difluoromethoxy)-1-((5-methoxy-7-methyl-1H-indol-4-yl)methyl)piperidin-2-yl)benzoic acid;
4-((2R,4S)-4-(difluoromethoxy)-1-((5-methoxy-7-methyl-1H-indol-4-yl)methyl)piperidin-2-yl)benzoic acid;
4-(4-(difluoromethoxy)-1-((5-methoxy-7-methyl-1H-indol-4-yl)methyl)piperidin-2-yl)benzoic acid;
4-((3R,5S)-1,1-difluoro-6-((5-methoxy-7-methyl-1H-indol-4-yl)methyl)-6-azaspiro[2.5]octan-5-yl)benzoic acid; (Example 30)
4-((3S,5S)-1,1-difluoro-6-((5-methoxy-7-methyl-1H-indol-4-yl)methyl)-6-azaspiro[2.5]octan-5-yl)benzoic acid (or Example 30)
4-((3S,5R)-1,1-difluoro-6-((5-methoxy-7-methyl-1H-indol-4-yl)methyl)-6-azaspiro[2.5]octan-5-yl)benzoic acid;
4-((3R,5R)-1,1-difluoro-6-((5-methoxy-7-methyl-1H-indol-4-yl)methyl)-6-azaspiro[2.5]octan-5-yl)benzoic acid;
4-(1,1-difluoro-6-((5-methoxy-7-methyl-1H-indol-4-yl)methyl)-6-azaspiro[2.5]octan-5-yl)benzoic acid;
(±)-4-(7-((5-methoxy-7-methyl-1H-indol-4-yl)methyl)-2-oxa-7-azaspiro[3.5]nonan-6-yl)benzoic acid; (Example 31)

(S)-4-(7-((5-methoxy-7-methyl-1H-indol-4-yl)methyl)-2-oxa-7-azaspiro[3.5]nonan-6-yl)benzoic acid; (Example 32)
(R)-4-(7-((5-methoxy-7-methyl-1H-indol-4-yl)methyl)-2-oxa-7-azaspiro[3.5]nonan-6-yl)benzoic acid;
4-(7-((5-methoxy-7-methyl-1H-indol-4-yl)methyl)-2-oxa-7-azaspiro[3.5]nonan-6-yl)benzoic acid;
4-((5S,7S)-8-((5-methoxy-7-methyl-1H-indol-4-yl)methyl)-1-oxa-8-azaspiro[4.5]decan-7-yl)benzoic acid; (Example 33)
4-((5R,7S)-8-((5-methoxy-7-methyl-1H-indol-4-yl)methyl)-1-oxa-8-azaspiro[4.5]decan-7-yl)benzoic acid; (or Example 33)
4-((5R,7R)-8-((5-methoxy-7-methyl-1H-indol-4-yl)methyl)-1-oxa-8-azaspiro[4.5]decan-7-yl)benzoic acid;
4-((5S,7R)-8-((5-methoxy-7-methyl-1H-indol-4-yl)methyl)-1-oxa-8-azaspiro[4.5]decan-7-yl)benzoic acid;
4-(8-((5-methoxy-7-methyl-1H-indol-4-yl)methyl)-1-oxa-8-azaspiro[4.5]decan-7-yl)benzoic acid;
4-((5S,7S)-8-((5-methoxy-7-methyl-1H-indol-4-yl)methyl)-2-oxa-8-azaspiro[4.5]decan-7-yl)benzoic acid; (Example 34)
4-((5R,7S)-8-((5-methoxy-7-methyl-1H-indol-4-yl)methyl)-2-oxa-8-azaspiro[4.5]decan-7-yl)benzoic acid; (or Example 34)
4-((5R,7R)-8-((5-methoxy-7-methyl-1H-indol-4-yl)methyl)-2-oxa-8-azaspiro[4.5]decan-7-yl)benzoic acid;
4-((5S,7R)-8-((5-methoxy-7-methyl-1H-indol-4-yl)methyl)-2-oxa-8-azaspiro[4.5]decan-7-yl)benzoic acid;
4-(8-((5-methoxy-7-methyl-1H-indol-4-yl)methyl)-2-oxa-8-azaspiro[4.5]decan-7-yl)benzoic acid;
4-(5R,7S)-2,2-difluoro-8-((5-methoxy-7-methyl-1H-indol-4-yl)methyl)-8-azaspiro[4.5]decan-7-yl)benzoic acid; (Example 35 or 36)
4-(5S,7S)-(2,2-difluoro-8-((5-methoxy-7-methyl-1H-indol-4-yl)methyl)-8-azaspiro[4.5]decan-7-yl)benzoic acid; (or Example 36 or 35)
4-(5S,7R)-(2,2-difluoro-8-((5-methoxy-7-methyl-1H-indol-4-yl)methyl)-8-azaspiro[4.5]decan-7-yl)benzoic acid;
4-(5R,7R)-(2,2-difluoro-8-((5-methoxy-7-methyl-1H-indol-4-yl)methyl)-8-azaspiro[4.5]decan-7-yl)benzoic acid;
4-(2,2-difluoro-8-((5-methoxy-7-methyl-1H-indol-4-yl)methyl)-8-azaspiro[4.5]decan-7-yl)benzoic acid;
(±)-trans-4-(1-((5-methoxy-7-methyl-1H-indol-4-yl)methyl)-4-phenylpiperidin-2-yl)benzoic acid; (Example 37)
4-((2S,4S)-4-(1-((5-methoxy-7-methyl-1H-indol-4-yl)methyl)-4-phenylpiperidin-2-yl)benzoic acid;
4-((2R,4R)-4-(1-((5-methoxy-7-methyl-1H-indol-4-yl)methyl)-4-phenylpiperidin-2-yl)benzoic acid;
4-((2S,4R)-4-(1-((5-methoxy-7-methyl-1H-indol-4-yl)methyl)-4-phenylpiperidin-2-yl)benzoic acid;
4-((2R,4S)-4-(1-((5-methoxy-7-methyl-1H-indol-4-yl)methyl)-4-phenylpiperidin-2-yl)benzoic acid;
4-(4-(1-((5-methoxy-7-methyl-1H-indol-4-yl)methyl)-4-phenylpiperidin-2-yl)benzoic acid;
4-((2S,4S)-1-((5-methoxy-7-methyl-1H-indol-4-yl)methyl)-4-(pyridin-2-yl)piperidin-2-yl)benzoic acid; (Example 38)
4-((2R,4R)-1-((5-methoxy-7-methyl-1H-indol-4-yl)methyl)-4-(pyridin-2-yl)piperidin-2-yl)benzoic acid;
4-((2S,4R)-1-((5-methoxy-7-methyl-1H-indol-4-yl)methyl)-4-(pyridin-2-yl)piperidin-2-yl)benzoic acid;
4-((2R,4S)-1-((5-methoxy-7-methyl-1H-indol-4-yl)methyl)-4-(pyridin-2-yl)piperidin-2-yl)benzoic acid;
4-(1-((5-methoxy-7-methyl-1H-indol-4-yl)methyl)-4-(pyridin-2-yl)piperidin-2-yl)benzoic acid;
4-(2-((5-methoxy-7-methyl-1H-indol-4-yl)methyl)-2-azaspiro[3.4]octan-1-yl)benzoic acid; (Example 39)
(S)-4-(2-((5-methoxy-7-methyl-1H-indol-4-yl)methyl)-2-azaspiro[3.4]octan-1-yl)benzoic acid;
(R)-4-(2-((5-methoxy-7-methyl-1H-indol-4-yl)methyl)-2-azaspiro[3.4]octan-1-yl)benzoic acid;
(R)-4-(2-((5-methoxy-7-methyl-1H-indol-4-yl)methyl)-2-azaspiro[3.3]heptan-1-yl)benzoic acid; (Example 40)
(S)-4-(2-((5-methoxy-7-methyl-1H-indol-4-yl)methyl)-2-azaspiro[3.3]heptan-1-yl)benzoic acid;
4-(2-((5-methoxy-7-methyl-1H-indol-4-yl)methyl)-2-azaspiro[3.3]heptan-1-yl)benzoic acid;
4-((2S,4S)-4-cyclopropyl-1-((5-methoxy-7-methyl-1H-indol-4-yl)methyl)piperidin-2-yl)benzoic acid; (Example 41)
4-((2R,4R)-4-cyclopropyl-1-((5-methoxy-7-methyl-1H-indol-4-yl)methyl)piperidin-2-yl)benzoic acid;
4-((2S,4R)-4-cyclopropyl-1-((5-methoxy-7-methyl-1H-indol-4-yl)methyl)piperidin-2-yl)benzoic acid;
4-((2R,4S)-4-cyclopropyl-1-((5-methoxy-7-methyl-1H-indol-4-yl)methyl)piperidin-2-yl)benzoic acid;
4-(4-cyclopropyl-1-((5-methoxy-7-methyl-1H-indol-4-yl)methyl)piperidin-2-yl)benzoic acid;
4-((2S,4S)-1-((5-methoxy-7-methyl-1H-indol-4-yl)methyl)-4-(3,3,3-trifluoropropyl)piperidin-2-yl)benzoic acid; (Example 42)
4-((2R,4R)-1-((5-methoxy-7-methyl-1H-indol-4-yl)methyl)-4-(3,3,3-trifluoropropyl)piperidin-2-yl)benzoic acid;
4-((2S,4R)-1-((5-methoxy-7-methyl-1H-indol-4-yl)methyl)-4-(3,3,3-trifluoropropyl)piperidin-2-yl)benzoic acid;
4-((2R,4S)-1-((5-methoxy-7-methyl-1H-indol-4-yl)methyl)-4-(3,3,3-trifluoropropyl)piperidin-2-yl)benzoic acid;
4-(1-((5-methoxy-7-methyl-1H-indol-4-yl)methyl)-4-(3,3,3-trifluoropropyl)piperidin-2-yl)benzoic acid;
4-((2S,4S)-4-cyclobutyl-1-((5-methoxy-7-methyl-1H-indol-4-yl)methyl)piperidin-2-yl)benzoic acid;
4-((2S,4R)-4-cyclobutyl-1-((5-methoxy-7-methyl-1H-indol-4-yl)methyl)piperidin-2-yl)benzoic acid;
4-((2R,4R)-4-cyclobutyl-1-((5-methoxy-7-methyl-1H-indol-4-yl)methyl)piperidin-2-yl)benzoic acid;
4-((2R,4S)-4-cyclobutyl-1-((5-methoxy-7-methyl-1H-indol-4-yl)methyl)piperidin-2-yl)benzoic acid;
4-(4-cyclobutyl-1-((5-methoxy-7-methyl-1H-indol-4-yl)methyl)piperidin-2-yl)benzoic acid; (mixture of Example 43)
4-((2S,4S)-4-(cyclopropylmethyl)-1-((5-methoxy-7-methyl-1H-indol-4-yl)methyl)piperidin-2-yl)benzoic acid; (Example 44)
4-((2R,4R)-4-(cyclopropylmethyl)-1-((5-methoxy-7-methyl-1H-indol-4-yl)methyl)piperidin-2-yl)benzoic acid;
4-((2S,4R)-4-(cyclopropylmethyl)-1-((5-methoxy-7-methyl-1H-indol-4-yl)methyl)piperidin-2-yl)benzoic acid;
4-((2R,4S)-4-(cyclopropylmethyl)-1-((5-methoxy-7-methyl-1H-indol-4-yl)methyl)piperidin-2-yl)benzoic acid;
4-(4-(cyclopropylmethyl)-1-((5-methoxy-7-methyl-1H-indol-4-yl)methyl)piperidin-2-yl)benzoic acid;
(S)-4-(2,2-difluoro-7-((5-methoxy-7-methyl-1H-indol-4-yl)methyl)-7-azaspiro[3.5]nonan-6-yl)benzoic acid; (Example 45)
(R)-4-(2,2-difluoro-7-((5-methoxy-7-methyl-1H-indol-4-yl)methyl)-7-azaspiro[3.5]nonan-6-yl)benzoic acid;

4-(2,2-difluoro-7-((5-methoxy-7-methyl-1H-indol-4-yl)methyl)-7-azaspiro[3.5]nonan-6-yl)benzoic acid;

4-((2R,4s,6S)-2-(difluoromethyl)-7-((5-methoxy-7-methyl-1H-indol-4-yl)methyl)-7-azaspiro[3.5]nonan-6-yl)benzoic acid; (Example 46 or 47)

4-((2S,4r,6S)-2-(difluoromethyl)-7-((5-methoxy-7-methyl-1H-indol-4-yl)methyl)-7-azaspiro[3.5]nonan-6-yl)benzoic acid; (Example 47 or 46)

4-((2S,4s,6R)-2-(difluoromethyl)-7-((5-methoxy-7-methyl-1H-indol-4-yl)methyl)-7-azaspiro[3.5]nonan-6-yl)benzoic acid;

4-((2R,4r,6R)-2-(difluoromethyl)-7-((5-methoxy-7-methyl-1H-indol-4-yl)methyl)-7-azaspiro[3.5]nonan-6-yl)benzoic acid;

4-(2-(difluoromethyl)-7-((5-methoxy-7-methyl-1H-indol-4-yl)methyl)-7-azaspiro[3.5]nonan-6-yl)benzoic acid;

4-((2R,4s,6S)-7-((5-methoxy-7-methyl-1H-indol-4-yl)methyl)-2-(trifluoromethyl)-7-azaspiro[3.5]nonan-6-yl)benzoic acid; (Example 48 or 49)

4-((2S,4r,6S)-7-((5-methoxy-7-methyl-1H-indol-4-yl)methyl)-2-(trifluoromethyl)-7-azaspiro[3.5]nonan-6-yl)benzoic acid; (Example 49 or 48)

4-((2S,4s,6R)-7-((5-methoxy-7-methyl-1H-indol-4-yl)methyl)-2-(trifluoromethyl)-7-azaspiro[3.5]nonan-6-yl)benzoic acid;

4-((2R,4r,6R)-7-((5-methoxy-7-methyl-1H-indol-4-yl)methyl)-2-(trifluoromethyl)-7-azaspiro[3.5]nonan-6-yl)benzoic acid;

4-(7-((5-methoxy-7-methyl-1H-indol-4-yl)methyl)-2-(trifluoromethyl)-7-azaspiro[3.5]nonan-6-yl)benzoic acid;

(S)-4-(2,2-difluoro-7-((5-methoxy-7-methyl-1H-indol-4-yl)methyl)-7-azaspiro[3.5]nonan-6-yl)-2-fluorobenzoic acid; (Example 50)

(R)-4-(2,2-difluoro-7-((5-methoxy-7-methyl-1H-indol-4-yl)methyl)-7-azaspiro[3.5]nonan-6-yl)-2-fluorobenzoic acid;

4-(2,2-difluoro-7-((5-methoxy-7-methyl-1H-indol-4-yl)methyl)-7-azaspiro[3.5]nonan-6-yl)-2-fluorobenzoic acid;

(S)-4-(8-((5-methoxy-7-methyl-1H-indol-4-yl)methyl)-8-azadispiro[$2.1.5^5.1^3$]undecan-7-yl)benzoic acid; (Example 51)

(R)-4-(8-((5-methoxy-7-methyl-1H-indol-4-yl)methyl)-8-azadispiro[$2.1.5^5.1^3$]undecan-7-yl)benzoic acid;

4-(8-((5-methoxy-7-methyl-1H-indol-4-yl)methyl)-8-azadispiro[$2.1.5^5.1^3$]undecan-7-yl)benzoic acid;

(S)-4-(7-((3-chloro-5-methoxy-7-methyl-1H-indol-4-yl)methyl)-2,2-difluoro-7-azaspiro[3.5]nonan-6-yl)benzoic acid; (Example 53)

(R)-4-(7-((3-chloro-5-methoxy-7-methyl-1H-indol-4-yl)methyl)-2,2-difluoro-7-azaspiro[3.5]nonan-6-yl)benzoic acid;

4-(7-((3-chloro-5-methoxy-7-methyl-1H-indol-4-yl)methyl)-2,2-difluoro-7-azaspiro[3.5]nonan-6-yl)benzoic acid;

(S)-4-(2,2-difluoro-7-((3-fluoro-5-methoxy-7-methyl-1H-indol-4-yl)methyl)-7-azaspiro[3.5]nonan-6-yl)benzoic acid; (Example 54)

(R)-4-(2,2-difluoro-7-((3-fluoro-5-methoxy-7-methyl-1H-indol-4-yl)methyl)-7-azaspiro[3.5]nonan-6-yl)benzoic acid;

4-(2,2-difluoro-7-((3-fluoro-5-methoxy-7-methyl-1H-indol-4-yl)methyl)-7-azaspiro[3.5]nonan-6-yl)benzoic acid;

4-((2R,4s,6S)-2-cyano-7-((5-methoxy-7-methyl-1H-indol-4-yl)methyl)-7-azaspiro[3.5]nonan-6-yl)benzoic acid; (Example 52 or 55)

4-((2S,4r,6S)-2-cyano-7-((5-methoxy-7-methyl-1H-indol-4-yl)methyl)-7-azaspiro[3.5]nonan-6-yl)benzoic acid; (Example 55 or 52)

4-((2S,4s,6R)-2-cyano-7-((5-methoxy-7-methyl-1H-indol-4-yl)methyl)-7-azaspiro[3.5]nonan-6-yl)benzoic acid;

4-((2R,4r,6R)-2-cyano-7-((5-methoxy-7-methyl-1H-indol-4-yl)methyl)-7-azaspiro[3.5]nonan-6-yl)benzoic acid;

4-(2-cyano-7-((5-methoxy-7-methyl-1H-indol-4-yl)methyl)-7-azaspiro[3.5]nonan-6-yl)benzoic acid;

4-((2R,4s,6S)-2-(difluoromethoxy)-7-((5-methoxy-7-methyl-1H-indol-4-yl)methyl)-7-azaspiro[3.5]nonan-6-yl)benzoic acid; (Example 56 or 57)

4-((2S,4r,6S)-2-(difluoromethoxy)-7-((5-methoxy-7-methyl-1H-indol-4-yl)methyl)-7-azaspiro[3.5]nonan-6-yl)benzoic acid; (Example 57 or 56)

4-((2S,4s,6R)-2-(difluoromethoxy)-7-((5-methoxy-7-methyl-1H-indol-4-yl)methyl)-7-azaspiro[3.5]nonan-6-yl)benzoic acid;

4-((2R,4r,6R)-2-(difluoromethoxy)-7-((5-methoxy-7-methyl-1H-indol-4-yl)methyl)-7-azaspiro[3.5]nonan-6-yl)benzoic acid;

4-(2-(difluoromethoxy)-7-((5-methoxy-7-methyl-1H-indol-4-yl)methyl)-7-azaspiro[3.5]nonan-6-yl)benzoic acid;

(S)-4-(7-((5-methoxy-7-methyl-1H-indol-4-yl)methyl)-2-oxo-7-azaspiro[3.5]nonan-6-yl)benzoic acid; (Example 58)

(R)-4-(7-((5-methoxy-7-methyl-1H-indol-4-yl)methyl)-2-oxo-7-azaspiro[3.5]nonan-6-yl)benzoic acid;

4-(7-((5-methoxy-7-methyl-1H-indol-4-yl)methyl)-2-oxo-7-azaspiro[3.5]nonan-6-yl)benzoic acid;

4-((2R,4s,6S)-2-hydroxy-7-((5-methoxy-7-methyl-1H-indol-4-yl)methyl)-2-methyl-7-azaspiro[3.5]nonan-6-yl)benzoic acid; (Example 59 or 60)

4-((2S,4r,6S)-2-hydroxy-7-((5-methoxy-7-methyl-1H-indol-4-yl)methyl)-2-methyl-7-azaspiro[3.5]nonan-6-yl)benzoic acid; (Example 60 or 59)

4-((2S,4s,6R)-2-hydroxy-7-((5-methoxy-7-methyl-1H-indol-4-yl)methyl)-2-methyl-7-azaspiro[3.5]nonan-6-yl)benzoic acid;

4-((2R,4r,6R)-2-hydroxy-7-((5-methoxy-7-methyl-1H-indol-4-yl)methyl)-2-methyl-7-azaspiro[3.5]nonan-6-yl)benzoic acid;

4-(2-hydroxy-7-((5-methoxy-7-methyl-1H-indol-4-yl)methyl)-2-methyl-7-azaspiro[3.5]nonan-6-yl)benzoic acid;

4-((2S)-2-fluoro-7-((5-methoxy-7-methyl-1H-indol-4-yl)methyl)-7-azaspiro[3.5]nonan-6-yl)benzoic acid; (Example 61)

4-((2R,4s,6S)-2-fluoro-7-((5-methoxy-7-methyl-1H-indol-4-yl)methyl)-7-azaspiro[3.5]nonan-6-yl)benzoic acid; (Example 62 or 63)

4-((2S,4r,6S)-2-fluoro-7-((5-methoxy-7-methyl-1H-indol-4-yl)methyl)-7-azaspiro[3.5]nonan-6-yl)benzoic acid; (Example 63 or 62)

4-((2S,4s,6R)-2-fluoro-7-((5-methoxy-7-methyl-1H-indol-4-yl)methyl)-7-azaspiro[3.5]nonan-6-yl)benzoic acid;

4-((2R,4r,6R)-2-fluoro-7-((5-methoxy-7-methyl-1H-indol-4-yl)methyl)-7-azaspiro[3.5]nonan-6-yl)benzoic acid;

4-(2-fluoro-7-((5-methoxy-7-methyl-1H-indol-4-yl)methyl)-7-azaspiro[3.5]nonan-6-yl)benzoic acid;

4-((2R,4s,6S)-4-(2-hydroxy-7-((5-methoxy-7-methyl-1H-indol-4-yl)methyl)-7-azaspiro[3.5]nonan-6-yl)benzoic acid; (Example 64)

4-((2S,4r,6S)-2-hydroxy-7-((5-methoxy-7-methyl-1H-indol-4-yl)methyl)-7-azaspiro[3.5]nonan-6-yl)benzoic acid; (Example 64)

4-((2S,4s,6R)-2-hydroxy-7-((5-methoxy-7-methyl-1H-indol-4-yl)methyl)-7-azaspiro[3.5]nonan-6-yl)benzoic acid;

4-((2R,4r,6R)-2-hydroxy-7-((5-methoxy-7-methyl-1H-indol-4-yl)methyl)-7-azaspiro[3.5]nonan-6-yl)benzoic acid;

4-(2-hydroxy-7-((5-methoxy-7-methyl-1H-indol-4-yl)methyl)-7-azaspiro[3.5]nonan-6-yl)benzoic acid;

(R)-4-(1-((5-methoxy-7-methyl-1H-indol-4-yl)methyl)-4-(2,2,2-trifluoroethyl)piperazin-2-yl)benzoic acid; (Example 65)

(S)-4-(1-((5-methoxy-7-methyl-1H-indol-4-yl)methyl)-4-(2,2,2-trifluoroethyl)piperazin-2-yl)benzoic acid;

4-(1-((5-methoxy-7-methyl-1H-indol-4-yl)methyl)-4-(2,2,2-trifluoroethyl)piperazin-2-yl)benzoic acid;

(R)-4-(4-(2,2-difluoroethyl)-1-((5-methoxy-7-methyl-1H-indol-4-yl)methyl)piperazin-2-yl)benzoic acid; (Example 66)

(S)-4-(4-(2,2-difluoroethyl)-1-((5-methoxy-7-methyl-1H-indol-4-yl)methyl)piperazin-2-yl)benzoic acid;

4-(4-(2,2-difluoroethyl)-1-((5-methoxy-7-methyl-1H-indol-4-yl)methyl)piperazin-2-yl)benzoic acid;

(R)-4-(4-((3,3-difluorocyclobutyl)methyl)-1-((5-methoxy-7-methyl-1H-indol-4-yl)methyl)piperazin-2-yl)benzoic acid; (Example 67)

(S)-4-(4-((3,3-difluorocyclobutyl)methyl)-1-((5-methoxy-7-methyl-1H-indol-4-yl)methyl)piperazin-2-yl)benzoic acid;

4-(4-((3,3-difluorocyclobutyl)methyl)-1-((5-methoxy-7-methyl-1H-indol-4-yl)methyl)piperazin-2-yl)benzoic acid;

(R)-4-(1-((5-methoxy-7-methyl-1H-indol-4-yl)methyl)-4-(3,3,3-trifluoropropyl)piperazin-2-yl)benzoic acid; (Example 68)

(S)-4-(1-((5-methoxy-7-methyl-1H-indol-4-yl)methyl)-4-(3,3,3-trifluoropropyl)piperazin-2-yl)benzoic acid;

4-(1-((5-methoxy-7-methyl-1H-indol-4-yl)methyl)-4-(3,3,3-trifluoropropyl)piperazin-2-yl)benzoic acid;

(R)-4-(4-((3-fluorooxetan-3-yl)methyl)-1-((5-methoxy-7-methyl-1H-indol-4-yl)methyl)piperazin-2-yl)benzoic acid; (Example 69)

(S)-4-(4-((3-fluorooxetan-3-yl)methyl)-1-((5-methoxy-7-methyl-1H-indol-4-yl)methyl)piperazin-2-yl)benzoic acid;

4-(4-((3-fluorooxetan-3-yl)methyl)-1-((5-methoxy-7-methyl-1H-indol-4-yl)methyl)piperazin-2-yl)benzoic acid;

(R)-4-(4-(2-fluoroethyl)-1-((5-methoxy-7-methyl-1H-indol-4-yl)methyl)piperazin-2-yl)benzoic acid; (Example 70)

(S)-4-(4-(2-fluoroethyl)-1-((5-methoxy-7-methyl-1H-indol-4-yl)methyl)piperazin-2-yl)benzoic acid;

4-(4-(2-fluoroethyl)-1-((5-methoxy-7-methyl-1H-indol-4-yl)methyl)piperazin-2-yl)benzoic acid;

(±)-trans-4-1-((5-methoxy-7-methyl-1H-indol-4-yl)methyl)-4-(3-(trifluoromethyl)azetidin-1-yl)piperidin-2-yl)benzoic acid; (Example 71)

4-((2S,4S)-1-((5-methoxy-7-methyl-1H-indol-4-yl)methyl)-4-(3-(trifluoromethyl)azetidin-1-yl)piperidin-2-yl)benzoic acid; (Example 81)

4-((2R,4R)-1-((5-methoxy-7-methyl-1H-indol-4-yl)methyl)-4-(3-(trifluoromethyl)azetidin-1-yl)piperidin-2-yl)benzoic acid;

4-((2S,4R)-1-((5-methoxy-7-methyl-1H-indol-4-yl)methyl)-4-(3-(trifluoromethyl)azetidin-1-yl)piperidin-2-yl)benzoic acid;

4-((2R,4S)-1-((5-methoxy-7-methyl-1H-indol-4-yl)methyl)-4-(3-(trifluoromethyl)azetidin-1-yl)piperidin-2-yl)benzoic acid;

4-(1-((5-methoxy-7-methyl-1H-indol-4-yl)methyl)-4-(3-(trifluoromethyl)azetidin-1-yl)piperidin-2-yl)benzoic acid;

4-((2S,4S)-1-((5-methoxy-7-methyl-1H-indol-4-yl)methyl)-4-(3-(trifluoromethoxy)azetidin-1-yl)piperidin-2-yl)benzoic acid; (Example 72)

4-((2R,4R)-1-((5-methoxy-7-methyl-1H-indol-4-yl)methyl)-4-(3-(trifluoromethoxy)azetidin-1-yl)piperidin-2-yl)benzoic acid;

4-((2S,4R)-1-((5-methoxy-7-methyl-1H-indol-4-yl)methyl)-4-(3-(trifluoromethoxy)azetidin-1-yl)piperidin-2-yl)benzoic acid;

4-((2R,4S)-1-((5-methoxy-7-methyl-1H-indol-4-yl)methyl)-4-(3-(trifluoromethoxy)azetidin-1-yl)piperidin-2-yl)benzoic acid;

4-(1-((5-methoxy-7-methyl-1H-indol-4-yl)methyl)-4-(3-(trifluoromethoxy)azetidin-1-yl)piperidin-2-yl)benzoic acid;

4-((2S,4S)-4-(3-cyanoazetidin-1-yl)-1-((5-methoxy-7-methyl-1H-indol-4-yl)methyl)piperidin-2-yl)benzoic acid; (Example 73)

4-((2R,4R)-4-(3-cyanoazetidin-1-yl)-1-((5-methoxy-7-methyl-1H-indol-4-yl)methyl)piperidin-2-yl)benzoic acid;

4-((2S,4R)-4-(3-cyanoazetidin-1-yl)-1-((5-methoxy-7-methyl-1H-indol-4-yl)methyl)piperidin-2-yl)benzoic acid;

4-((2R,4S)-4-(3-cyanoazetidin-1-yl)-1-((5-methoxy-7-methyl-1H-indol-4-yl)methyl)piperidin-2-yl)benzoic acid;

4-(4-(3-cyanoazetidin-1-yl)-1-((5-methoxy-7-methyl-1H-indol-4-yl)methyl)piperidin-2-yl)benzoic acid;

4-((2S,4S)-4-(3-(difluoromethyl)azetidin-1-yl)-1-((5-methoxy-7-methyl-1H-indol-4-yl)methyl)piperidin-2-yl)benzoic acid; (Example 74)

4-((2R,4R)-4-(3-(difluoromethyl)azetidin-1-yl)-1-((5-methoxy-7-methyl-1H-indol-4-yl)methyl)piperidin-2-yl)benzoic acid;

4-((2S,4R)-4-(3-(difluoromethyl)azetidin-1-yl)-1-((5-methoxy-7-methyl-1H-indol-4-yl)methyl)piperidin-2-yl)benzoic acid;

4-((2R,4S)-4-(3-(difluoromethyl)azetidin-1-yl)-1-((5-methoxy-7-methyl-1H-indol-4-yl)methyl)piperidin-2-yl)benzoic acid;

4-(4-(3-(difluoromethyl)azetidin-1-yl)-1-((5-methoxy-7-methyl-1H-indol-4-yl)methyl)piperidin-2-yl)benzoic acid;

4-((2S,4S)-1-((3-chloro-5-methoxy-7-methyl-1H-indol-4-yl)methyl)-4-(3-(trifluoromethyl)azetidin-1-yl)piperidin-2-yl)benzoic acid; (Example 75)

4-((2R,4R)-1-((3-chloro-5-methoxy-7-methyl-1H-indol-4-yl)methyl)-4-(3-(trifluoromethyl)azetidin-1-yl)piperidin-2-yl)benzoic acid;

4-((2S,4R)-1-((3-chloro-5-methoxy-7-methyl-1H-indol-4-yl)methyl)-4-(3-(trifluoromethyl)azetidin-1-yl)piperidin-2-yl)benzoic acid;

4-((2R,4S)-1-((3-chloro-5-methoxy-7-methyl-1H-indol-4-yl)methyl)-4-(3-(trifluoromethyl)azetidin-1-yl)piperidin-2-yl)benzoic acid;

4-(1-((3-chloro-5-methoxy-7-methyl-1H-indol-4-yl)methyl)-4-(3-(trifluoromethyl)azetidin-1-yl)piperidin-2-yl)benzoic acid;

4-((2S,4S)-1-((5-cyclopropyl-7-methyl-1H-indol-4-yl)methyl)-4-(3-(trifluoromethyl)azetidin-1-yl)piperidin-2-yl)benzoic acid; (Example 76)

4-((2R,4R)-1-((5-cyclopropyl-7-methyl-1H-indol-4-yl)methyl)-4-(3-(trifluoromethyl)azetidin-1-yl)piperidin-2-yl)benzoic acid;

4-((2S,4R)-1-((5-cyclopropyl-7-methyl-1H-indol-4-yl)methyl)-4-(3-(trifluoromethyl)azetidin-1-yl)piperidin-2-yl)benzoic acid;

4-((2R,4S)-1-((5-cyclopropyl-7-methyl-1H-indol-4-yl)methyl)-4-(3-(trifluoromethyl)azetidin-1-yl)piperidin-2-yl)benzoic acid;

4-(1-((5-cyclopropyl-7-methyl-1H-indol-4-yl)methyl)-4-(3-(trifluoromethyl)azetidin-1-yl)piperidin-2-yl)benzoic acid;

4-((2S,4S)-4-(3-cyanoazetidin-1-yl)-1-((5-cyclopropyl-7-methyl-1H-indol-4-yl)methyl)piperidin-2-yl)benzoic acid; (Example 77)

4-((2R,4R)-4-(3-cyanoazetidin-1-yl)-1-((5-cyclopropyl-7-methyl-1H-indol-4-yl)methyl)piperidin-2-yl)benzoic acid;

4-((2S,4R)-4-(3-cyanoazetidin-1-yl)-1-((5-cyclopropyl-7-methyl-1H-indol-4-yl)methyl)piperidin-2-yl)benzoic acid;

4-((2R,4S)-4-(3-cyanoazetidin-1-yl)-1-((5-cyclopropyl-7-methyl-1H-indol-4-yl)methyl)piperidin-2-yl)benzoic acid;

4-(4-(3-cyanoazetidin-1-yl)-1-((5-cyclopropyl-7-methyl-1H-indol-4-yl)methyl)piperidin-2-yl)benzoic acid;

4-((2S,4S)-1-((5-cyclopropyl-7-methyl-1H-indol-4-yl)methyl)-4-(5-azaspiro[2.3]hexan-5-yl)piperidin-2-yl)benzoic acid; (Example 78)

4-((2R,4R)-1-((5-cyclopropyl-7-methyl-1H-indol-4-yl)methyl)-4-(5-azaspiro[2.3]hexan-5-yl)piperidin-2-yl)benzoic acid;

4-((2S,4R)-1-((5-cyclopropyl-7-methyl-1H-indol-4-yl)methyl)-4-(5-azaspiro[2.3]hexan-5-yl)piperidin-2-yl)benzoic acid;

4-((2R,4S)-1-((5-cyclopropyl-7-methyl-1H-indol-4-yl)methyl)-4-(5-azaspiro[2.3]hexan-5-yl)piperidin-2-yl)benzoic acid;

4-(1-((5-cyclopropyl-7-methyl-1H-indol-4-yl)methyl)-4-(5-azaspiro[2.3]hexan-5-yl)piperidin-2-yl)benzoic acid;

4-((2S,4S)-1-((5-methoxy-7-methyl-1H-indol-4-yl)methyl)-4-(3-(methylsulfonyl)azetidin-1-yl)piperidin-2-yl)benzoic acid; (Example 79)

4-((2R,4R)-1-((5-methoxy-7-methyl-1H-indol-4-yl)methyl)-4-(3-(methylsulfonyl)azetidin-1-yl)piperidin-2-yl)benzoic acid;

4-((2S,4R)-1-((5-methoxy-7-methyl-1H-indol-4-yl)methyl)-4-(3-(methylsulfonyl)azetidin-1-yl)piperidin-2-yl)benzoic acid;

4-((2R,4S)-1-((5-methoxy-7-methyl-1H-indol-4-yl)methyl)-4-(3-(methylsulfonyl)azetidin-1-yl)piperidin-2-yl)benzoic acid;

4-(1-((5-methoxy-7-methyl-1H-indol-4-yl)methyl)-4-(3-(methylsulfonyl)azetidin-1-yl)piperidin-2-yl)benzoic acid;

4-((2S,4S)-4-(3-fluoroazetidin-1-yl)-1-((5-methoxy-7-methyl-1H-indol-4-yl)methyl)piperidin-2-yl)benzoic acid; (Example 80)

4-((2R,4R)-4-(3-fluoroazetidin-1-yl)-1-((5-methoxy-7-methyl-1H-indol-4-yl)methyl)piperidin-2-yl)benzoic acid;

4-((2S,4R)-4-(3-fluoroazetidin-1-yl)-1-((5-methoxy-7-methyl-1H-indol-4-yl)methyl)piperidin-2-yl)benzoic acid;

4-((2R,4S)-4-(3-fluoroazetidin-1-yl)-1-((5-methoxy-7-methyl-1H-indol-4-yl)methyl)piperidin-2-yl)benzoic acid;

4-(4-(3-fluoroazetidin-1-yl)-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(oxetan-3-yloxy)piperidin-2-yl)benzoic acid; (Example 82)

4-((2R,4R)-1-((5-methoxy-7-methyl-1H-indol-4-yl)methyl)-4-(oxetan-3-yloxy)piperidin-2-yl)benzoic acid;

4-((2S,4R)-1-((5-methoxy-7-methyl-1H-indol-4-yl)methyl)-4-(oxetan-3-yloxy)piperidin-2-yl)benzoic acid;

4-((2R,4S)-1-((5-methoxy-7-methyl-1H-indol-4-yl)methyl)-4-(oxetan-3-yloxy)piperidin-2-yl)benzoic acid;

4-(1-((5-methoxy-7-methyl-1H-indol-4-yl)methyl)-4-(oxetan-3-yloxy)piperidin-2-yl)benzoic acid;

4-((2S,4S)-4-(2,2-difluoroethoxy)-1-((5-methoxy-7-methyl-1H-indol-4-yl)methyl)piperidin-2-yl)benzoic acid; (Example 83)

4-((2R,4R)-4-(2,2-difluoroethoxy)-1-((5-methoxy-7-methyl-1H-indol-4-yl)methyl)piperidin-2-yl)benzoic acid;

4-((2S,4R)-4-(2,2-difluoroethoxy)-1-((5-methoxy-7-methyl-1H-indol-4-yl)methyl)piperidin-2-yl)benzoic acid;

4-((2R,4S)-4-(2,2-difluoroethoxy)-1-((5-methoxy-7-methyl-1H-indol-4-yl)methyl)piperidin-2-yl)benzoic acid;

4-(4-(2,2-difluoroethoxy)-1-((5-methoxy-7-methyl-1H-indol-4-yl)methyl)piperidin-2-yl)benzoic acid;

4-((2S,4S)-4-cyclobutoxy-1-((5-methoxy-7-methyl-1H-indol-4-yl)methyl)piperidin-2-yl)benzoic acid; (Example 84)

4-((2R,4R)-4-cyclobutoxy-1-((5-methoxy-7-methyl-1H-indol-4-yl)methyl)piperidin-2-yl)benzoic acid;

4-((2S,4R)-4-cyclobutoxy-1-((5-methoxy-7-methyl-1H-indol-4-yl)methyl)piperidin-2-yl)benzoic acid;

4-((2R,4S)-4-cyclobutoxy-1-((5-methoxy-7-methyl-1H-indol-4-yl)methyl)piperidin-2-yl)benzoic acid;

4-(4-cyclobutoxy-1-((5-methoxy-7-methyl-1H-indol-4-yl)methyl)piperidin-2-yl)benzoic acid;

4-((2S,4S)-1-((5-methoxy-7-methyl-1H-indol-4-yl)methyl)-4-(2,2,2-trifluoroethoxy)piperidin-2-yl)benzoic acid; (Example 85)

4-((2R,4R)-1-((5-methoxy-7-methyl-1H-indol-4-yl)methyl)-4-(2,2,2-trifluoroethoxy)piperidin-2-yl)benzoic acid;

4-((2S,4R)-1-((5-methoxy-7-methyl-1H-indol-4-yl)methyl)-4-(2,2,2-trifluoroethoxy)piperidin-2-yl)benzoic acid;

4-((2R,4S)-1-((5-methoxy-7-methyl-1H-indol-4-yl)methyl)-4-(2,2,2-trifluoroethoxy)piperidin-2-yl)benzoic acid; and 4-(1-((5-methoxy-7-methyl-1H-indol-4-yl)methyl)-4-(2,2,2-trifluoroethoxy)piperidin-2-yl)benzoic acid.

Embodiment 111: A pharmaceutical composition comprising a compound of any one of embodiments 1 to 110, or a pharmaceutically acceptable salt thereof; and a pharmaceutically acceptable carrier.

Embodiment 112: A method of treating a disease or disorder associated with complement factor B (CFB), comprising administering to a subject having such disease or disorder, a therapeutically effective amount of a compound of any one of embodiments 1 to 110 or a pharmaceutically acceptable salt thereof, or a pharmaceutical composition of embodiment 111.

Embodiment 113: A method of treating or preventing a disease or disorder selected from autoimmune disease or disorder, inflammatory disease or disorder, metabolic disease or disorder, neurological disease or disorder, pulmonary disease, respiratory disease or disorder, ophthalmic disease, cardiovascular disease, and kidney disease, comprising administering to a subject having such disease or disorder, a therapeutically effective amount of a compound of any one of embodiments 1 to 110, a pharmaceutically acceptable salt thereof, or a pharmaceutical composition of embodiment 111.

Embodiment 114: A method of treating or preventing a disease or disorder selected from multiple sclerosis, Guillain Barre Syndrome, traumatic brain injury, Parkinson's disease, age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retinochoroiditis, sympathetic ophthalmia, ocular cicatricial pemphigoid, ocular pemphigus, nonarteritic ischemic optic neuropathy, post-operative inflammation, retinal vein occlusion, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, stroke, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis, obesity and metabolic syndrome, comprising administering to a subject having such disease or disorder, a therapeutically effective amount of a compound of any one of embodiments 1 to 110, a pharmaceutically acceptable salt thereof, or a pharmaceutical composition of embodiment 111.

Embodiment 115: A method of treating or preventing a disease or disorder selected from kidney disease, chronic kidney disease, diabetic nephropathy, glomerular kidney disease, complement C3 glomerulopathy (C3G), IgA nephropathy (IgAN), membranous nephropathy (MN), focal segmental glomerulosclerosis (FSGS), atypical hemolytic uremic syndrome (aHUS), dense-deposit disease (DDD), minimal change disease (MCD), paroxysmal nocturnal hemoglobinuria (PNH), ANCA-associated vasculitis, lupus nephritis and polycystic kidney disease (PKD), comprising administering to a subject having such disease or disorder, a therapeutically effective amount of a compound of any one of embodiments 1 to 110, a pharmaceutically acceptable salt thereof, or a pharmaceutical composition of embodiment 111.

Embodiment 116: The method of any one of embodiments 112 to 115 further comprising administering to the subject a therapeutically effective amount of a second therapeutic agent.

Embodiment 117: Use of a compound of any one of embodiments 1 to 110 or a pharmaceutically acceptable salt thereof, or a pharmaceutical composition of embodiment 111, for preparing, or for the manufacture of, a medicament for use in treating a disease or disorder associated with CFB.

Embodiment 118: The use of a compound of any one of embodiments 1 to 110, a pharmaceutically acceptable salt thereof, or a pharmaceutical composition of embodiment 111, for preparing, or for the manufacture of, a medicament for use in treating or preventing a disease or disorder selected from multiple sclerosis, Guillain Barre Syndrome, traumatic brain injury, Parkinson's disease, age-related macular degeneration, geographic atrophy, diabetic retinopathy, uveitis, retinitis pigmentosa, macular edema, Behcet's uveitis, multifocal choroiditis, Vogt-Koyangi-Harada syndrome, intermediate uveitis, birdshot retinochoroiditis, sympathetic ophthalmia, ocular cicatricial pemphigoid, ocular pemphigus, nonarteritic ischemic optic neuropathy, post-operative inflammation, retinal vein occlusion, hemodialysis complications, hyperacute allograft rejection, xenograft rejection, interleukin-2 induced toxicity during IL-2 therapy, inflammatory disorders, inflammation of autoimmune diseases, Crohn's disease, adult respiratory distress syndrome, myocarditis, post-ischemic reperfusion conditions, myocardial infarction, stroke, balloon angioplasty, post-pump syndrome in cardiopulmonary bypass or renal bypass, atherosclerosis, hemodialysis, renal ischemia, mesenteric artery reperfusion after aortic reconstruction, infectious disease or sepsis, immune complex disorders and autoimmune diseases, rheumatoid arthritis, systemic lupus erythematosus (SLE), SLE nephritis, proliferative nephritis, liver fibrosis, hemolytic anemia, myasthenia gravis, tissue regeneration, neural regeneration, dyspnea, hemoptysis, ARDS, asthma, chronic obstructive pulmonary disease (COPD), emphysema, pulmonary embolisms and infarcts, pneumonia, fibrogenic dust diseases, pulmonary fibrosis, asthma, allergy, bronchoconstriction, hypersensitivity pneumonitis, parasitic diseases, Goodpasture's Syndrome, pulmonary vasculitis, Pauci-immune vasculitis, immune complex-associated inflammation, antiphospholipid syndrome, glomerulonephritis, obesity, metabolic syndrome, kidney disease, chronic kidney disease, diabetic nephropathy, glomerular kidney disease, Complement C3 glomerulopathy (C3G), IgA nephropathy (IgAN), membranous nephropathy (MN), focal segmental glomerulosclerosis (FSGS), atypical hemolytic uremic syndrome (aHUS), dense-deposit disease (DDD), minimal change disease (MCD), paroxysmal nocturnal hemoglobinuria (PNH), ANCA-associated vasculitis, lupus nephritis and polycystic kidney disease (PKD).

F. Examples

The starting materials used for the synthesis were synthesized according to known literature procedures or obtained from commercial sources, such as, but not limited to, Sigma-Aldrich, Fluka, Acros Organics, Alfa Aesar, VWR Scientific, and the like. Nuclear Magnetic Resonance (NMR) analysis was conducted using a Bruker Acuity 300 MHz or 400 MHz spectrometer with an appropriate deuterated solvent. NMR chemical shift (6) is expressed in units of parts per million (ppm). LCMS analysis was conducted using a Waters Acquity UPLC with a QDA MS detector using a Waters C18 BEH 1.7 μm, 2.1×50 mm column, eluting with 95:5 to 0:100 H2O:MeCN+0.1% formic acid at a flow rate of 0.6 mL/min over 3.5 minutes. Alternatively, LCMS was conducted using a Shimadzu LCMS-2020 using a Ascentis Express C18 2.7 μm, 3.0×50 mm column, eluting with 95:5 to 0:100 H2O:MeCN+0.05% trifluoroacetic acid at a flow rate of 1.5 mL/min over 3.0 minutes. The MS detector was set up to scan under both positive and negative mode ions ranging from 100-1200 Daltons. General methods for the preparation of compounds can be modified using appropriate reagents and conditions for the introduction of the various moieties found in the structures as provided herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. Various alternatives to the embodiments of the invention described herein may be employed in practicing the invention. It is intended that the following claims define the scope of the invention and that methods and structures within the scope of these claims and their equivalents be covered thereby.

Standard abbreviations and acronyms as defined in Journal of Organic Chemistry's Author's Guideline at https://pubs.acs.orf/userimages/ContentEditor/1218717864819/joceah_abbreviations.pdf are used herein. Other abbreviations and acronyms used herein are as follows:

TABLE 1

| Abbreviations | |
|---|---|
| Ac | acetate |
| aq. | aqueous |
| $B_2pin_2$ | (pinacolato)diboron |
| C | Celsius |
| Cbz-Cl | benzyl chloroformate |
| 4-CzIPN | 2,4,5,6-tetra(9H-carbazol-9-yl)isophthalonitrile |
| DAST | diethylaminosulfur trifluoride |
| DIAD | diisopropyl azodicarboxylate |
| DCE | dichloroethane |
| DMF | dimethylformamide |
| DMSO | dimethylsulfoxide |
| EtOAc | ethyl acetate |
| Et | ethyl |
| equiv | equivalents |
| h | hours |
| HBpin | 4,4,5,5-tetramethyl-1,3,2-dioxaborolane |
| Hünig's base | N,N-diisopropylethylamine |
| g | grams |
| L | liter |
| LCMS | liquid chromatography - mass spectrometry |
| LiHMDS | lithium bis(trimethylsilyl)amide |
| liq. | liquid |
| M | molar |
| Me | methyl |
| MeCN | acetonitrile |
| mg | milligrams |
| mL | milliliter |
| mm | millimeters |
| mmol | millimoles |
| mol | moles |
| MS | mass spectrometry |
| MsCl | methanesulfonyl chloride |
| NBS | N-bromosuccinimide |
| nm | nanometers |
| Pd/C | palladium supported on carbon |
| $Pd(dppf)Cl_2•CH_2Cl_2$ | [1,1'-bis(diphenylphosphino)ferrocene]dichloropalladium(II), complex with dichloromethane |
| $Pd(PPh_3)_4$ | tetrakis(triphenylphosphine)palladium(0) |
| $Pd(PPh_3)Cl_2$ | bis(triphenylphosphine)palladium(II) dichloride |
| $PPh_3$ | triphenylphosphine |
| Pr | propyl |
| sat. | saturated |
| $scCO_2$ | super critical carbon dioxide |
| TBDPS | tert-butyldiphenylsilyl |
| TBAF | tetra-n-butylammonium fluoride |
| tBuXPhos-Pd-G3 | [(2-di-tert-butylphosphino-2',4',6'-triisopropyl-1,1'-biphenyl)-2-(2'-amino-1,1'-biphenyl)]palladium(II) methanesulfonate |
| THF | tetrahydrofuran |
| TFA | trifluoroacetic acid |
| μL | microliter |
| μW | microwave reactor |
| μm | micrometers |
| v/v | volume/volume |
| wt | weight |
| XPhos-Pd-G3 | (2-dicyclohexylphosphino-2',4',6'-triisopropyl-1,1'-biphenyl)[2-(2'-amino-1,1'-biphenyl)]palladium(II) methanesulfonate |
| $Zn(CN)_2$ | zinc cyanide |

General Synthetic Schemes

In some embodiments, compounds described herein can be prepared as outlined in the following general synthetic schemes. The methods below may be conducted on pure enantiomers, mixture of enantiomers, pure diastereomers or mixture of diastereomers. The diastereomers may be separated by normal, reverse or $scCO_2$ column chromatography, utilizing achiral or chiral stationary phases. The enantiomers may be separated by normal, reverse or $scCO_2$ column chromatography, utilizing chiral stationary phases.

Method A: Heteroaryl Substituted Analogs

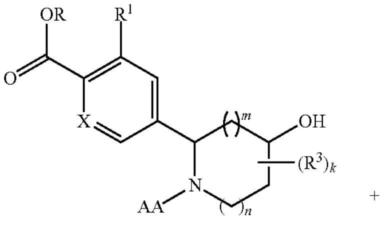

A-1
Heteroaryl
e.g.

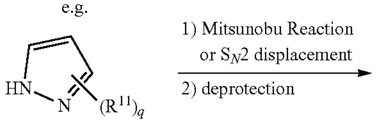

A-2

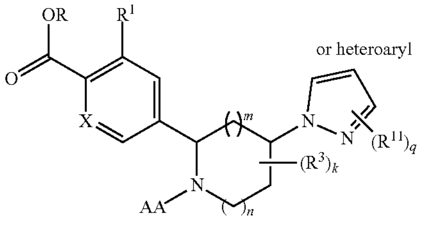

A-3

AA = PG or AA =

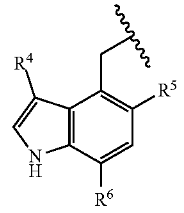

The hydroxy intermediate A-1 can be converted into a leaving group (e.g., mesylate, halide) or used directly via an Mitsunobu reaction, reacting with a heteroaryl compound (A-2, such as a pyrazole), in order to yield the heteroaryl intermediate (not shown). The nitrogen of the central heterocycle can be substituted with a protecting group, or it may contain the indole moiety. In the case of the later, ester hydrolysis and removal of the protection groups, yields the corresponding carboxylic acid targets A-3.

Method B: Amination Reaction for Amine/Amide Analogs

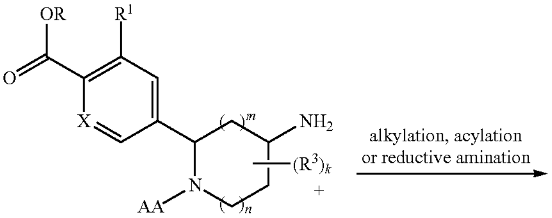

B-1

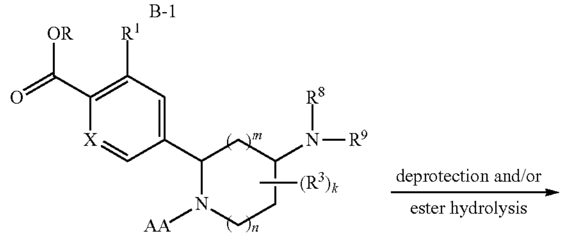

B-2

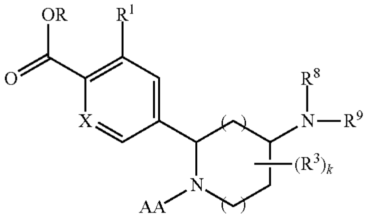

B-3

AA = PG or AA =

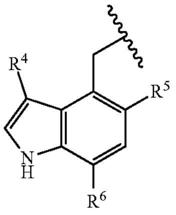

Amine intermediate B-1 is reacted with an alkylating reagent, and acylating reagent or an aldehyde or ketone, yielding the desired alkylated product B-2. This can be conducted more than one time to yield a disubstituted amine. The B-2 product can be further deprotected to yield an intermediate or hydrolyzed to yield the corresponding carboxylic acid targets B-3. Once again, the nitrogen of the central heterocycle can be substituted with a protecting group, or it may contain the indole moiety.

Method C: Reductive Amination

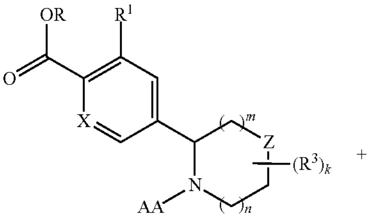

C-1

-continued

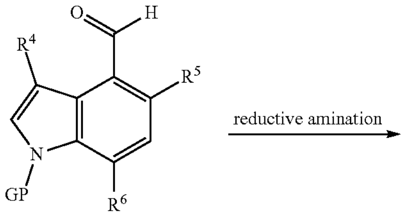

C-2

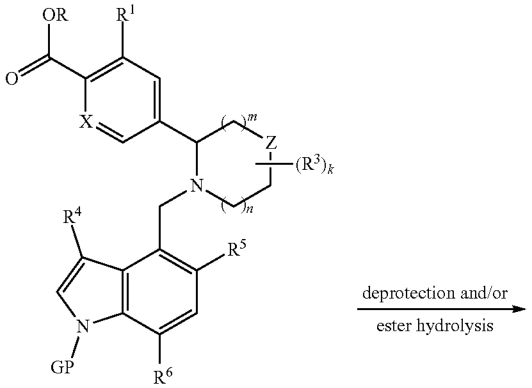

C-3

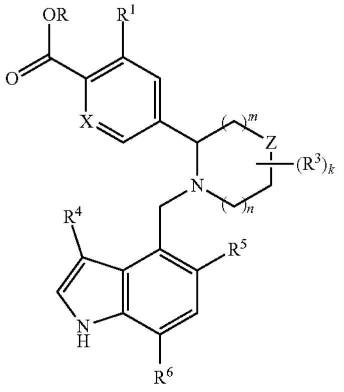

C-4

The cyclic amine C-1, which can be obtained from any of the methods listed here, either directly, or via deprotection of an N-protected analog (e.g. hydrogenation of a N-Cbz protected piperidine) is treated with C-2 under reductive amination conditions to yield product C-3. This is then followed by protecting group cleavage and ester hydrolysis, to yield the corresponding carboxylic acid or related targets C-4.

Method D: Alpha-Arylation of NH-Heterocycles

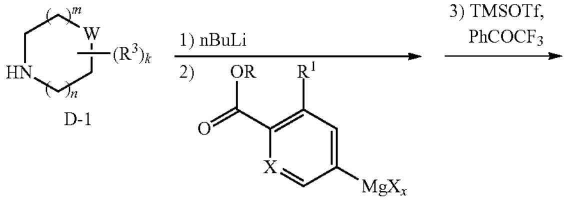

D-1 D-2

-continued

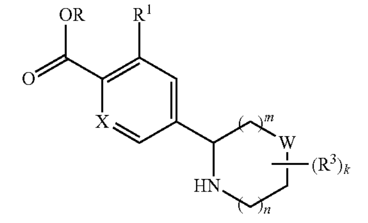

D-3

Amine intermediate D-1 is treated with a strong base, such as n-BuLi at cold temperature (e.g., −78 to −40° C.) followed by treated with an aryl-organometallic aryl, such as a Grignard reagent D-2. The product is warmed with reagents such as TMSOTf to yield the desired amine product D-3. A similar procedure is described by Siedel et. al. in *Nature Chemistry* 2018, pages 165-169.

Method E: Alpha-Arylation of NBoc-Heterocycles

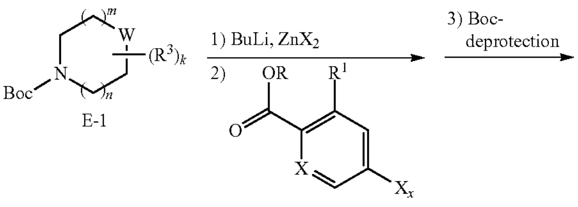

E-1

Pd/L catalyst
E-2

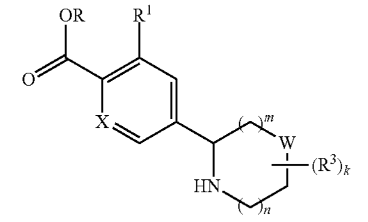

E-3

$X_x$ = Cl, Br, I, OTf

A Boc-protected cyclic amine E-1 is treated with a strong base, such as n-BuLi and an organozinc salt at cold temperature (e.g., −78 to −40° C.) followed by treated with an aryl halide E-2, under typical Pd-catalyzed cross-coupling conditions. The product can be deprotected using strong acid, such as TFA, to afford free amine E-3. A similar procedure is described by Coldham et. al. in *Organic Letters* 2008, pages 3923-3925.

Method F: Alpha-Arylation of N-Protected-Heterocycles Via Photocatalysis

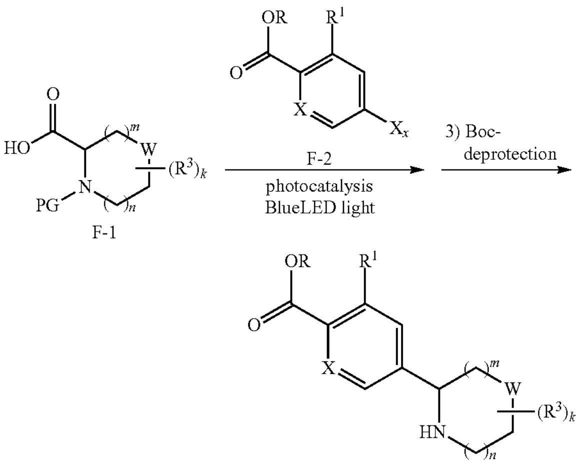

F-1

F-2

F-3

$X_x$ = CN or Br, I

A protected cyclic amino carboxylic acid intermediate F-1 is reacted with an aryl halide or aryl nitrile F-2 under photocatalysis condition (e.g., blueLED light, 4CzIPN), yielding the desired product E-3. This compound can be N-deprotected under standard conditions (e.g., TFA, when PG=Boc) to yield the desired product F-3. Similar procedures have been described by MacMillan et. al. in *Journal of the American Chemical Society* 2014, pages 5257-5260; *Science,* 2014, pages 437-440 and Zhu et. al. in *Advanced Synthesis and Catalysis,* 2020, pages 1502-1508.

Method G: Reductive Amination for Amine Analogs

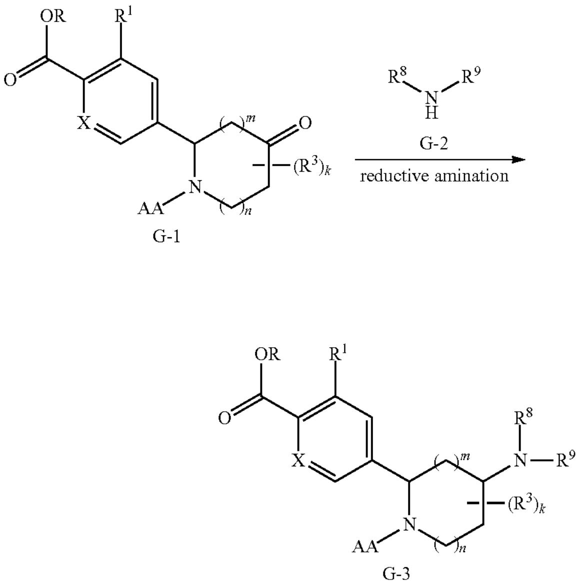

G-1

G-2

G-3

-continued

AA = PG or
AA =

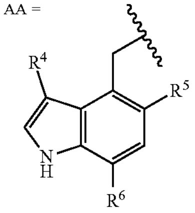

Ketone intermediate G-1 can be reacted with an amine G-2, under standard reductive amination conditions (e.g., $NaBH(OAc)_3$, DCE) to yield the desired product G-3. The nitrogen of the central heterocycle can be substituted with a protecting group, or it may contain the indole moiety.

Method H: Preparation of Alkyl Analogs Via Hydrazide-Boronic Acid Coupling

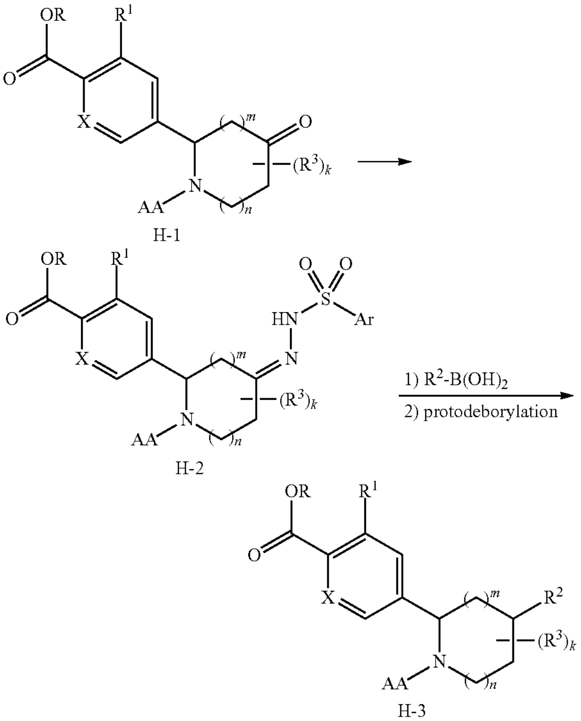

H-1

H-2

H-3

AA = PG or AA =

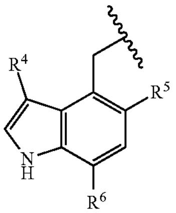

Ketone intermediate H-1 is reacted with a sulfonylhydrazine, yielding the sulfonylhydrazone H-2. This can be reacted with a boronic acid under thermal conditions, in the presence of a strong base, such as $Cs_2CO_3$, followed by in situ proto-deborylation, to yield the corresponding compound H-3, which can be further functionalized to the final products using the procedures described in the other methods. This method was described by Ley et. al. in *The Journal of Organic Chemistry,* 2014, pages 328-338.

Method I: 4-Piperidine Analogs, Including 4-Piperidine Ethers

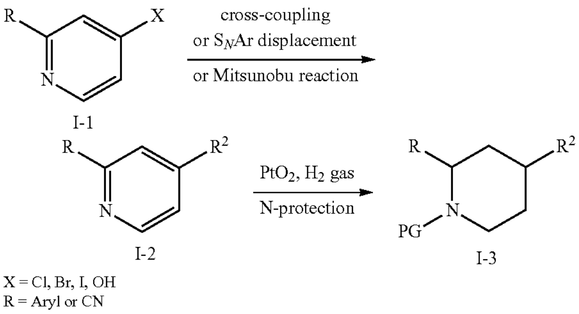

I-1 I-2 I-3

X = Cl, Br, I, OH
R = Aryl or CN

A pyridine intermediate I-1 can be further functionalized at the 4-position to introduce the $R^2$ group, using standard chemistry such as a metal-catalyzed cross-coupling from the pyridine halide, or a Mitsunobu reaction from the 4-hydroxypyridine. The intermediate I-2 is reduced under standard conditions (e.g., catalytic $PtO_2$, AcOH, hydrogen gas) to afford the protected piperidine analog I-3, which can be further transformed to the final products using the methods described within.

Method J: Conversion of Heterocyclic Alcohols to Heterocycles and Heteroaryls

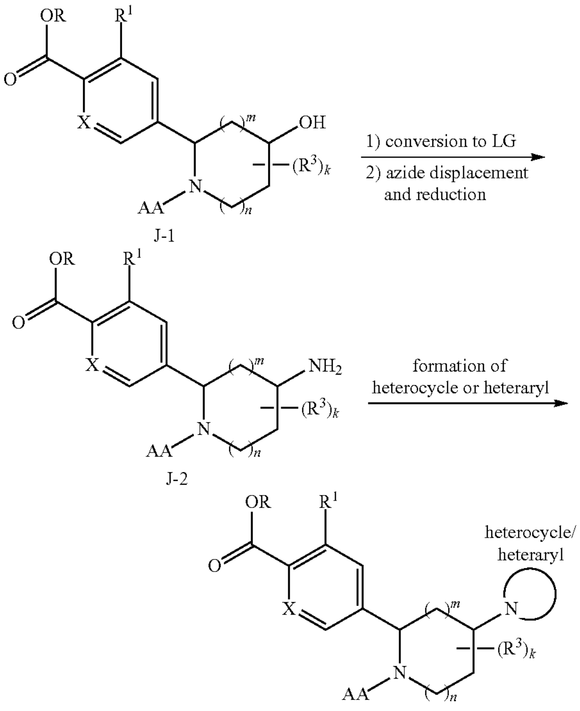

J-1 J-2 J-3

-continued

AA = PG or AA =

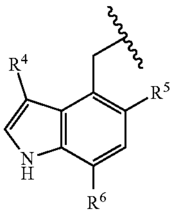

The alcohol intermediate J-1 can be transformed into a primary amine by converting the alcohol to a leaving group (e.g., OTs or OMs) followed by displacement with a nucleophilic azide and reduction under standard conditions (e.g., $PPh_3$, $H_2O$) to afford the primary amine J-2. This amine can be further transformed to a heterocycle or heteroaryl analog J-3 and then to the final products claimed using the methods described within. Alternatively, it is possible to convert J-1 directly to J-3 using conditions, such as conversion of the alcohol in J-1 to a leaving group (e.g., bromide) and coupling with a heterocycle halide under nickel catalysis to afford J-3 (reference: Baran et. al. *J. Am. Chem. Soc.,* 2016, pages 2174-2177 and Gong et. al. *Org. Lett.,* 2012, pages 3352-3355).

Method K: Conversion of Alcohols to Ether Analogs

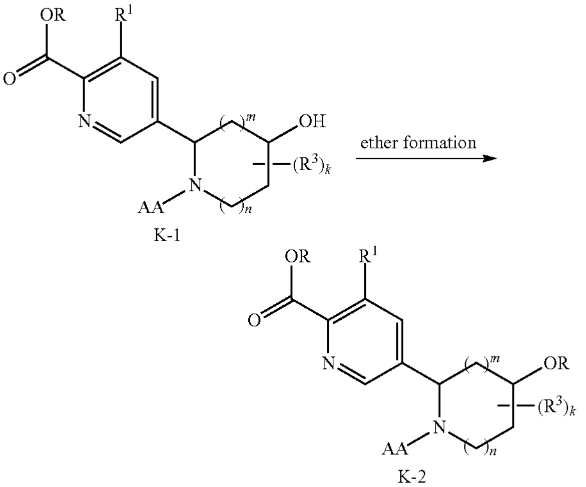

K-1 K-2

AA = PG or AA =

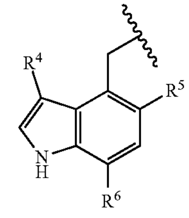

The alcohol intermediate K-1 can be converted to an ether K-2 using standard conditions described in the literature (e.g., alkyl halide, base). The ether can contain the indole moiety or be protected and converted to the final products of the claim using chemistry described in the methods within.

Method L: Cycloaddition Chemistry for Spiro Analogs

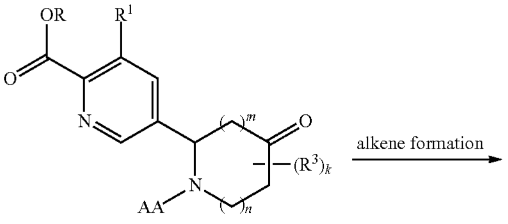

L-1

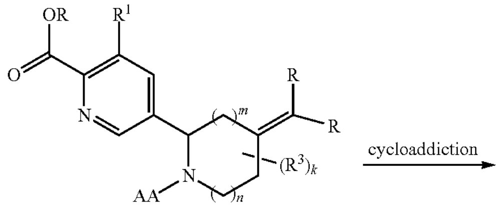

L-2

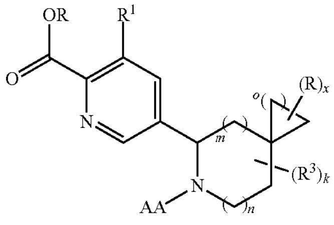
L-3

AA = PG or AA =

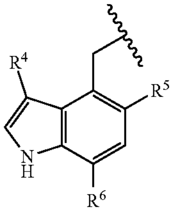

The ketone compound L-1 can be converted to an alkene L-2 using standard chemistry, such as a Wittig olefination. The olefin serves as a suitable partner for a cycloaddition reaction which, in the presence of a suitable reagent (e.g., carbene, ketene) can afford a spirocyclic compound L-3. The spirocycle can contain the indole moiety or be protected and converted to the final products of the claim using chemistry described in the methods within.

Method M: Cross-Coupling and Reduction for Analogs

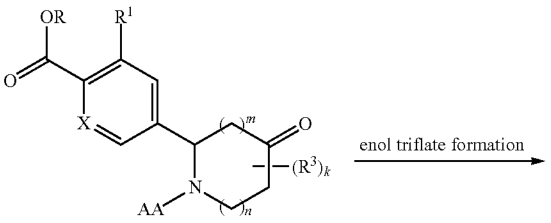

M-1

-continued

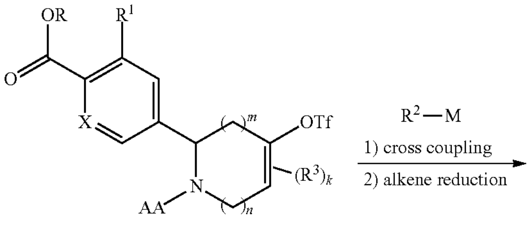

M-2

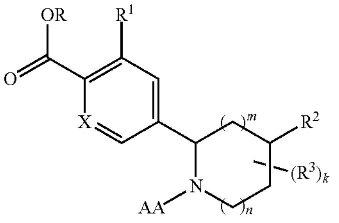
M-3

AA = PG or AA =

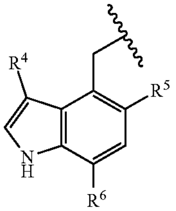

The ketone compound M-1 can be converted to an enol triflate M-2 and then coupled under standard metal-catalyzed cross-coupling conditions with an organometallic reagent, followed by reduction of the alkene to afford the product M-3. The product can contain the indole moiety or be protected and converted to the final products of the claim using chemistry described in the methods within.

Method N: N-Alkylation or Reduction Amination for Central Dinitrogen Analogs

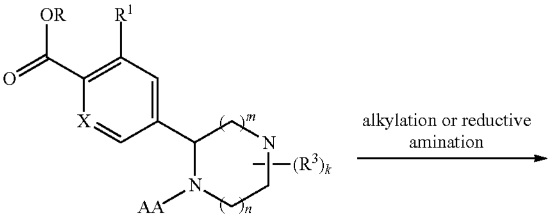

N-1

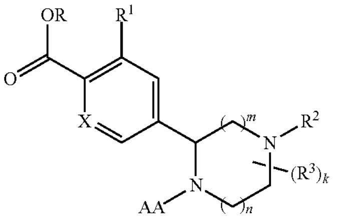
N-2

-continued

AA = PG or AA =

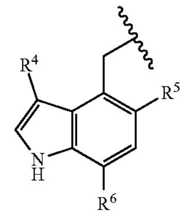

The diamine compound N-1 can be converted to N-2 via standard alkylation (e.g., an alkyl bromide, $K_2CO_3$) or via reductive amination with a ketone or aldehyde. The product can contain the indole moiety or be protected and converted to the final products of the claim using chemistry described in the methods within.

PREPARATION OF INTERMEDIATES

Intermediate A: Preparation of (+) cis and trans-benzyl 4-((tert-butyldiphenylsilyl)oxy)-2-(4-(methoxycarbonyl)phenyl)piperidine-1-carboxylate Intermediate A

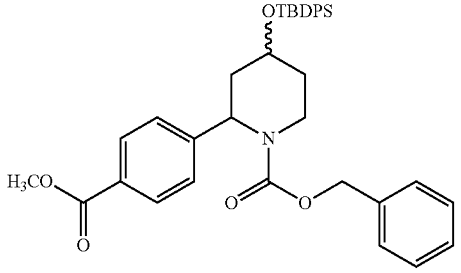

Intermediate A was prepared in a similar fashion as described in *J. Med. Chem.* 2020, 63, 11, 5697-5722, using methyl 4-iodobenzoate instead of 4-bromobenzonitrile.

Intermediate B: Preparation of (+) trans-benzyl 4-((tert-butyldiphenylsilyl)oxy)-2-(4-(methoxycarbonyl)phenyl)piperidine-1-carboxylate Intermediate B

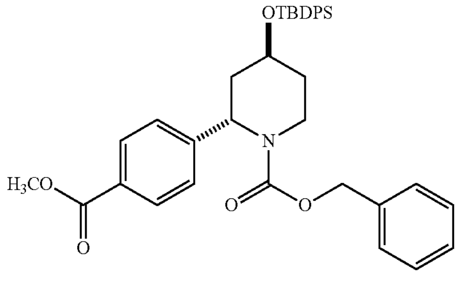

Intermediate A was loaded a silica gel column and purified by column chromatography eluting with a 0-100% EtOAc in hexanes as a gradient to afford the title product.

Intermediate C: Preparation of (±)-cis-benzyl 4-((tert-butyldiphenylsilyl)oxy)-2-(4-(methoxycarbonyl)phenyl)piperidine-1-carboxylate Intermediate C

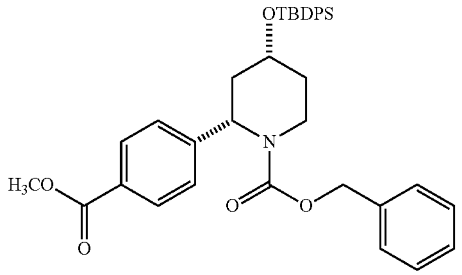

Intermediate A was loaded a silica gel column and purified by column chromatography eluting with a 0-100% EtOAc in hexanes as a gradient to afford the title product.

Intermediate D: Preparation of (W)-tert-butyl 4-((4-hydroxy-2-(4-(methoxycarbonyl)phenyl)piperidin-1-yl)methyl)-5-methoxy-7-methyl-1H-indole-1-carboxylate Intermediate D

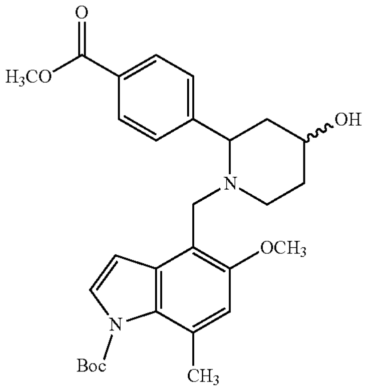

Step 1: Preparation of methyl 4-(4-((tert-butyldiphenylsilyl)oxy)piperidin-2-yl)benzoate: To a solution of Intermediate A (1.0 equiv) in THE (0.03 M) and EtOAc (0.03 M) was added 10 wt % Pd/C (0.1 equiv). The mixture was degassed with $N_2$ and then stirred at 20-25° C. for 16 hours under an H2 atmosphere. The reaction mixture was degassed with $N_2$, filtered through a plug of celite to remove the Pd/C, washed with $CH_2Cl_2$, and concentrated under reduced pressure to give a residue. The mixture was purified by column chromatography through silica gel using an eluent of 0% to 10% MeOH in $CH_2Cl_2$ as a gradient. The desired product containing fractions were concentrated and dried under vacuum to afford a grey oil (99% yield).

Step 2: Preparation of tert-butyl 4-((4-((tert-butyldiphenylsilyl)oxy)-2-(4-(methoxycarbonyl)phenyl)piperidin-1-yl)methyl)-5-methoxy-7-methyl-1H-indole-1-carboxylate: To a solution of methyl 4-(4-((tert-butyldiphenylsilyl)oxy) piperidin-2-yl)benzoate (1.0 equiv) in DCE (0.2 M) was added tert-butyl 4-formyl-5-methoxy-7-methyl-indole-1-carboxylate (1.2 equiv) and $NaBH(OAc)_3$ (2.8 equiv). The resulting mixture was stirred at 20-25° C. for 16 hours while monitoring by LCMS and TLC analysis. The solution was quenched by addition of saturated aqueous $NH_4Cl$ solution, and the mixture was extracted with EtOAc. The combined organic layers were washed with brine, dried over $Na_2SO_4$, filtered, and concentrated under reduced pressure to afford a residue. The mixture was purified by column chromatography through silica gel, using an eluent of 0% to 30% ethyl acetate in petroleum ether as a gradient. The desired product containing fractions were concentrated and dried under vacuum to afford a colorless oil (63% yield). LCMS (ESI) m/z 747 $(M+1)^+$.

Step 3: Preparation of tert-butyl 4-((4-hydroxy-2-(4-(methoxycarbonyl)phenyl)piperidin-1-yl)methyl)-5-methoxy-7-methyl-1H-indole-1-carboxylate: To a solution of tert-butyl 4-((4-((tert-butyldiphenylsilyl)oxy)-2-(4-(methoxycarbonyl)phenyl)piperidin-1-yl)methyl)-5-methoxy-7-methyl-1H-indole-1-carboxylate (1.0 equiv) in THE (0.15 M) was added TBAF (2.0 equiv) at 0° C. and the mixture was stirred at 20-25° C. for 16 hours. The reaction was monitored by LCMS and TLC analysis and stopped at completion. The reaction mixture was concentrated under reduced pressure, the resulting crude residue was diluted with $H_2O$ and extracted with EtOAc several times. The combined organic layers were washed with brine, dried over $Na_2SO_4$, filtered, and concentrated under reduced pressure to give a residue. The mixture was purified by column chromatography through silica gel, eluting with 0% to 10% ethyl acetate in petroleum ether as a gradient. The desired product containing fractions were concentrated and dried under vacuum to afford a colorless oil (75% yield). LCMS (ESI) m/z 509 $(M+1)^+$.

Intermediate E: Preparation of (W)-cis-tert-butyl 4-((4-hydroxy-2-(4-(methoxycarbonyl)phenyl)piperidin-1-yl)methyl)-5-methoxy-7-methyl-1H-indole-1-carboxylate Intermediate E

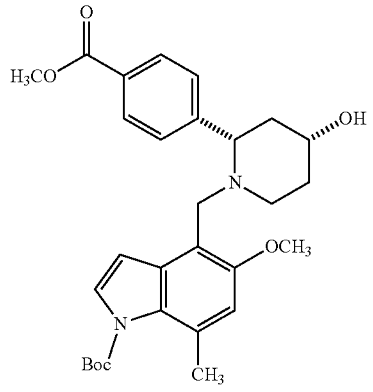

(+/-)-cis

Intermediate E was synthesized in a similar fashion as Intermediate D, using Intermediate C as starting material instead of Intermediate A.

Intermediate F: Preparation of (±)-tert-butyl 4-(((trans)-4-amino-2-(4-(methoxycarbonyl)phenyl)piperidin-1-yl)methyl)-5-methoxy-7-methyl-1H-indole-1-carboxylate Intermediate F

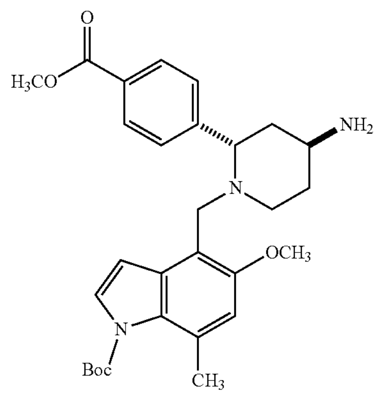

(+/-)-trans

Step 1: Preparation of (±)-methyl 4-((cis)-4-((tert-butyldiphenylsilyl)oxy)piperidin-2-yl)benzoate: To a solution of (±)-(cis)-benzyl 4-((tert-butyldiphenylsilyl)oxy)-2-(4-(methoxycarbonyl)phenyl)piperidine-1-carboxylate (Intermediate C, 1.0 equiv) in MeOH (0.33 M) was added Pd/C (10 wt %, 0.12 equiv) under a nitrogen atmosphere. The suspension was degassed and purged with H2 a total of 3 times. The mixture was stirred at 20-25° C. for 7 hours under a H2 (15 psi) atmosphere. After this time, LCMS indicated the completion of the reaction. The reaction mixture was filtered through a pad of celite, and the filtrate concentrated under reduced pressure to afford (±)-methyl 4-((cis)-4-((tert-butyldiphenylsilyl)oxy)piperidin-2-yl)benzoate as a colorless gum. The crude product was used for the next step without further purification. LCMS (ESI) m/z 475 $(M+1)^+$.

Step 2: Preparation of (±)-tert-butyl 4-(((cis)-4-((tert-butyldiphenylsilyl)oxy)-2-(4-(methoxycarbonyl)phenyl)piperidin-1-yl)methyl)-5-methoxy-7-methyl-1H-indole-1-carboxylate: (±)-Methyl 4-((cis)-4-((tert-butyldiphenylsilyl)oxy)piperidin-2-yl)benzoate (1.0 equiv) and tert-butyl 4-formyl-5-methoxy-7-methyl-1H-indole-1-carboxylate (0.5 equiv) were dissolved in MeOH (0.7 M, mixture A) and stirred at 20-25° C. In another round bottom flask, $NaBH_3CN$ (2.0 equiv) and $ZnCl_2$ (1.0 equiv) were dissolved in MeOH (0.7 M, mixture B). Both mixtures were vigorous stirred under a nitrogen atmosphere at 20-25° C. After 1.5 hours, mixture B was added to mixture A, and the final combined reaction mixture was stirred under a nitrogen atmosphere for 20 hours at 35° C. After this time, another portion of tert-butyl 4-formyl-5-methoxy-7-methyl-1H-indole-1-carboxylate (0.5 equiv) was added to the mixture at 20-25° C. and stirring was continued at 35° C. for another 24.5 hours. The reaction mixture was evaporated under vacuum to remove the solvent and the residue was diluted with EtOAc. The suspension was then washed with $H_2O$, dried over anhydrous $Na_2SO_4$, filtered and concentrated under reduced pressure to give a residue. The residue was purified by column chromatography through silica gel, eluting with 0% to 5% ethyl acetate in petroleum ether as a gradient, to yield the title product as a white solid (52% yield). $^1H$-NMR (400 MHz, $CDCl_3$): δ 8.04 (d, J=8.4 Hz, 2H), 7.65-7.62 (m, 4H), 7.56 (d, J=7.2 Hz, 2H), 7.47 (d, J=3.6 Hz, 1H), 7.42-7.39 (m, 2H), 7.37-7.33 (m, 4H), 6.64-6.62 (m, 2H), 3.92 (s, 3H), 3.75 (s, 3H), 3.74-3.73 (m, 1H), 3.52 (d, J=12.4 Hz, 1H), 3.13 (d, J 12.4 Hz, 1H), 3.05 (dd, J=11.6, 2.8 Hz, 1H), 2.74-2.69 (m, 1H), 2.57 (s, 3H), 1.91-1.88 (m, 1H), 1.84-1.78 (m, 2H), 1.64 (s, 2H), 1.62 (s, 9H), 1.01 (s, 9H). LCMS (ESI) m/z 747 $(M+1)^+$.

Step 3: Preparation of (±)-tert-butyl 4-(((cis)-4-hydroxy-2-(4-(methoxycarbonyl)phenyl)piperidin-1-yl)methyl)-5-methoxy-7-methyl-1H-indole-1-carboxylate: To a solution of (±)-tert-butyl 4-(((cis)-4-((tert-butyldiphenylsilyl)oxy)-2-(4-(methoxycarbonyl)phenyl)piperidin-1-yl)methyl)-5-methoxy-7-methyl-1H-indole-1-carboxylate (1.0 equiv) in THE (0.22 M) was added TBAF (1 M, 4.0 equiv) at 0° C. The mixture was stirred at 20-25° C. for 4 hours. The reaction mixture was quenched by addition of saturated aqueous $NH_4Cl$ solution at 20-25° C., and the mixture was extracted with EtOAc. The combined organic layers were dried over anhydrous $Na_2SO_4$, filtered and concentrated under reduced pressure to afford a residue. The residue was purified by column chromatography through silica gel, eluting with 0 to 67% ethyl acetate in petroleum ether as a gradient, to yield the title compound as a yellow solid (83% yield). $^1$H-NMR (400 MHz, $CDCl_3$): δ 8.07 (d, J=8.4 Hz, 2H), 7.62 (d, J=7.6 Hz, 2H), 7.49 (d, J=3.6 Hz, 1H), 6.68 (s, 1H), 6.62 (d, J=3.6 Hz, 1H), 3.93 (s, 3H), 3.80 (s, 3H), 3.77-3.71 (m, 1H), 3.60 (d, J=12.4 Hz, 1H), 3.28-3.22 (m, 2H), 2.92-2.87 (m, 1H), 2.59 (s, 3H), 2.11-2.07 (m, 1H), 2.03-2.02 (m, 1H), 1.89-1.84 (m, 1H), 1.70-1.64 (m, 1H), 1.62 (s, 9H), 1.55-1.45 (m, 2H). LCMS (ESI) m/z 509 $(M+1)^+$.

Step 4: Preparation of (±)-tert-butyl 5-methoxy-4-(((cis)-2-(4-(methoxycarbonyl)phenyl)-4-((methylsulfonyl)oxy)piperidin-1-yl)methyl)-7-methyl-1H-indole-1-carboxylate: To a solution of (±)-tert-butyl 4-(((cis)-4-hydroxy-2-(4-(methoxycarbonyl)phenyl)piperidin-1-yl)methyl)-5-methoxy-7-methyl-1H-indole-1-carboxylate (1.0 equiv) in $CH_2Cl_2$ (0.15 M) was added $Et_3N$ (2.5 equiv) followed by MsCl (1.8 equiv) at 0° C. The mixture was then stirred at 20-25° C. for 0.5 hours. TLC analysis indicated the completion of the mixture. The reaction mixture was diluted with $CH_2Cl_2$, washed with $H_2O$, brine, dried over anhydrous $Na_2SO_4$, filtered and concentrated under reduced pressure to afford a residue. The residue was purified by column chromatography through silica gel, eluting with 0% to 20% ethyl acetate in petroleum ether as a gradient, to give the title compound as a yellow solid (87% yield). $^1$H-NMR (400 MHz, $CDCl_3$): δ 8.08 (d, J=8.4 Hz, 2H), 7.61 (d, J=7.6 Hz, 2H), 7.49 (d, J=3.6 Hz, 1H), 6.68 (s, 1H), 6.55 (d, J=4.0 Hz, 1H), 4.78-4.71 (m, 1H), 3.93 (s, 3H), 3.80 (s, 3H), 3.59 (d, J=12.0 Hz, 1H), 3.33 (dd, J=11.6, 2.6 Hz, 1H), 3.24 (d, J=12.4 Hz, 1H), 2.98 (s, 3H), 2.97-2.92 (m, 1H), 2.59 (s, 3H), 2.27-2.22 (m, 1H), 2.17-2.10 (m, 1H), 2.02-2.01 (m, 1H), 1.96-1.90 (m, 1H), 1.84-1.74 (m, 1H), 1.62 (s, 9H).

Step 5: Preparation of (±)-tert-butyl 4-(((trans)-4-azido-2-(4-(methoxycarbonyl)phenyl)piperidin-1-yl)methyl)-5-methoxy-7-methyl-1H-indole-1-carboxylate: A mixture of (±)-tert-butyl 5-methoxy-4-(((cis)-2-(4-(methoxycarbonyl)phenyl)-4-((methylsulfonyl)oxy)piperidin-1-yl)methyl)-7-methyl-1H-indole-1-carboxylate (1.0 equiv), $NaN_3$ (3.0 equiv) in DMF (0.17 M) was heated to 100° C. for 3 hours. TLC indicated completion of the reaction, and the mixture was cooled to 20-25° C., diluted with EtOAc and quenched with saturated aqueous $NaHCO_3$ solution to pH ~9. The organic phase was then separated, washed with water, brine, dried over anhydrous $Na_2SO_4$, and then evaporated under reduced pressure to afford a residue. The residue was purified by column chromatography through silica gel, eluting with 0% to 10% EtOAc in petroleum ether as a gradient, to give the title compound a white solid (71% yield). $^1$H-NMR (400 MHz, $CDCl_3$): δ 8.06 (d, J=8.4 Hz, 2H), 7.63 (d, J=8.0 Hz, 2H), 7.49 (d, J 4.0 Hz, 1H), 6.68 (s, 1H), 6.62 (d, J=3.6 Hz, 1H), 3.98-3.94 (m, 1H), 3.93 (s, 3H), 3.81 (s, 3H), 3.64 (d, J=12.0 Hz, 1H), 3.54-3.51 (m, 1H), 3.31 (d, J=12.0 Hz, 1H), 2.71-2.67 (m, 1H), 2.59 (s, 3H), 2.41-2.34 (m, 1H), 1.91-1.82 (m, 2H), 1.80-1.70 (m, 2H), 1.62 (s, 9H).

Step 6: Preparation of (±)-tert-butyl 4-(((trans)-4-amino-2-(4-(methoxycarbonyl)phenyl)piperidin-1-yl)methyl)-5-methoxy-7-methyl-1H-indole-1-carboxylate formic acid salt: A mixture of (±)-tert-butyl 4-(((trans)-4-azido-2-(4-(methoxycarbonyl)phenyl)piperidin-1-yl)methyl)-5-methoxy-7-methyl-1H-indole-1-carboxylate (1.0 equiv), $PPh_3$ (1.5 equiv) in THE (0.20 M) was degassed and purged with nitrogen a total of 3 times, after which the mixture was heated to 50° C. for 3 hours with stirring. An aqueous solution of $NH_3 \cdot H_2O$ (12 M, 60 equiv) was added to the mixture and the mixture was stirred at 50° C. for another 16 hours. The reaction mixture was diluted with EtOAc, and the organic phase separated, washed with brine, dried over anhydrous $Na_2SO_4$, filtered and concentrated under reduced pressure to give a residue. The residue was purified by column chromatography through silica gel, eluting with 100:0 to 90:10 $CH_2Cl_2$:MeOH as a gradient to afford the title compound as a formic acid salt (white solid, 69% yield). $^1$H-NMR (1 equiv formic acid salt, 400 MHz, $CD_3OD$): δ 8.54 (s, 1H), 8.05 (d, J=8.4 Hz, 2H), 7.65 (d, J=8.4 Hz, 2H), 7.55 (d, J=4.0 Hz, 1H), 6.76 (s, 1H), 6.61 (d, J=4.0 Hz, 1H), 3.91 (s, 3H), 3.81 (s, 3H), 3.76 (d, J=12.1 Hz, 1H), 3.72 (dd, J=10.4, 3.1 Hz, 1H), 3.53-3.50 (m, 2H), 2.83-2.77 (m, 1H), 2.57-2.51 (m, 4H), 2.22-2.15 (m, 1H), 2.00-1.91 (m, 2H), 1.80 (d, J=14.0 Hz, 1H), 1.63 (s, 9H). LCMS (ESI) m/z 508 $(M+1)^+$.

Intermediate G: Preparation of (±)-tert-butyl 5-methoxy-4-((2-(4-(methoxycarbonyl)phenyl)-4-oxopiperidin-1-yl)methyl)-7-methyl-1H-indole-1-carboxylate Intermediate G

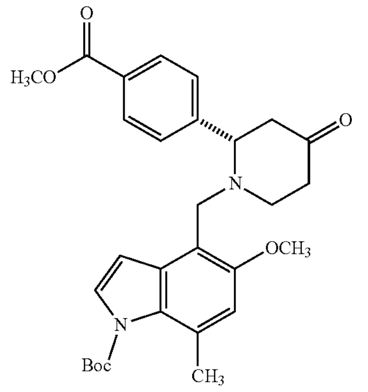

To a solution of $(COCl)_2$ (1.2 equiv) in $CH_2Cl_2$ (0.2 M) at −78° C. was added DMSO (2.5 equiv) and the mixture was stirred at −78° C. for 5 minutes. A solution of tert-butyl 4-((4-hydroxy-2-(4-(methoxycarbonyl)phenyl)piperidin-1-yl)methyl)-5-methoxy-7-methyl-1H-indole-1-carboxylate (Intermediate E, 1 equiv) in $CH_2Cl_2$ (0.16 M) was added to the above mixture while maintaining the reaction temperature at −78° C. Stirring at this temperature was continued for 30 minutes and was followed by addition of $Et_3N$ (5 equiv). The cooling bath was removed, and the reaction mixture was stirred for 1 hour at 20-25° C. Analysis by TLC revealed starting material was consumed and one major new spot had formed. The solution was quenched by addition of saturated aqueous $NH_4Cl$ solution at 0° C. and the mixture was extracted with EtOAc. Then the combined organic layers were washed with brine, dried over $Na_2SO_4$, filtered, and concentrated under reduced pressure. The residue was purified by column chromatography through silica gel, eluting with 0% to 50% ethyl acetate in petroleum ether as a gradient. The desired product containing fractions were concentrated and dried under vacuum to afford a white solid (75% yield). $^1$H-NMR (400 MHz, $CDCl_3$) δ 8.09 (d, J=8 Hz, 2H), 7.62 (d, J=8 Hz, 2H), 7.52 (d, J=4 Hz, 1H), 6.71 (s, 1H), 6.61 (d, J=4 Hz, 1H), 3.94 (s, 3H), 3.82 (s, 3H), 3.77 (d, J=12 Hz, 1H), 3.70 (dd, J=12, 4 Hz, 1H), 3.41 (d, J=12 Hz, 1H), 3.17-3.09 (m, 1H), 2.78-2.66 (m, 1H), 2.61 (s, 3H), 2.59-2.51 (m, 2H), 2.50-2.42 (m, 1H), 2.32 (dd, J=12, 4 Hz, 1H), 1.63 (s, 9H). LCMS (ESI) m/z 525 $(M+19)^+$.

Intermediate H: Preparation of benzyl (S)-2-(4-(methoxycarbonyl)phenyl)-4-oxopiperidine-1-carboxylate Intermediate H

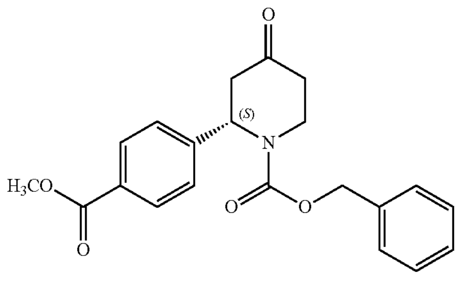

The racemic ketone derived from Intermediate A route was purified by chiral SFC method to obtain Intermediate H.

Intermediate I: Preparation of (±)-trans-benzyl-4-hydroxy-2-(4-(methoxycarbonyl)phenyl)piperidine-1-carboxylate Intermediate I

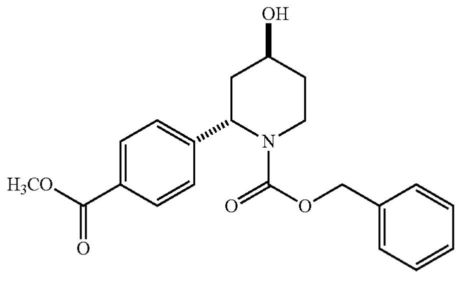

To a solution of (±)-trans-benzyl 4-((tert-butyldiphenylsilyl)oxy)-2-(4-(methoxycarbonyl)phenyl)piperidine-1-carboxylate (Intermediate B, 1.0 equiv) in THE (0.15 M) was slowly added TBAF (1.0 M, 4.0 equiv) dropwise at 0° C. After addition, the reaction mixture was stirred at 20-25° C. for 16 hours. Analysis by TLC (petroleum ether:ethyl acetate=1:1) indicated no reactant remained and a new spot had formed. The reaction mixture was concentrated under reduced pressure, diluted with $H_2O$, and extracted with ethyl acetate (3×). The combined organic layers were dried and concentrated under reduced pressure. The residue was purified by column chromatography through silica gel (eluent of 0% to 70% ethyl acetate in petroleum ether as a gradient). The desired product containing fractions were concentrated and dried under vacuum to afford a yellow oil (85% yield).

Intermediate J: Preparation of benzyl (S)-6-(4-(methoxycarbonyl)phenyl)-2-oxo-7-azaspiro[3.5]nonane-7-carboxylate Intermediate J

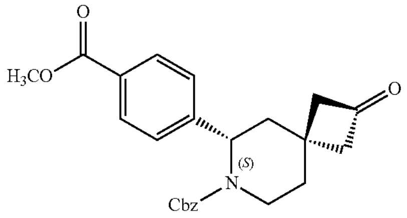

Step 1: Preparation of benzyl(S)-2-(4-(methoxycarbonyl)phenyl)-4-methylenepiperidine-1-carboxylate: To a nitrogen-purged, flame-dried flask, containing a cooled (−20° C.) suspension of methyltriphenylphosphonium bromide (1.5 equiv) in THF (0.17 M) was added a solution of lithium bis(trimethylsilyl)amide (1 M in THF, 1.5 equiv). The mixture was stirred for 2 hours at −20° C. under a nitrogen atmosphere, after which a solution of benzyl(S)-2-(4-(methoxycarbonyl)phenyl)-4-oxopiperidine-1-carboxylate (Intermediate H, 1.0 equiv) in THF (0.57 M) was added. The reaction mixture was slowly warmed to 20-25° C. and stirred for 64 hours under a nitrogen atmosphere. The reaction mixture was quenched with saturated aqueous $NH_4Cl$ and diluted with EtOAc. The aqueous layer was separated and extracted three times with EtOAc. The combined organic layers were washed with brine, concentrated under reduced pressure, applied to a silica precartridge and purified by column chromatography through silica gel, eluting with a 0-100% EtOAc in hexanes as a gradient. The fractions from the major peak eluting at 35% EtOAc in hexanes were combined and concentrated under reduced pressure to afford a colourless oil (14% yield). LCMS (ESI) m/z 366 $(M+1)^+$.

Step 2: Preparation of benzyl (6S)-1,1-dichloro-6-(4-(methoxycarbonyl)phenyl)-2-oxo-7-azaspiro[3.5]nonane-7-carboxylate: To a suspension of benzyl (S)-2-(4-(methoxycarbonyl)phenyl)-4-methylenepiperidine-1 carboxylate (1.0 equiv) and zinc-copper couple (14 equiv) in ether (0.18 M) under a nitrogen atmosphere was added, dropwise, a solution of 2,2,2-trichloroacetyl chloride (3.3 equiv) in 1,2-dimethoxyethane (3.3 M). The reaction mixture was stirred at 20-25° C. for 18 hours, after which additional 2,2,2-trichloroacetyl chloride (9.75 equiv) in 1,2-dimethoxyethane (3.3 M) was added and the reaction mixture was stirred at 20-25° C. for another 6 hours. The reaction mixture was quenched with saturated aqueous $NaHCO_3$ solution at 0° C., filtered, and the solids were washed with EtOAc. The aqueous layer was separated and extracted three times with EtOAc. The combined organic layers were washed with brine, dried over $MgSO_4$, concentrated under reduced pressure, and purified by column chromatography, eluting with a 0-100% EtOAc in hexanes gradient. The fractions from the major peaks eluting near 80% EtOAc in hexanes were combined and concentrated under vacuum to afford an orange oil (92% yield). LCMS (ESI) m/z 476 $(M+1)^+$.

Step 3: Preparation of benzyl (S)-6-(4-(methoxycarbonyl)phenyl)-2-oxo-7-azaspiro[3.5]nonane-7-carboxylate: To a solution of benzyl (6S)-1,1-dichloro-6-(4-(methoxycarbonyl)phenyl)-2-oxo-7-azaspiro[3.5]nonane-7-carboxylate (1.0 equiv) in saturated $NH_4Cl$ in methanol (0.2 M) was added zinc powder (5.8 equiv) at 20-25° C. The reaction mixture was stirred at 20-25° C. for 19 hours. The mixture was applied to a silica gel precartridge and purified by column chromatography through silica gel, eluting with a 0-100% EtOAc in hexanes gradient. The fractions from the major peak eluting at 78% EtOAc in hexanes were combined and concentrated under reduced pressure to afford a white solid (86% yield). LCMS (ESI) m/z 408 $(M+1)^+$.

PREPARATION OF EXAMPLES

Example 1: Preparation of 4-((2S,4S)-4-(4-fluoro-1H-pyrazol-1-yl)-1-((5-methoxy-7-methyl-1H-indol-4-yl)methyl)piperidin-2-yl)benzoic acid Example 1

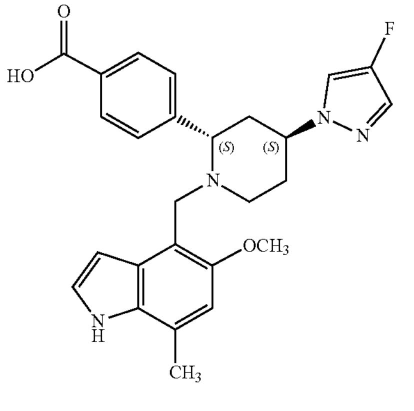

Step 1: Preparation of (±)-trans-tert-butyl 4-((4-(4-fluoro-1H-pyrazol-1-yl)-2-(4-(methoxycarbonyl)phenyl)piperidin-1-yl)methyl)-5-methoxy-7-methyl-1H-indole-1-carboxylate: A mixture of 4-fluoro-1H-pyrazole (3.0 equiv), (±)-cis-tert-butyl 4-((4-hydroxy-2-(4-(methoxycarbonyl)phenyl)piperidin-1-yl)methyl)-5-methoxy-7-methyl-1H-indole-1-carboxylate (Intermediate E, 1.0 equiv), triphenylphosphine (3.0 equiv) in THE (0.5 M) was degassed and purged with $N_2$ a total of 3 times and the mixture cooled to 0° C. After this time, di-isopropyl diazene-1,2-dicarboxylate (3.0 equiv) was added to the reaction mixture at 0° C. The mixture was stirred at 10° C. for 16 hours, then the mixture was stirred at 30° C. for 20 hours. LCMS showed that approx. 19% of desired product was detected. The reaction mixture was diluted with ethyl acetate and extracted with water. The organic layers were filtered and concentrated under reduced pressure to give a residue. The mixture was purified by column chromatography through silica gel, using an eluent of 0% to 21% ethyl acetate in petroleum ether as a gradient. The crude product was isolated as a yellow gum. LCMS (ESI) m/z 576 $(M+1)^+$.

Step 2: Preparation of (±)-trans-4-((4-(4-fluoro-1H-pyrazol-1-yl)-1-((5-methoxy-7-methyl-1H-indol-4-yl)methyl)piperidin-2-yl)benzoic acid formic acid salt: To a solution of (±)-trans-tert-butyl 4-((4-(4-fluoro-1H-pyrazol-1-yl)-2-(4-(methoxycarbonyl)phenyl)piperidin-1-yl)methyl)-5-methoxy-7-methyl-1H-indole-1-carboxylate (1.0 equiv) was added a 5.6 M aqueous LiOH/THF/MeOH solution (13.0 equiv LiOH, v/v/v, 4/7/7). The mixture was stirred while heating at 70° C. for 16 hours. LCMS indicated completion of hydrolysis, after which the mixture was cooled, and the reaction quenched with acetic acid to pH ~6. The mixture was purified by preparative-HPLC (column: Welch Xtimate C18; mobile phase: 18% to 48% $CH_3CN$ in water+0.225% formic acid as a gradient over 6 min). The desired product containing fractions were concentrated and lyophilized overnight to yield the title product as a yellow gum (formic acid salt, 22% yield). LCMS (ESI) m/z 462 $(M+1)^+$.

Step 3: Preparation of 4-((2S,4S)-4-(4-fluoro-1H-pyrazol-1-yl)-1-((5-methoxy-7-methyl-1H-indol-4-yl)methyl)piperidin-2-yl)benzoic acid: The racemic compound (±)-trans-tert-butyl 4-((2S,4S)-4-(4-fluoro-1H-pyrazol-1-yl)-1-((5-methoxy-7-methyl-1H-indol-4-yl)methyl)piperidin-2-yl)benzoic (1.0 equiv) was separated by chiral SFC column chromatography (column: Phenomenex-Cellulose-2 (250 mm×30 mm, 10 μm); mobile phase: 50% EtOH+0.1% $NH_3 \cdot H_2O$/50% $scCO_2$) to give the title compound as a light pink solid (25% yield). $^1$H-NMR (400 MHz, $CD_3OD$): δ 8.44 (bs, 1H), 8.15 (d, J=8.0 Hz, 2H), 7.83 (d, J=4.8 Hz, 1H), 7.66 (d, J 8.0 Hz, 2H), 7.55 (d, J=4.0 Hz, 1H), 7.29 (d, J=3.2 Hz, 1H), 6.74 (s, 1H), 6.27 (d, J=2.8 Hz, 1H), 4.81-4.85 (m, 1H), 4.61 (bs, 1H), 4.32 (d, J=12.4 Hz, 1H), 4.09 (d, J=12.4 Hz, 1H), 3.75 (s, 3H), 3.48-3.56 (m, 1H), 3.36-3.45 (m, 1H), 2.66 (d, J=6.0 Hz, 2H), 2.49 (s, 3H), 2.44 (d, J 2.8 Hz, 2H). $^{19}$F-NMR (376 MHz, $CD_3OD$): δ 179.54 (s). LCMS (ESI) m/z 462 $(M+1)^+$.

The following compounds were prepared in a similar manner as Example 1 replacing 4-fluoro-1H-pyrazole with the corresponding commercially available pyrazoles in the table in step 1.

| Example | Intermediate Used | Structure | MW | MS (ESI+) |
| --- | --- | --- | --- | --- |
| Example 2 | 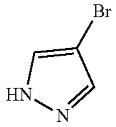 | 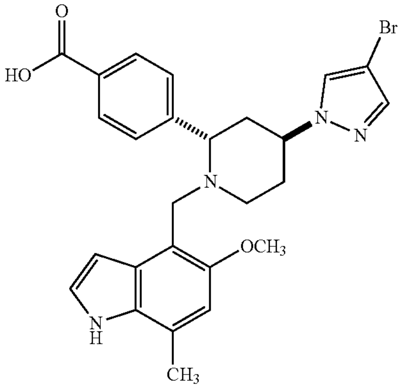 (+/-)-trans<br>(±)-trans-4-(4-(4-bromo-1H-pyrazol-1-yl)-1-((5-methoxy-7-methyl-1H-indol-4-yl)methyl)piperidin-2-yl)benzoic acid | 522.13 | 523 (M + 1)⊕ |
| Example 3 | 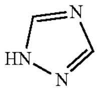 | 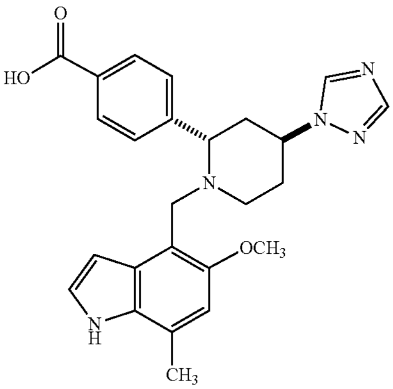 (+/-)-trans<br>(±)-trans-4-(1-((5-methoxy-7-methyl-1H-indol-4-yl)methyl)-4-(1H-1,2,4-triazol-1-yl)piperidin-2-yl)benzoic acid | 445.52 | 446 (M + 1)⊕ |
| Example 4 | 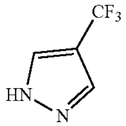 | 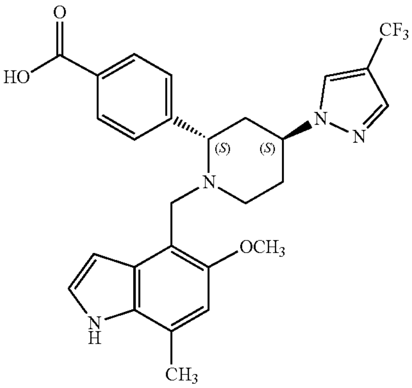 4-((2S,4S)-1-((5-methoxy-7-methyl-1H-indol-4-yl)methyl)-4-(4-(trifluoromethyl)-1H-pyrazol-1-yl)piperidin-2-yl)benzoic acid | 512.53 | 513 (M + 1)⊕ |

-continued

| Example | Intermediate Used | Structure | MW | MS (ESI+) |
|---|---|---|---|---|
| Example 5 | 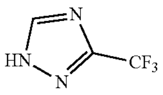 | 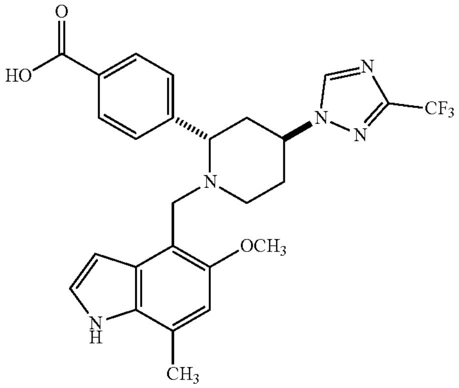<br>(+/-)-trans<br>(±)-trans-4-(1-((5-methoxy-7-methyl-1H-indol-4-yl)methyl)-4-(3-(trifluoromethyl)-1H-1,2,4-triazol-1-yl)piperidin-2-yl)benzoic acid | 513.52 | 514 (M + 1)⊕ |
| Example 6 | 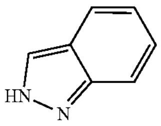 | 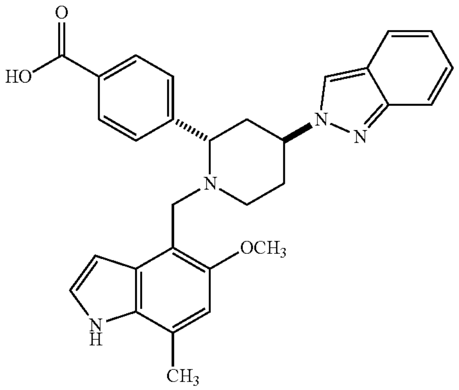<br>(+/-)-trans<br>(±)-trans-4-(4-(2H-indazol-2-yl)-1-((5-methoxy-7-methyl-1H-indol-4-yl)methyl)piperidin-2-yl)benzoic acid | 494.60 | 495 (M + 1)⊕ |
| Example 7 | 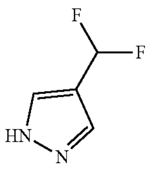 | 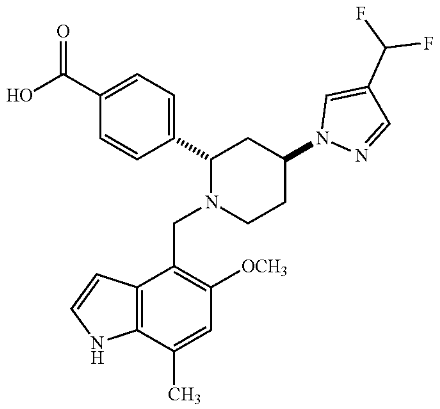<br>(+/-)-trans<br>(±)-trans-4-(4-(4-(difluoromethyl)-1H-pyrazol-1-yl)-1-((5-methoxy-7-methyl-1H-indol-4-yl)methyl)piperidin-2-yl)benzoic acid | 494.54 | 495 (M + 1)⊕ |

-continued

| Example | Intermediate Used | Structure | MW | MS (ESI+) |
|---|---|---|---|---|
| Example 8 | 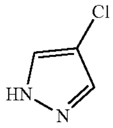 | 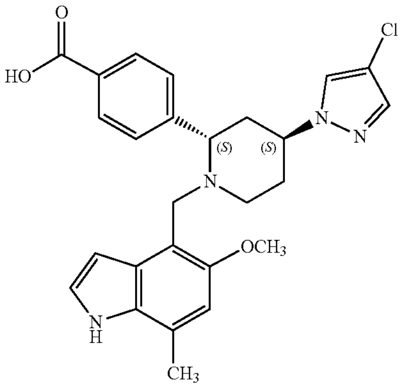 4-((2S,4S)-4-chloro-1H-pyrazol-1-yl)-1-((5-methoxy-7-methyl-1H-indol-4-yl)methyl)piperidin-2-yl)benzoic acid | 478.98 | 479 (M + 1)$^{\oplus}$ |

Example 9: Preparation of (±)-trans-4-(1-((5-methoxy-7-methyl-1H-indol-4-yl)methyl)-4-(1H-pyrazol-1-yl)piperidin-2-yl)benzoic acid Example 9

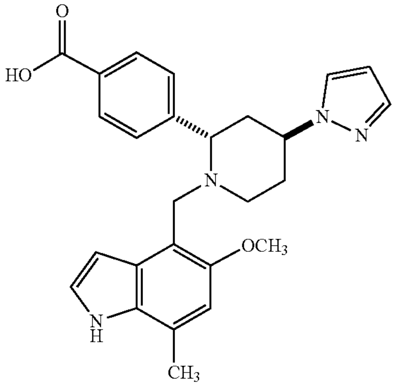

(+/-)-trans

Into a glass vial, equipped with a magnetic stir bar, a Teflon cap and under nitrogen was added (±)-trans-tert-butyl 4-((4-(4-bromo-1H-pyrazol-1-yl)-2-(4-(methoxycarbonyl) phenyl)piperidin-1-yl)methyl)-5-methoxy-7-methyl-1H-indole-1-carboxylate (1.0 equiv, synthesized as per Example 2, step 1), tBuBrettPhos-Pd-G3 (0.05 equiv), sodium tert-pentoxide (1.2 equiv), methanol (2.0 equiv) and 1,4-dioxane (0.3 M). The resulting mixture was purged with nitrogen for 10 min, before being heated under nitrogen at 60° C. for 18 hours. After this time, LCMS indicated production formation. The reaction mixture was loaded directly onto a reverse phase pre-cartridge. Purification by reverse phase column chromatography through a $C_{18}$ column, eluting with 90:10 to 0:100 water:MeCN+0.1% formic acid as a gradient, collecting all peaks. The desired product containing fractions were concentrated and lyophilized overnight to yield the title product as a white powder (52% yield). LCMS (ESI) m/z 445 $(M+1)^+$.

Example 10: Preparation of 4-((2S,4S)-4-(4-cyano-1H-pyrazol-1-yl)-1-((5-methoxy-7-methyl-1H-indol-4-yl)methyl)piperidin-2-yl)benzoic acid Example 10

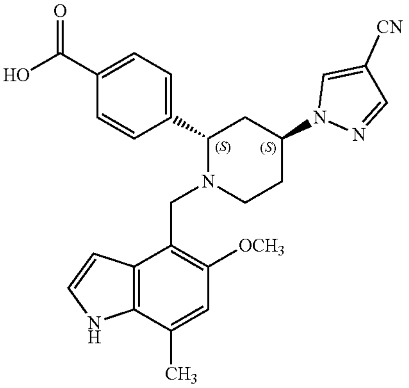

Step 1: Preparation of (±)-cis-benzyl 4-hydroxy-2-(4-(methoxycarbonyl)phenyl)piperidine-1-carboxylate: To a solution of (±)-cis-benzyl 4-((tert-butyldiphenylsilyl)oxy)-2-(4-(methoxycarbonyl)phenyl)piperidine-1-carboxylate (Intermediate C, 1.0 equiv) in THE (0.17 M) was added TBAF (1 M in THF, 2.0 equiv) at 0° C. and the mixture was warmed and stirred at 20-25° C. for 2 hours. The residue was diluted with $H_2O$ and extracted with EtOAc. The combined organic layers were washed with brine, dried over $Na_2SO_4$, filtered, and concentrated under reduced pressure to afford a residue. The mixture was purified by column chromatography through silica gel, using an eluent of 0% to 50% ethyl acetate in petroleum ether as a gradient. The desired product containing fractions were concentrated and dried under vacuum to afford a white solid (95% yield).

Step 2: Preparation of (±)-trans-benzyl 4-(4-cyano-1H-pyrazol-1-yl)-2-(4-(methoxycarbonyl)phenyl)piperidine-1-carboxylate: To a solution of (±)-cis-benzyl 4-hydroxy-2-(4-(methoxycarbonyl)phenyl)piperidine-1-carboxylate (1.0 equiv) in THE (0.11 M) was added $PPh_3$ (1.2 equiv), 1H-pyrazole-4-carbonitrile (1.2 equiv) and DIAD (1.2 equiv) at 0° C. The mixture was stirred at 20-25° C. for 16 hours. LCMS and TLC analysis reveals product formation.

The reaction mixture was concentrated under reduced pressure to give a residue. The residue was diluted with $H_2O$ and extracted with $CH_2Cl_2$. The combined organic layers were washed with brine, dried over $Na_2SO_4$, filtered, and concentrated under reduced pressure to afford a residue. The residue was purified by column chromatography through silica gel, eluting with 0% to 30% ethyl acetate in petroleum ether as a gradient. The desired product containing fractions were concentrated and dried under vacuum to afford colorless oil (35% yield). LCMS (ESI) m/z 445 $(M+1)^+$.

Step 3: Preparation of (±)-trans-methyl 4-(4-(4-cyano-1H-pyrazol-1-yl)piperidin-2-yl)benzoate: To a solution of (±)-trans-benzyl 4-(4-cyano-1H-pyrazol-1-yl)-2-(4-(methoxycarbonyl)phenyl)piperidine-1-carboxylate (1.0 equiv) in THE (0.34 M) was added 10 wt % Pd/C (0.2 equiv) and the mixture was degassed and purged with $N_2$ three times, after which the $N_2$ was replaced with H2 and the mixture purged another three times. The mixture was stirred at 20-25° C. for 2 hours under a H2 (15 psi) atmosphere. LCMS revealed desired product. The reaction mixture was filtered through a pad of celite, the cake was washed with $CH_2Cl_2$, and the filtrate concentrated under reduced pressure to give crude product as yellow oil. The crude title product was used for the next step without further purification. LCMS (ESI) m/z 311 $(M+1)^+$.

Step 4: Preparation of (±)-trans-tert-butyl 4-((4-(4-cyano-1H-pyrazol-1-yl)-2-(4-(methoxycarbonyl)phenyl)piperidin-1-yl)methyl)-5-methoxy-7-methyl-1H-indole-1-carboxylate: To a solution of (±)-trans-methyl 4-((4-(4-cyano-1H-pyrazol-1-yl)piperidin-2-yl)benzoate (1.0 equiv) in DCE (0.13 M) was added tert-butyl 4-formyl-5-methoxy-7-methyl-indole-1-carboxylate (1.2 equiv) and $NaBH(OAc)_3$ (2.8 equiv). The resulting mixture was stirred at 20-25° C. for 12 hours. TLC revealed starting material was completely consumed, and one main new spot formed. The reaction mixture was concentrated under reduced pressure to afford a residue. The residue was purified by column chromatography through silica gel, eluting with 0% to 35% ethyl acetate in petroleum ether as a gradient. The desired product containing fractions were concentrated and dried under vacuum to afford colorless oil (72% yield). LCMS (ESI) m/z 606 $(M+23)^+$.

Step 5: Preparation of tert-butyl 4-(((2S,4S)-4-(4-cyano-1H-pyrazol-1-yl)-2-(4-(methoxycarbonyl)phenyl)piperidin-1-yl)methyl)-5-methoxy-7-methyl-1H-indole-1-carboxylate: The sample of (±)-trans-tert-butyl 4-[[(4-(4-cyanopyrazol-1-yl)-2-(4-methoxycarbonylphenyl)-1-piperidyl]methyl]-5-methoxy-7-methyl-indole-1-carboxylate (1.0 equiv) was separated into each of the corresponding enantiomers using chiral SFC column chromatography (column: Phenomenex-Cellulose-2 (250 mm×50 mm, 10 μm); mobile phase: 45% EtOH+0.1% $NH_3 \cdot H_2O$ EtOH in 55% $scCO_2$) to give the title compound (39% yield) as a white solid. LCMS (ESI) m/z 606 $(M+23)^+$.

Step 6: Preparation of 4-((2S,4S)-1-((1-(tert-butoxycarbonyl)-5-methoxy-7-methyl-1H-indol-4-yl)methyl)-4-(4-cyano-1H-pyrazol-1-yl)piperidin-2-yl)benzoic acid: To a solution of tert-butyl 4-(((2S,4S)-4-(4-cyano-1H-pyrazol-1-yl)-2-(4-(methoxycarbonyl)phenyl)piperidin-1-yl)methyl)-5-methoxy-7-methyl-1H-indole-1-carboxylate (1.0 equiv) in THF (0.06 M) and $H_2O$ (0.06 M) was added $LiOH \cdot H_2O$ (4.0 equiv). The mixture was stirred at 20-25° C. for 2 hours after which LCMS analysis showed formation of the desired product. The residue was diluted with $H_2O$ and extracted with EtOAc three times. The combined organic layers were washed with brine, dried over $Na_2SO_4$, filtered, and concentrated under reduced pressure to give a white solid, which was used for the next step without further purification. LCMS (ESI) m/z 570 $(M+1)^+$.

Step 7: Preparation of 4-((2S,4S)-4-(4-cyano-1H-pyrazol-1-yl)-1-((5-methoxy-7-methyl-1H-indol-4-yl)methyl)piperidin-2-yl)benzoic acid: A solution of 4-((2S,4S)-1-((1-(tert-butoxycarbonyl)-5-methoxy-7-methyl-1H-indol-4-yl)methyl)-4-(4-cyano-1H-pyrazol-1-yl)piperidin-2-yl)benzoic acid (1.0 equiv) in $CH_2Cl_2$ (0.1 M) and TFA (0.005 M) was stirred at 20-25° C. for 2 hours. LCMS showed formation of product. The reaction mixture was concentrated under reduced pressure to give a residue. $^1H$-NMR (400 MHz, $CD_3OD$): δ 8.51 (s, 1H), 8.25 (bs, 1H), 8.19 (d, J=8.0 Hz, 2H), 8.09 (s, 1H), 7.71 (d, J=8.0 Hz, 2H), 7.31 (d, J=4.0 Hz, 1H), 6.77 (s, 1H), 6.30 (d, J=4.0 Hz, 1H), 4.91-5.00 (m, 2H), 4.36 (d, J=12.0 Hz, 1H), 4.17 (d, J=12.0 Hz, 1H), 3.77 (s, 3H), 3.54-3.67 (m, 1H), 3.43-3.51 (m, 1H), 2.71 (bs, 2H), 2.42-2.59 (m, 5H). LCMS (ESI) m/z 470 $(M+1)^+$.

The following compounds were prepared in a similar manner as Example 10 replacing 1H-pyrazole-4-carbonitrile in step 2 with the corresponding pyrazole listed in the table below.

| Example | Intermediate Used | Structure | MW | MS (ESI+) |
|---|---|---|---|---|
| Example 11 | 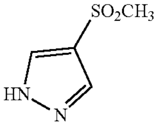 | 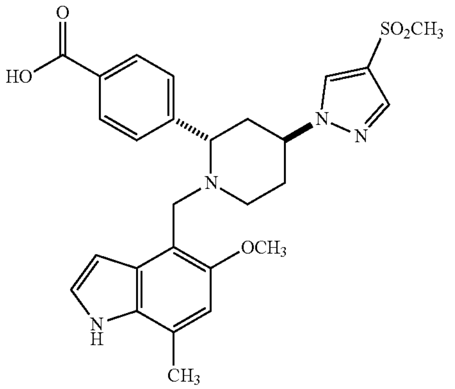 (+/-)-trans<br>(±)-trans-4-(1-((5-methoxy-7-methyl-1H-indol-4-yl)methyl)-4-(4-methylsulfonyl)-1H-pyrazol-1-yl)piperidin-2-yl)benzoic acid | 522.19 | 523 (M + 1)$^{\oplus}$ |

Example 12: Preparation of (±)-trans-4-(1-((5-methoxy-7-methyl-1H-indol-4-yl)methyl)-4-(2-oxopyrrolidin-1-yl)piperidin-2-yl)benzoic acid

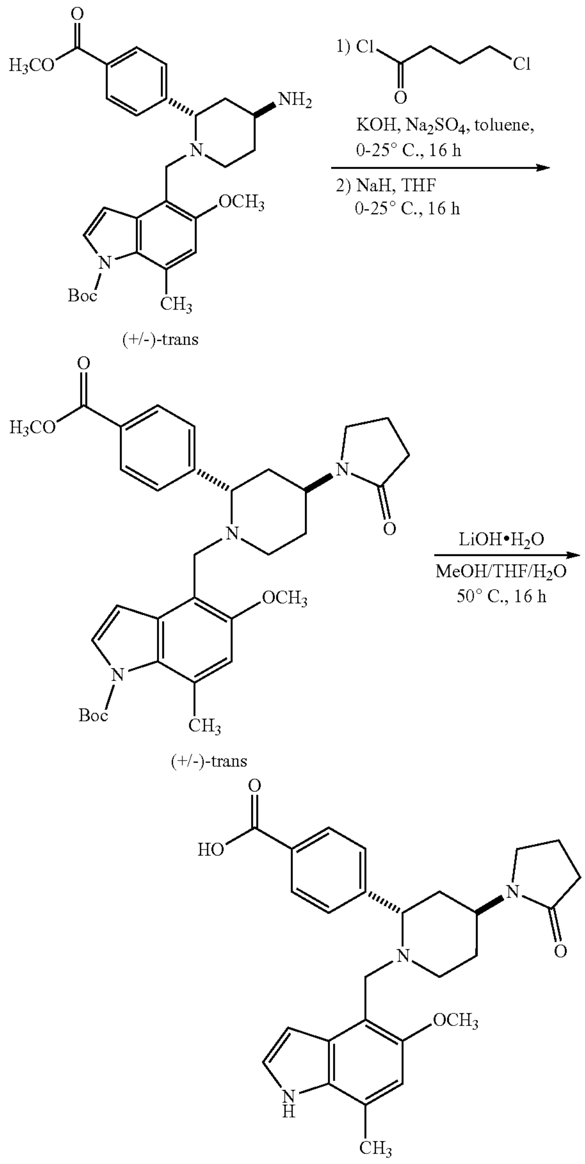

(+/-)-trans
Example 12

Step 1: Preparation of (±)-tert-butyl 5-methoxy-4-(((trans)-2-(4-(methoxycarbonyl)phenyl)-4-(2-oxopyrrolidin-1-yl)piperidin-1-yl)methyl)-7-methyl-1H-indole-1-carboxylate: To a solution of (±)-tert-butyl 4-(((trans)-4-amino-2-(4-(methoxycarbonyl)phenyl)piperidin-1-yl)methyl)-5-methoxy-7-methyl-1H-indole-1-carboxylate (1.0 equiv) and $Na_2SO_4$ (1.2 equiv) in toluene (0.25 M) was added KOH (3.0 equiv) followed by the addition of 4-chlorobutanoyl chloride (1.0 equiv) in toluene (1.48 M) at 0° C. The mixture was then stirred at 20-25° C. for 16 hours. After this time, the mixture was filtered and concentrated under vacuum to remove the solvent. The residue was diluted with THE (0.03 M) and the suspension was cooled down to 0° C. Solid NaH (60% in mineral oil, 10.0 equiv) was slowly added and the resulting mixture was stirred at 20-25° C. for 16 hours. The reaction mixture was quenched by addition of saturated aqueous $NaHCO_3$ solution, and the aqueous layer extracted with EtOAc. The combined organic layers were washed with brine, dried over anhydrous $Na_2SO_4$, filtered and concentrated under reduced pressure to give a residue. The residue was purified by column chromatography through silica gel, eluting with 0 to 10% MeOH in $CH_2Cl_2$ as a gradient, to yield the title compound as a colorless liquid (42% yield). LCMS (ESI) m/z 576 $(M+1)^+$.

Step 2: Preparation of (±)-trans-4-(1-((5-methoxy-7-methyl-1H-indol-4-yl)methyl)-4-(2-oxopyrrolidin-1-yl)piperidin-2-yl)benzoic acid: To a solution of (±)-tert-butyl 5-methoxy-4-(((trans)-2-(4-(methoxycarbonyl)phenyl)-4-(2-oxopyrrolidin-1-yl)piperidin-1-yl)methyl)-7-methyl-1H-indole-1-carboxylate (1.0 equiv) was added 0.8 M aqueous LiOH/THF/MeOH solution (13.0 equiv LiOH, v/v/v, 2/1/1). The mixture was heating to 50° C. while stirring for 16 hours. LCMS analysis indicated hydrolysis, and the mixture was cooled and concentrated under reduced pressure to afford a residue. $^1$H-NMR (400 MHz, $CD_3OD$): δ 8.40 (s, 0.5H), 8.16 (d, J=8.0 Hz, 2H), 7.69 (d, J=8.0 Hz, 2H), 7.33 (d, J=2.8 Hz, 1H), 6.78 (s, 1H), 6.38 (d, J=2.8 Hz, 1H), 4.68 (d, J=9.2 Hz, 1H), 4.39 (d, J=12.4 Hz, 1H), 4.23 (d, J=12.4 Hz, 1H), 4.11 (s, 1H), 3.80 (s, 3H), 3.77-3.72 (m, 2H), 3.42-3.40 (m, 2H), 2.57-2.52 (m, 1H), 2.49 (s, 3H), 2.48-2.44 (m, 2H), 2.38-2.34 (m, 2H), 2.19-2.07 (m, 3H). LCMS (ESI) m/z 462 $(M+1)^+$.

Example 13: Preparation of 4-((2S,4S)-1-((5-methoxy-7-methyl-1H-indol-4-yl)methyl)-4-(2-oxopyrrolidin-1-yl)piperidin-2-yl)benzoic acid Example 13

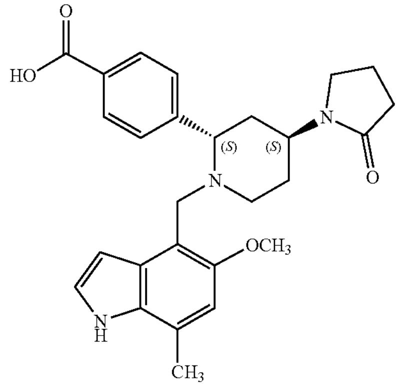

Step 1: Preparation of tert-butyl 5-methoxy-4-(((2S,4S)-2-(4-(methoxycarbonyl)phenyl)-4-(2-oxopyrrolidin-1-yl)piperidin-1-yl)methyl)-7-methyl-1H-indole-1-carboxylate: The racemic compound (±)-tert-butyl 5-methoxy-4-(((trans)-2-(4-(methoxycarbonyl)phenyl)-4-(2-oxopyrrolidin-1-yl)piperidin-1-yl)methyl)-7-methyl-1H-indole-1-carboxylate (step 1 of Example 12) was further separated via chiral column SFC chromatography through a REGIS(S,S) WHELK-O1 (250 mm×25 mm, 10 μm) column eluting with 40:60 heptane:EtOH+0.1% $NH_3 \cdot H_2O$ as a gradient, with a 80 mL/min flow rate and 40° C. column temperature. The desired product containing fractions were concentrated to yield the title compound as a yellow solid (33% yield) $^1$H-NMR (400 MHz, $CDCl_3$): δ 7.99 (d, J=8.3 Hz, 2H), 7.58

(d, J=8.3 Hz, 2H), 7.53 (d, J=3.8 Hz, 1H), 6.70-6.69 (m, 2H), 4.22-4.18 (m, 1H), 4.02 (d, J=12.3 Hz, 1H), 3.90 (s, 3H), 3.88-3.87 (m, 1H), 3.84 (s, 3H), 3.82-3.79 (m, 1H), 3.61-3.52 (m, 2H), 3.41-3.37 (m, 1H), 2.84-2.78 (m, 1H), 2.61 (s, 3H), 2.43-2.36 (m, 3H), 2.27-2.22 (m, 1H), 2.11-2.01 (m, 4H), 1.63 (s, 9H). LCMS (ESI) m/z 576 $(M+1)^+$.

Step 2: Preparation of 4-((2S,4S)-1-((5-methoxy-7-methyl-1H-indol-4-yl)methyl)-4-(2-oxopyrrolidin-1-yl)piperidin-2-yl)benzoic acid: To a solution of tert-butyl 5-methoxy-4-(((2S,4S)-2-(4-(methoxycarbonyl)phenyl)-4-(2-oxopyrrolidin-1-yl)piperidin-1-yl)methyl)-7-methyl-1H-indole-1-carboxylate (1.0 equiv) was added 2.14 M aqueous LiOH/THF/MeOH solution (18.0 equiv LiOH, v/v/v, 2/1/1). The mixture was stirred at 50° C. for 16 hours. LCMS indicated completion of reaction. The reaction mixture was filtered, and the filter cake was washed with MeOH. The resulting filtrate was acidified with acetic acid to pH-7 and concentrated under reduced pressure to afford a residue. $^1$H-NMR (400 MHz, $CD_3OD$): δ 8.38 (s, 0.5H), 8.14 (d, J 8.4 Hz, 2H), 7.67 (d, J=8.4 Hz, 2H), 7.31 (d, J=3.2 Hz, 1H), 6.77 (s, 1H), 6.37 (d, J=3.0 Hz, 1H), 4.66 (dd, J=11.2, 2.8 Hz, 1H), 4.38 (d, J=12.8 Hz, 1H), 4.21 (d, J=12.8 Hz, 1H), 4.18-4.10 (m, 1H), 3.78 (s, 3H), 3.76-3.70 (m, 2H), 3.40-3.37 (m, 2H), 2.58-2.54 (m, 1H), 2.50 (s, 3H), 2.50-2.44 (m, 2H), 2.39-2.32 (m, 2H), 2.19-2.09 (m, 2H), 2.09-2.01 (m, 1H). LCMS (ESI) m/z 462 $(M+1)^+$.

Example 14: Preparation of (+)-trans-4-(1-((5-methoxy-7-methyl-1H-indol-4-yl)methyl)-4-((2,2,2-trifluoroethyl)amino)piperidin-2-yl)benzoic acid Example 14

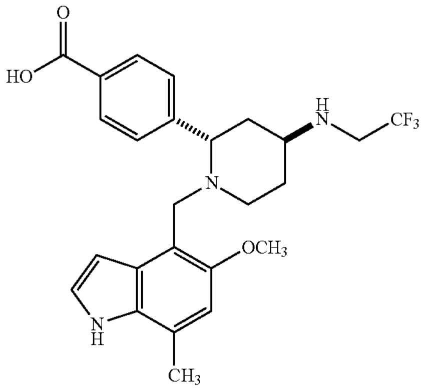

(+/-)-trans

Step 1: Preparation of (±)-tert-butyl 5-methoxy-4-(((trans)-2-(4-(methoxycarbonyl)phenyl)-4-((2,2,2-trifluoroethyl)amino)piperidin-1-yl)methyl)-7-methyl-1H-indole-1-carboxylate: A mixture of (±)-tert-butyl 4-(((trans)-4-amino-2-(4-(methoxycarbonyl)phenyl)piperidin-1-yl)methyl)-5-methoxy-7-methyl-1H-indole-1-carboxylate (Intermediate F, 1.0 equiv), 2,2,2-trifluoroethyl trifluoromethanesulfonate (2.0 equiv) and $EtN(iPr)_2$ (6.0 equiv) in dioxane (0.10 M) was heated to 80° C. for 16 hours under a $N_2$ atmosphere. LCMS indicated completion of reaction after this time. The reaction mixture was concentrated under reduced pressure to afford a residue. The residue was purified by preparative-TLC ($SiO_2$, hexanes:EtOAc=1:1) to yield the title compound as a yellow solid (95% yield). LCMS (ESI) m/z 590 $(M+1)^+$.

Step 2: Preparation of (+)-trans-4-(1-((5-methoxy-7-methyl-1H-indol-4-yl)methyl)-4-((2,2,2-trifluoroethyl)amino)piperidin-2-yl)benzoic acid: To a solution of (±)-tert-butyl 5-methoxy-4-(((trans)-2-(4-(methoxycarbonyl)phenyl)-4-((2,2,2-trifluoroethyl)amino)piperidin-1-yl)methyl)-7-methyl-1H-indole-1-carboxylate (1.0 equiv) was added 1.98 M aqueous LiOH/THF/MeOH solution (18.0 equiv LiOH, v/v/v, 2/1/1). The mixture was stirred at 50° C. for 16 hours after which LCMS analysis indicated completion. The reaction mixture was filtered, the filter cake was washed with MeOH, and the filtrate was acidified with acetic acid to pH-7. The resulting mixture was concentrated under reduced pressure. $^1$H-NMR (400 MHz, $CD_3OD$): δ 8.34 (s, 1H), 8.18 (d, J=8.4 Hz, 2H), 7.68 (d, J=8.0 Hz, 2H), 7.32 (d, J=3.2 Hz, 1H), 6.77 (s, 1H), 6.32 (s, 1H), 4.90 (s, 1H), 4.34 (d, J=12.4 Hz, 1H), 4.21 (d, J=12.4 Hz, 1H), 3.76 (s, 3H), 3.69-3.62 (m, 1H), 3.35-3.32 (m, 2H), 3.30-3.26 (m, 1H), 3.26-3.18 (m, 1H), 2.51 (s, 3H), 2.34-2.26 (m, 1H), 2.16-2.12 (m, 1H), 2.05-2.04 (m, 1H), 1.95-1.91 (m, 1H). LCMS (ESI) m/z 476 $(M+1)^+$.

Example 15: Preparation of 4-((2S,4S)-1-((5-methoxy-7-methyl-1H-indol-4-yl)methyl)-4-((2,2,2-trifluoroethyl)amino)piperidin-2-yl)benzoic acid Example 15

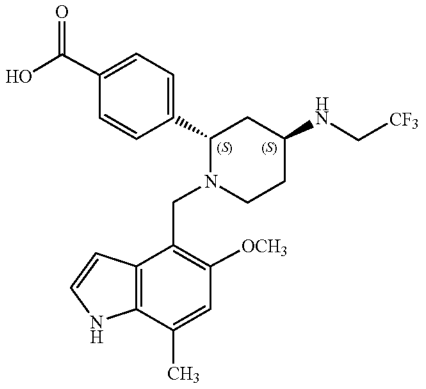

Step 1: Preparation of tert-butyl 5-methoxy-4-(((2S,4S)-2-(4-(methoxycarbonyl)phenyl)-4-((2,2,2-trifluoroethyl)amino)piperidin-1-yl)methyl)-7-methyl-1H-indole-1-carboxylate: The racemic compound, (±)-tert-butyl 5-methoxy-4-(((trans)-2-(4-(methoxycarbonyl)phenyl)-4-((2,2,2-trifluoroethyl)amino)piperidin-1-yl)methyl)-7-methyl-1H-indole-1-carboxylate was obtained from step 1 of Example 14. The trans-configuration enantiomers were further separated via Chiral SFC through a DAICEL CHIRALPAK AD (250 mm×30 mm, 10 μm) column eluting with 85:15 EtOH+0.1% $NH_3{\cdot}H_2O$:iPrOH as a gradient, with a 60 mL/min flow rate and 40° C. column temperature. The desired product containing fractions were concentrated to yield the title compound as a yellow solid (29% yield). $^1$H-NMR (400 MHz, $CD_3OD$): δ 7.95 (d, J=8.0 Hz, 2H), 7.54 (d, J=8.0 Hz, 2H), 7.43 (d, J=3.6 Hz, 1H), 6.65 (s, 1H), 6.48 (d, J=3.6 Hz, 1H), 3.82 (s, 3H), 3.69 (s, 3H), 3.59-3.64 (m, 2H), 3.08-3.18 (m, 2H), 2.92 (s, 1H), 2.58-2.60 (m, 2H), 2.44 (s, 3H), 1.60-1.89 (m, 4H), 1.52 (s, 9H). LC-MS (ESI) m/z 590 $(M+1)^+$.

Step 2: Preparation of 4-((2S,4S)-1-((5-methoxy-7-methyl-1H-indol-4-yl)methyl)-4-((2,2,2-trifluoroethyl)amino)piperidin-2-yl)benzoic acid: To a solution of tert-butyl 5-methoxy-4-(((2S,4S)-2-(4-(methoxycarbonyl)phenyl)-4-((2,2,2-trifluoroethyl)amino)piperidin-1-yl)methyl)-7-methyl-1H-indole-1-carboxylate (1.0 equiv) was added 1.53 M aqueous LiOH/THF/MeOH solution (18.0 equiv LiOH, v/v/v, 2/1/1). The mixture was stirred at 50° C. for 16 hours after which LCMS indicated completion of reaction. The reaction mixture was concentrated under reduced pressure to remove the THF and MeOH and water was added to the remaining reaction mixture. The resulting mixture was neutralized with saturated aqueous $KHSO_4$ solution to pH-7 and extracted with EtOAc. The combined organic layers were washed with brine, dried over anhydrous $Na_2SO_4$, filtered and concentrated under reduced pressure to give a residue. $^1H$-NMR (400 MHz, $CD_3OD$): δ 8.34 (s, 1H), 8.18 (d, J=8.0 Hz, 2H), 7.68 (d, J=8.0 Hz, 2H), 7.32 (d, J=3.2 Hz, 1H), 6.77 (s, 1H), 6.32 (s, 1H), 4.84 (s, 1H), 4.34 (d, J=11.2 Hz, 1H), 4.21 (d, J=12.8 Hz, 1H), 3.76 (s, 3H), 3.69-3.62 (m, 1H), 3.36-3.32 (m, 2H), 3.28-3.26 (m, 1H), 3.23 (s, 1H), 2.51 (s, 3H), 2.34-2.26 (m, 1H), 2.16-2.03 (m, 2H), 1.95-1.91 (m, 1H). LCMS (ESI) m/z 476 $(M+1)^+$.

Example 16: Preparation of (±)-trans-4-(1-((5-methoxy-7-methyl-1H-indol-4-yl)methyl)-4-(sulfamoylamino)piperidin-2-yl)benzoic acid Example 16

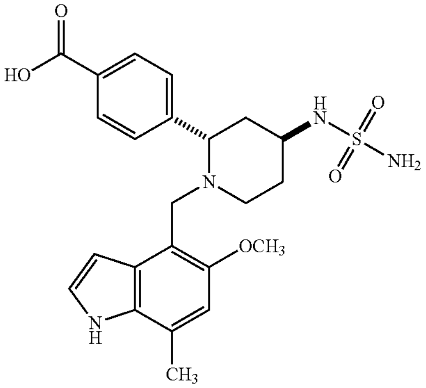

(+/-)-trans

Step 1: Preparation of (±)-tert-butyl 5-methoxy-4-(((trans)-2-(4-(methoxycarbonyl)phenyl)-4-(sulfamoylamino)piperidin-1-yl)methyl)-7-methyl-1H-indole-1-carboxylate: To a solution of (±)-tert-butyl 4-(((trans)-4-amino-2-(4-(methoxycarbonyl)phenyl)piperidin-1-yl)methyl)-5-methoxy-7-methyl-1H-indole-1-carboxylate (Intermediate F, 1.0 equiv) in $CH_2Cl_2$ (0.05 M) was added $Et_3N$ (3.0 equiv) and $NH_2SO_2Cl$ (2.0 equiv) at 0° C. The mixture was then stirred at 25° C. for 16 hours. The crude mixture was purified by column chromatography through silica gel using an eluent of 0 to 10% of MeOH in $CH_2Cl_2$ as a gradient to yield the title compound as a colorless liquid (23% yield). LCMS (ESI) m/z 587 $(M+1)^+$.

Step 2: Preparation of (+)-trans-4-(1-((5-methoxy-7-methyl-1H-indol-4-yl)methyl)-4-(sulfamoylamino)piperidin-2-yl)benzoic acid formic acid salt: To a solution of (±)-tert-butyl 5-methoxy-4-(((trans)-2-(4-(methoxycarbonyl)phenyl)-4-(sulfamoylamino)piperidin-1-yl)methyl)-7-methyl-1H-indole-1-carboxylate (1.0 equiv) was added 0.12 M aqueous LiOH/THF/MeOH solution (13.0 equiv LiOH, v/v/v, 2/1/1). The mixture was heating under stirring at 50° C. for 16 hours. LCMS indicated completion of hydrolysis, after which the mixture was cooled and concentrated under reduced pressure to give a residue. $^1H$-NMR (400 MHz, $CD_3OD$): δ 8.29 (s, 1H), 8.19 (d, J=8.0 Hz, 2H), 7.69 (d, J=7.6 Hz, 2H), 7.33 (d, J=3.2 Hz, 1H), 6.77 (s, 1H), 6.33 (s, 1H), 4.38 (d, J=12.4 Hz, 1H), 4.20 (d, J=12.4 Hz, 1H), 3.83 (s, 1H), 3.77 (s, 3H), 3.63-3.56 (m, 1H), 3.41-3.37 (m, 2H), 2.51 (s, 3H), 2.43-2.40 (m, 1H), 2.36-2.32 (m, 1H), 2.20-2.14 (m, 1H). LCMS (ESI) m/z 473 $(M+1)^+$.

Example 17: Preparation of (+)-trans-4-(1-((5-methoxy-7-methyl-1H-indol-4-yl)methyl)-4-(oxetan-3-ylamino)piperidin-2-yl)benzoic acid Example 17

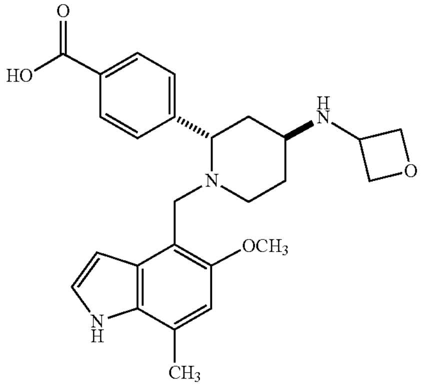

(+/-)-trans

Step 1: Preparation of (±)-tert-butyl 5-methoxy-4-(((trans)-2-(4-(methoxycarbonyl)phenyl)-4-(oxetan-3-ylamino)piperidin-1-yl)methyl)-7-methyl-1H-indole-1-carboxylate: To a solution of (±)-tert-butyl 4-(((trans)-4-amino-2-(4-(methoxycarbonyl)phenyl)piperidin-1-yl)methyl)-5-methoxy-7-methyl-1H-indole-1-carboxylate (Intermediate F, 1.0 eq) in MeOH (0.08 M) was added oxetan-3-one (3.0 equiv), $ZnCl_2$ (4.0 equiv) and $NaBH_3CN$ (3.0 equiv) at 0° C. The mixture was heated to 50° C. and stirred at this temperature for 14 hours or until LCMS indicated completion. The reaction mixture was filtered, and the filter cake was washed with MeOH. The resulting filtrate was concentrated under reduced pressure to give a residue which was purified by preparative TLC ($SiO_2$, 100% EtOAc) to yield the title compound as a yellow solid (68% yield). LCMS (ESI) m/z 564 $(M+1)^+$.

Step 2: Preparation of (+)-trans-4-(1-((5-methoxy-7-methyl-1H-indol-4-yl)methyl)-4-(oxetan-3-ylamino)piperidin-2-yl)benzoic acid: To a solution of (±)-tert-butyl 5-methoxy-4-(((trans)-2-(4-(methoxycarbonyl)phenyl)-4-(oxetan-3-ylamino)piperidin-1-yl)methyl)-7-methyl-1H-indole-1-carboxylate (1.0 equiv) was added 0.96 M aqueous LiOH/THF/MeOH solution (18.0 equiv LiOH, v/v/v, 2/1/1). The mixture was stirred at 50° C. for 16 hours after which LCMS indicated reaction completion. The reaction mixture was filtered, and the filter cake was washed with MeOH. The resulting filtrate was acidified with acetic acid to pH=6-7 (18% yield). $^1H$-NMR (400 MHz, $CD_3OD$): δ 8.37 (s, 1H), 8.18 (d, J=8.0 Hz, 2H), 7.68 (d, J=8.0 Hz, 2H), 7.32 (d, J=3.2 Hz, 1H), 6.76 (s, 1H), 6.32 (d, J=3.2 Hz, 1H), 4.84-4.83 (m, 4H), 4.59-4.55 (m, 2H), 4.35 (d, J=12.8 Hz, 1H), 4.16 (d, J=12.8 Hz, 1H), 4.14-4.06 (m, 1H), 3.75 (s, 3H), 3.68-3.60

(m, 1H), 3.11 (s, 1H), 2.51 (s, 3H), 2.35-2.32 (m, 1H), 2.07-2.02 (m, 2H), 1.84 (d, J=15.2 Hz, 1H). LCMS (ESI) m/z 450 $(M+1)^+$.

Example 18: Preparation of 4-((2S,4S)-1-((5-methoxy-7-methyl-1H-indol-4-yl)methyl)-4-(oxetan-3-ylamino)piperidin-2-yl)benzoic acid Example 18

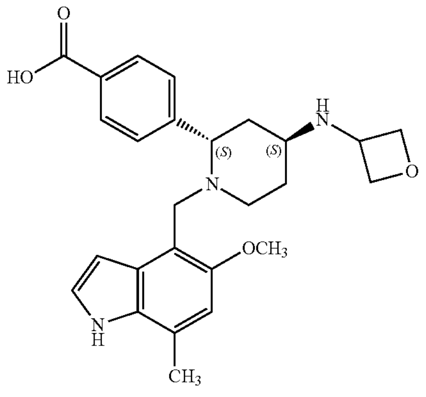

Step 1: Preparation of tert-butyl 5-methoxy-4-(((2S,4S)-2-(4-(methoxycarbonyl)phenyl)-4-(oxetan-3-ylamino)piperidin-1-yl)methyl)-7-methyl-1H-indole-1-carboxylate: The racemic (±)-tert-butyl 5-methoxy-4-(((trans)-2-(4-(methoxycarbonyl)phenyl)-4-(oxetan-3-ylamino)piperidin-1-yl)methyl)-7-methyl-1H-indole-1-carboxylate was prepared as per step 1, Example 17. The trans-configuration enantiomers were further separated via chiral SFC chromatography through a DAICEL CHIRALPAK IG (250 mm×50 mm, 10 μm column), eluting with 60:40 $scCO_2$:EtOH+0.1% $NH_3 \cdot H_2O$ as a gradient, with 140 mL/min flow rate and 40° C. column temperature. The desired product containing fractions were concentrated to yield the title product as a yellow solid (37% yield). LCMS (ESI) m/z 564 $(M+1)^+$.

Step 2: Preparation of 4-((2S,4S)-1-((5-methoxy-7-methyl-1H-indol-4-yl)methyl)-4-(oxetan-3-ylamino)piperidin-2-yl)benzoic acid formic acid salt: To a mixture of tert-butyl 5-methoxy-4-(((2S,4S)-2-(4-(methoxycarbonyl)phenyl)-4-(oxetan-3-ylamino)piperidin-1-yl)methyl)-7-methyl-1H-indole-1-carboxylate (1.0 equiv) was added 2.6 M aqueous LiOH/THF/MeOH solution (13.0 equiv LiOH, v/v/v, 2/1/1). The mixture was heating under stirring at 50° C. for 16 hours. LCMS indicated completion of hydrolysis, after which the mixture was cooled, and the reaction quenched (43% yield). $^1$H-NMR (400 MHz, $CD_3OD$): δ 8.28 (s, 1H), 8.18 (d, J=8.0 Hz, 2H), 7.69 (d, J=8.0 Hz, 2H), 7.32 (d, J=3.2 Hz, 1H), 6.77 (s, 1H), 6.32 (d, J 2.8 Hz, 1H), 4.83 (m, 2H), 4.60-4.54 (m, 2H), 4.35-4.17 (m, 2H), 4.12-4.10 (m, 1H), 3.76 (s, 3H), 3.69-3.62 (m, 1H), 3.29-3.28 (m, 2H), 3.11 (s, 1H), 2.51 (s, 3H), 2.35-2.28 (m, 1H), 2.07-2.01 (m, 2H), 1.86-1.82 (m, 1H). LCMS (ESI) m/z 450 $(M+1)^+$.

Example 19: Preparation of 4-((2S,4S)-4-((3,3-difluorocyclobutyl)amino)-1-((5-methoxy-7-methyl-1H-indol-4-yl)methyl)piperidin-2-yl)benzoic acid Example 19

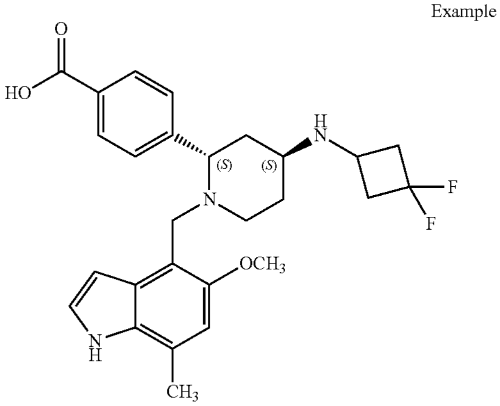

Step 1: Preparation of benzyl (2S)-4-((3,3-difluorocyclobutyl)amino)-2-(4-(methoxycarbonyl)phenyl)piperidine-1-carboxylate: A solution of 3,3-difluorocyclobutanamine hydrochloride (1.2 equiv) and N,N-diisopropylethylamine (1.2 equiv) in DCE (0.58 M) was stirred for 30 minutes at 20-25° C. Benzyl (S)-2-(4-(methoxycarbonyl)phenyl)-4-oxopiperidine-1-carboxylate (Intermediate H, 1.0 equiv) was added, and the mixture was stirred for 1 hour. Sodium triacetoxyborohydride (2.5 equiv) was added and the reaction mixture was stirred at 20-25° C. for another 20 hours. The reaction was quenched with water and concentrated under reduced pressure. The residue was purified by reverse phase column chromatography using a C18 column, eluting with 0-100% MeCN in water+0.1% formic acid as gradient. The fractions from the major peak eluting at 60% MeCN in water were combined and concentrated under reduced pressure to yield a colourless oil (92% yield). LCMS (ESI) m/z 459 $(M+1)^+$.

Step 2: Preparation of benzyl (2S,4S)-4-((tert-butoxycarbonyl)(3,3-difluorocyclobutyl)amino)-2-(4-(methoxycarbonyl)phenyl)piperidine-1-carboxylate: To a solution of benzyl (2S)-4-((3,3-difluorocyclobutyl)amino)-2-(4-(methoxycarbonyl)phenyl)piperidine-1-carboxylate (1.0 equiv) in THE (0.16 M) was added di-tert-butyl dicarbonate (2.0 equiv) and N,N-diisopropylethylamine (3.0 equiv). The solution was stirred at 23° C. for 3 hours. The temperature was increased to 80° C. and the solution was stirred for 18 hours under reflux. The solution was concentrated under reduced pressure and purified by column chromatography through silica gel, eluting with 20-60% ethyl acetate in hexanes as a gradient. The product containing fractions were concentrated under reduced pressure to afford a colourless oil (9% yield). LCMS (ESI) m/z 590 $(M+1)^+$.

Step 3: Preparation of methyl 4-((2S,4S)-4-((tert-butoxycarbonyl)(3,3-difluorocyclobutyl)amino)piperidin-2-yl)benzoate: To a solution of benzyl (2S,4S)-4-((tert-butoxycarbonyl)(3,3-difluorocyclobutyl)amino)-2-(4-(methoxycarbonyl)phenyl)piperidine-1-carboxylate (1 equiv) in MeOH (0.07 M) was added palladium on carbon, 10 wt %(0.052 equiv) and the mixture was purged with $N_2$. A balloon containing H2 gas was fitted onto the flask, the contents were purged, and the mixture was stirred under a H2 atmosphere at 20-25° C. for 90 minutes. The reaction mixture was filtered through a pad of celite, and the filtrate was concentrated under reduced pressure to afford a clear colourless oil which was directly used in the next step without further purification. LCMS (ESI) m/z 425 $(M+1)^+$.

Step 4: Preparation of tert-butyl 4-(((2S,4S)-4-((tert-butoxycarbonyl)(3,3-difluorocyclobutyl)amino)-2-(4-(methoxycarbonyl)phenyl)piperidin-1-yl)methyl)-5-methoxy-7-methyl-1H-indole-1-carboxylate: To a solution of methyl 4-((2S,4S)-4-((tert-butoxycarbonyl)(3,3-difluorocyclobutyl)amino)piperidin-2-yl)benzoate (1.0 equiv) in DCE (0.10 M) was added tert-butyl 4-formyl-5-methoxy-7-methyl-1H-indole-1-carboxylate (1.0 equiv) and 0.3 Å molecular sieves. The reaction mixture was stirred at 20-25° C. for 60 minutes. Sodium triacetoxyborohydride (2.5 equiv) was added and the reaction mixture was stirred for 64 hours at 20-25° C. The reaction was quenched with water, then the mixture was purified by column chromatography through silica gel, eluting with 0-100% ethyl acetate in hexanes as a gradient. The fractions from the major peak eluting at 65% ethyl acetate were combined and concentrated under reduced pressure to afford a colourless oil (91% yield). LCMS (ESI) m/z 698 $(M+1)^+$.

Step 5: Preparation of 4-((2S,4S)-4-((3,3-difluorocyclobutyl)amino)-1-((5-methoxy-7-methyl-1H-indol-4-yl)methyl)piperidin-2-yl)benzoic acid: To tert-butyl 4-(((2S,4S)-4-((tert-butoxycarbonyl)(3,3-difluorocyclobutyl)amino)-2-(4-(methoxycarbonyl)phenyl)piperidin-1-yl)methyl)-5-methoxy-7-methyl-1H-indole-1-carboxylate (1.0 equiv) in $CH_2Cl_2$ (0.06 M) was added trifluoroacetic acid (18 equiv). The reaction mixture was stirred at 20-25° C. for 4 hours. The reaction mixture was concentrated under reduced pressure and the residue was redissolved in THF/MeOH (1:1, v/v) (0.03 M). A solution of 1 M aqueous lithium hydroxide solution (14 equiv) was added, and the solution was stirred at 80° C. for 2 hours. The reaction mixture was concentrated under reduced pressure to afford the title compound (67% yield). $^1$H-NMR (400 MHz, DMSO): δ 7.88 (d, J=7.7 Hz, 2H), 7.42 (d, J=7.7 Hz, 2H), 7.23 (d, J=3.2 Hz, 1H), 6.63 (d, J=5.1 Hz, 1H), 6.48 (d, J=3.2 Hz, 1H), 3.71 (s, 3H), 3.59-3.47 (m, 2H), 3.27-3.10 (m, 2H), 2.83-2.68 (m, 3H), 2.41 (m, 7H), 2.17 (dd, J=9.5, 3.9 Hz, 1H), 1.78-1.68 (m, 1H), 1.64 (d, J=13.2 Hz, 1H), 1.48 (s, 2H). LCMS (ESI) m/z 484 $(M+1)^+$.

The following compounds were prepared in a similar manner as Example 19 replacing 3,3-difluorocyclobutanamine with the corresponding commercially available amines in the table in step 1.

| Example | Intermediate Used | Structure | MW | MS (ESI+) |
|---|---|---|---|---|
| Example 20 | 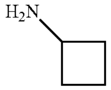 | 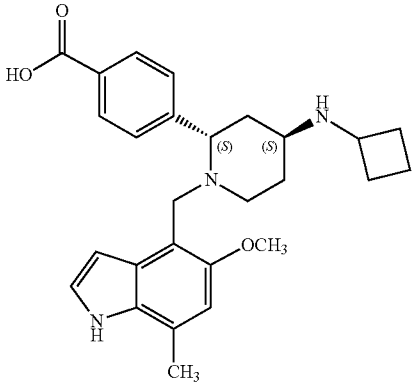 4-((2S,4S)-4-(cyclobutylamino)-1-((5-methoxy-7-methyl-1H-indol-4-yl)methyl)piperidin-2-yl)benzoic acid | 447.25 | 448 $(M + 1)^{\oplus}$ |
| Example 21 | 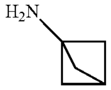 | 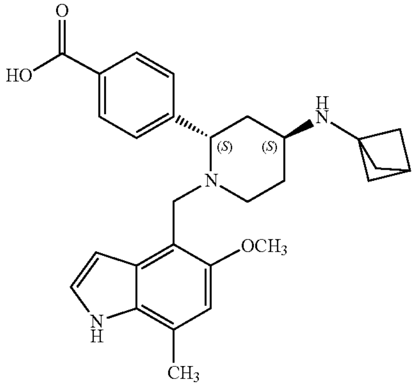 4-((2S,4S)-4-(bicyclo[1.1.1]pentan-1-ylamino)-1-((5-methoxy-7-methyl-1H-indol-4-yl)methyl)pyiperidin-2-yl)benzoic acid | 459.25 | 460 $(M + 1)^{\oplus}$ |

-continued

| Example | Intermediate Used | Structure | MW | MS (ESI+) |
|---|---|---|---|---|
| Example 22 | 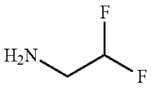 | 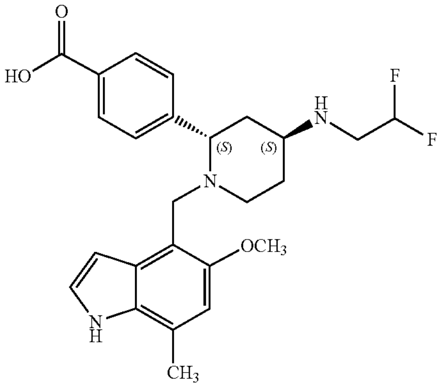<br>4-((2S,4S)-4-((2,2-difluoroethyl)amino)-1-((5-methoxy-7-methyl-1H-indol-4-yl)methyl)piperidin-2-yl)benzoic acid<br>$^1$H NMR (400 MHz, $d_4$-MeOD): δ 8.32 (br s, 1H), 8.21 (br d, J = 8.0 Hz, 2H), 7.73 (br d, J = 8.0 Hz, 2H), 7.33 (d, J = 8.0 Hz, 1H), 6.75 (s, 1H), 6.33 (br d, J = 2.0 Hz, 1H), 6.16-5.84 (m, 1H), 4.90 (br s, 1H), 4.35 (br d, J = 12.8 Hz, 1H), 4.17 (br d, J = 12.8 Hz, 1H), 3.75 (s, 3H), 3.71-3.65 (m, 1H), 3.29 (br s, 1H), 3.20 (br s, 1H), 3.08-2.96 (m, 2H), 2.51 (s, 3H), 2.40-2.32 (m, 1H), 2.16-2.04 (m, 2H), 1.96-1.88 (m, 1H). | 457.22 | 458 (M + 1)$^{\oplus}$ |
| Example 23 | 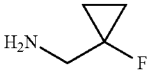 | 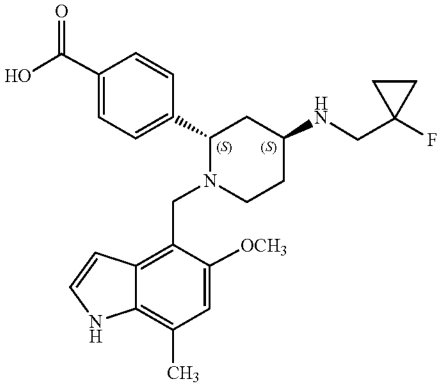<br>4-((2S,4S)-4-(((1-fluorocyclopropyl)methyl)amino)-1-((5-methoxy-7-methyl-1H-indol-4-yl)methyl)piperidin-2-yl)benzoic acid<br>$^1$H NMR (400 MHz, $d_6$-DMSO): δ 7.85 (d, J = 7.7 Hz, 2H), 7.41 (d, J = 7.7 Hz, 2H), 7.21 (d, J = 2.8 Hz, 1H), 6.60-6.49 (m, 1H), 6.42 (t, J = 3.0 Hz, 1H), 3.69 (s, 3H), 3.63-3.42 (m, 2H), 3.19 (s, 1H), 2.88 (M, 2H), 2.40 (s, 3H), 1.85-1.62 (m, 3H), 1.51 (d, J = 13.0 Hz, 2H), 0.94 (dd, J = 19.2, 6.1 Hz, 2H), 0.69 (d, J = 8.8 Hz, 2H). | 465.57 | 466 (M + 1)$^{\oplus}$ |

-continued

| Example | Intermediate Used | Structure | MW | MS (ESI+) |
|---|---|---|---|---|
| Example 24 | 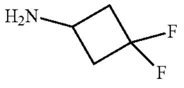 | 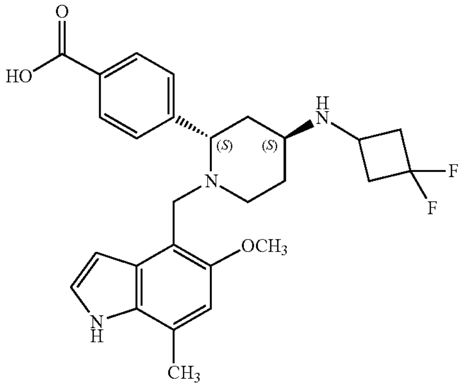<br>4-((2S,4S)-4-((3,3-difluorocyclobutyl)amino)-1-((5-methoxy-7-methyl-1H-indol-4-yl)methyl)piperidin-2-yl)benzoic acid | 483.56 | 484 (M + 1)⊕ |
| Example 25 | 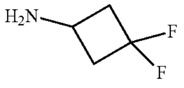 | 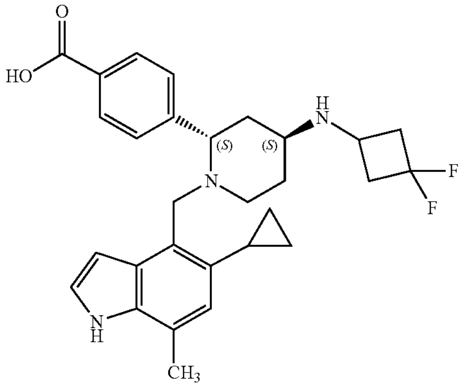<br>4-((2S,4S)-1-((5-cyclopropyl-7-methyl-1H-indol-4-yl)methyl)-4-((3,3-difluorocyclobutyl)amino)piperidin-2-yl)benzoic acid | 493.60 | 494 (M + 1)⊕ |
| Example 26 | 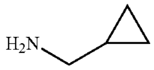 | 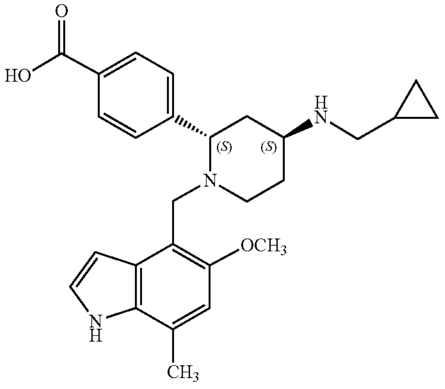<br>4-((2S,4S)-4-((cyclopropylmethyl)amino)-1-((5-methoxy-7-methyl-1H-indol-4-yl)methyl)piperidin-2-yl)benzoic acid | 447.58 | 448 (M + 1)⊕ |

-continued

| Example | Intermediate Used | Structure | MW | MS (ESI+) |
|---|---|---|---|---|
| Example 27 | 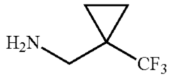 | 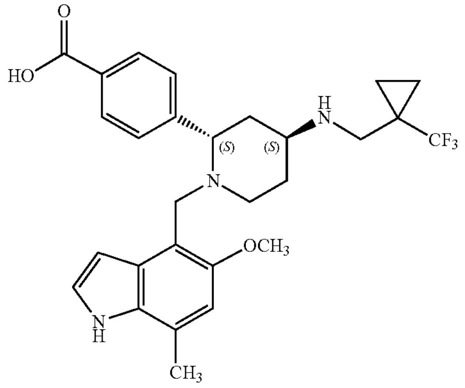 4-((2S,4S)-1-((5-methoxy-7-methyl-1H-indol-4-yl)methyl)-4-(((1-(trifluoromethyl)cyclopropyl)methyl)amino)piperidin-2-yl)benzoic acid | 515.58 | 516 (M + 1)$^{\oplus}$ |

Example 25: Preparation of 4-((2S,4S)-1-((5-cyclopropyl-7-methyl-1H-indol-4-yl)methyl)-4-((3,3-difluorocyclobutyl)amino)piperidin-2-yl)benzoic acid Example 25

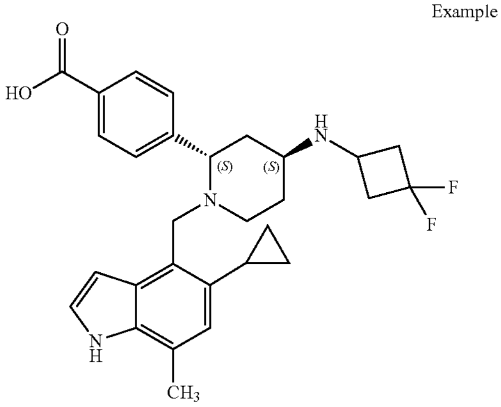

Step 1: Preparation of benzyl (2S,4S)-4-((3,3-difluorocyclobutyl)amino)-2-(4-(methoxycarbonyl)phenyl)piperidine-1-carboxylate: A solution of 3,3-difluorocyclobutanamine hydrochloride (1.5 equiv) and N,N-diisopropylethylamine (1.5 equiv), and benzyl (S)-2-(4-(methoxycarbonyl)phenyl)-4-oxopiperidine-1-carboxylate (Intermediate H, 1.0 equiv) in DCE (0.58 M) was stirred with 0.3 Å molecular sieves for 1 hour at 45° C. Sodium triacetoxyborohydride (2.0 equiv) was added and the reaction mixture was stirred at 20-25° C. for another 18 hours. The reaction was quenched with water, extracted with $CH_2Cl_2$ using a phase separator and the combined organic layers were concentrated under reduced pressure. The residue was purified by column chromatography through silica gel, eluting with 0-5% MeOH in $CH_2Cl_2$ as gradient. The fractions from the minor peak corresponding to the minor diastereomer eluting at 3% MeOH in $CH_2Cl_2$ were combined and concentrated under reduced pressure to yield a white solid (27% yield). LCMS (ESI) m/z 459 $(M+1)^+$.

Step 2: Preparation of methyl 4-((2S,4S)-4-((3,3-difluorocyclobutyl)amino)piperidin-2-yl)benzoate: To a solution benzyl (2S,4S)-4-((3,3-difluorocyclobutyl)amino)-2-(4-(methoxycarbonyl)phenyl)piperidine-1-carboxylate (1 equiv) in MeOH (0.4 M) was added palladium on carbon, 15 wt. % (10% Pd on carbon) and the mixture was purged with $N_2$. A balloon containing H2 gas was fitted onto the flask, the contents were purged, and the mixture was stirred under a H2 atmosphere at 23° C. for 15 hours. The reaction mixture was filtered through a pad of celite, and the filtrate was concentrated under reduced pressure to afford a clear colourless oil which was directly used in the next step without further purification. LCMS (ESI) m/z 325 $(M+1)^+$.

Step 3: Preparation of tert-butyl 5-cyclopropyl-4-(((2S,4S)-4-((3,3-difluorocyclobutyl)amino)-2-(4-(methoxycarbonyl)phenyl)piperidin-1-yl)methyl)-7-methyl-1H-indole-1-carboxylate: To a solution of methyl 4-((2S,4S)-4-((3,3-difluorocyclobutyl)amino)piperidin-2-yl)benzoate (1.5 equiv) in MeCN (0.4 M) was added tert-butyl 5-cyclopropyl-4-formyl-7-methyl-1H-indole-1-carboxylate (1.0 equiv) and 0.3 Å molecular sieves. The reaction mixture was stirred at 45° C. for 62 hours. Sodium triacetoxyborohydride (2.5 equiv) was added and the reaction mixture was stirred for 18 hours at 23° C. The reaction was quenched with water, then the mixture was purified by column chromatography through silica gel, eluting with 0-60% ethyl acetate in hexanes as a gradient. The fractions from the major peak were combined and concentrated under reduced pressure to afford a pale-yellow oil (48% yield). LCMS (ESI) m/z 608 $(M+1)^+$.

Step 4: Preparation of 4-((2S,4S)-1-((5-cyclopropyl-7-methyl-1H-indol-4-yl)methyl)-4-((3,3-difluorocyclobutyl)amino)piperidin-2-yl)benzoic acid: To tert-butyl 5-cyclopropyl-4-(((2S,4S)-4-((3,3-difluorocyclobutyl)amino)-2-(4-(methoxycarbonyl)phenyl)piperidin-1-yl)methyl)-7-methyl-1H-indole-1-carboxylate (1.0 equiv) in THF/MeOH (1:1, v/v) (0.15 M). A solution of 1 M aqueous lithium hydroxide (5.0 equiv) was added, and the solution was stirred at 50° C. for 6 hours. The reaction mixture was concentrated under reduced pressure and was acidified to pH ~2 by addition of formic acid. The mixture was purified by reverse phase column chromatography through a C18 column, eluting with 10-100% MeCN in water+0.1% formic acid as a gradient. The fractions from the major peak eluting at 45% MeCN were combined and lyophilized to afford the title compound as a white powder (62% yield). LCMS (ESI) m/z 494 $(M+1)^+$. $^1H$ NMR (400 MHz, $d_6$-DMSO): δ 10.83 (s, 1H), 8.16 (s, 1H), 7.93 (d, J=7.9 Hz, 2H), 7.61 (d, J=7.9 Hz, 2H), 7.24 (t, J=2.7 Hz, 1H), 6.56 (t, J=2.4 Hz, 1H), 6.44 (s, 1H), 3.76 (d, J=12.0 Hz, 1H), 3.68 (s, 1H), 3.46 (d, J=12.0 Hz, 1H), 3.25-3.15 (m, 1H), 2.85 (t, J=3.4 Hz, 1H), 2.76 (dtt, J=13.2, 8.3, 3.8 Hz, 2H), 2.42 (m, 3H), 2.35 (s, 3H), 2.18 (td, J=8.5, 4.4 Hz, 1H), 1.85 (t, J=13.1 Hz, 1H), 1.70 (d, J=13.4 Hz, 1H), 1.53 (d, J 8.9 Hz, 2H), 0.82 (dp, J=8.9, 4.5 Hz, 1H), 0.67 (dq, J=9.9, 5.2 Hz, 1H), 0.52 (dq, J=13.1, 8.0, 6.2 Hz, 1H), 0.17 (h, J=4.8 Hz, 1H).

Examples 28 and 29: Preparation of 4-((2S,4S)-4-(difluoromethoxy)-1-((5-methoxy-7-methyl-1H-indol-4-yl)methyl)piperidin-2-yl)benzoic acid and 4-((2R,4R)-4-(difluoromethoxy)-1-((5-methoxy-7-methyl-1H-indol-4-yl)methyl)piperidin-2-yl)benzoic acid Example 28

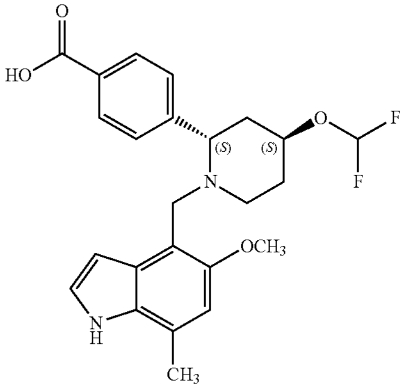

Example 29

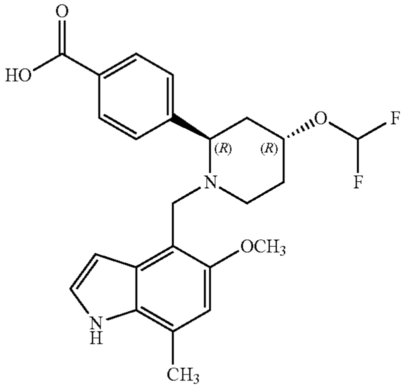

Step 1: Preparation of (±)-benzyl (trans)-4-(difluoromethoxy)-2-(4-(methoxycarbonyl)phenyl)piperidine-1-carboxylate: Into a round bottom flask equipped with a magnetic stir bar and under an atmosphere of $N_2$ was added (±)-benzyl (trans)-4-hydroxy-2-(4-(methoxycarbonyl)phenyl)piperidine-1-carboxylate (Intermediate I, 1.0 equiv), copper (I) iodide (0.2 equiv) and MeCN (0.2 M). The mixture was heated to 50° C. using an oil bath and 2-(fluorosulphonyl)difluoroacetic acid (2.0 equiv) was added to the heated mixture via syringe pump over 1 h. LCMS analysis reveals product formation. The reaction mixture was cooled to room temperature and poured into a separatory funnel containing sat. aqueous $Na_2CO_3$ solution (2.0 volumes) and the mixture was extracted with EtOAc (3×1 volume). The combined organic layers were washed with brine (1 volume), dried over $MgSO_4$, filtered, and concentrated under reduced pressure. Purification by column chromatography through silica gel, eluting with 100:0 to 40:60 Hexanes: EtOAc as a gradient afforded the title compound as a clear oil (53% yield). LCMS (ESI) m/z 420 $(M+1)^+$.

Step 2: Preparation of (±)-methyl 4-((trans)-4-(difluoromethoxy)piperidin-2-yl)benzoate: Into a round-bottom flask equipped with a magnetic stir bar and under an atmosphere of $N_2$ was added (±)-benzyl (trans)-4-(difluoromethoxy)-2-(4-(methoxycarbonyl)phenyl)piperidine-1-carboxylate (1.0 equiv), EtOAc (0.15 M) and 10 wt % palladium on carbon. The flask was first degassed with $N_2$ then fitted with a balloon filled with H2 gas and further degassed with H2. After bubbling in H2 for 15 minutes, the bubbler was removed, and the contents of the flask stirred at room temperature under an atmosphere of H2 for 1 h. LCMS analysis after this time reveals complete conversion of starting material. The reaction was degassed with $N_2$ and filtered through a pad of celite, washing with $CH_2Cl_2$ (3 volumes). The resulting clear filtrate was concentrated under reduced pressure and used directly in the next step without further purification. LCMS (ESI) m/z 286 $(M+1)^+$.

Step 3: Preparation of (±)-tert-butyl 4-(((trans)-4-(difluoromethoxy)-2-(4-(methoxycarbonyl)phenyl)piperidin-1-yl)methyl)-5-methoxy-7-methyl-1H-indole-1-carboxylate: Into a round-bottom flask equipped with a magnetic stir bar and under $N_2$ was added (±)-methyl 4-((trans)-4-(difluoromethoxy)piperidin-2-yl)benzoate (1.0 equiv), tert-butyl 4-formyl-5-methoxy-7-methyl-1H-indole-1-carboxylate (1.3 equiv), DCE (0.29 M) and 3 Å molecular sieves. The reaction mixture was heated to 40° C. for 1 h and then sodium triacetoxyborohydride (1.5 equiv) was added and the mixture was heated for 18 h overnight. The reaction mixture was cooled to room temperature, diluted with water and dichloromethane, and filtered through a pad of celite on a plastic fritted funnel. The clear filtrate was concentrated under reduced pressure. Purification by reverse-phase column chromatography using a C18 column, eluting with 95:5 to 20:80 $H_2O$:MeCN+0.1% formic acid as a gradient afforded the title compound as a slight yellow oil (66% yield). LCMS (ESI) m/z 559 $(M+1)^+$.

Step 4: Separation of enantiomers (2S,4S) and (2R,4R)-tert-butyl 4-(((trans)-4-(difluoromethoxy)-2-(4-(methoxycarbonyl)phenyl)piperidin-1-yl)methyl)-5-methoxy-7-methyl-1H-indole-1-carboxylate: The racemic compound (±)-tert-butyl 4-(((trans)-4-(difluoromethoxy)-2-(4-(methoxycarbonyl)phenyl)piperidin-1-yl)methyl)-5-methoxy-7-methyl-1H-indole-1-carboxylate was separated into each enantiomer using chiral SFC column chromatography, eluting through a ChiralPak IG column with 5% to 60% MeOH as a gradient. The first peak eluted at 3.7 min, and the second peak eluted at 4.2 min, both with >99% ee purity. Both compounds were concentrated separately and lyophilyzed to afford a white solid (37% yield and 29% yield respectively).

Step 5: Preparation of 4-((2S,4S)-4-(difluoromethoxy)-1-((5-methoxy-7-methyl-1H-indol-4-yl)methyl)piperidin-2-yl)benzoic acid: Into a round-bottom flask equipped with a magnetic stir bar was added the first eluting peak from tert-butyl 4-(((trans)-4-(difluoromethoxy)-2-(4-(methoxycarbonyl)phenyl)piperidin-1-yl)methyl)-5-methoxy-7-methyl-1H-indole-1-carboxylate (1.0 equiv), THF:MeOH (1:1 v/v, 0.2 M) and 1.0 M aqueous LiOH solution (3.0 equiv). The mixture was heated to 70° C. for 4 h, after which LCMS analysis reveals complete conversion of starting material to afford Example 28 (92% yield). $^1$H-NMR (400 MHz, $d_4$-MeOD): δ 12.86 (bs, 1H), 10.81 (s, 1H), 7.96 (d, J=8.0 Hz, 2H), 7.65 (d, J=8.0 Hz, 2H), 7.23 (s, 1H), 6.74 (t, $J_{F-H}$=76 Hz, 1H), 6.63 (s, 1H), 6.40 (s 1H), 4.39 (s, 1H), 3.69 (s, 3H), 3.51 (d, J 12.0 Hz, 2H), 3.23 (d, J=12.0 Hz, 1H), 2.58-2.52 (m, 1H), 2.39 (s, 3H), 2.35-2.30 (m, 1H), 1.86-1.81 (m, 2H), 1.68-1.60 (m, 2H). LCMS (ESI) m/z 445 $(M+1)^+$.

Using a similar procedure, the second eluting enantiomer from tert-butyl 4-(((trans)-4-(difluoromethoxy)-2-(4-(methoxycarbonyl)phenyl)piperidin-1-yl)methyl)-5-methoxy-7-methyl-1H-indole-1-carboxylate was hydrolyzed and purified to afford a white solid, corresponding to Example 29 (89% yield). LCMS (ESI) m/z 445 $(M+1)^+$.

Example 30: Preparation of 4-((3R,5S)- or ((3S, 5S)-1,1-difluoro-6-((5-methoxy-7-methyl-1H-indol-4-yl)methyl)-6-azaspiro[2.5]octan-5-yl)benzoic acid Example 30

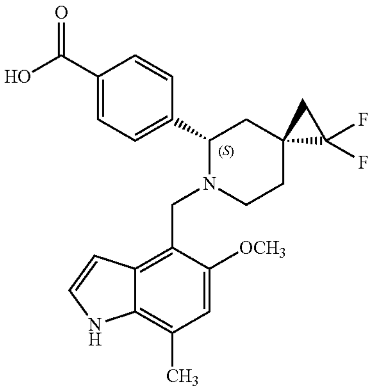

or

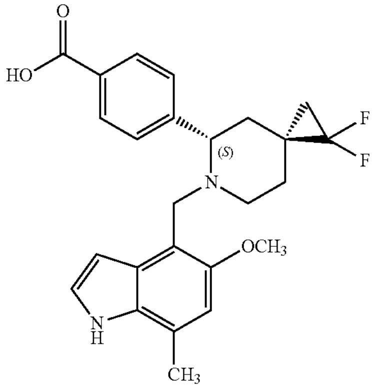

Step 1: Preparation of benzyl (S)-2-(4-(methoxycarbonyl)phenyl)-4-methylenepiperidine-1-carboxylate: To a cooled (−20° C.) suspension of methyltriphenylphosphonium bromide (1.5 equiv) in THE (0.33 M) in a flame-dried flask under a nitrogen atmosphere was added LiHMDS (1.0 M solution in THF, 1.5 equiv). After 90 minutes at this temperature, a solution of benzyl (S)-2-(4-(methoxycarbonyl)phenyl)-4-oxopiperidine-1-carboxylate (Intermediate H, 1.0 equiv) in THE (1.09 M) was added. The reaction mixture was slowly warmed to 23° C. and stirred for 18 hours. The temperature was increased to 50° C. and the mixture was stirred for 3 hours. Additional LiHMDS (1.0 equiv) was added, and the mixture was stirred for 4 hours at 50° C. The temperature was decreased to 20-25° C. and the mixture was stirred for another 18 hours. The reaction was quenched with a small amount of water and concentrated under reduced pressure. The residue was applied to a silica gel precartridge and purified by column chromatography through silica gel, eluting with a 0-100% EtOAc in hexanes as a gradient. The fractions from the major peak eluting at 45% EtOAc in hexanes were combined and concentrated under reduced pressure to afford a yellow oil (13% yield). LCMS (ESI) m/z 366 $(M+1)^+$.

Step 2: Preparation of benzyl (5S)-1,1-difluoro-5-(4-(methoxycarbonyl)phenyl)-6-azaspiro[2.5]octane-6-carboxylate: To a solution of benzyl (S)-2-(4-(methoxycarbonyl)phenyl)-4-methylenepiperidine-1-carboxylate (1.0 equiv) in THE (0.29 M) in a thick-walled glass tube was added NaI (2.2 equiv) and trimethyl(trifluoromethyl)silane (2.0 equiv). The reaction mixture was heated at 115° C. for 1 hour. After cooling, additional NaI (2.2 equiv) and trimethyl(trifluoromethyl)silane (2.0 equiv) were added and the reaction was heated at 115° C. for another hour. After cooling, additional trimethyl(trifluoromethyl)silane (2.0 equiv) was added and the reaction was heated at 115° C. for another hour. The reaction mixture was cooled, applied onto a silica precartridge and purified by column chromatography through silica gel, eluting with 30-90% EtOAc in hexanes as a gradient. The fractions from the first peak eluting at 44% EtOAc in hexanes were combined and concentrated under reduced pressure to afford a colorless oil (64% yield) as a single diastereomer. LCMS (ESI) m/z 416 $(M+1)^+$.

Step 3: Preparation of methyl 4-((5S)-1,1-difluoro-6-azaspiro[2.5]octan-5-yl)benzoate: To a solution of benzyl (5S)-1,1-difluoro-5-(4-(methoxycarbonyl)phenyl)-6-azaspiro[2.5]octane-6-carboxylate (1.0 equiv) in MeOH (0.19 M) was added palladium on carbon, 10 wt % (0.038 equiv). The mixture was purged with $N_2$ for 10 minutes and a balloon of H2 gas was then fitted to the flask. The contents were degassed, and the mixture was stirred under an atmosphere of H2 at 20-25° C. for 2 hours. The reaction mixture was filtered, and the filtrate was concentrated under reduced pressure to afford a colourless oil (92% yield) which was directly used in the next step without further purification. LCMS (ESI) m/z 282 $(M+1)^+$.

Step 4: Preparation of tert-butyl 4-(((5S)-1,1-difluoro-5-(4-(methoxycarbonyl)phenyl)-6-azaspiro[2.5]octan-6-yl)methyl)-5-methoxy-7-methyl-1H-indole-1-carboxylate: To a solution of methyl 4-((5S)-1,1-difluoro-6-azaspiro[2.5]octan-5-yl)benzoate in DCE (0.17 M) was added tert-butyl 4-formyl-5-methoxy-7-methyl-1H-indole-1-carboxylate (1.1 equiv) and 3 Å molecular sieves. The reaction mixture was stirred at 20-25° C. for 30 minutes. After this time, sodium triacetoxyborohydride (2.5 equiv) was added and the reaction mixture was stirred for 90 hours at 20-25° C. The reaction was quenched with a small amount of water, then the mixture was applied to a silica precartridge and purified by column chromatography through silica gel to obtain a single diastereomer, eluting with 0-100% EtOAc in hexanes as a gradient. The fractions from the peak eluting at 55%

EtOAc in hexanes were combined and concentrated under reduced pressure to afford a colourless oil (81% yield). LCMS (ESI) m/z 555 $(M+1)^+$.

Step 5: Preparation of 4-((3R,5S)- or ((3S,5S)-1,1-difluoro-6-((5-methoxy-7-methyl-1H-indol-4-yl)methyl)-6-azaspiro[2.5]octan-5-yl)benzoic acid: A solution of tert-butyl 4-(((5S)-1,1-difluoro-5-(4-(methoxycarbonyl)phenyl)-6-azaspiro[2.5]octan-6-yl)methyl)-5-methoxy-7-methyl-1H-indole-1-carboxylate in 1 M aqueous LiOH/THF/MeOH solution (5 equiv LiOH, v/v/v, 1/1/1) was heated at 70° C. and stirred for 3 hours, then heated to 80° C. and stirred for another 1 hour. The reaction mixture was cooled to afford the title compound as a single diastereomer (75% yield). $^1$H-NMR (400 MHz, DMSO): δ 10.84 (t, J=2.3 Hz, 1H), 8.04-7.93 (m, 2H), 7.68 (d, J=7.9 Hz, 2H), 7.26 (t, J=2.8 Hz, 1H), 6.66 (d, J=0.9 Hz, 1H), 6.44 (dd, J=3.1, 1.9 Hz, 1H), 3.72 (s, 3H), 3.56 (d, J=11.8 Hz, 1H), 3.23-3.16 (m, 2H), 2.84 (dd, J=11.7, 3.4 Hz, 1H), 2.46-2.37 (m, 3H), 2.05-1.92 (m, 2H), 1.81-1.70 (m, 1H), 1.49 (d, J=13.5 Hz, 1H), 1.36 (d, J=13.4 Hz, 1H), 1.24 (q, J=10.1, 7.5 Hz, 2H). LCMS (ESI) m/z 441.5 $(M+1)^+$.

Example 31: Preparation of (±)-4-(7-((5-methoxy-7-methyl-1H-indol-4-yl)methyl)-2-oxa-7-azaspiro[3.5]nonan-6-yl)benzoic acid Example 31

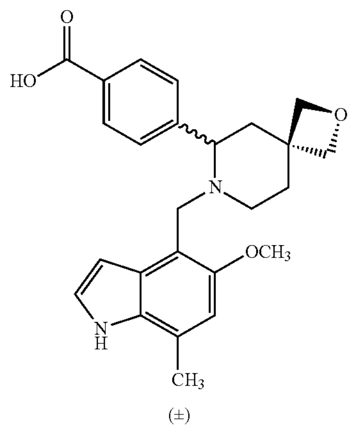

Step 1: Preparation of (±) tert-butyl-4-(2-oxa-7-azaspiro[3.5]nonan-6-yl)benzoate: To a solution of tert-butyl 4-iodobenzoate (1.5 equiv) in diethyl ether (0.25 M) under nitrogen and cooled over a dry ice/acetone bath adjusted to −40° C. was added dropwise chloro(isopropyl) magnesium·lithium chloride (1.5 equiv, 1.3 M in THF). This mixture was stirred over the dry ice/acetone cooling bath adjusted to −35 to −40° C. by incremental addition of dry ice to the cooling bath for 2 hours. To a solution of 2-oxa-7-azaspiro[3.5]nonane (1.0 equiv) in diethyl ether (0.25 M) under nitrogen and cooled over a dry ice/acetone bath at −78° C. was added butyllithium (1.0 equiv, 1.6 M in hexanes) and the reaction was stirred over the dry ice/acetone cooling bath for 10 minutes. To this mixture was added 2,2,2-trifluoroacetophenone (1.0 equiv) and the mixture stirred for 10 minutes at −78° C. To this reaction was added via canula the solution of the prepared magnesium complex over 5 minutes. Finally, trimethylsilyl trifluoromethanesulphonate (1.2 equiv) was added and the resulting mixture was stirred over a wet ice cooling bath (0 to 4° C.) for 30 minutes and then warmed to 20-25° C. for 1 hour. This mixture was diluted with water and extracted twice with EtOAc. The combined extracts were dried over $MgSO_4$, filtered and concentrated under reduced pressure. The residue was purified by reverse phase column chromatography using a C18 column, eluting with 0-50% MeCN in water gradient containing 0.1% $HCO_2H$. The fractions from the major peak eluting at 35% MeCN in water were combined and concentrated under vacuum to afford a gum (6% yield).

Step 2: Preparation of (±) tert-butyl-4-((6-(4-(tert-butoxycarbonyl)phenyl)-2-oxa-7-azaspiro[3.5]nonan-7-yl)methyl)-5-methoxy-7-methyl-1H-indole-1-carboxylate: To a solution of tert-butyl 4-(2-oxa-7-azaspiro[3.5]nonan-6-yl)benzoate in dichloroethane (0.12 M) was added tert-butyl 4-formyl-5-methoxy-7-methyl-1H-indole-1-carboxylate (1.3 equiv) and 3 Å molecular sieves. The reaction mixture was stirred for 30 minutes at 20-25° C. Sodium triacetoxyborohydride (2.50 equiv) was added, and the reaction mixture was stirred for 24 hours at 20-25° C. The reaction was quenched with a small amount of water, then the mixture was applied to a silica precartridge and purified by column chromatography through silica gel, eluting with a 0-100% ethyl acetate in hexanes gradient. The fractions from the major peak eluting at 80% EtOAc in hexanes were combined and concentrated under reduced pressure to afford a colourless oil (51% yield). LCMS (ESI) m/z 577 $(M+1)^+$.

Step 3: Preparation of (±)-4-(7-((5-methoxy-7-methyl-1H-indol-4-yl)methyl)-2-oxa-7-azaspiro[3.5]nonan-6-yl) benzoic acid: To a solution of tert-butyl-4-((6-(4-(tert-butoxycarbonyl)phenyl)-2-oxa-7-azaspiro[3.5]nonan-7-yl)methyl)-5-methoxy-7-methyl-1H-indole-1-carboxylate (1.0 equiv) in 1:1 v/v THF/MeOH (0.10 M) was added 1 M aqueous LiOH solution (5.0 equiv). The reaction mixture was stirred at 70° C. for 3 hours, then 80° C. for 5 hours. Additional 1 M aqueous LiOH solution (5.0 equiv) was added, and the reaction mixture was stirred at 80° C. for 3 more hours (53% yield). $^1$H-NMR (400 MHz, DMSO): δ 10.81 (s, 1H), 7.95 (d, J=7.9 Hz, 2H), 7.64 (d, J=7.9 Hz, 2H), 7.22 (t, J=2.8 Hz, 1H), 6.62 (s, 1H), 6.40 (d, J=2.6 Hz, 1H), 4.50 (d, J=5.8 Hz, 1H), 4.39 (d, J=5.8 Hz, 1H), 4.15 (d, J=6.8 Hz, 2H), 3.67 (s, 3H), 3.49 (d, J=11.9 Hz, 1H), 3.14-3.02 (m, 2H), 2.65 (d, J=11.5 Hz, 1H), 2.39 (s, 3H), 2.06 (d, J 12.9 Hz, 1H), 1.85 (t, J=14.1 Hz, 2H), 1.63 (t, J=12.3 Hz, 1H), 1.43 (t, J=12.8 Hz, 1H). LCMS (ESI) m/z 421.5 $(M+1)^+$.

The following compound was obtained by chiral separation of the racemic mixture above.

| Example | Structure | MW | MS (ESI+) |
|---|---|---|---|
| Example 32 | 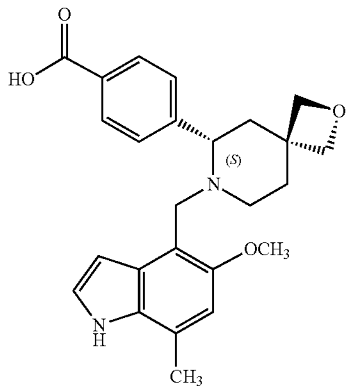 (S)-4-(7-((5-methoxy-7-methyl-1H-indol-4-yl)methyl)-2-oxa-7-azaspiro[3.5]nonan-6-yl)benzoic acid | 420.51 | 421 (M + 1)$^{\oplus}$ |

The following compounds were prepared in a similar manner as Example 31 replacing 2-oxa-7-azaspiro[3.5] nonane with the corresponding commercially available amines in the table in step 1.

| Example | Intermediate Used | Structure | MW | MS (ESI+) |
|---|---|---|---|---|
| Example 33 | 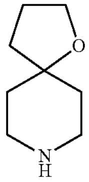 | 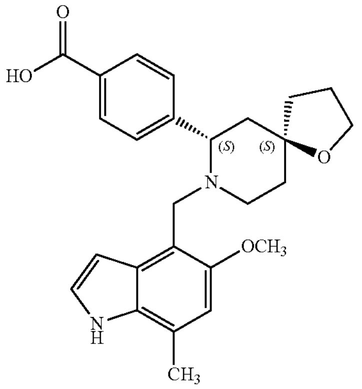 or 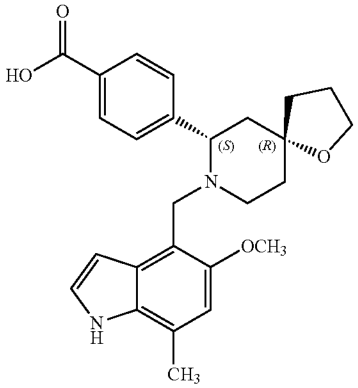 4-((5S,7S)-8-((5-methoxy-7-methyl-1H-indol-4-yl)methyl)-1-oxa-8-azaspiro[4.5]decan-7-yl)benzoic acid or 4-((5R,7S)-8-((5-methoxy-7-methyl-1H-indol-4-yl)methyl)-1-oxa-8-azaspiro[4.5]decan-7-yl)benzoic acid | 434.22 | 435 (M + 1)$^{\oplus}$ |

-continued
| Example | Intermediate Used | Structure | MW | MS (ESI+) |
| --- | --- | --- | --- | --- |
| Example 34 | 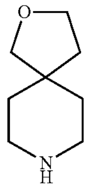 | 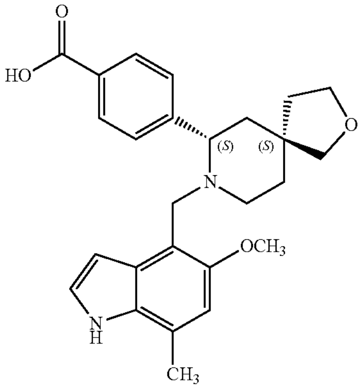 or 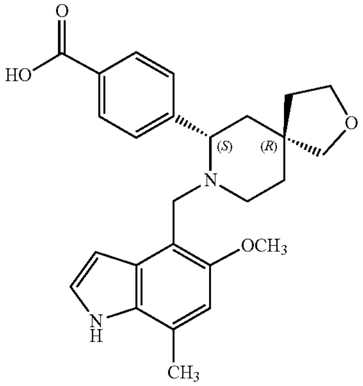 4-((5S,7S)-8-((5-methoxy-7-methyl-1H-indol-4-yl)methyl)-2-oxa-8-azaspiro[4.5]decan-7-yl)benzoic acid or 4-((5R,7S)-8-((5-methoxy-7-methyl-1H-indol-4-yl)methyl)-2-oxa-8-azaspiro[4.5]decan-7-yl)benzoic acid | 434.22 | 435 (M + 1)⊕ |

-continued
| Example | Intermediate Used | Structure | MW | MS (ESI+) |
|---|---|---|---|---|
| Example 35 | 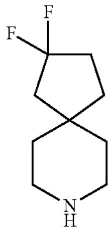 [SMILES: FC1(F)CCC2(CCNCC2)C1] | 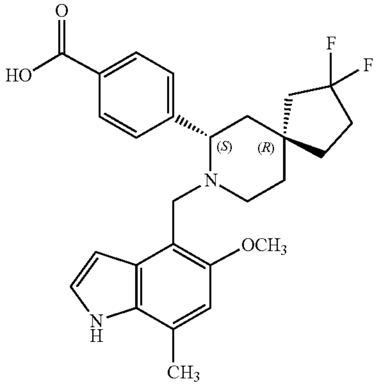 or 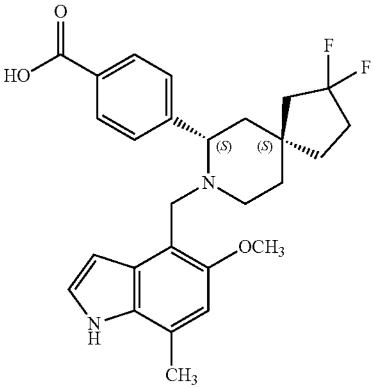 4-(5R,7S)-(2,2-difluoro-8-((5-methoxy-7-methyl-1H-indol-4-yl)methyl)-8-azaspiro[4.5]decan-7-yl)benzoic acid or 4-(5S,7S)-(2,2-difluoro-8-((5-methoxy-7-methyl-1H-indol-4-yl)methyl)-8-azaspiro[4.5]decan-7-yl)benzoic acid | 468.54 | 469 (M + 1)$^{\oplus}$ |

-continued

| Example | Intermediate Used | Structure | MW | MS (ESI+) |
|---|---|---|---|---|
| Example 36 | 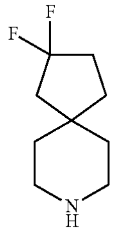 [SMILES: FC1(F)CCC2(CCNCC2)C1] | 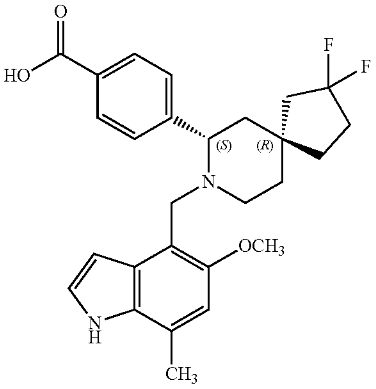 or 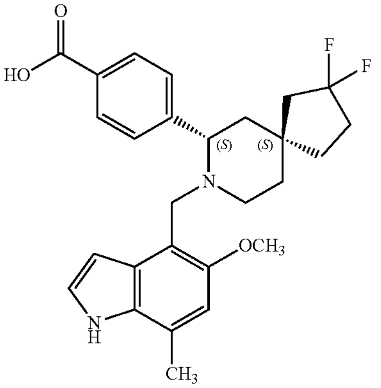 4-(5R,7S)-(2,2-difluoro-8-((5-methoxy-7-methyl-1H-indol-4-yl)methyl)-8-azaspiro[4.5]decan-7-yl)benzoic acid or 4-(5S,7S)-(2,2-difluoro-8-((5-methoxy-7-methyl-1H-indol-4-yl)methyl)-8-azaspiro[4.5]decan-7-yl)benzoic acid | 468.54 | 469 $(M + 1)^{\oplus}$ |

Example 35 & 36: Preparation of 4-((5S,7S)-2,2-difluoro-8-((5-methoxy-7-methyl-1H-indol-4-yl)methyl)-8-azaspiro[4.5]decan-7-yl)benzoic acid and 4-((5R,7S)-2,2-difluoro-8-((5-methoxy-7-methyl-11H-indol-4-yl)methyl)-8-azaspiro[4.5]decan-7-yl)benzoic acid Example 35 and 36

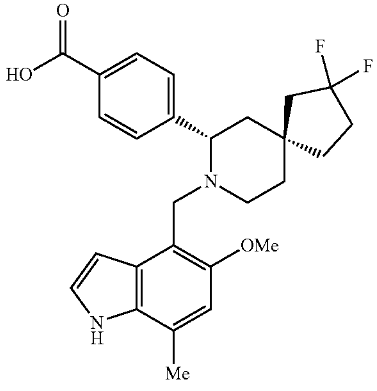

-continued

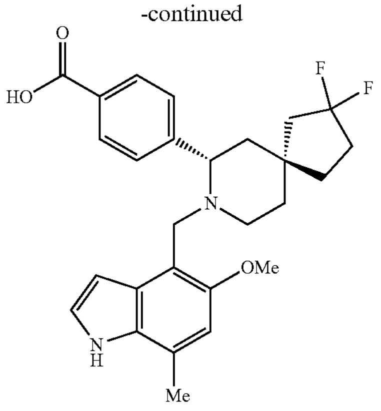

Step 1: Preparation of tert-butyl 2,2-difluoro-8-azaspiro[4.5]decane-8-carboxylate. A round bottom flask was charged with 3,3-difluoro-8-azaspiro[4.5]decane hydrochloride (1.0 equiv), $CH_2Cl_2$ (0.5 M), tert-butoxycarbonyl tert-butyl carbonate (1.2 equiv) and cooled to 0° C. Diisopropylethylamine (2.5 equiv) was added dropwise, and the mixture was allowed to warm to room temperature overnight. The next day the reaction was quenched with water and extracted three times with $CH_2C12$. The combined organic layers were dried over sodium sulphate, filtered, concentrated under vacuum, and purified by silica gel column chromatography to afford tert-butyl 3,3-difluoro-8-azaspiro[4.5]decane-8-carboxylate (98% yield).

Step 2: Preparation of (±) tert-butyl 2,2-difluoro-7-(4-(methoxycarbonyl)phenyl)-8-azaspiro[4.5]decane-8-carboxylate. A flame dried microwave vial, equipped with a stir bar, rubber septum and needle temperature probe, was put under an atmosphere of nitrogen, charged with tert-butyl 3,3-difluoro-8-azaspiro[4.5]decane-8-carboxylate (1.0 equiv), N,N,N',N'-tetramethylethane-1,2-diamine (1.3 equiv), THE (0.5 M) and cooled to −78° C. with a dry ice/acetone bath. sec-Butyllithium, 12% (ca 1.4 M) in cyclohexane/hexane (1.3 equiv) was added dropwise, not allowing internal temperature to rise above −70° C. and allowed to stir for 10 min. Zinc chloride anhydrous (1.35 equiv), was added dropwise, maintaining internal temperature below −70° C. After complete addition of the zinc chloride, the solution was allowed to mix for 5 min followed by removal of the dry ice/acetone bath, the mixture was allowed to warm to room temperature and was allowed to mix for a further 10 min once at room temperature. Methyl 4-iodobenzoate (1.4 equiv) and [2-(2-aminophenyl)phenyl]-methylsulfonyloxy-palladium; dicyclohexyl-[2-(2,4,6-triisopropylphenyl)phenyl]phosphane (0.10 equiv) were added as a solid under a stream of nitrogen. The microwave vial was sealed and heated at 65° C. for 2 hours. The reaction mixture was then allowed to cool to room temperature and 5% $NH_4OH$ solution (0.5 M) was added to the reaction mixture. The reaction mixture was then extracted three times with EtOAc. The combined organic extracts were dried over sodium sulphate, concentrated in vacuo. The crude mixture was purified by column chromatography through silica gel using an eluent of 0 to 25% of EtOAc in hexanes as a gradient to yield the title compound as a colorless liquid (81% yield).

Step 3: Preparation of (±) methyl 4-(2,2-difluoro-8-azaspiro[4.5]decan-7-yl)benzoate hydrochloride: tert-butyl 3,3-difluoro-9-(4-methoxycarbonylphenyl)-8-azaspiro[4.5]decane-8-carboxylate (1.0 equiv) and hydrochloric acid 4 M in dioxane (3.7 equiv) was stirred for 1 hour under nitrogen. The reaction mixture was resuspended in methanol and concentrated in vacuo to dryness. Crude material carried through to next step without further purification.

Step 4: Preparation of (I) tert-butyl 4-((2,2-difluoro-7-(4-(methoxycarbonyl)phenyl)-8-azaspiro[4.5]decan-8-yl)methyl)-5-methoxy-7-methyl-1H-indole-1-carboxylate: Methyl 4-(3,3-difluoro-8-azaspiro[4.5]decan-9-yl)benzoate hydrochloride (1.0 equiv), tert-butyl 4-formyl-5-methoxy-7-methyl-indole-1-carboxylate (1.2 equiv), diisopropylethylamine (4.0 equiv), and $CH_2Cl_2$ (0.15 M) were heated at 40° C. for 30 min. Sodium triacetoxyborohydride (2.0 equiv) was added. The reaction mixture was allowed to stir overnight at 40° C. The reaction was quenched with water and extracted three times with $CH_2Cl_2$. Combined organic extracts were dried over sodium sulphate concentrated in vacuo. The crude mixture was purified by column chromatography through silica gel using an eluent of 0 to 25% of EtOAc in hexanes as a gradient to yield the title compound as a colorless liquid (96% yield).

Step 5: Preparation of (±) 4-(2,2-difluoro-8-((5-methoxy-7-methyl-1H-indol-4-yl)methyl)-8-azaspiro[4.5]decan-7-yl)benzoic acid: tert-butyl 4-[[3,3-difluoro-9-(4-methoxycarbonylphenyl)-8-azaspiro[4.5]decan-8-yl]methyl]-5-methoxy-7-methyl-indole-1-carboxylate (1.0 equiv), THE (0.2 M), methanol (0.2 M), lithium hydroxide (5.2 equiv, 1M solution in water) were heated overnight at 65° C. The reaction was acidified with formic acid (8 equiv), the volatiles were removed in vacuo and the crude mixture was redissolved to a homogeneous mixture with DMSO. The crude mixture was purified by reverse phase column chromatography using an eluent of 15 to 70% of water (0.1% formic acid) in acetonitrile (0.1% formic acid) as a gradient to yield the title compound as a colorless liquid (77% yield).

Step 6: Preparation of 4-((5S,7S)-2,2-difluoro-8-((5-methoxy-7-methyl-1H-indol-4-yl)methyl)-8-azaspiro[4.5]decan-7-yl)benzoic acid and 4-((5R,7S)-2,2-difluoro-8-((5-methoxy-7-methyl-1H-indol-4-yl)methyl)-8-azaspiro[4.5]decan-7-yl)benzoic acid: The crude material from step 5 was separated by chiral chromatography using a ChiralPak Ad 4.6×150 nm column, 5 to 60% IPA. (First eluting peak)$^1$H NMR (400 MHz, $d_4$-MeOD): δ 8.16 (d, J=7.8 Hz, 2H), 7.66 (d, J=7.4 Hz, 2H), 7.32 (d, J=3.1 Hz, 1H), 6.75 (s, 1H), 6.32 (d, J=3.2 Hz, 1H), 4.49 (d, J 12.0 Hz, 1H), 4.34 (d, J=12.7 Hz, 1H), 4.13 (d, J=12.6 Hz, 1H), 3.75 (s, 3H), 3.47 (d, J=13.1 Hz, 1H), 3.35-3.25 (m, 1H), 2.50 (s, 3H), 2.40 (td, J=14.4, 4.5 Hz, 2H), 2.18 (tt, J=14.1, 7.8 Hz, 3H), 2.02 (d, J=14.4 Hz, 1H), 1.92-1.81 (m, 2H), 1.76 (t, J=7.8 Hz, 2H). (second eluting peak) $^1$H NMR (400 MHz, $d_4$-MeOD): δ 8.16 (d, J=6.1 Hz, 2H), 7.68 (d, J=5.8 Hz, 2H), 7.33 (d, J=3.0 Hz, 1H), 6.78 (s, 1H), 6.34 (s, 1H), 4.55 (d, J=12.4 Hz, 1H), 4.35 (d, J=12.5 Hz, 1H), 4.14 (d, J=12.6 Hz, 1H), 3.77 (s, 3H), 3.52-3.35 (m, 2H), 2.52 (s, 3H), 2.38-1.82 (m, 10H).

Example 37: Preparation of (±)-trans-4-(1-((5-methoxy-7-methyl-1H-indol-4-yl)methyl)-4-phenylpiperidin-2-yl)benzoic acid Example 37

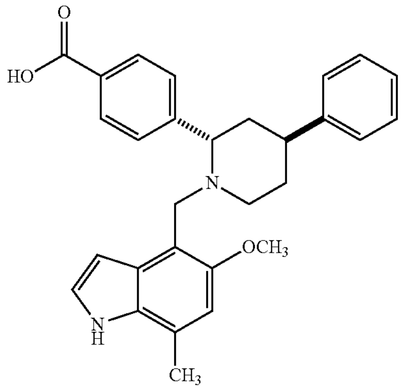

(+/-)-trans

Step 1: Preparation of (±) tert-butyl 2-(4-cyanophenyl)-4-phenylpiperidine-1-carboxylate: A mixture of terephthalonitrile (1.0 equiv), 1-(tert-butoxycarbonyl)-4-phenylpiperidine-2-carboxylic acid (2.0 equiv), 2,4,5,6-tetra(9H-carbazol-9-yl)isophthalonitrile (0.05 equiv) and $K_2HPO_4$ (3.0 equiv) in DMSO (0.08 M) was degassed and purged with $N_2$ for 30 min. The mixture was stirred at 20-25° C. for 16 hours and irradiated with a blue LED light (365 nm) under a $N_2$ atmosphere. Several new peaks were shown on LCMS and approx. 51% of desired compound was detected. The reaction mixture was diluted with $H_2O$ and extracted with ethyl acetate. The organic layers were washed with $H_2O$, dried over $Na_2SO_4$, filtered, and concentrated under reduced pressure to afford a residue. The residue was purified by column chromatography through silica gel (eluent of 0% to 5% ethyl acetate in petroleum ether as a gradient). The desired product containing fractions were concentrated and dried under vacuum to afford a light-yellow oil (41% yield). LCMS (ESI) m/z 307 $(M-56+1)^+$.

Step 2: Preparation of (±)-4-(4-phenylpiperidin-2-yl)benzonitrile: To a solution of (±) tert-butyl 2-(4-cyanophenyl)-4-phenylpiperidine-1-carboxylate (1.0 equiv) in $CH_2Cl_2$ (0.6 M) was added TFA (4.5 M). The mixture was stirred at 20-25° C. for 1.5 hours after which LCMS indicated completion of reaction. The reaction mixture was treated with saturated aqueous $NaHCO_3$ solution to pH=7 and extracted with EtOAc (3 x). The combined organic layers were dried over $Na_2SO_4$, filtered, and concentrated under reduced pressure to afford a residue. The crude product 4-(4-phenylpiperidin-2-yl)benzonitrile was obtained as a yellow oil, which was directly used in the next step without further purification. LCMS (ESI) m/z 263 $(M+1)^+$.

Step 3: Preparation of (±)-trans-tert-butyl 4-(((2S,4S)-2-(4-cyanophenyl)-4-phenylpiperidin-1-yl)methyl)-5-methoxy-7-methyl-1H-indole-1-carboxylate: To a solution of 4-(4-phenylpiperidin-2-yl)benzonitrile (1.0 equiv) and tert-butyl 4-formyl-5-methoxy-7-methyl-1H-indole-1-carboxylate (1.0 equiv) in MeOH (0.05 M) was added $ZnCl_2$ (5.0 equiv) and the mixture was stirred at 20-25° C. for 2 hours. Solid $NaBH_3CN$ (3.0 equiv) was then added, and the mixture was stirred at 20-25° C. for 16 hours. Several new peaks were shown on LCMS and approx. 82% of the desired compound was detected. The reaction mixture was diluted with ethyl acetate and extracted with water. The organic layers were filtered and concentrated under reduced pressure to afford a residue. The residue was purified by column chromatography through silica gel (eluent of 0 to 6% MeOH in $CH_2Cl_2$ as a gradient). The desired product containing fractions were concentrated and lyophilized overnight to yield the title product as a yellow gum (75% yield). LCMS (ESI) m/z 536 $(M+1)^+$.

Step 4: Preparation of (+)-trans-4-(1-((5-methoxy-7-methyl-1H-indol-4-yl)methyl)-4-phenylpiperidin-2-yl)benzoic acid: To a solution of (±)-trans-tert-butyl 4-((-2-(4-cyanophenyl)-4-phenylpiperidin-1-yl)methyl)-5-methoxy-7-methyl-1H-indole-1-carboxylate (1.0 equiv) was added 1.4 M aqueous KOH/EtOH solution (15.0 equiv KOH, v/v, 2/5). The mixture was heating under stirring at 100° C. for 40 hours and 120° C. for 144 hours. LCMS indicated completion of hydrolysis, after which the mixture was cooled to 20-25° C., and the reaction quenched with 1:1 saturated aqueous $KHSO_4$ solution: water to pH ~6. The mixture was diluted with $H_2O$ and extracted with ethyl acetate (62% yield). $^1H$-NMR (400 MHz, $CD_3OD$): δ 8.36 (bs, 1H), 8.18 (d, J=8.4 Hz, 2H), 7.68 (d, J=8.4 Hz, 2H), 7.46 (d, J=4.4 Hz, 4H), 7.29-7.34 (m, 2H), 6.74 (s, 1H), 6.25 (d, J=4.8 Hz, 1H), 4.49-4.53 (m, 1H), 4.30 (d, J=12.8 Hz, 1H), 4.12 (d, J 12.8 Hz, 1H), 3.74 (s, 3H), 3.40-3.49 (m, 2H), 3.23-3.29 (m, 1H), 2.64-2.71 (m, 2H), 2.49 (s, 3H), 2.38-2.47 (m, 2H). LCMS (ESI) m/z 455 $(M+1)^+$.

Example 38: Preparation of 4-((2S,4S)-1-((5-methoxy-7-methyl-1H-indol-4-yl)methyl)-4-(pyridin-2-yl)piperidin-2-yl)benzoic acid Example 38

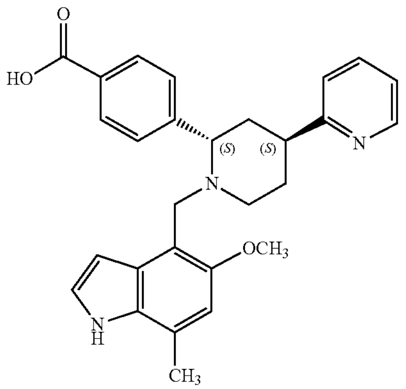

Step 1: Preparation of (±)-trans-benzyl 4-hydroxy-2-(4-(methoxycarbonyl)phenyl)piperidine-1-carboxylate: To a solution of (±)-trans-benzyl 4-((tert-butyldiphenylsilyl)oxy)-2-(4-(methoxycarbonyl)phenyl)piperidine-1-carboxylate (Intermediate B, 1.0 equiv) in THF (0.15 M) was slowly added TBAF (1.0 M, 4.0 equiv) dropwise at 0° C. After addition, the reaction mixture was stirred at 20-25° C. for 16 hours. TLC (Petroleum ether: Ethyl acetate=1:1) analysis indicated no reactant remained and a new spot had formed. The reaction mixture was concentrated under reduced pressure, diluted with $H_2O$, and extracted with ethyl acetate (3×). The combined organic layers were dried and concentrated under reduced pressure. The residue was purified by column chromatography through silica gel (eluent of 0% to 70% ethyl acetate in petroleum ether as a gradient). The desired product containing fractions were concentrated and dried under vacuum to afford a yellow oil (85% yield).

Step 2: Preparation of (±)-cis-benzyl 4-bromo-2-(4-(methoxycarbonyl)phenyl)piperidine-1-carboxylate: To a mixture of (±)-trans-benzyl 4-hydroxy-2-(4-(methoxycarbonyl)phenyl)piperidine-1-carboxylate (1.0 equiv) and $CBr_4$ (3.0 equiv) in $CH_2Cl_2$ (0.55 M) was added $PPh_3$ (3.0 equiv). The reaction mixture was stirred at 40° C. for 16 hours. TLC (Petroleum ether: Ethyl acetate=2:1) analysis indicated no reactant remained and a new spot formed. The reaction mixture was diluted with $H_2O$ and extracted with ethyl acetate (3×). The combined organic layers were dried, filtered and concentrated under reduced pressure. The residue was purified by column chromatography through silica gel (eluent of 0% to 40% ethyl acetate in petroleum ether as a gradient). The desired product containing fractions were concentrated and dried under vacuum to afford a yellow oil (85% yield).

Step 3: Preparation of (±)-trans-benzyl 2-(4-(methoxycarbonyl)phenyl)-4-(pyridin-2-yl)piperidine-1-carboxylate: To an oven-dried flask, (±)-cis-benzyl 4-bromo-2-(4-(methoxycarbonyl)phenyl)piperidine-1-carboxylate (1.0 equiv), Zn metal (2.0 equiv) and anhydrous $MgCl_2$ (1.0 equiv) in anhydrous N,N-dimethylacetamide (0.091 M) were combined with a mixture of $NiI_2$ (0.10 equiv) and 4,4'-di-tert-butyl-2,2'-bipyridine (0.10 equiv). The system was degassed under vacuum and purged with $N_2$ several times. Finally, pyridine (1.0 equiv) and 2-bromopyridine (1.0 equiv) were added to the flask and the black suspension was stirred under an atmosphere of $N_2$ at 20-25° C. for 16 hours. Several peaks were observed by LCMS and the desired compound was detected. The reaction mixture was diluted with $H_2O$ and extracted with ethyl acetate (3×). The combined organic layers were dried over $MgSO_4$, filtered, and concentrated under reduced pressure. The residue was purified by column chromatography through silica gel (eluent of 0 to 70% ethyl acetate in petroleum ether as a gradient). The desired product containing fractions were concentrated and dried under vacuum to afford a colorless oil (35% yield). LCMS (ESI) m/z 431 $(M+1)^+$.

Step 4: Preparation of (±)-trans-methyl 4-(4-(pyridin-2-yl)piperidin-2-yl)benzoate: To a solution of (±)-trans-benzyl 2-(4-(methoxycarbonyl)phenyl)-4-(pyridin-2-yl)piperidine-1-carboxylate (1.0 equiv) in THE and MeOH (0.065 M, v/v=3:2) was added Pd on carbon (10 wt %, 0.10 equiv). The system was degassed and purged with $N_2$, followed by the addition of $H_2$ and purging with $H_2$ gas three more times. The mixture was stirred under an atmosphere of $H_2$ (15 psi) at 20-25° C. for 2 hours. TLC (dichloromethane:methanol=10:1) analysis indicated no reactant remained at this time. The reaction mixture was filtered through celite and the filtrate was concentrated under reduced pressure. The desired product was obtained without further purification as colorless oil (94% yield). LCMS (ESI) m/z 297 $(M+1)^+$.

Step 5: Preparation of (±)-trans-tert-butyl 5-methoxy-4-((2-(4-(methoxycarbonyl)phenyl)-4-(pyridin-2-yl)piperidin-1-yl)methyl)-7-methyl-1H-indole-1-carboxylate: To a solution of (±)-trans-methyl 4-(4-(pyridin-2-yl)piperidin-2-yl) benzoate (1.0 equiv), tert-butyl 4-formyl-5-methoxy-7-methyl-1H-indole-1-carboxylate (1.0 equiv) in MeOH (0.034 M) was added $ZnCl_2$ (3.0 equiv). The solution was stirred at 50° C. for 2 hours under a $N_2$ atmosphere, after which $NaBH_3CN$ (4.0 equiv) was added, and the suspension was stirred at the same temperature for 16 hours. TLC (dichloromethane:methanol=10:1) indicated a new spot had formed and no reactant remained. The reaction mixture was diluted with water and extracted with ethyl acetate (3×). The combined organic layers were dried over $MgSO_4$, filtered, and concentrated under reduced pressure. The residue was purified by column chromatography through silica gel (eluent of 0 to 7% methanol in dichloromethane as a gradient). The desired product containing fractions were concentrated and dried under vacuum to afford a colorless oil (31% yield). LCMS (ESI) m/z 570 $(M+1)^+$.

Step 6: Preparation of (±)-trans-4-(1-((5-methoxy-7-methyl-1H-indol-4-yl)methyl)-4-(pyridin-2-yl)piperidin-2-yl)benzoic acid: To a solution of (±)-trans-tert-butyl 5-methoxy-4-((2-(4-(methoxycarbonyl)phenyl)-4-(pyridin-2-yl)piperidin-1-yl)methyl)-7-methyl-1H-indole-1-carboxylate (1.0 equiv) was added 1 M aqueous LiOH/THF/MeOH solution (10.0 equiv LiOH, v/v/v, 1/1/1). The mixture was stirred at 70° C. for 2 hours. LCMS indicated completion of hydrolysis, the reaction mixture was diluted with $H_2O$, then washed with ethyl acetate. The pH of the aqueous layer was adjusted to pH-7 using 1.0 M aqueous HCl solution and then extracted with butanol (3×). The combined organic layers were dried over $MgSO_4$, filtered, and concentrated under reduced pressure to yield the title product (30% yield). LCMS (ESI) m/z 456 $(M+1)^+$.

Step 7: Preparation of 4-((2S,4S)-1-((5-methoxy-7-methyl-1H-indol-4-yl)methyl)-4-(pyridin-2-yl)piperidin-2-yl)benzoic acid: The enantiomers of (+)-trans-4-(1-((5-methoxy-7-methyl-1H-indol-4-yl)methyl)-4-(pyridin-2-yl) piperidin-2-yl)benzoic acid (Example 37, 1.0 equiv) were separated by chiral SFC chromatography (column: DAICEL CHIRALPAK AD (250 mm×30 mm, 10 μm); mobile phase: A: [0.1% $NH_3H_2O$ in EtOH](45%), B: $scCO_2$ (55%) to give 4-((2S,4S)-1-((5-methoxy-7-methyl-1H-indol-4-yl)methyl)-4-(pyridin-2-yl)piperidin-2-yl)benzoic acid (42% yield) as a white solid. $^1$H-NMR (400 MHz, $CD_3OD$): δ 8.69 (s, 1H), 8.13 (d, J=8 Hz, 2H), 7.81-7.85 (m, 1H), 7.62 (d, J=8 Hz, 2H), 7.48 (d, J=8 Hz, 1H), 7.32-7.35 (m, 1H), 7.29 (d, J=3 Hz, 1H), 6.76 (s, 1H), 6.26 (s, 1H), 4.93-4.99 (m, 1H), 4.60 (m, 1H), 4.31-4.39 (m, 1H), 4.12 (d, J=13 Hz, 1H), 3.76 (s, 3H), 3.51-3.60 (m, 1H), 3.35-3.50 (m, 2H), 2.58-2.67 (m, 2H), 2.50 (s, 3H), 2.33-2.45 (m, 2H). LCMS (ESI) m/z 456 $(M+1)^+$.

Example 39: Preparation of (±)-4-(2-((5-methoxy-7-methyl-1H-indol-4-yl)methyl)-2-azaspiro[3.4]octan-1-yl)benzoic acid Example 39

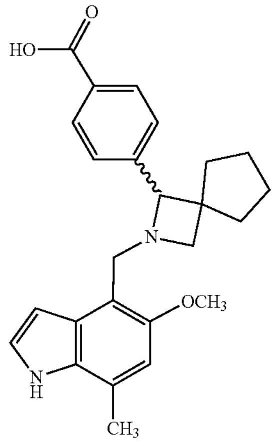

(±)

Step 1: Preparation of (±) tert-butyl 1-(4-(methoxycarbonyl)phenyl)-2-azaspiro[3.4]octane-2-carboxylate: A mixture of methyl 4-cyanobenzoate (1.0 equiv), 2-tert-butoxycarbonyl-2-azaspiro[3.4]octane-3-carboxylic acid (1.5 equiv), $K_2HPO_4$ (3.0 equiv), 2,4,5,6-tetra(9H-carbazol-9-yl)isophthalonitrile (4-CzIPN, 0.05 equiv) in DMSO (0.03 M) was degassed and purged with $N_2$ (3 times), and then the mixture was stirred at 20-25° C. for 18 hours under a $N_2$ atmosphere while being irradiated with a blue LED light (365 nm). Several new peaks were observed by LCMS and approx. 52% of desired compound was detected. The mixture was purified by column chromatography through silica gel (eluent of 0% to 10% ethyl acetate in petroleum ether as a gradient). The desired product containing fractions were concentrated and dried under vacuum to afford a colourless oil (49% yield). LCMS (ESI) m/z 290 $(M-56+1)^+$.

Step 2: Preparation of (±) methyl 4-(2-azaspiro[3.4]octan-1-yl)benzoate: To a solution of tert-butyl 3-(4-methoxycarbonylphenyl)-2-azaspiro[3.4]octane-2-carboxylate (1.0 equiv) in $CH_2Cl_2$ (0.03 M) and TFA (0.1 M) was stirred at 20-25° C. for 1 hour after which LCMS analysis indicated completion of reaction. The reaction mixture was washed with saturated aqueous $NaHCO_3$ and extracted with EtOAc. The combined organic layers were dried over $MgSO_4$, filtered, and concentrated under reduced pressure to afford a residue. The crude product methyl 4-(2-azaspiro[3.4]octan-3-yl)benzoate was obtained as a yellow oil, which was directly used in the next step without further purification.

Step 3: Preparation of (±)-tert-butyl 5-methoxy-4-((1-(4-(methoxycarbonyl)phenyl)-2-azaspiro[3.4]octan-2-yl) methyl)-7-methyl-1H-indole-1-carboxylate: To a solution of methyl 4-(2-azaspiro[3.4]octan-3-yl)benzoate (1.0 equiv) and tert-butyl 4-formyl-5-methoxy-7-methyl-indole-1-carboxylate (1.5 equiv) in MeOH (0.03 M) was added tetraisopropoxytitanium (4.0 equiv). The mixture was stirred at 20-25° C. for 2 hours. After this time, $NaBH_3CN$ (2.0 equiv) was added, and the resulting mixture was stirred at 50° C. for 16 hours. Several new peaks were observed by LCMS and approx. 60% of the desired compound was detected. The mixture was purified by column chromatography through silica gel (eluent of 0 to 10% ethyl acetate in petroleum ether as a gradient). The desired product containing fractions were concentrated and dried under vacuum to afford a colourless oil (54% yield). LCMS (ESI) m/z 519 $(M+1)^+$.

Step 4: Preparation of (+)-4-(2-((5-methoxy-7-methyl-1H-indol-4-yl)methyl)-2-azaspiro[3.4]octan-1-yl)benzoic acid formic acid salt: To a solution of tert-butyl 5-methoxy-4-[[3-(4-methoxycarbonylphenyl)-2-azaspiro[3.4]octan-2-yl]methyl]-7-methyl-indole-1-carboxylate (1.0 equiv) was added 1 M aqueous LiOH/THF/MeOH solution (3.0 equiv LiOH, v/v/v, 1/1/1). The mixture was heating under stirring at 70° C. for 2 hours. LCMS indicated completion of hydrolysis, after which the mixture was cooled to 20-25° C. and the reaction quenched with dilute acetic acid to pH ~5 to yield the title product (47% yield). $^1$H-NMR (400 MHz, $d_4$-MeOD): δ 8.38 (bs, 0.5H), 7.93 (d, J=8 Hz, 2H), 7.35 (d, J=4 Hz, 1H), 7.18 (d, J=8 Hz, 2H), 6.63 (s, 1H), 6.52 (d, J=8 Hz, 1H), 5.34 (s, 1H), 4.69 (q, J=12 Hz, 2H), 4.14 (d, J=8 Hz, 1H), 3.95 (d, J=12 Hz, 1H), 3.78 (s, 3H), 2.45 (s, 3H), 1.88-1.97 (m, 2H), 1.71-1.75 (m, 1H), 1.46-1.56 (m, 4H), 1.24-1.29 (m, 1H). LCMS (ESI) m/z 405 $(M+1)^+$.

Example 40: Preparation of (R)-4-(2-((5-methoxy-7-methyl-1H-indol-4-yl)methyl)-2-azaspiro[3.3]heptan-1-yl)benzoic acid Example 40

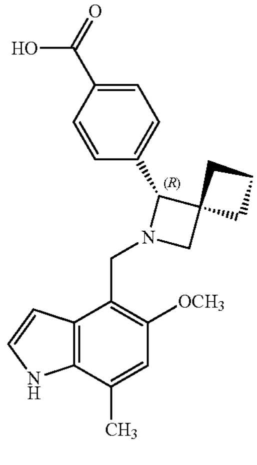

Step 1: Preparation of (±)-tert-butyl 1-(4-(methoxycarbonyl)phenyl)-2-azaspiro[3.3]heptane-2-carboxylate: A mixture of methyl 4-cyanobenzoate (1.0 equiv), 2-(tert-butoxycarbonyl)-2-azaspiro[3.3]heptane-1-carboxylic acid (2.0 equiv), 2,4,5,6-tetra(9H-carbazol-9-yl)isophthalonitrile (4-CzIPN, 0.05 equiv) and $K_2HPO_4$ (3.0 equiv) in DMSO (0.06 M) was degassed and purged with $N_2$ for 30 min. The mixture was irradiated with a blue LED light (365 nm) under a $N_2$ atmosphere while being stirred at 20-25° C. for 16 hours. The reaction mixture was diluted with $H_2O$ and extracted with ethyl acetate. The organic layers were washed with $H_2O$, dried over $Na_2SO_4$, filtered, and concentrated under reduced pressure to afford a residue. The residue was purified by column chromatography through silica gel (eluent of 0% to 10% ethyl acetate in petroleum ether as a gradient). The crude product tert-butyl 1-(4-(methoxycarbonyl)phenyl)-2-azaspiro[3.3]heptane-2-carboxylate was obtained as a yellow gum, which was directly used in the next step without further purification. LCMS (ESI) m/z 276 $(M-56+1)^+$.

Step 2: Preparation of (1)-methyl 4-(2-azaspiro[3.3]heptan-1-yl)benzoate: To a solution of tert-butyl 1-(4-(methoxycarbonyl)phenyl)-2-azaspiro[3.3]heptane-2-carboxylate (1.0 equiv) in $CH_2Cl_2$ (0.3 M) was added TFA (2.7 M). The mixture was stirred at 15° C. for 16 hours after which LCMS indicated completion of reaction. The reaction mixture was neutralized with saturated aqueous $NaHCO_3$ solution to pH-7. The combined organic layers were dried over $Na_2SO_4$, filtered, and concentrated under reduced pressure to afford a residue. The residue was purified by column chromatography through silica gel (eluent of 0% to 4% MeOH in $CH_2Cl_2$ as a gradient). The crude product methyl 4-(2-azaspiro[3.3]heptan-1-yl)benzoate was obtained as a yellow gum, which was directly used in the next step without further purification. LCMS (ESI) m/z 231 $(M+1)^+$.

Step 3: Preparation of (1) tert-butyl 5-methoxy-4-((1-(4-(methoxycarbonyl)phenyl)-2-azaspiro[3.3]heptan-2-yl) methyl)-7-methyl-1H-indole-1-carboxylate: To a solution of methyl 4-(2-azaspiro[3.3]heptan-1-yl)benzoate (1.0 equiv) and tert-butyl 4-formyl-5-methoxy-7-methyl-1H-indole-1-carboxylate (1.0 equiv) in MeOH (0.07 M) was added $ZnCl_2$ (5.0 equiv) and the mixture was stirred at 50° C. for 2 hours. Solid $NaBH_3CN$ (3.0 equiv) was then added, and the mixture was stirred at 50° C. for 40 hours. Several new peaks were observed by LCMS and approx. 42% of the desired compound was detected. The reaction mixture was diluted with ethyl acetate and washed with water. The organic layers were dried over $MgSO_4$, filtered, and concentrated under reduced pressure to afford a residue. The residue was purified by column chromatography through silica gel (eluent of 0 to 6% MeOH in $CH_2Cl_2$ as a gradient). The crude product was obtained as a yellow gum, which was directly used in the next step without further purification. LCMS (ESI) m/z 505 $(M+1)^+$.

Step 4: Preparation of (+)-4-(2-((5-methoxy-7-methyl-1H-indol-4-yl)methyl)-2-azaspiro[3.3]heptan-1-yl)benzoic acid: To a solution of tert-butyl 5-methoxy-4-((1-(4-(methoxycarbonyl)phenyl)-2-azaspiro[3.3]heptan-2-yl) methyl)-7-methyl-1H-indole-1-carboxylate (1.0 equiv) was added 1.5 M aqueous $LiOH{\cdot}H_2O$/THF/MeOH solution (13.0 equiv $LiOH{\cdot}H_2O$, v/v/v, 3/2/2). The mixture was heated to 70° C. under stirring for 1.5 hours. LCMS indicated completion of hydrolysis, after which the mixture was cooled to 20-25° C. and the reaction mixture was quenched with dilute acetic acid to pH~6. The mixture was purified by preparative-HPLC (column: Welch Xtimate C18; mobile phase: 23% to 53% $CH_3CN$ in water+0.225% formic acid as a gradient over 6 min). The desired product containing fractions were concentrated and lyophilized to yield the title product as a white solid (formic acid salt, 41% yield).

Step 5: Preparation of ((R)-4-(2-((5-methoxy-7-methyl-1H-indol-4-yl)methyl)-2-azaspiro[3.3]heptan-1-yl)benzoic acid: The sample of racemic tert-butyl 4-(2-((5-methoxy-7-methyl-1H-indol-4-yl)methyl)-2-azaspiro[3.3]heptan-1-yl) benzoic acid (1.0 equiv) was separated into the corresponding pure enantiomers by chiral SFC chromatography (column: Phenomenex-Cellulose-2 (250 mm×30 mm, 10 μm); mobile phase: 30% A, [0.1% $NH_1H_2O$ EtOH], 70% B, $scCO_2$) to give ((R)-4-(2-((5-methoxy-7-methyl-1H-indol-4-yl)methyl)-2-azaspiro[3.3]heptan-1-yl)benzoic acid (38% yield) as a white solid. $^1$H-NMR (400 MHz, $CD_3OD$): δ 7.92 (d, J=8.0 Hz, 2H), 7.33 (d, J=3.2 Hz, 1H), 7.16 (d, J=8.0 Hz, 2H), 6.62 (s, 1H), 6.50 (d, J=2.8 Hz, 1H), 5.08 (s, 1H), 4.53-4.61 (m, 2H), 4.12-4.19 (m, 2H), 3.76 (s, 3H), 2.45 (s, 3H), 2.19-2.23 (m, 2H), 2.04-2.10 (m, 1H), 1.91-1.98 (m, 1H), 1.75-1.86 (m, 1H), 1.48-1.59 (m, 1H). LCMS (ESI) m/z 391 $(M+1)^+$.

Example 41: Preparations of 4-((2S,4S)-4-cyclopropyl-1-((5-methoxy-7-methyl-1H-indol-4-yl)methyl) piperidin-2-yl)benzoic acid Example 41

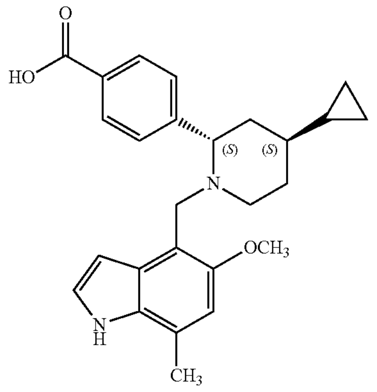

Step 1: Preparation of tert-butyl (S)-4-((4-(2-(mesitylsulfonyl)hydrazono)-2-(4-(methoxycarbonyl)phenyl)piperidin-1-yl)methyl)-5-methoxy-7-methyl-1H-indole-1-carboxylate: Into a reaction vial was added tert-butyl (S)-5-methoxy-4-((2-(4-(methoxycarbonyl)phenyl)-4-oxopiperidin-1-yl)methyl)-7-methyl-1H-indole-1-carboxylate (Intermediate G, 1.0 equiv) and methanol (0.5 M). Solid 2,4,6-trimethylbenzenesulfonohydrazide (1.0 equiv) was added and the mixture was stirred at 20-25° C. and monitored by LCMS. Analysis by LCMS indicated completion of reaction after 2 hours. The mixture was concentrated, yielding a yellow foam, which was further dried under high vacuum and used in directly in the next step without further purification.

Step 2: Preparation of tert-butyl 4-(((2S)-4-cyclopropyl-2-(4-(methoxycarbonyl)phenyl)piperidin-1-yl)methyl)-5-methoxy-7-methyl-1H-indole-1-carboxylate: Into a sealed reaction vial under a nitrogen atmosphere was added cesium carbonate (3 equiv), tert-butyl (S)-4-((4-(2-(mesitylsulfonyl)hydrazono)-2-(4-(methoxycarbonyl)phenyl)piperidin-1-yl)methyl)-5-methoxy-7-methyl-1H-indole-1-carboxylate (1.0 equiv), cyclopropylboronic acid (4.0 equiv) and chlorobenzene (0.3 M). The mixture was purged with nitrogen for 5 minutes before being heated to 100° C. for 5 hours. After this time, LCMS indicated the boronic acid product formation.

The mixture was cooled to 20-25° C., filtered through Celite, washed with $CH_2Cl_2$ and concentrated. The residue was diluted with chlorobenzene (0.3 M) and treated with 4-tert-butylcatechol (10 equiv). The mixture was heated to 80° C. and monitored for protodeboronation product. LCMS indicated product formation after 3 hours. The mixture was concentrated to remove most of chlorobenzene. The resulting yellow residue was loaded onto a silica gel pre-cartridge and dried under vacuum. The mixture was purified by column chromatography through silica gel, eluting with 100:0 to 0:100 hexanes:EtOAc as a gradient, collecting all peaks. The desired product containing fractions were concentrated and dried under vacuum to afford a light-yellow oil (46% yield).

Step 3: Preparation of 4-((2S)-4-cyclopropyl-1-((5-methoxy-7-methyl-1H-indol-4-yl)methyl)piperidin-2-yl) benzoic acid: Into a reaction vial was added tert-butyl 4-(((2S)-4-cyclopropyl-2-(4-(methoxycarbonyl)phenyl)piperidin-1-yl)methyl)-5-methoxy-7-methyl-1H-indole-1-carboxylate (1.0 equiv), 1 M aqueous LiOH solution (3.0 equiv), and THF/MeOH (v/v, 1/1, 0.3 M). The resulting suspension was heated to 60° C. with stirring and monitored by LCMS. LCMS analysis indicated completion of hydrolysis after 18 hours. The reaction was cooled to 20-25° C. and quenched with conc. formic acid to pH-2. The mixture was concentrated and loaded onto a reverse phase C18 precartridge. The mixture was purified by a reverse phase column chromatography through a C18 column, eluting with 90:10 to 0:100 water:MeCN+0.1% formic acid as a gradient, collecting all peaks. The desired product containing fractions were concentrated and lyophilized to yield the title product as a white powder (95% yield). Chiral HPLC analysis indicated the title product was a mixture of diastereomers.

Step 4: Preparation of 4-((2S,4S)-4-cyclopropyl-1-((5-methoxy-7-methyl-1H-indol-4-yl)methyl) piperidin-2-yl) benzoic acid: The diastereomeric mixture of 4-((2S)-4-cyclopropyl-1-((5-methoxy-7-methyl-1H-indol-4-yl) methyl)piperidin-2-yl)benzoic acid, prepared above, was purified into each diastereomer and clean enantiomer using chiral preparative-HPLC column chromatography under the following conditions: column, Phenomenex Lux Cellulose-4, 10×250 mm, 5 mm; eluents, 55% MeOH+10 mM ammonium formate/45% $scCO_2$; flow rate, 10 mL/min; wavelength, 254 nm. The resulting fractions from the first eluting peak were combined and lyophilized to afford 4-((2S,4S)-4-cyclopropyl-1-((5-methoxy-7-methyl-1H-indol-4-yl) methyl)piperidin-2-yl)benzoic acid (99% ee) as a white solid. $^1$H NMR (400 MHz, DMSO): δ 12.84 (s, 1H), 10.82 (s, 1H), 7.99 (d, J=7.9 Hz, 2H), 7.70 (d, J=7.9 Hz, 2H), 7.25 (t, J=2.8 Hz, 1H), 6.65 (s, 1H), 6.45 (t, J=2.5 Hz, 1H), 5.15 (t, J=7.4 Hz, 1H), 3.70 (s, 3H), 3.55 (d, J=11.9 Hz, 1H), 3.22-3.11 (m, 3H), 2.89-2.77 (m, 1H), 2.42 (s, 3H), 2.15-1.85 (m, 6H), 0.91 (t, J 7.5 Hz, 3H). LCMS (ESI) m/z 419 $(M+H)^+$.

The following compounds were prepared in a similar manner as Example 41 replacing cyclopropylboronic acid with the corresponding pyrazole in the table in the second step.

| Example | Intermediate Used | Structure | MW | MS (ESI+) |
|---|---|---|---|---|
| Example 42 | 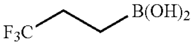 | 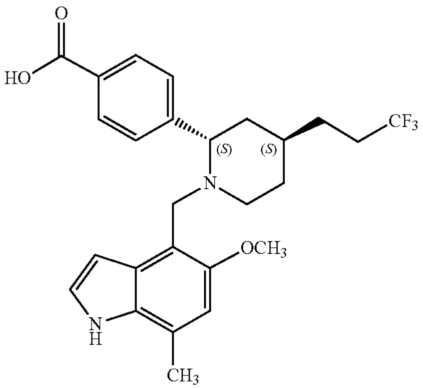 4-((2S,4S)-1-((5-methoxy-7-methyl-1H-indol-4-yl)methyl)-4-(3,3,3-trifluoropropyl)piperidin-2-yl)benzoic acid | 474.52 | 475 (M + 1)⊕ |
| Example 43 | 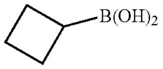 | 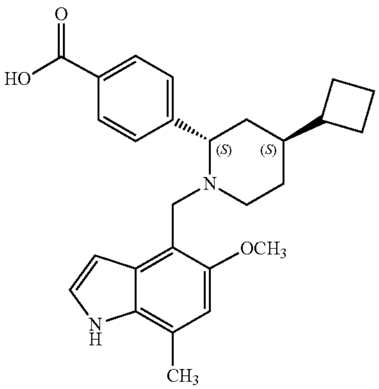 and 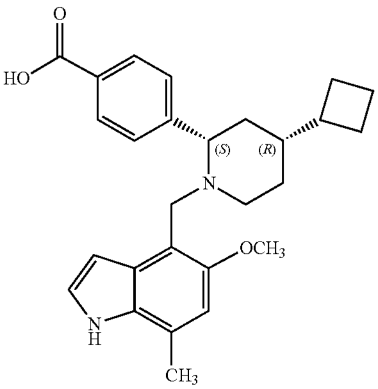 4-((2S,4S)-4-cyclobutyl-1-((5-methoxy-7-methyl-1H-indol-4-yl)methyl)piperidin-2-yl)benzoic acid and 4-((2S,4R)-4-cyclobutyl-1-((5-methoxy-7-methyl-1H-indol-4-yl)methyl)piperidin-2-yl)benzoic acid | 432.24 | 433 (M + 1)⊕ |

-continued

| Example | Intermediate Used | Structure | MW | MS (ESI+) |
|---|---|---|---|---|
| Example 44 | 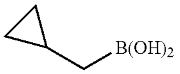 | 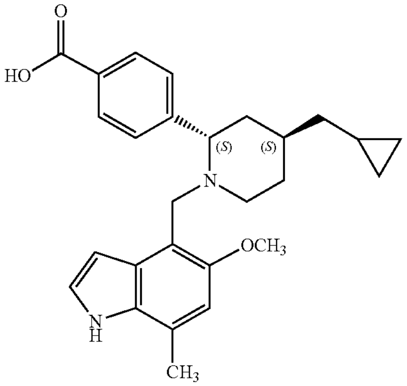 4-((2S,4S)-4-(cyclopropylmethyl)-1-((5-methoxy-7-methyl-1H-indol-4-yl)methyl)piperidin-2-yl)benzoic acid | 432.56 | 433 (M + 1)$^{\oplus}$ |

Example 45: Preparation of (S)-4-(2,2-difluoro-7-((5-methoxy-7-methyl-1H-indol-4-yl)methyl)-7-azaspiro[3.5]nonan-6-yl)benzoic acid Example 45

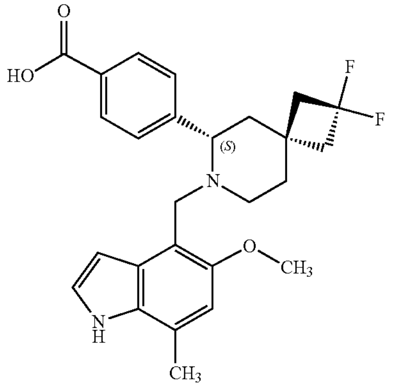

Step 1: Preparation of benzyl (S)-2,2-difluoro-6-(4-(methoxycarbonyl)phenyl)-7-azaspiro[3.5]nonane-7-carboxylate: To a solution of benzyl (S)-6-(4-(methoxycarbonyl)phenyl)-2-oxo-7-azaspiro[3.5]nonane-7-carboxylate (Intermediate J, 1.0 equiv) in $CH_2Cl_2$ (0.3 M) at 0° C. was added dropwise, di ethyl aminosulfur trifluoride (3.0 equiv), over 1 hour using a syringe pump. The reaction mixture was stirred at 0° C. for 2 hours and at 20-25° C. for 19 hours. The reaction was cooled to 0° C. and quenched by dropwise addition of saturated aqueous saturated $NaHCO_3$ solution. The mixture was stirred at 0° C. for 1 hour, the organic layer was separated, and the aqueous layer was further extracted three times with $CH_2Cl_2$. The combined organic layers were dried over anhydrous $MgSO_4$, concentrated under reduced pressure, applied to a silica precartridge, and purified by column chromatography through silica gel, eluting with a 0-100% EtOAc in hexanes gradient. The fraction from the major peak eluting at 82% EtOAc in hexanes was concentrated under reduced pressure to afford the desired product as a white solid (53% yield). LCMS (ESI) m/z 430 $(M+1)^+$.

Step 2: Preparation of methyl (S)-4-(2,2-difluoro-7-azaspiro[3.5]nonan-6-yl)benzoate: To a solution of benzyl (S)-2,2-difluoro-6-(4-(methoxycarbonyl)phenyl)-7-azaspiro[3.5]nonane-7-carboxylate (1.0 equiv) in methanol (0.06 M) was added palladium on carbon (10 wt %, 0.02 equiv). The flask was purged with $N_2$, followed by purging with $H_2$, and the mixture was stirred under a $H_2$ atmosphere at 20-25° C. for 18 hours. Additional palladium on carbon (10 wt %, 0.02 equiv) was added and the reaction mixture was stirred at 20-25° C. for 2 hours under an atmosphere of $H_2$. The reaction mixture was filtered through celite, and the filtrate was concentrated under reduced pressure to afford a colourless solid (96% yield) which was used in the next step without further purification. LCMS (ESI) m/z 296 $(M+1)^+$.

Step 3: Preparation of tert-butyl (S)-4-((2,2-difluoro-6-(4-(methoxycarbonyl)phenyl)-7-azaspiro[3.5]nonan-7-yl)methyl)-5-methoxy-7-methyl-1H-indole-1-carboxylate: To a solution of methyl (S)-4-(2,2-difluoro-7-azaspiro[3.5]nonan-6-yl)benzoate (1.0 equiv) in DCE (0.15 M) was added tert-butyl 4-formyl-5-methoxy-7-methyl-1H-indole-1-carboxylate (1.3 equiv) and 3 Å molecular sieves. The reaction mixture was stirred at 20-25° C. for 1 hour. Sodium triacetoxyborohydride (2.50 equiv) was added, and the reaction mixture was stirred for 18 hours at 20-25° C. The reaction was quenched with a small amount of water, applied to a silica precartridge, and purified by column chromatography through silica gel, eluting with a 0-100% EtOAc in hexanes as a gradient. The fractions from the peaks eluting at 80% EtOAc in hexanes were combined and concentrated under reduced pressure to afford a colourless oil (80% yield). LCMS (ESI) m/z 569 $(M+1)^+$.

Step 4: Preparation of (S)-4-(2,2-difluoro-7-((5-methoxy-7-methyl-1H-indol-4-yl)methyl)-7-azaspiro[3.5]nonan-6-yl)benzoic acid: To a solution of tert-butyl (S)-4-((2,2-difluoro-6-(4-(methoxycarbonyl)phenyl)-7-azaspiro[3.5]nonan-7-yl)methyl)-5-methoxy-7-methyl-1H-indole-1-carboxylate (1.0 equiv) in 1:1 v/v THF/MeOH (0.09 M) was added 1 M aqueous LiOH solution (5.0 equiv). The reaction mixture was heated to 80° C. with stirring for 2 hours. The reaction mixture was acidified with dilute formic acid, applied to a C18 precartridge, and purified by reverse phase column chromatography through a C18 column, eluting with a 10-100% MeCN in water as a gradient containing 0.1% $HCO_2H$. The fractions from the peak eluting at 46% MeCN in water were combined and lyophilized to afford a light pink powder (63% yield). $^1H$-NMR (400 MHz, DMSO): δ

10.82 (s, 1H), 7.97 (d, J=7.9 Hz, 2H), 7.68 (d, J=7.8 Hz, 2H), 7.25 (t, J=2.9 Hz, 1H), 6.65 (s, 1H), 6.45 (s, 1H), 3.70 (s, 3H), 3.53 (d, J=11.8 Hz, 1H), 3.23 (s, 1H), 3.16 (d, J=11.9 Hz, 1H), 2.67 (d, J=12.4 Hz, 1H), 2.59 (d, J=13.1 Hz, 1H), 2.46 (s, 1H), 2.43 (s, 3H), 2.29 (t, J=13.3 Hz, 2H), 1.98 (s, 1H), 1.70 (d, J=9.0 Hz, 2H), 1.53 (d, J=9.5 Hz, 2H). LCMS (ESI) m/z 455 $(M+1)^+$.

The following compounds were prepared in a similar manner as Example 45, where the corresponding ketone moiety can be further functionalized using known chemistry described as in the literature, such as ketone reduction, alcohol to fluorine conversion, ketone addition followed by deoxygenation or indole halogenation.

| Example | Structure | MW | MS (ESI+) |
|---|---|---|---|
| Example 46 | 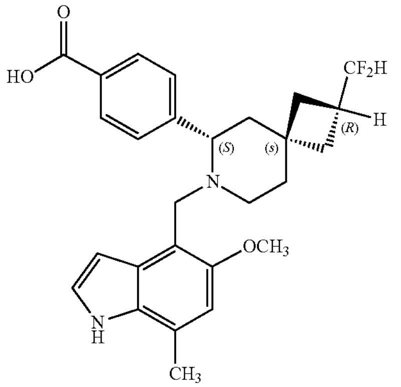 or 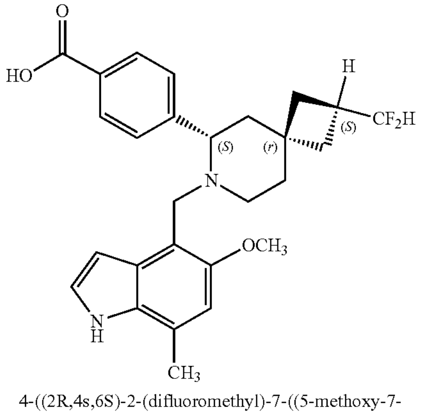 4-((2R,4s,6S)-2-(difluoromethyl)-7-((5-methoxy-7-methyl-1H-indol-4-yl)methyl)-7-azaspiro[3.5]nonan-6-yl)benzoic acid or 4-((2S,4r,6S)-2-(difluoromethyl)-7-((5-methoxy-7-methyl-1H-indol-4-yl)methyl)-7-azaspiro[3.5]nonan-6-yl)benzoic acid $^1H$ NMR (400 MHz, $d_6$-DMSO): δ 10.82 (s, 1H), 8.29 (s, 1H), 7.95 (d, J = 7.9 Hz, 2H), 7.63 (d, J = 7.8 Hz, 2H), 7.25 (d, J = 3.0 Hz, 1H), 6.65 (s, 1H), 6.47 (s, 1H), 6.27-5.83 (m, 2H), 3.71 (s, 3H), 3.52 (d, J = 11.9 Hz, 1H), 3.14 (d, J = 12.4 Hz, 3H), 2.64 (d, J = 11.0 Hz, 2H), 2.42 (s, 2H), 2.08-1.94 (m, 2H), 1.92-1.81 (m, 1H), 1.77-1.61 (m, 3H), 1.53 (t, J = 12.4 Hz, 1H), 1.37 (t, J = 12.6 Hz, 1H). | 468.54 | 469 $(M + 1)^{\oplus}$ |

-continued
| Example | Structure | MW | MS (ESI+) |
|---|---|---|---|
| Example 47 | 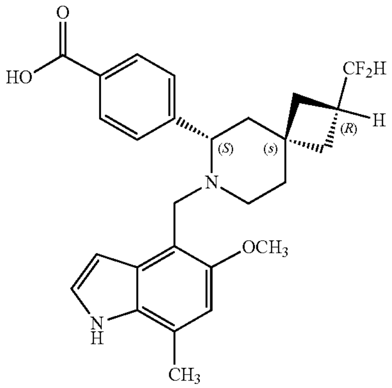 or 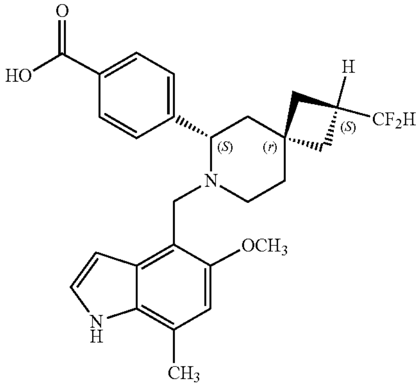 4-((2R,4s,6S)-2-(difluoromethyl)-7-((5-methoxy-7-methyl-1H-indol-4-yl)methyl)-7-azaspiro[3.5]nonan-6-yl)benzoic acid or 4-((2S,4r,6S)-2-(difluoromethyl)-7-((5-methoxy-7-methyl-1H-indol-4-yl)methyl)-7-azaspiro[3.5]nonan-6-yl)benzoic acid $^{1}$H NMR (400 MHz, $d_6$-DMSO): δ 10.81 (s, 1H), 7.97 (s, 2H), 7.69 (s, 2H), 7.24 (d, J = 3.4 Hz, 1H), 6.65 (s, 1H), 6.45 (s, 1H), 6.24-5.81 (m, 2H), 3.70 (s, 3H), 3.52 (d, J = 11.9 Hz, 1H), 3.27-3.15 (m, 3H), 2.58 (d, J = 11.4 Hz, 1H), 2.42 (s, 3H), 2.13 (t, J = 10.4 Hz, 1H), 1.91 (dd, J = 26.9, 13.0 Hz, 2H), 1.80-1.65 (m, 3H), 1.63-1.27 (m, 2H). | 468.54 | 469 (M + 1)$^{\oplus}$ |

-continued
| Example | Structure | MW | MS (ESI+) |
|---|---|---|---|
| Example 48 | 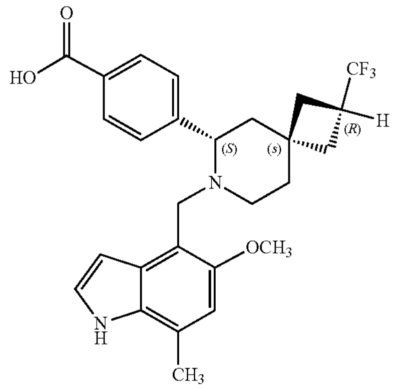 or<br>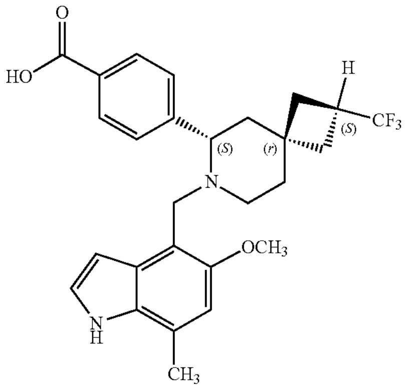<br>4-((2R,4s,6S)-7-((5-methoxy-7-methyl-1H-indol-4-yl)methyl)-2-(trifluoromethyl)-7-azaspiro[3.5]nonan-6-yl)benzoic acid or 4-((2S,4r,6S)-7-((5-methoxy-7-methyl-1H-indol-4-yl)methyl)-2-(trifluoromethyl)-7-azaspiro[3.5]nonan-6-yl)benzoic acid<br>$^1$H NMR (400 MHz, $d_6$-DMSO): δ 10.82 (s, 1H), 7.96 (d, J = 7.6 Hz, 2H), 7.66 (d, J = 7.7 Hz, 2H), 7.25 (d, J = 3.1 Hz, 1H), 6.66 (s, 1H), 6.46 (s, 1H), 3.71 (s, 3H), 3.52 (d, J = 11.7 Hz, 2H), 3.14 (d, J = 10.5 Hz, 4H), 2.42 (s, 3H), 2.15 (t, J = 10.8 Hz, 1H), 1.99 (dt, J = 21.0, 11.4 Hz, 2H), 1.82 (p, J = 11.6 Hz, 2H), 1.71 (d, J = 13.0 Hz, 1H), 1.67-1.52 (m, 2H), 1.39 (t, J = 12.6 Hz, 1H). | 486.54 | 487 (M + 1)$^{\oplus}$ |

-continued

| Example | Structure | MW | MS (ESI+) |
|---|---|---|---|
| Example 49 | 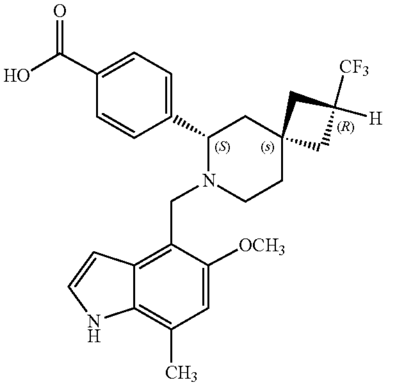 or 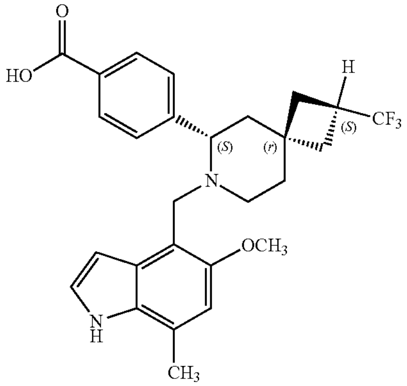<br>4-((2R,4s,6S)-7-((5-methoxy-7-methyl-1H-indol-4-yl)methyl)-2-(trifluoromethyl)-7-azaspiro[3.5]nonan-6-yl)benzoic acid or 4-((2S,4r,6S)-7-((5-methoxy-7-methyl-1H-indol-4-yl)methyl)-2-(trifluoromethyl)-7-azaspiro[3.5]nonan-6-yl)benzoic acid<br>$^1$H NMR (400 MHz, $d_6$-DMSO): δ 10.81 (s, 1H), 7.98 (d, J = 7.8 Hz, 2H), 7.69 (d, J = 7.7 Hz, 2H), 7.25 (s, 1H), 6.65 (s, 1H), 6.45 (s, 1H), 3.70 (s, 3H), 3.52 (d, J = 11.9 Hz, 2H), 3.15 (d, J = 11.4 Hz, 4H), 2.42 (s, 3H), 2.28 (t, J = 10.4 Hz, 1H), 1.86 (dp, J = 31.8, 11.6, 11.2 Hz, 4H), 1.55 (t, J = 12.3 Hz, 1H), 1.49-1.32 (m, 2H). | 486.54 | 487 (M + 1)$^{\oplus}$ |
| Example 50 | 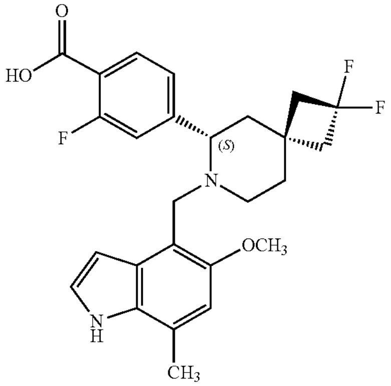<br>(S)-4-(2,2-difluoro-7-((5-methoxy-7-methyl-1H-indol-4-yl)methyl)-7-azaspiro[3.5]nonan-6-yl)-2-fluorobenzoic acid<br>$^1$H NMR (400 MHz, $d_4$-MeOD): δ 7.89 (t, J = 7.6 Hz, 1H), 7.44 (t, J = 9.2 Hz, 2H), 7.35 (d, J = 3.1 Hz, 1H), 6.78 (s, 1H), 6.38 (d, J = 3.2 Hz, 1H), 4.48-4.30 (m, 2H), 4.09 (d, J = 12.7 Hz, 1H), 3.80 (s, 3H), 3.48 (d, J = 13.2 Hz, 1H), 3.24 (td, J = 13.3, 3.1 Hz, 1H), 2.83-2.59 (m, 2H), 2.53 (s, 5H), 2.26 (d, J = 14.2 Hz, 1H), 2.18-1.98 (m, 2H), 1.91 (d, J = 14.5 Hz, 1H). | 472.51 | 473 (M + 1)$^{\oplus}$ |

-continued

| Example | Structure | MW | MS (ESI+) |
| --- | --- | --- | --- |
| Example 51 | 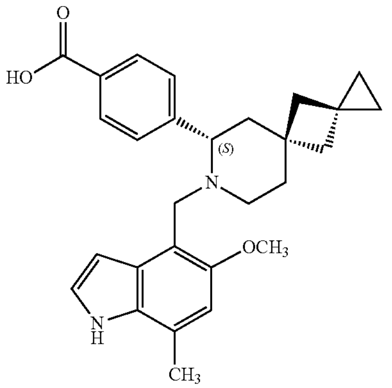<br>(S)-4-(8-((5-methoxy-7-methyl-1H-indol-4-yl)methyl)-8-azadispiro[2.1.5⁵.1³]undecan-7-yl)benzoic acid<br>$^1$H NMR (400 MHz, $d_6$-DMSO): δ 10.82 (s, 1H), 8.19 (s, 1H), 7.98 (d, J = 7.8 Hz, 2H), 7.68 (d, J = 7.8 Hz, 2H), 7.25 (d, J = 3.1 Hz, 1H), 6.66 (s, 1H), 6.47 (s, 1H), 3.71 (s, 3H), 3.54-3.11 (m, 3H), 2.65 (d, J = 12.3 Hz, 1H), 2.42 (s, 3H), 2.00 (dt, J = 32.6, 11.0 Hz, 3H), 1.89-1.72 (m, 3H), 1.71-1.56 (m, 2H), 1.47 (dt, J = 14.5, 7.1 Hz, 1H), 0.46-0.27 (m, 4H). | 444.57 | 445 (M + 1)$^\oplus$ |
| Example 52 | 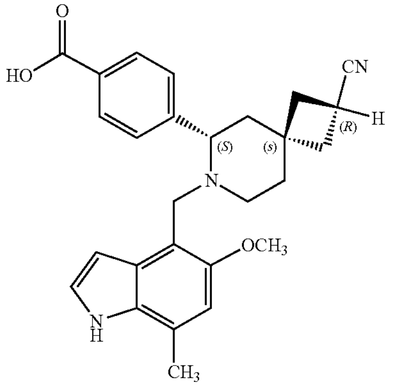 or<br>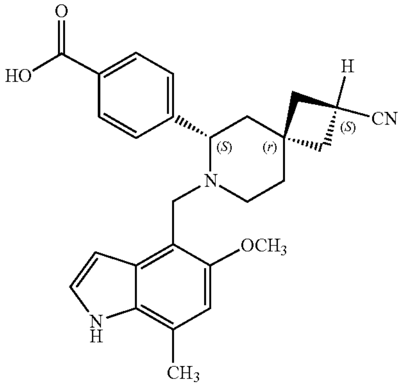<br>4-((2R,4s,6S)-2-cyano-7-((5-methoxy-7-methyl-1H-indol-4-yl)methyl)-7-azaspiro[3.5]nonan-6-yl)benzoic acid or 4-((2S,4r,6S)-2-cyano-7-((5-methoxy-7-methyl-1H-indol-4-yl)methyl)-7-azaspiro[3.5]nonan-6-yl)benzoic acid | 443.55 | 444 (M + 1)$^\oplus$ |

-continued

| Example | Structure | MW | MS (ESI+) |
|---|---|---|---|
| Example 53 | 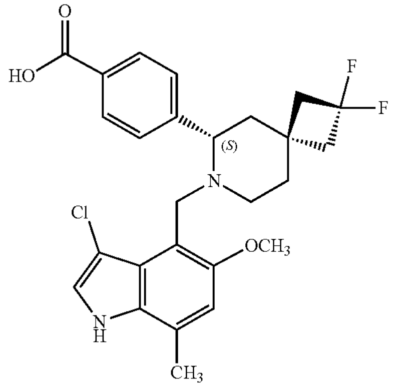<br>(S)-4-(7-((3-chloro-5-methoxy-7-methyl-1H-indol-4-yl)methyl)-2,2-difluoro-7-azaspiro[3.5]nonan-6-yl)benzoic acid<br>$^1$H NMR (400 MHz, $d_4$-MeOD): δ 8.11 (d, J = 7.9 Hz, 2H), 7.62 (d, J = 7.8 Hz, 2H), 7.29 (s, 1H), 6.76 (s, 1H), 4.55 (d, J = 12.7 Hz, 1H), 4.48-4.14 (m, 2H), 3.71 (s, 3H), 3.29-3.16 (m, 2H), 2.81-2.67 (m, 1H), 2.64-2.53 (m, 1H), 2.46 (s, 5H), 2.38-2.21 (m, 1H), 2.04 (dt, J = 14.5, 3.4 Hz, 2H), 1.85 (dd, J = 14.5, 2.9 Hz, 1H). | 488.96 | 489 (M + 1)$^\oplus$ |
| Example 54 | 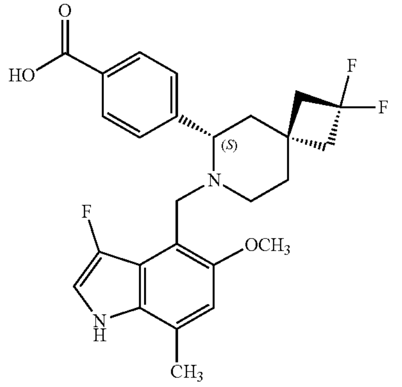<br>(S)-4-(2,2-difluoro-7-((3-fluoro-5-methoxy-7-methyl-1H-indol-4-yl)methyl)-7-azaspiro[3.5]nonan-6-yl)benzoic acid<br>$^1$H NMR (400 MHz, $d_4$-MeOD): δ 8.13 (d, J = 7.9 Hz, 2H), 7.63 (d, J = 7.9 Hz, 2H), 7.17 (d, J = 2.4 Hz, 1H), 6.82 (s, 1H), 4.50-4.30 (m, 2H), 4.15 (d, J = 12.7 Hz, 1H), 3.74 (s, 3H), 3.46 (d, J = 12.0 Hz, 1H), 3.18 (dd, J = 14.6, 11.5 Hz, 1H), 2.84-2.66 (m, 2H), 2.55-2.39 (m, 5H), 2.28 (d, J = 15.4 Hz, 1H), 2.07 (d, J = 14.5 Hz, 2H), 1.91 (d, J = 14.2 Hz, 1H). | 472.51 | 473 (M + 1)$^\oplus$ |

-continued
| Example | Structure | MW | MS (ESI+) |
|---|---|---|---|
| Example 55 | 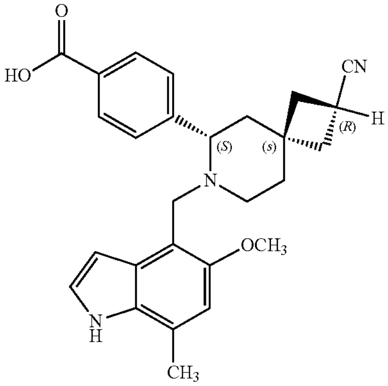 or 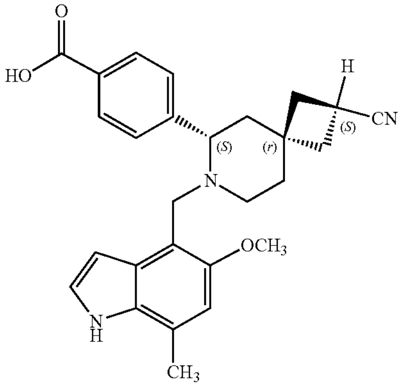 4-((2R,4s,6S)-2-cyano-7-((5-methoxy-7-methyl-1H-indol-4-yl)methyl)-7-azaspiro[3.5]nonan-6-yl)benzoic acid or 4-((2S,4r,6S)-2-cyano-7-((5-methoxy-7-methyl-1H-indol-4-yl)methyl)-7-azaspiro[3.5]nonan-6-yl)benzoic acid | 443.55 | 444 (M + 1)$^{\oplus}$ |

-continued
| Example | Structure | MW | MS (ESI+) |
|---|---|---|---|
| Example 56 | 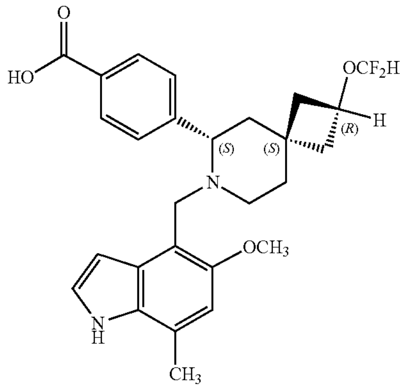 or 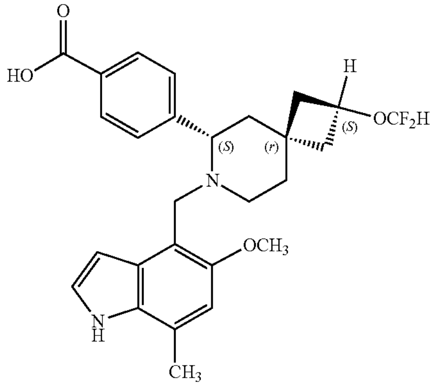 4-((2R,4s,6S)-2-(difluoromethoxy)-7-((5-methoxy-7-methyl-1H-indol-4-yl)methyl)-7-azaspiro[3.5]nonan-6-yl)benzoic acid or 4-((2S,4r,6S)-2-(difluoromethoxy)-7-((5-methoxy-7-methyl-1H-indol-4-yl)methyl)-7-azaspiro[3.5]nonan-6-yl)benzoic acid $^1$H NMR (400 MHz, $d_6$-DMSO): δ 10.81 (d, J = 2.4 Hz, 1H), 8.19 (s, 1H), 7.96 (d, J = 8.0 Hz, 2H), 7.65 (d, J = 7.8 Hz, 2H), 7.25 (t, J = 2.8 Hz, 1H), 6.65 (s, 1H), 6.58 (t, J = 76 Hz, 1H), 6.46 (dd, J = 3.0, 1.9 Hz, 1H), 4.59 (p, J = 7.2 Hz, 1H), 3.70 (s, 3H), 3.52 (d, J = 11.9 Hz, 1H), 3.22-3.09 (m, 3H), 2.64 (d, J = 12.2 Hz, 2H), 2.42 (s, 3H), 2.14-1.76 (m, 3H), 1.65 (d, J = 7.3 Hz, 2H), 1.52 (d, J = 13.1 Hz, 1H), 1.39 (t, J = 12.4 Hz, 1H). | 484.54 | 485 (M + 1)$^{\oplus}$ |

-continued

| Example | Structure | MW | MS (ESI+) |
| --- | --- | --- | --- |
| Example 57 | 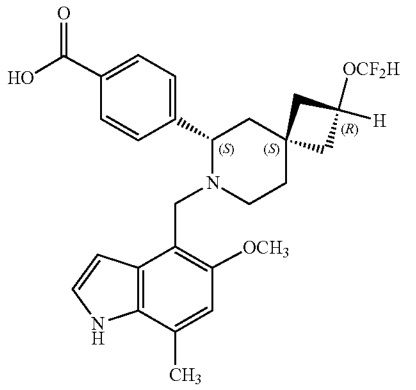 or<br>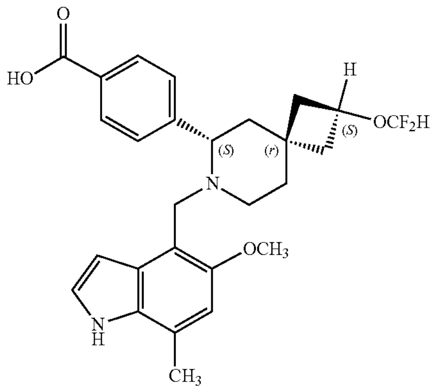<br>4-((2R,4s,6S)-2-(difluoromethoxy)-7-((5-methoxy-7-methyl-1H-indol-4-yl)methyl)-7-azaspiro[3.5]nonan-6-yl)benzoic acid or 4-((2S,4r,6S)-2-(difluoromethoxy)-7-((5-methoxy-7-methyl-1H-indol-4-yl)methyl)-7-azaspiro[3.5]nonan-6-yl)benzoic acid<br>$^1$H NMR (400 MHz, $d_6$-DMSO): δ 10.81 (t, J = 2.4 Hz, 1H), 8.19 (s, 1H), 7.97 (d, J = 8.0 Hz, 2H), 7.68 (d, J = 7.8 Hz, 2H), 7.25 (t, J = 2.8 Hz, 1H), 6.65 (s, 1H), 6.58 (t, J = 76 Hz, 1H), 6.44 (t, J = 2.5 Hz, 1H), 4.62 (p, J = 7.2 Hz, 1H), 3.70 (s, 3H), 3.52 (d, J = 11.9 Hz, 1H), 3.19 (dd, J = 30.2, 10.9 Hz, 3H), 2.58 (dd, J = 14.3, 10.1 Hz, 2H), 2.42 (s, 3H), 2.08 (dt, J = 11.9, 6.8 Hz, 1H), 1.96 (q, J = 12.6, 9.1 Hz, 1H), 1.82 (dt, J = 12.2, 6.3 Hz, 2H), 1.72 (d, J = 12.9 Hz, 1H), 1.62-1.40 (m, 2H). | 484.54 | 485 (M + 1)$^{\oplus}$ |

-continued

| Example | Structure | MW | MS (ESI+) |
|---|---|---|---|
| Example 58 | 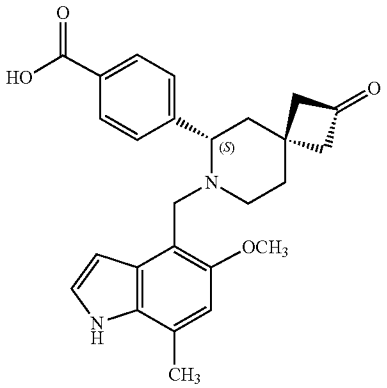 (S)-4-(7-((5-methoxy-7-methyl-1H-indol-4-yl)methyl)-2-oxo-7-azaspiro[3.5]nonan-6-yl)benzoic acid $^1$H NMR (400 MHz, $d_6$-DMSO): δ 10.83 (d, J = 2.3 Hz, 1H), 8.29 (s, 1H), 7.97 (d, J = 8.0 Hz, 2H), 7.68 (d, J = 7.7 Hz, 2H), 7.26 (t, J = 2.8 Hz, 1H), 6.66 (s, 1H), 6.48 (dd, J = 3.1, 1.9 Hz, 1H), 3.71 (s, 3H), 3.57-3.15 (m, 2H), 3.04 (s, 2H), 2.87 (d, J = 17.4 Hz, 1H), 2.74 (s, 2H), 2.42 (s, 3H), 2.01 (t, J = 11.3 Hz, 1H), 1.90-1.52 (m, 5H). | 432.52 | 433 (M + 1)$^{\oplus}$ |
| Example 59 | 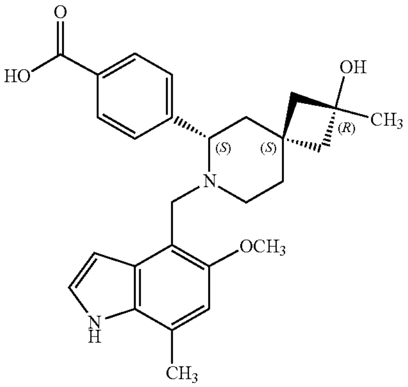 or 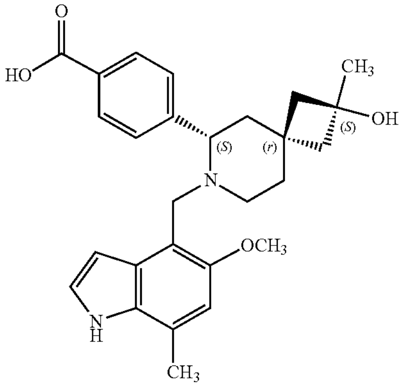 4-((2R,4s,6S)-2-hydroxy-7-((5-methoxy-7-methyl-1H-indol-4-yl)methyl)-2-methyl-7-azaspiro[3.5]nonan-6-yl)benzoic acid or 4-((2S,4r,6S)-2-hydroxy-7-((5-methoxy-7-methyl-1H-indol-4-yl)methyl)-2-methyl-7-azaspiro[3.5]nonan-6-yl)benzoic acid $^1$H NMR (400 MHz, $d_6$-DMSO): δ 10.81 (t, J = 2.4 Hz, 1H), 8.19 (s, 1H), 7.96 (d, J = 8.0 Hz, 2H), 7.65 (d, J = 7.7 Hz, 2H), 7.24 (t, J = 2.8 Hz, 1H), 6.65 (s, 1H), 6.45 (dd, J = 3.0, 1.9 Hz, 1H), 4.70 (s, 1H), 3.70 (s, 3H), 3.50 (d, J = 12.0 Hz, 2H), 3.20-3.10 (m, 3H), 2.59 (d, J = 11.9 Hz, 1H), 2.42 (s, 3H), 2.13-1.34 (m, 7H), 1.21 (s, 3H). | 502.53 | 503 (M + 1)$^{\oplus}$ |

-continued
| Example | Structure | MW | MS (ESI+) |
| --- | --- | --- | --- |
| Example 60 | 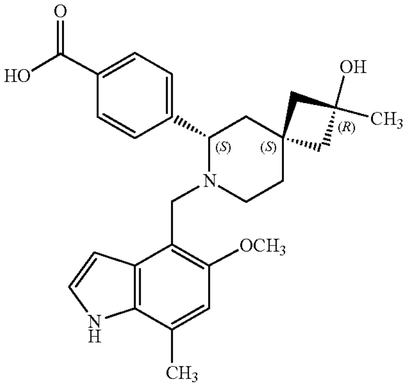 or<br>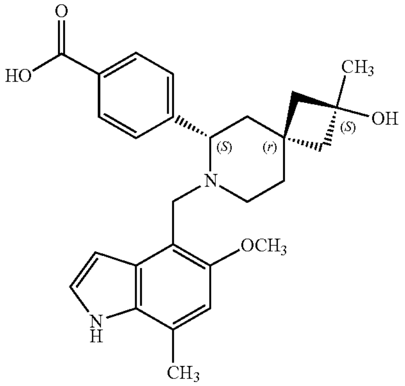<br>4-((2R,4s,6S)-2-hydroxy-7-((5-methoxy-7-methyl-1H-indol-4-yl)methyl)-2-methyl-7-azaspiro[3.5]nonan-6-yl)benzoic acid or 4-((2S,4r,6S)-2-hydroxy-7-((5-methoxy-7-methyl-1H-indol-4-yl)methyl)-2-methyl-7-azaspiro[3.5]nonan-6-yl)benzoic acid<br>$^{1}H$ NMR (400 MHz, $d_6$-DMSO): δ 10.81 (t, J = 2.3 Hz, 1H), 8.19 (s, 1H), 8.02-7.89 (m, 2H), 7.65 (d, J = 7.9 Hz, 2H), 7.24 (t, J = 2.8 Hz, 1H), 6.65 (s, 1H), 6.45 (dd, J = 3.1, 1.9 Hz, 1H), 4.70 (s, 1H), 3.70 (s, 3H), 3.52 (d, J = 11.9 Hz, 2H), 3.15 (t, J = 11.7 Hz, 3H), 2.61 (d, J = 11.7 Hz, 1H), 2.42 (s, 3H), 2.04-1.90 (m, 3H), 1.81 (d, J = 12.7 Hz, 1H), 1.63-1.30 (m, 3H), 1.21 (s, 3H). | 448.56 | 449 (M + 1)⊕ |

Example 52 & 55: Preparation of 4-((2R,4s,6S)-2-cyano-7-((5-methoxy-7-methyl-1H-indol-4-yl)methyl)-7-azaspiro[3.5]nonan-6-yl)benzoic acid and 4-((2S,4r,6S)-2-cyano-7-((5-methoxy-7-methyl-1H-indol-4-yl)methyl)-7-azaspiro[3.5]nonan-6-yl)benzoic acid Example 52 and Example 55

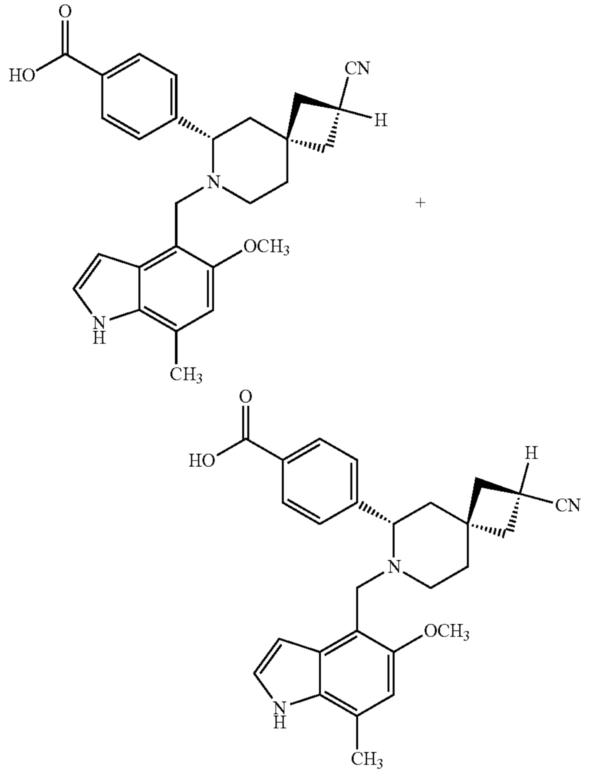

Step 1: Preparation of (S)-benzyl 2-cyano-6-(4-(methoxycarbonyl)phenyl)-7-azaspiro[3.5]nonane-7-carboxylate: To a mixture of (S)-benzyl 6-(4-(methoxycarbonyl)phenyl)-2-oxo-7-azaspiro[3.5]nonane-7-carboxylate (Intermediate J, 1.0 equiv) in MeOH (0.01 M) was added 2,4,6-trimethylbenzenesulfonohydrazide (1 equiv). The reaction mixture was stirred at 50° C. for 2 hours. The mixture was concentrated, co-evaporated with toluene to remove most solvents then further dried under high vacuum. The resulting crude product was dissolved in dioxane (0.02 M), treated with KCN (4.0 equiv), the reaction mixture was stirred at 110° C. for 16 hours. The reaction mixture was diluted with water (1 volume) and extracted with EtOAc (3×1 volume). The organic layers were concentrated under reduced pressure. The residue was purified by column chromatography through silica gel, eluting with 0-30% ethyl acetate in petroleum ether as a gradient. The product containing fractions were concentrated and dried under vacuum to give (S)-benzyl 2-cyano-6-(4-(methoxycarbonyl)phenyl)-7-azaspiro[3.5]nonane-7-carboxylate (52% yield) as a light-yellow liquid. LCMS (ESI) m/z 441.1 $(M+23)^+$.

Step 2: Preparation of (S)-methyl 4-(2-cyano-7-azaspiro[3.5]nonan-6-yl)benzoate: To a solution of (S)-benzyl 2-cyano-6-(4-(methoxycarbonyl)phenyl)-7-azaspiro[3.5]nonane-7-carboxylate (1.0 equiv) in EtOAc (0.04 M) was added Pd/C (1.0 equiv, 10% w/w) under $N_2$. The suspension was degassed under vacuum and purged with $H_2$ 3 times. The mixture was stirred under H2 (15 psi) at 25° C. for 16 hours. The reaction mixture was filtered, and the solvent was concentrated to give (S)-methyl 4-(2-cyano-7-azaspiro[3.5]nonan-6-yl)benzoate (78% yield) as a white solid. LCMS (ESI) m/z 284.9 $(M+23)^+$.

Step 3: Preparation of (S)-tert-butyl 4-((2-cyano-6-(4-(methoxycarbonyl)phenyl)-7-azaspiro[3.5]nonan-7-yl)methyl)-5-methoxy-7-methyl-1H-indole-1-carboxylate: To a mixture of (S)-methyl 4-(2-cyano-7-azaspiro[3.5]nonan-6-yl)benzoate (1.1 equiv) in MeOH (0.02 M) was added $ZnCl_2$ (2.0 equiv). The mixture was stirred at 30° C. for 1 hour. $NaBH_3CN$ (3.0 equiv) was added. The reaction mixture was stirred at 50° C. for 16 hours. The reaction mixture was concentrated and diluted with $H_2O$ (1 volume) and extracted with EtOAc (3×1 volume). The combined layers were concentrated. The mixture was purified by column chromatography through silica gel, eluting with 0-100% ethyl acetate in petroleum ether as a gradient, the product containing fractions were concentrated to give (S)-tert-butyl 4-((2-cyano-6-(4-(methoxycarbonyl)phenyl)-7-azaspiro[3.5]nonan-7-yl)methyl)-5-methoxy-7-methyl-1H-indole-1-carboxylate (56% yield) as a white solid. LCMS (ESI) m/z 580.1 $(M+23)^+$.

Step 4: Preparation of tert-butyl 4-(((2R,4s,6S)-2-cyano-6-(4-(methoxycarbonyl)phenyl)-7-azaspiro[3.5]nonan-7-yl)methyl)-5-methoxy-7-methyl-1H-indole-1-carboxylate and tert-butyl 4-(((2S,4r,6S)-2-cyano-6-(4-(methoxycarbonyl)phenyl)-7-azaspiro[3.5]nonan-7-yl)methyl)-5-methoxy-7-methyl-1H-indole-1-carboxylate: The residue was purified by prep-SFC (column: DAICEL CHIRALCEL OD (250 mm×50 mm, 10 μm); mobile phase: 5% to 40% MeOH in $CO_2$+0.05% diethylamine as a gradient over 2.5 min). The fractions of first peak (penultimate product of Example 55) were concentrated and lyophilized overnight and carried out to the next step. LCMS (ESI) m/z 580.2 $(M+23)^+$. The second peak (penultimate product of Example 52) were concentrated and lyophilized overnight and carried out to the next step. LCMS (ESI) m/z 580.2 $(M+23)^+$.

Step 5: Preparation of 4-((2R,4s,6S)-2-cyano-7-((5-methoxy-7-methyl-1H-indol-4-yl)methyl)-7-azaspiro[3.5]nonan-6-yl)benzoic acid or 4-((2S,4r,6S)-2-cyano-7-((5-methoxy-7-methyl-1H-indol-4-yl)methyl)-7-azaspiro[3.5]nonan-6-yl)benzoic acid: To the first peak product from step 4 (1.0 equiv) was added 1 M aqueous LiOH/THF/MeOH solution (10.0 equiv LiOH, v/v/v, 1/1/1). The reaction mixture was stirred at 30° C. for 16 hours. The mixture was quenched with acetic acid to pH~5 and extracted with EtOAc (3×100 mL). The organic layers were concentrated under reduced pressure. The residue was purified by prep-SFC (column: DAICEL CHIRALPAK AD; mobile phase: 5% to 40% isopropanol in $CO_2$+0.05% diethylamine as a gradient over 2.5 min). The desired product containing fractions were concentrated and lyophilized overnight to give Example 55: 4-((2R,4s,6S)-2-cyano-7-((5-methoxy-7-methyl-1H-indol-4-yl)methyl)-7-azaspiro[3.5]nonan-6-yl)benzoic acid or 4-((2S,4r,6S)-2-cyano-7-((5-methoxy-7-methyl-1H-indol-4-yl)methyl)-7-azaspiro[3.5]nonan-6-yl)

benzoic acid (60% yield) as a white solid. $^1H$ NMR (400 MHz, $d_4$-MeOD): δ 8.14 (br d, J=8.0 Hz, 2H), 7.62 (br d, J=8.0 Hz, 2H), 7.30 (d, J=4.0 Hz, 1H), 6.74 (s, 1H), 6.30 (br s, 1H), 4.39-4.22 (m, 2H), 4.02 (br d, J=12.0 Hz, 1H), 3.74 (s, 3H), 3.39 (br d, J=12.0 Hz, 1H), 3.28-3.16 (m, 1H), 2.67-2.57 (m, 1H), 2.49 (s, 3H), 2.47-2.40 (m, 1H), 2.25 (m, 2H), 2.17 (m, 2H), 2.05-1.95 (m, 1H), 1.87 (m, 1H). LCMS (ESI) m/z 444.2 $(M+1)^+$. The second peak from step 4 was processed in a similar manner, yielding Example 52: 4-((2R,4s,6S)-2-cyano-7-((5-methoxy-7-methyl-1H-indol-4-yl)methyl)-7-azaspiro[3.5]nonan-6-yl)benzoic acid or 4-((2S,4r,6S)-2-cyano-7-((5-methoxy-7-methyl-1H-indol-4-yl)methyl)-7-azaspiro[3.5]nonan-6-yl)benzoic acid (55% yield) as white solid. 1H NMR (400 MHz, $d_6$-DMSO): δ 10.82 (br s, 1H), 7.97 (d, J=8.0 Hz, 2H), 7.66 (d, J=8.0 Hz, 2H), 7.24 (t, J=4.0 Hz, 1H), 6.64 (s, 1H), 6.42 (s, 1H), 3.69 (s, 3H), 3.50 (d, J=12.0 Hz, 1H), 3.22-3.08 (m, 2H), 2.59 (d, J=12.0 Hz, 2H), 2.45 (d, J=12.0 Hz, 1H), 2.41 (s, 3H), 1.82-2.11 (m, 5H), 1.36-1.63 (m, 3H).

Example 61: Preparation of 4-((2S,4r,6S)-2-fluoro-7-((5-methoxy-7-methyl-1H-indol-4-yl)methyl)-7-azaspiro[3.5]nonan-6-yl)benzoic acid and 4-((2R,4s,6S)-2-fluoro-7-((5-methoxy-7-methyl-1H-indol-4-yl)methyl)-7-azaspiro[3.5]nonan-6-yl)benzoic acid Example 61

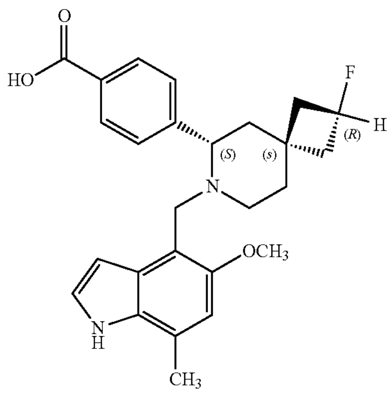

diastereomic mixture and

-continued

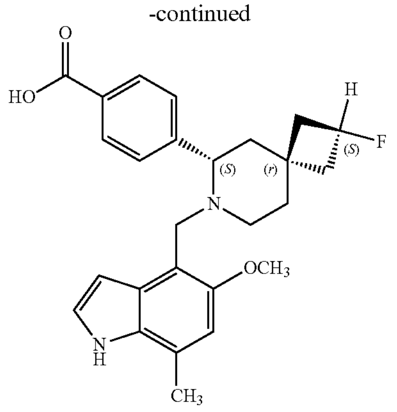

Step 1: Preparation of benzyl (S)-2-hydroxy-6-(4-(methoxycarbonyl)phenyl)-7-azaspiro[3.5]nonane-7-carboxylate: To a solution of benzyl (S)-6-(4-(methoxycarbonyl)phenyl)-2-oxo-7-azaspiro[3.5]nonane-7-carboxylate (Intermediate J, 1.0 equiv) in 10:1 THF/water (0.13 M) was added sodium borohydride (3.0 equiv). The reaction mixture was stirred at 20-25° C. for 17 hours. The reaction mixture was quenched with water, diluted with ethyl acetate, and the aqueous layer was extracted three times with ethyl acetate. The combined organics were dried over anhydrous $MgSO_4$, concentrated under reduced pressure, applied to a precartridge, and purified by column chromatography through silica gel, eluting with a 0-100% ethyl acetate/hexanes gradient. The fractions from the major peak eluting at 100% ethyl acetate in hexanes were combined and concentrated under reduced pressure to afford a white solid (82% yield). LCMS (ESI) m/z 410 $(M+1)^+$.

Step 2: Preparation of benzyl (S)-2-fluoro-6-(4-(methoxycarbonyl)phenyl)-7-azaspiro[3.5]nonane-7-carboxylate: To a solution of benzyl (S)-2-hydroxy-6-(4-(methoxycarbonyl)phenyl)-7-azaspiro[3.5]nonane-7-carboxylate (1.0 equiv) in $CH_2Cl_2$ (0.5 M) at 0° C. was added dropwise diethylaminosulfur trifluoride (2.2 equiv). The reaction was slowly warmed up to 20-25° C. and stirred for 22 hours. The reaction mixture was quenched with saturated aqueous $NaHCO_3$ solution and extracted three times with ethyl acetate. The combined organics were dried over anhydrous $MgSO_4$, filtered, and concentrated under reduced pressure. The residue was applied to a precartridge and purified by column chromatography through silica gel, eluting with a 0-100% ethyl acetate in hexanes gradient. The fractions from the major peak eluting at 82% ethyl acetate in hexanes were combined and concentrated under reduced pressure to afford a light-yellow oil (41% yield). LCMS (ESI) m/z 412 $(M+1)^+$.

Steps 3 to 5 were conducted as described in steps 2 to 4 of Example 45 to yield (S)-4-(2-fluoro-7-((5-methoxy-7-methyl-1H-indol-4-yl)methyl)-7-azaspiro[3.5]nonan-6-yl)benzoic acid as a mixture of diasteromers. LCMS (ESI) m/z 437 $(M+1)^+$.

The diasteromeric mixture in Example 61 above, was purified into each diastereomer using chiral preparative-HPLC column chromatography.

| Example | Structure | MW | MS (ESI+) |
|---|---|---|---|
| Example 62 | 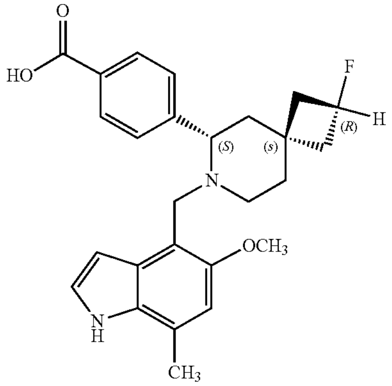 or | 436.53 | 437 (M + 1)⊕ |
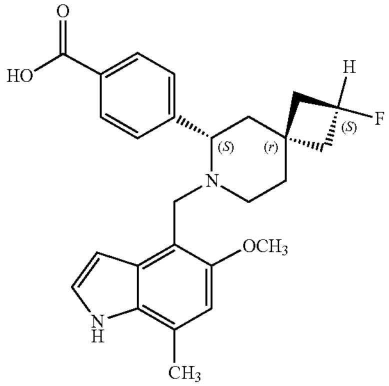
4-((2R,4s,6S)-2-fluoro-7-((5-methoxy-7-methyl-1H-indol-4-yl)methyl)-7-azaspiro[3.5]nonan-6-yl)benzoic acid or 4-((2S,4r,6S)-2-fluoro-7-((5-methoxy-7-methyl-1H-indol-4-yl)methyl)-7-azaspiro[3.5]nonan-6-yl)benzoic acid
$^1$H NMR (400 MHz, $d_6$-DMSO): δ 10.81 (s, 1H), 8.20 (s, 1H), 7.96 (d, J = 8.0 Hz, 2H), 7.64 (d, J = 7.8 Hz, 2H), 7.25 (t, J = 2.8 Hz, 1H), 6.65 (s, 1H), 6.45 (t, J = 2.4 Hz, 1H), 5.13 (t, J = 6.4 Hz, 1H), 4.99 (t, J = 6.5 Hz, 1H), 3.70 (s, 3H), 3.52 (d, J = 11.9 Hz, 1H), 3.16 (t, J = 10.6 Hz, 2H), 2.64 (d, J = 12.0 Hz, 1H), 2.42-1.80 (m, 6H), 1.67 (d, J = 7.4 Hz, 1H), 1.42 (s, 1H), 1.35-1.09 (m, 2H), 0.88 (t, J = 7.2 Hz, 1H).

-continued
| Example | Structure | MW | MS (ESI+) |
|---|---|---|---|
| Example 63 | 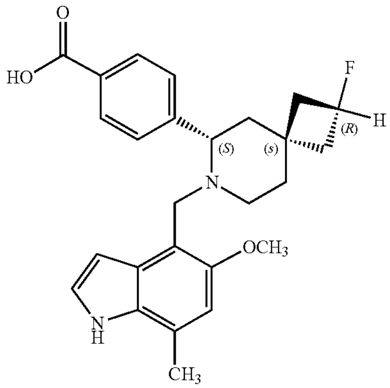 or 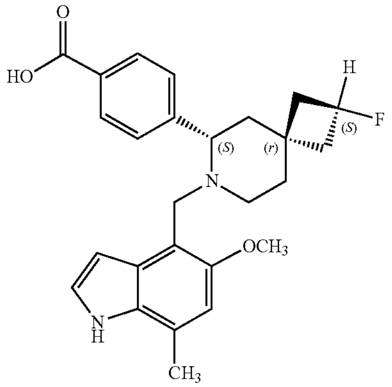 4-((2R,4s,6S)-2-fluoro-7-((5-methoxy-7-methyl-1H-indol-4-yl)methyl)-7-azaspiro[3.5]nonan-6-yl)benzoic acid or 4-((2S,4r,6S)-2-fluoro-7-((5-methoxy-7-methyl-1H-indol-4-yl)methyl)-7-azaspiro[3.5]nonan-6-yl)benzoic acid <br> $^1$H NMR (400 MHz, $d_6$-DMSO): δ 10.81 (s, 1H), 8.20 (s, 1H), 7.96 (d, J = 8.0 Hz, 2H), 7.65 (s, 2H), 7.24 (d, J = 2.9 Hz, 1H), 6.65 (s, 1H), 6.44 (s, 1H), 5.16 (s, 1H), 5.02 (s, 1H), 3.70 (s, 3H), 3.51 (d, J = 11.7 Hz, 2H), 3.18 (dd, J = 18.6, 11.1 Hz, 4H), 2.61 (d, J = 11.9 Hz, 1H), 2.42 (s, 2H), 2.11 (s, 2H), 1.90 (d, J = 25.8 Hz, 2H), 1.71-1.40 (m, 2H). | 436.53 | 437 (M + 1)$^\oplus$ |

Example 64: Preparation of 4-((2R,4s,6S)-4-(2-hydroxy-7-((5-methoxy-7-methyl-1H-indol-4-yl)methyl)-7-azaspiro[3.5]nonan-6-yl)benzoic acid and 4-((2S,4r,6S)-2-hydroxy-7-((5-methoxy-7-methyl-1H-indol-4-yl)methyl)-7-azaspiro[3.5]nonan-6-yl)benzoic acid Example 64

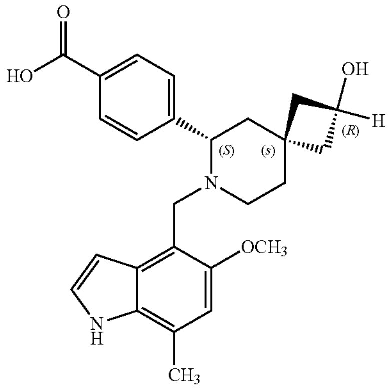

mixture of diasteromers and

-continued

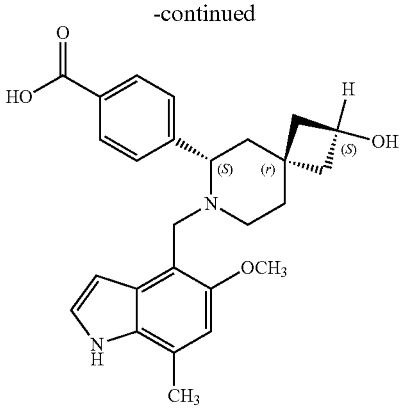

This compound was obtained in a similar manner to Example 61, utilizing the alcohol in step 2 and skipping the fluorination step 3.

| Example | Structure | MW | MS (ESI+) |
|---|---|---|---|
| Example 64 | 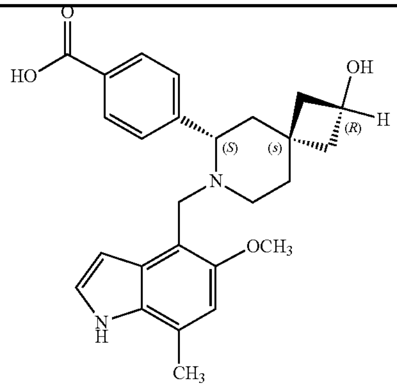 and<br>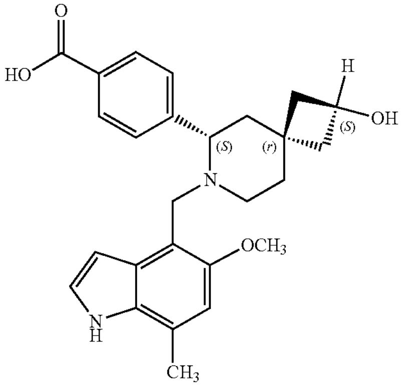<br>4-((2R,4s,6S)-4-(2-hydroxy-7-((5-methoxy-7-methyl-1H-indol-4-yl)methyl)-7-azaspiro[3.5]nonan-6-yl)benzoic acid and 4-((2S,4r,6S)-2-hydroxy-7-((5-methoxy-7-methyl-1H-indol-4-yl)methyl)-7-azaspiro[3.5]nonan-6-yl)benzoic acid<br>$^1$H NMR (400 MHz, $d_6$-DMSO): δ 10.81 (s, 1H), 8.23 (s, 1H), 7.95 (d, J = 8.0 Hz, 2H), 7.63 (d, J = 7.9 Hz, 2H), 7.25 (t, J = 2.8 Hz, 1H), 6.65 (s, 1H), 6.49-6.43 (m, 1H), 4.06 (q, J = 7.2 Hz, 2H), 3.70 (s, 3H), 3.51 (d, J = 11.9 Hz, 1H), 3.14 (d, J = 11.5 Hz, 1H), 2.62 (d, J = 11.9 Hz, 1H), 2.42 (s, 3H), 2.36-2.25 (m, 2H), 2.10-1.89 (m, 2H), 1.69-1.49 (m, 2H), 1.38 (dt, J = 24.0, 12.4 Hz, 4H). | 434.22 | 435 (M + 1)$^{\oplus}$ |

Example 65: Preparation of (R)-4-(1-((5-methoxy-7-methyl-1H-indol-4-yl)methyl)-4-(2,2,2-trifluoroethyl)piperazin-2-yl)benzoic acid

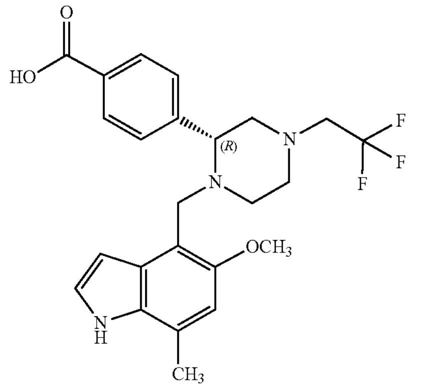

Example 65

Step 1: Preparation of 4-benzyl 1-tert-butyl 2-(4-(methoxycarbonyl)phenyl)piperazine-1,4-dicarboxylate: A mixture of methyl 4-cyanobenzoate (1.0 equiv), 4-((benzyloxy)carbonyl)-1-(tert-butoxycarbonyl)piperazine-2-carboxylic acid (2.0 equiv), 2,4,5,6-tetra(9H-carbazol-9-yl) isophthalonitrile (CzIPN, 0.05 equiv) and $K_2HPO_4$ (3.0 equiv) in DMSO (0.06 M) was degassed and purged with $N_2$ for 30 min and the mixture was irradiated with blue LED light (365 nm) while being stirred at 20-25° C. under a $N_2$ atmosphere for 16 hours. Several new peaks were identified by LCMS with approx. 34% of the desired compound detected. The reaction mixture was diluted with $H_2O$ and extracted with ethyl acetate (3×). The combined organic layers were washed with $H_2O$, dried over $Na_2SO_4$, filtered, and concentrated under reduced pressure. The residue was purified by column chromatography through silica gel, eluting with 0% to 13% ethyl acetate in petroleum ether as a gradient. The crude product was obtained as a yellow gum, which was directly used in the next step without further purification. LCMS (ESI) m/z 399 $(M-56+1)^+$.

Step 2: Preparation of tert-butyl 2-(4-(methoxycarbonyl) phenyl)piperazine-1-carboxylate: To a solution of 4-benzyl 1-tert-butyl 2-(4-(methoxycarbonyl)phenyl)piperazine-1,4-dicarboxylate (1.0 equiv) in MeOH (0.2 M) was added Pd/C (10 wt %, 0.01 equiv) under a $N_2$ atmosphere. The suspension was degassed and purged with H2 a total of three times. The mixture was stirred under an atmosphere of $H_2$ (15 psi) at 10° C. for 16 hours. The reaction mixture was filtered and concentrated under reduced pressure and the crude product was obtained as a yellow gum, which was directly used in the next step without further purification. LCMS (ESI) m/z 265 $(M-56+1)^+$.

Step 3: Preparation of tert-butyl 2-(4-(methoxycarbonyl) phenyl)-4-(2,2,2-trifluoroethyl)piperazine-1-carboxylate: A mixture of tert-butyl 2-(4-(methoxycarbonyl)phenyl)piperazine-1-carboxylate (1.0 equiv), 2,2,2-trifluoroethyl trifluoromethanesulfonate (4.0 equiv) and $EtN(iPr)_2$ (6.0 equiv) in dioxane (0.09 M) was degassed and purged with $N_2$ three times, and the mixture was stirred at 80° C. for 40 hours under a $N_2$ atmosphere. The reaction mixture was concentrated under reduced pressure and purified by column chromatography through silica gel (eluent of 0% to 12% ethyl acetate in petroleum ether as a gradient). The desired product containing fractions were concentrated to yield the title product as a light-yellow solid (67% yield). LCMS (ESI) m/z 347 $(M-56+1)^+$.

Step 4: Preparation of methyl 4-(4-(2,2,2-trifluoroethyl) piperazin-2-yl)benzoate: To a solution of tert-butyl 2-(4-(methoxycarbonyl)phenyl)-4-(2,2,2-trifluoroethyl)piperazine-1-carboxylate (1.0 equiv) in $CH_2Cl_2$ (0.2 M) was added TFA (2.7 M). The mixture was stirred at 10° C. for 2.5 hours after which LCMS indicated completion of reaction. The reaction mixture was neutralized with saturated aqueous $NaHCO_3$ solution to pH-7. The combined organic layers were dried over $Na_2SO_4$, filtered, and concentrated under reduced pressure. The crude product was obtained as a yellow solid, which was directly used in the next step without further purification. LCMS (ESI) m/z 303 $(M+1)^+$.

Step 5: Preparation of tert-butyl 5-methoxy-4-((2-(4-(methoxycarbonyl)phenyl)-4-(2,2,2-trifluoroethyl)piperazin-1-yl)methyl)-7-methyl-1H-indole-1-carboxylate: To a solution of methyl 4-(4-(2,2,2-trifluoroethyl)piperazin-2-yl) benzoate (1.0 equiv) and tert-butyl 4-formyl-5-methoxy-7-methyl-1H-indole-1-carboxylate (1.0 equiv) in MeOH (0.04 M) was added $ZnCl_2$ (5.0 equiv) and the mixture was stirred at 50° C. for 2 hours. Solid $NaBH_3CN$ (3.0 equiv) was then added, and the mixture was heated with stirring at 50° C. for 40 hours. Several new peaks were identified by LCMS analysis, including approx. 55% of the desired compound. The reaction mixture was diluted with ethyl acetate and washed with water. The combined organic layers were dried over $MgSO_4$, filtered, and concentrated under reduced pressure. The residue was purified by column chromatography through silica gel (eluent of 0% to 11% ethyl acetate in petroleum ether as a gradient). The desired product containing fractions were concentrated to yield the title product as a light-yellow oil (84% yield). LCMS (ESI) m/z 576 $(M+1)^+$.

Step 6: Preparation of 4-(1-((5-methoxy-7-methyl-1H-indol-4-yl)methyl)-4-(2,2,2-trifluoroethyl)piperazin-2-yl) benzoic acid: To a solution of tert-butyl 5-methoxy-4-((2-(4-(methoxycarbonyl)phenyl)-4-(2,2,2-trifluoroethyl) piperazin-1-yl)methyl)-7-methyl-1H-indole-1-carboxylate (1.0 equiv) was added 3.0 M aqueous $LiOH{\cdot}H_2O$/THF/MeOH solution (13.0 equiv $LiOH{\cdot}H_2O$, v/v/v, 5/5/3). The mixture was heated under stirring at 70° C. for 16 hours. LCMS indicated completion of hydrolysis, after which the mixture was cooled to 20-25° C. and quenched with dilute acetic acid to pH ~6. The reaction mixture was diluted with ethyl acetate and washed with water. The combined organic layers were filtered and concentrated under reduced pressure. The crude was obtained as a yellow solid, which was directly used in the next step without further purification. LCMS (ESI) m/z 462 $(M+1)^+$.

Step 7: Preparation of (R)-4-(1-((5-methoxy-7-methyl-1H-indol-4-yl)methyl)-4-(2,2,2-trifluoroethyl)piperazin-2-yl)benzoic acid: The racemic sample of tert-butyl 4-(1-((5-methoxy-7-methyl-1H-indol-4-yl)methyl)-4-(2,2,2-trifluoroethyl)piperazin-2-yl)benzoic acid (1.0 equiv) was separated into the corresponding pure enantiomers using chiral SFC chromatography (column: DAICEL CHIRALPAK AD (250 mm×30 mm, 10 μm); mobile phase: 40% A, 0.1% $NH_3{\cdot}H_2O$ in iPrOH; 60% B, $scCO_2$, to give product (R)-4-(1-((5-methoxy-7-methyl-1H-indol-4-yl)methyl)-4-(2,2,2-trifluoroethyl)piperazin-2-yl)benzoic acid (39% yield). $^1H$-NMR (formic acid salt, 400 MHz, $CD_3OD$): δ 8.34 (bs, 1H), 8.15 (d, J=8.0 Hz, 2H), 7.69 (d, J=8.0 Hz, 2H), 7.29 (d, J=2.8 Hz, 1H), 6.73 (s, 1H), 6.36 (d, J=3.2 Hz, 1H), 4.34-4.38 (m, 1H), 4.21 (d, J=12.4 Hz, 1H), 3.96 (d, J=12.4 Hz, 1H), 3.77 (s, 3H), 3.16-3.27 (m, 4H), 3.12 (d, J=12.4 Hz, 1H), 3.05 (d, J=12.4 Hz, 1H), 2.92-2.98 (m, 1H), 2.81-2.87 (m, 1H), 2.49 (s, 3H). $^{19}F$-NMR (376 MHz, $CD_3OD$): δ −71.11 (s, 3F). LCMS (ESI) m/z 462 $(M+1)^+$.

The following compounds were prepared in a similar manner as Example 65 using different alkylating agents with piperazine.

| Example | Intermediate Used | Structure | MW | MS (ESI+) |
|---|---|---|---|---|
| Example 66 | 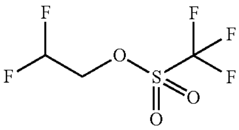 [SMILES: O=S(=O)(OCC(F)F)C(F)(F)F] | 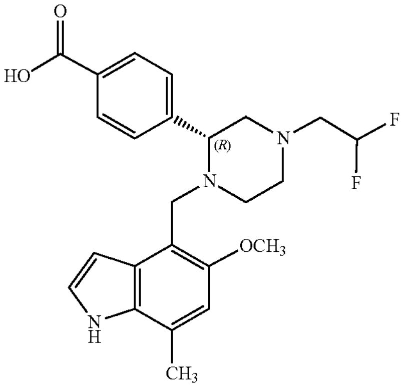 (R)-4-(4-(2,2-difluoroethyl)-1-((5-methoxy-7-methyl-1H-indol-4-yl)methyl)piperazin-2-yl)benzoic acid | 443.22 | 444 (M + 1)⊕ |
| Example 67 | 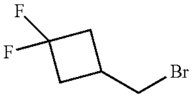 | 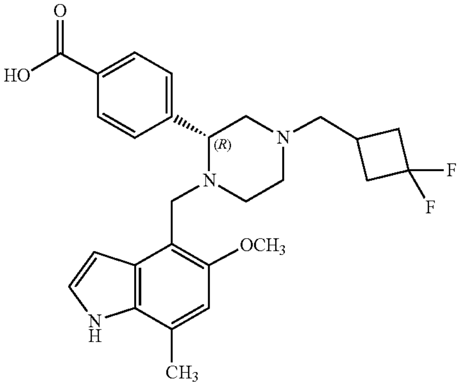 (R)-4-(4-((3,3-difluorocyclobutyl)methyl)-1-((5-methoxy-7-methyl-1H-indol-4-yl)methyl)piperazin-2-yl)benzoic acid | 483.23 | 484 (M + 1)⊕ |
| Example 68 | 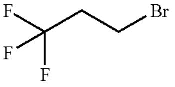 | 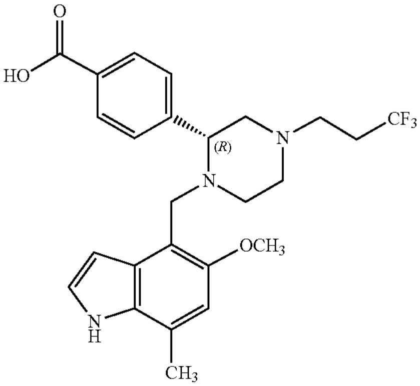 (R)-4-(1-((5-methoxy-7-methyl-1H-indol-4-yl)methyl)-4-(3,3,3-trifluoropropyl)piperazin-2-yl)benzoic acid | 475.21 | 476 (M + 1)⊕ |

-continued
| Example | Intermediate Used | Structure | MW | MS (ESI+) |
|---|---|---|---|---|
| Example 69 | 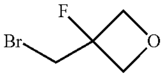 | 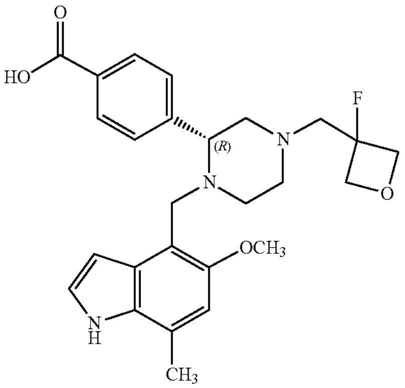 (R)-4-(4-((3-fluorooxetan-3-yl)methyl)-1-((5-methoxy-7-methyl-1H-indol-4-yl)methyl)piperazin-2-yl)benzoic acid | 467.54 | 468 (M + 1)$^{\oplus}$ |
| Example 70 | 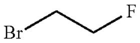 | 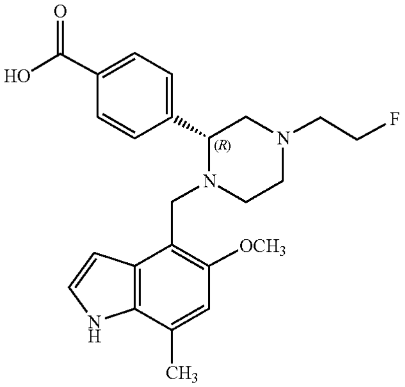 (R)-4-(4-(2-fluoroethyl)-1-((5-methoxy-7-methyl-1H-indol-4-yl)methyl)piperazin-2-yl)benzoic acid | 425.50 | 426 (M + 1)$^{\oplus}$ |

Example 71: Preparation of (±)-trans-4-1-((5-methoxy-7-methyl-1H-indol-4-yl)methyl)-4-(3-(trifluoromethyl)azetidin-1-yl)piperidin-2-yl)benzoic acid Example 71

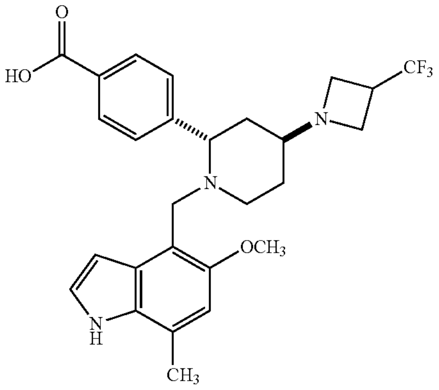

(+/-)-trans

Step 1: Preparation of tert-butyl 5-methoxy-4-((2-(4-(methoxycarbonyl)phenyl)-4-(3-(trifluoromethyl)azetidin-1-yl)piperidin-1-yl)methyl)-7-methyl-1H-indole-1-carboxylate: To a mixture of tert-butyl 5-methoxy-4-((2-(4-(methoxycarbonyl)phenyl)-4-oxopiperidin-1-yl)methyl)-7-methyl-1H-indole-1-carboxylate (Intermediate G, 1.0 equiv), 3-(trifluoromethyl)azetidine hydrochloride (2.0 equiv) in MeOH (0.08 M) was added $ZnCl_2$ (2.0 equiv). The mixture was stirred at 15° C. for 1 hour after which solid $NaBH_3CN$ (3 equiv) was added. The reaction mixture was stirred at 50° C. for 16 hours. Analysis by TLC ($CH_2Cl_2$: MeOH=10:1, UV 254 nm) demonstrated the formation of a new spot. The reaction mixture was concentrated, and the residue was purified by column chromatography through silica gel (eluent of 0% to 10% methanol in dichloromethane as a gradient). The desired product containing fractions were concentrated and dried under vacuum to afford a white solid (82% yield).

Step 2: Preparation of (±)-trans-4-1-((5-methoxy-7-methyl-1H-indol-4-yl)methyl)-4-(3-(trifluoromethyl)azetidin-1-yl)piperidin-2-yl)benzoic acid formic acid salt: To a mixture of tert-butyl 5-methoxy-4-((2-(4-(methoxycarbonyl)phenyl)-4-(3-(trifluoromethyl)azetidin-1-yl)piperidin-1-yl)methyl)-7-methyl-1H-indole-1-carboxylate (1.0 equiv) in THF (0.11 M), MeOH (0.11 M) and $H_2O$ (0.11 M) was added $LiOH{\cdot}H_2O$ (10 equiv). The reaction mixture was heated to 70° C. with stirring for 16 hours. The reaction mixture was concentrated, and the residue was purified by preparative HPLC (column: Welch Xtimate C18 150×25 mm, 5 μm; mobile phase: 8-38% MeCN in water+0.225% formic acid as a gradient). The desired trans isomer was isolated, concentrated, and dried under vacuum to afford a white solid (15% yield). $^1H$ NMR (formic acid salt, 400 MHz, $CD_3OD$): δ 8.37 (br s, 1H), 8.17 (d, J=8 Hz, 2H), 7.67 (d, J=8 Hz, 2H), 7.32 (d, 1H), 6.76 (s, 1H), 6.32 (br s, 1H), 4.77 (br d, J=12 Hz, 1H), 4.35 (br d, J=16 Hz, 1H), 4.18 (br d, J=12 Hz, 1H), 3.75 (s, 3H), 3.63-3.50 (m, 3H), 3.30-3.24 (m, 3H), 2.68 (br d, J=16 Hz, 1H), 2.50 (s, 3H), 2.36-2.11 (m, 1H), 2.01 (br d, J=12 Hz, 2H), 1.89-1.74 (m, 1H). LCMS (ESI) m/z 502 $(M+1)^+$.

The following compounds were prepared in a similar manner as Example 71, using the appropriately substituted azetidine hydrochloride in place of 3-(trifluoromethyl)azetidine hydrochloride, and using the appropriately substituted Intermediate G.

| Example | Intermediate Used | Structure | MW | MS (ESI+) |
|---|---|---|---|---|
| Example 72 | 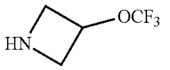 | 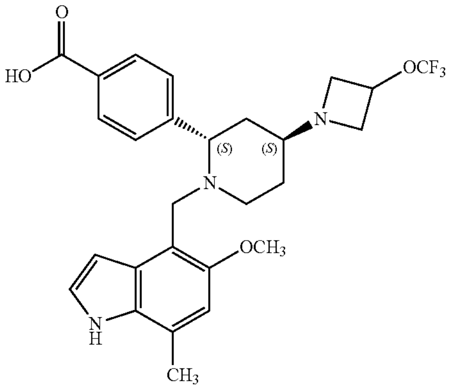 4-((2S,4S)-1-((5-methoxy-7-methyl-1H-indol-4-yl)methyl)-4-(3-(trifluoromethoxy)azetidin-1-yl)piperidin-2-yl)benzoic acid | 517.55 | 518 $(M + 1)^{\oplus}$ |

-continued

| Example | Intermediate Used | Structure | MW | MS (ESI+) |
|---|---|---|---|---|
| Example 73 | 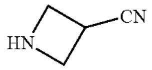 | 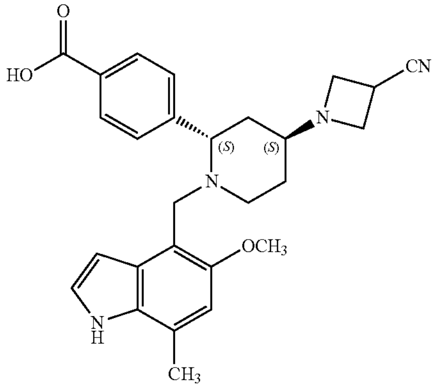 4-((2S,4S)-4-(3-cyanoazetidin-1-yl)-1-((5-methoxy-7-methyl-1H-indol-4-yl)methyl)piperidin-2-yl)benzoic acid | 458.56 | 459 (M + 1)⊕ |
| Example 74 | 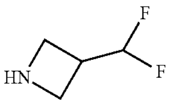 | 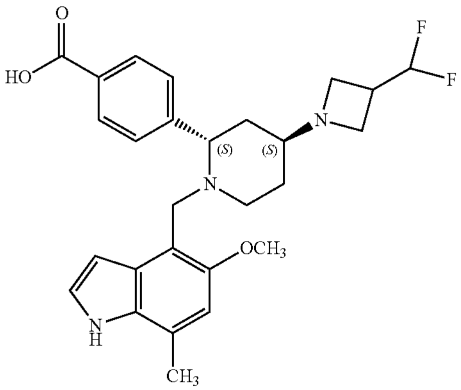 4-((2S,4S)-4-(3-(difluoromethyl)azetidin-1-yl)-1-((5-methoxy-7-methyl-1H-indol-4-yl)methyl)piperidin-2-yl)benzoic acid | 483.56 | 484 (M + 1)⊕ |
| Example 75 | 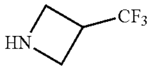 | 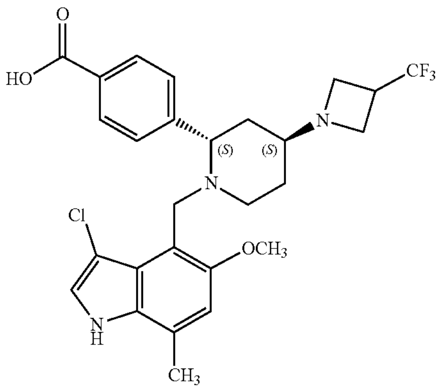 4-((2S,4S)-1-((3-chloro-5-methoxy-7-methyl-1H-indol-4-yl)methyl)-4-(3-(trifluoromethyl)azetidin-1-yl)piperidin-2-yl)benzoic acid | 535.99 | 536 (M + 1)⊕ |

-continued

| Example | Intermediate Used | Structure | MW | MS (ESI+) |
|---|---|---|---|---|
| Example 76 | 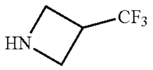 | 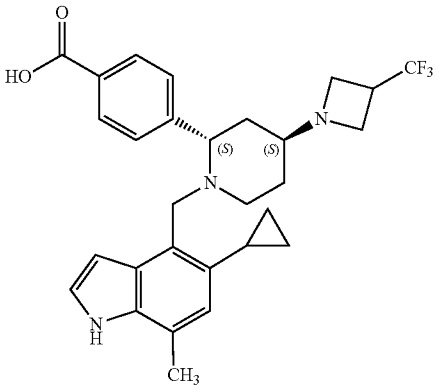<br>4-((2S,4S)-1-((5-cyclopropyl-7-methyl-1H-indol-4-yl)methyl)-4-(3-(trifluoromethyl)azetidin-1-yl)piperidin-2-yl)benzoic acid | 511.59 | 512 (M + 1)⊕ |
| Example 77 | 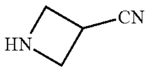 | 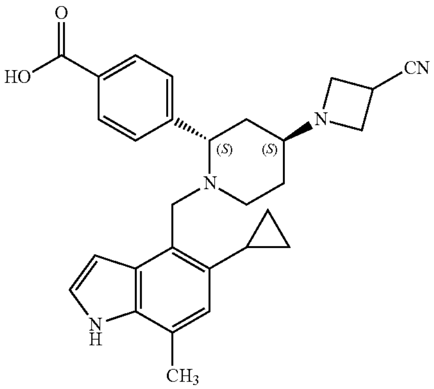<br>4-((2S,4S)-4-(3-cyanoazetidin-1-yl)-1-((5-cyclopropyl-7-methyl-1H-indol-4-yl)methyl)piperidin-2-yl)benzoic acid | 468.60 | 469 (M + 1)⊕ |
| Example 78 | 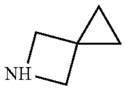 | 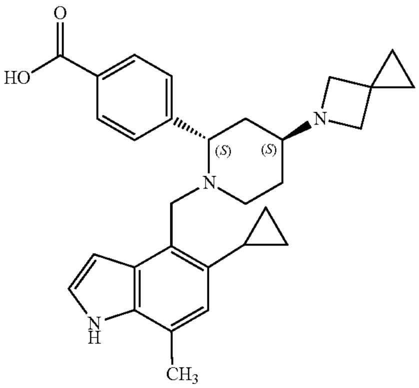<br>4-((2S,4S)-1-((5-cyclopropyl-7-methyl-1H-indol-4-yl)methyl)-4-(5-azaspiro[2.3]hexan-5-yl)piperidin-2-yl)benzoic acid | 469.63 | 470 (M + 1)⊕ |

-continued
| Example | Intermediate Used | Structure | MW | MS (ESI+) |
|---|---|---|---|---|
| Example 79 | 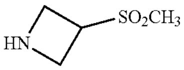 | 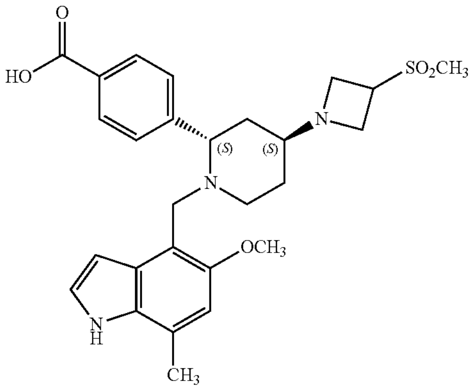 4-((2S,4S)-1-((5-methoxy-7-methyl-1H-indol-4-yl)methyl)-4-(3-(methylsulfonyl)azetidin-1-yl)piperidin-2-yl)benzoic acid | 511.64 | 512 (M + 1)⊕ |
| Example 80 | 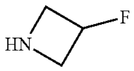 | 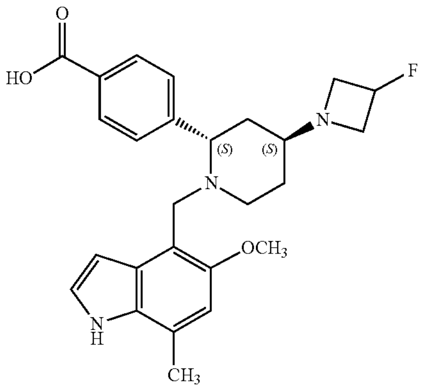 4-((2S,4S)-4-(3-fluoroazetidin-1-yl)-1-((5-methoxy-7-methyl-1H-indol-4-yl)methyl)piperidin-2-yl)benzoic acid | 451.54 | 452 (M + 1)⊕ |
| Example 81 | 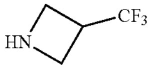 | 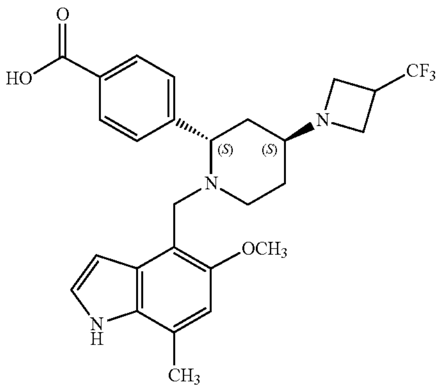 4-((2S,4S)-1-((5-methoxy-7-methyl-1H-indol-4-yl)methyl)-4-(3-(trifluoromethyl)azetidin-1-yl)piperidin-2-yl)benzoic acid | 501.55 | 502 (M + 1)⊕ |

Example 82: Preparation of 4-((2S,4S)-1-((5-methoxy-7-methyl-1H-indol-4-yl)methyl)-4-(oxetan-3-yloxy)piperidin-2-yl)benzoic acid Example 82

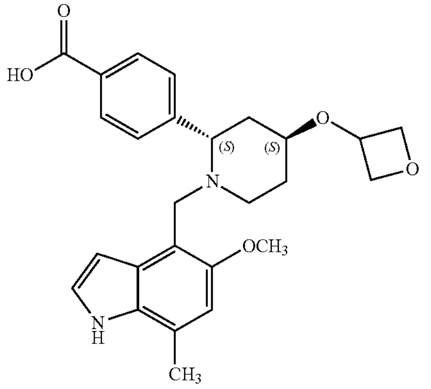

Step 1: Preparation of 4-(oxetan-3-yloxy)picolinonitrile: To a mixture of oxetan-3-ol (2.0 equiv) in DMF (0.6 M) was added NaH (2.0 equiv) at 0° C. The mixture was stirred at 15° C. for 30 min and then 4-chloropyridine-2-carbonitrile (1.0 equiv) was added. The reaction mixture was stirred at 15° C. for 1 hour after which TLC analysis (petroleum ether:EtOAc=2:1, UV 254 nm) indicated a new spot had formed. The reaction mixture was quenched by $H_2O$ and extracted with EtOAc. The organic layers were concentrated, and the crude product was triturated with petroleum ether at 15° C. for 60 minutes and then filtered. The cake was dried under vacuum to afford a light white solid (82% yield). LCMS (ESI) m/z 177 $(M+1)^+$.

Step 2: Preparation of 4-(oxetan-3-yloxy)picolinic acid: To a mixture of 4-(oxetan-3-yloxy) pyridine-2-carbonitrile (1.0 equiv) in dioxane (1.9 M) was added 2 M aqueous NaOH solution (1.06 equiv). The reaction mixture was heated to 100° C. with stirring for 16 hours. LCMS indicated starting material was consumed and the desired product mass was detected. The reaction mixture was adjusted to pH=7.0 with 1 M aqueous HCl solution and concentrated. The crude product was triturated with MeOH at 15° C. for 60 min and then filtered and dried under vacuum to afford a white solid (90% yield).

Step 3: Preparation of 4-(oxetan-3-yloxy)piperidine-2-carboxylic acid: To a solution of 4-(oxetan-3-yloxy)pyridine-2-carboxylic acid (1.0 equiv) in glacial acetic acid (2.05 M) and MeOH (0.51 M) was added $PtO_2$ (0.5 equiv). The suspension was degassed under vacuum and purged with H2 a total of 3 times. The mixture was stirred under H2 (50 psi) at 60° C. for 16 hours. The reaction mixture was filtered, and the solvent was concentrated. The desired unpurified product (96%) was used into the next step without further purification. LCMS (ESI) m/z 201 $(M+1)^+$.

Step 4: Preparation of 1-(tert-butoxycarbonyl)-4-(oxetan-3-yloxy)piperidine-2-carboxylic acid: To a mixture of 4-(oxetan-3-yloxy)piperidine-2-carboxylic acid (1.0 equiv) in dioxane (0.9 M) was added 2 M aqueous NaOH solution (1.0 equiv), followed by $Boc_2O$ (2.0 equiv). The reaction mixture was stirred at 20° C. for 16 hours. Analysis by TLC ($CH_2Cl_2$:MeOH=10:1, UV 254 nm) indicated formation of a new spot. The reaction mixture was adjusted to pH=7.0 with 1 M aqueous HCl solution and concentrated. The reaction mixture was diluted with $H_2O$ and extracted with EtOAc, and the combined organic layers were concentrated under reduced pressure. The resulting residue was purified by column chromatography through silica gel (eluent of 0% to 10% methanol in dichloromethane as a gradient). The desired product containing fractions were concentrated and dried under vacuum to afford a white gum (52% yield). LCMS (ESI) m/z 202 $(M-100+1)^+$.

Step 5: Preparation of tert-butyl 2-(4-(methoxycarbonyl)phenyl)-4-(oxetan-3-yloxy)piperidine-1-carboxylate: To a mixture of methyl 4-cyanobenzoate (1.0 equiv), 1-tert-butoxycarbonyl-4-(oxetan-3-yloxy)piperidine-2-carboxylic acid (1.5 equiv), 2,4,5,6-tetrakis(carbazol-9-yl)-1,3-dicyanobenzene (4-CzIPN, 0.02 equiv) and $K_2HPO_4$ (3.0 equiv) in DMSO (0.03 M) was degassed by bubbling a $N_2$ stream for 30 minutes. The reaction mixture irradiated with a blue LED light (365 nm) while stirring at 30° C. for 16 hours. LCMS indicated the desired product of correct mass was detected. The reaction mixture was diluted with $H_2O$ and extracted with EtOAc, and the combined organic layers were washed with $H_2O$, dried over $Na_2SO_4$ filtered and concentrated. The resulting residue was purified by column chromatography through silica gel (eluent of 0% to 20% ethyl acetate in petroleum ether as a gradient). The desired product containing fractions were concentrated and dried under vacuum to afford a light-yellow oil (29% yield). LCMS (ESI) m/z 292 $(M-100+1)^+$.

Step 6: Preparation of methyl 4-(4-(oxetan-3-yloxy)piperidin-2-yl)benzoate: To a mixture of tert-butyl 2-(4-methoxycarbonylphenyl)-4-(oxetan-3-yloxy)piperidine-1-carboxylate (1.0 equiv) in $CH_2Cl_2$ (0.18 M) was added TFA (15 equiv). The reaction mixture was stirred at 20-25° C. for 16 hours. The reaction mixture was adjusted to pH=9.0 using a saturated aqueous $NaHCO_3$ solution. The reaction mixture was further diluted with $H_2O$ and extracted with EtOAc. The combined organic layers were concentrated, and the residue was purified by column chromatography through silica gel (eluent of 0% to 10% methanol in dichloromethane as a gradient). The desired product containing fractions were concentrated and dried under vacuum to afford a light-yellow oil (61% yield). LCMS (ESI) m/z 292 $(M+1)^+$.

Step 7: Preparation of tert-butyl 5-methoxy-4-((2-(4-(methoxycarbonyl)phenyl)-4-(oxetan-3-yloxy)piperidin-1-yl)methyl)-7-methyl-1H-indole-1-carboxylate: To a mixture of methyl 4-[4-(oxetan-3-yloxy)-2-piperidyl]benzoate (1.0 equiv), tert-butyl 4-formyl-5-methoxy-7-methyl-indole-1-carboxylate (1.1 equiv) in MeOH (0.1 M) was added $ZnCl_2$ (2.0 equiv). The mixture was stirred at 15° C. for 1 hour. Solid $NaBH_3CN$ (3.0 equiv) was added, and the reaction mixture was stirred at 50° C. for 16 hours. Analysis by TLC ($CH_2Cl_2$:MeOH=10:1, UV 254 nm) indicated a new spot had formed. The reaction mixture was concentrated, and the residue was purified by column chromatography through silica gel (eluent of 0% to 10% methanol in dichloromethane as a gradient). The desired product containing fractions were concentrated and dried under vacuum to afford a white solid (62% yield). LCMS (ESI) m/z 565 $(M+1)^+$.

Step 8: Preparation of (±)-trans-4-(−1-((5-methoxy-7-methyl-1H-indol-4-yl)methyl)-4-(oxetan-3-yloxy)piperidin-2-yl)benzoic acid: To a mixture of tert-butyl 5-methoxy-4-[[−2-(4-methoxycarbonylphenyl)-4-(oxetan-3-yloxy)-1-piperidyl]methyl]-7-methyl-indole-1-carboxylate (1.0 equiv) in THF (0.09 M), MeOH (0.09 M), and $H_2O$ (0.09 M) was added $LiOH{\cdot}H_2O$ (10 equiv). The reaction mixture was heated to 70° C. with stirring for 16 hours. The reaction mixture was cooled to 20-25° C., adjusted to pH=5.0 with 1.0 M aqueous HCl solution and concentrated. The residue was purified by preparative HPLC (column: Welch Xtimate C18 150×25 mm, 5 μm; mobile phase: 18-48% MeCN in water+0.225% formic acid as a gradient). The desired product containing fractions were concentrated and dried under vacuum to afford a white solid (31% yield). LCMS (ESI) m/z 451 $(M+1)^+$.

Step 9: Preparation of 4-((2S,4S)-1-((5-methoxy-7-methyl-1H-indol-4-yl)methyl)-4-(oxetan-3-yloxy)piperidin-2-yl)benzoic acid: The racemic (±)-trans-4-(−1-((5-methoxy-7-methyl-1H-indol-4-yl)methyl)-4-(oxetan-3-yloxy)piperidin-2-yl)benzoic acid was separated into each of the enantiomers using a chiral SFC chromatography (column: DAICEL CHIRALPAK IC (250 mm×30 mm, 10 μm); mobile phase: 45% EtOH+0.1% $NH_3H_2O$ in $scCO_2$). The title compound was concentrated and dried under vacuum to afford a white solid. $^1$H-NMR (400 MHz, $CD_3OD$): δ 8.13 (d, J=8 Hz, 2H), 7.62 (br d, J=8 Hz, 2H), 7.32 (br s, 1H), 6.76 (s, 1H), 6.35 (br s, 1H), 4.84 (d, J=8 Hz, 2H), 4.81-4.66 (m, 3H), 4.62 (s, 1H), 4.30 (br d, J=8 Hz, 1H), 4.17 (br s, 1H), 3.83 (br s, 1H), 3.76 (s, 3H), 3.48 (br s, 1H), 3.39-3.33 (m, 1H), 2.50 (s, 3H), 2.29-2.09 (m, 2H), 1.97 (br s, 2H); LCMS (ESI) m/z 451 $(M+1)^+$.

The following compounds were prepared in a similar manner as Example 82 using different alcohol starting materials.

| Example | Intermediate Used | Structure | MW | MS (ESI+) |
|---|---|---|---|---|
| Example 83 | 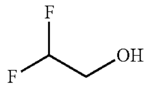 | 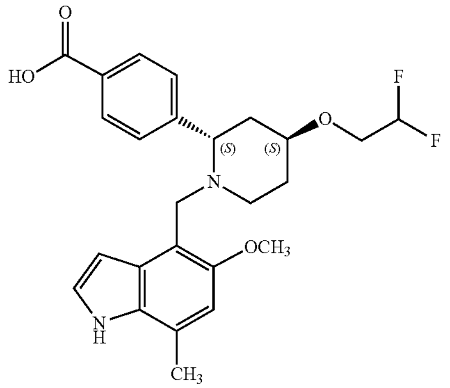 4-((2S,4S)-4-(2,2-difluoroethoxy)-1-((5-methoxy-7-methyl-1H-indol-4-yl)methyl)piperidin-2-yl)benzoic acid | 458.20 | 459 $(M + 1)^{\oplus}$ |
| Example 84 | 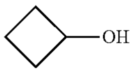 | 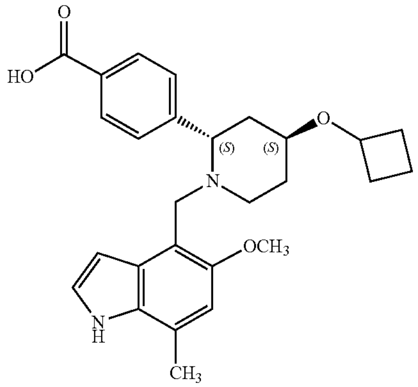 4-((2S,4S)-4-cyclobutoxy-1-((5-methoxy-7-methyl-1H-indol-4-yl)methyl)piperidin-2-yl)benzoic acid | 448.56 | 449 $(M + 1)^{\oplus}$ |

-continued

| Example | Intermediate Used | Structure | MW | MS (ESI+) |
|---|---|---|---|---|
| Example 85 | 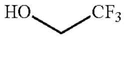 | 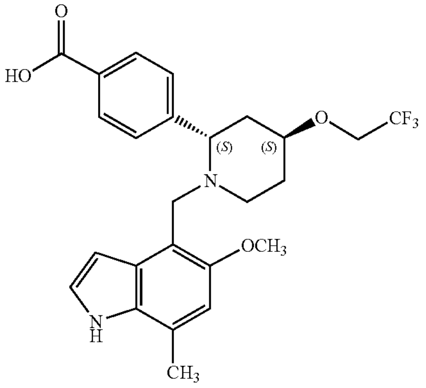 4-((2S,4S)-1-((5-methoxy-7-methyl-1H-indol-4-yl)methyl)-4-(2,2,2-trifluoroethoxy)piperidin-2-yl)benzoic acid | 476.50 | 477 (M + 1)$^{\oplus}$ |

Example 85: Human C3bBb Enzyme Assay

Compounds disclosed herein were evaluated for their potency to inhibit human C3bBb in a biochemical assay. To generate active C3bBb complex in vitro, purified human C3b (Complement Technology, A114), CFB (Complement Technology, A135) and CFD (Complement Technology, A136) were mixed in a 1:1:1 ratio to a final concentration of 1 μM each in the C3bBb assay buffer (PBS pH 7.4, 100 μM $NiCl_2$, 0.05% (w/v) CHAPS). The reaction mix was incubated at room temperature for 30 minutes on a rotating platform. After the incubation, a sample was taken to confirm the cleavage of CFB by Western blot using a polyclonal anti-human factor B antibody (Quidel, A311), and the rest of the reaction was immediately aliquoted on ice and stored at −80° C. On the day of the enzyme assay, a reaction mixture containing 3 nM C3bBb complex and 1 μM purified human C3 (Complement Technology, A113) was prepared in the C3bBb assay buffer. Compounds were serial diluted 3-fold in 100% DMSO for a 10-point dose-response curve. A 0.5 μL aliquot of diluted compound solution was transferred to a conical bottom 96-well plate, before 49.5 μL of the reaction mix was added to each well to initiate the reaction. The plate was incubated for 1 hour at room temperature. The reaction was terminated by adding 0.5 μL of Protease Inhibitor Cocktail (Thermo Fisher, 75446) to each well. The generation of C3a from C3 by the C3bBb complex was measured using the MicroVue C3a Plus EIA ELISA kit (Quidel, A031). The concentration of C3a from each well was calculated using a standard curve. Percent inhibition values were generated using the baseline (C3 only) and the maximum control (DMSO instead of compound), and $IC_{50}$ of each compound was calculated using 4-parameter logistic regression. Table 2 below (middle column) shows the $IC_{50}$ values obtained for the compounds disclosed herein. $IC_{50}$ values are categorized according to potency: A≤10 nM, 10 nM<B≤25 nM, 25 nM<C≤50 nM, 50 nM<D≤100 nM, 100 nM<E and "N.D." means "not determined".

Example 86: Human Serum MAC Formation Assay

MAC deposition assay using normal human serum was applied to evaluate compound potency under physiologically relevant conditions. Black Maxisorp plates (Thermo Fisher, 437111) were coated with preactivated zymosan (Complement Technology, B400) at 0.5 mg/mL in carbonate buffer (pH 9.5, Sigma, C3041) at room temperature overnight. Compounds were serial diluted 3-fold in 100% DMSO for a 10-point dose-response curve. Normal human serum (Complement Technology, NHS) was diluted to 50% (v/v) with the gelatin buffer (4.2 mM HEPES pH 7.4, 0.15 mM $CaCl_2$, 141 mM NaCl, 4.5 mM $MgCl_2$, 0.1% gelatin) containing 20 mM EGTA or 20 mM EDTA. In conical bottom 96-well plates, 1 μL compound and 99 μL of serum-EGTA were mixed. Serum-EDTA was used as baseline control. The serum-compound mixture was incubated at room temperature for 15 minutes before being transferred to the washed zymosan plate for complement activation at 37° C. for 30 minutes. The reaction was terminated by decanting the reaction mixture and adding blocking buffer (Thermo Fisher, 37539) for 20 minutes. MAC formation on the ELISA plate was detected using 0.2 μg/mL mouse anti-human C9 neoepitope monoclonal antibody (Thermo Fisher, MA5-33373) diluted in phosphate-buffered saline with 0.05% Tween-20 (PBST). A goat anti-mouse IgG-HRP antibody (Thermo Fisher, A16072) was used at 1:2000 in PBST as secondary antibody. After washing, the reaction was developed using QuantaBlu (Thermo Fisher, 15169) for 20 minutes at room temperature. The plates were read at 325 nm excitation and 420 nm emission wavelengths. Percent inhibition values were generated using the baseline (EDTA-serum) and the maximum control (EGTA-serum). An $IC_{50}$ for each compound was calculated using 4-parameter logistic regression. Table 2 below (last column) shows the $IC_{50}$ values obtained for the compounds disclosed herein. $IC_{50}$ values are categorized according to potency: 0<A≤100 nM, 100 nM<B≤200 nM, 200 nM<C≤300 nM, 300 nM<D≤500 nM, 500 nM<E.

TABLE 2

| Example Number | Human C3b:Bb $IC_{50}$ Avg (nM) | Human serum MAC formation $IC_{50}$ Avg (nM) |
|---|---|---|
| Example 1 | D | E |
| Example 2 | D | D |
| Example 3 | B | E |
| Example 4 | A | C |
| Example 5 | N.D. | E |
| Example 6 | N.D. | E |
| Example 7 | A* | B |
| Example 8 | A* | A |
| Example 9 | E | E |
| Example 10 | D | D |
| Example 11 | E | E |
| Example 12 | E | D |
| Example 13 | D* | B |
| Example 14 | B | B |
| Example 15 | A* | A |
| Example 16 | E | D |
| Example 17 | B | B |
| Example 18 | A* | B |
| Example 19 | A* | A |
| Example 20 | C | D |
| Example 21 | E | B |
| Example 22 | A* | B |
| Example 23 | D* | D |
| Example 24 | B* | C |
| Example 25 | A* | A |
| Example 26 | D* | B |
| Example 27 | N.D. | B |
| Example 28 | A* | B |
| Example 29 | E | E |
| Example 30 | A* | B |
| Example 31 | A* | E |
| Example 32 | A* | A |
| Example 33 | E* | E |
| Example 34 | A* | B |
| Example 35 | A* | A |
| Example 36 | A* | A |
| Example 37 | E | E |
| Example 38 | D | C |
| Example 39 | E | D |
| Example 40 | E | D |
| Example 41 | A* | B |
| Example 42 | A* | C |
| Example 43 | D* | E |
| Example 44 | A* | A |
| Example 45 | A* | A |
| Example 46 | A* | B |
| Example 47 | A* | A |
| Example 48 | A* | A |
| Example 49 | A* | A |
| Example 50 | A* | A |
| Example 51 | A* | A |
| Example 52 | A* | A |
| Example 53 | A* | A |
| Example 54 | A* | A |
| Example 55 | A* | A |
| Example 56 | A* | A |
| Example 57 | A* | A |
| Example 58 | A* | B |
| Example 59 | A* | B |
| Example 60 | B* | B |
| Example 61 | A* | A |
| Example 62 | A* | A |
| Example 63 | A* | A |
| Example 64 | B* | C |
| Example 65 | B* | C |
| Example 66 | C* | B |
| Example 67 | D* | D |
| Example 68 | A* | B |
| Example 69 | D* | B |
| Example 70 | C* | C |
| Example 71 | A* | D |
| Example 72 | C* | C |
| Example 73 | A* | B |
| Example 74 | A* | B |
| Example 75 | B* | C |
| Example 76 | A* | B |
| Example 77 | A* | A |

TABLE 2-continued

| Example Number | Human C3b:Bb $IC_{50}$ Avg (nM) | Human serum MAC formation $IC_{50}$ Avg (nM) |
|---|---|---|
| Example 78 | C* | B |
| Example 79 | D* | B |
| Example 80 | C* | C |
| Example 81 | A* | A |
| Example 82 | B* | C |
| Example 83 | A* | B |
| Example 84 | C* | C |
| Example 85 | A* | B |

*Complement assay conducted with 1 nM C3b:Bb enzyme

Example 87: C3bBb Enzyme Jump Dilution Assay

Compound residency time was examined in the C3bBb enzyme jump dilution assay. C3bBb was generated in house with commercially acquired human C3b (Complement Technologies, A114) and human FB (Complement Technologies, A135). Compounds described herein (e.g., compounds of Formula I) were serially diluted in DMSO, and 1 μL of diluted compound was added to 50 μL of C3bBb (2 nM) in assay buffer consisting of PBS at pH 7.4, 100 μM $NiCl_2$, and 0.05% (w/v) CHAPS. After incubating at room temperature for 15 min, 10 μL of the compound-enzyme mixture was combined with equal volume of human C3 at 2 M (Complement Technologies, A113) in assay buffer. For jump dilution, 1 μL of the compound-enzyme mixture was added to 19 μL of C3 at 1.05 μM. After incubating at room temperature for 1 h, the reaction was stopped by adding protease inhibitor cocktail. The amount of C3a generated was measured using the MicroVue C3a Plus EIA kit according to manufacturer's protocol (Quidel, A031). The amount of C3a was calculated from the standard curve and plotted against compound concentrations to determine $IC_{50}$ values.

Example 88: 50% Human Whole Blood Assay for Membrane Attack Complex (MAC) Formation Quantification Human whole blood was collected from healthy volunteers and immediately anticoagulated using the thrombin-specific inhibitor Hirudin (Creative BioMart, #Hirudin-02) at 50 μg/mL. Gelatin Veronal Buffer (GVB) (Complement Technology Inc, #B103) containing 2 mM $MgCl_2$ and 10 mM EGTA or EDTA was added to whole blood in equal volume to allow for alternative pathway-specific complement activation (EGTA), or to serve as a negative control (EDTA). The anti-coagulated 50% whole blood mixtures were then added to a 96-well plate in the presence or absence of compounds serial diluted in DMSO (1% final (v/v)) and incubated for 15 minutes at room temperature (21-25° C., RT). The alternative pathway was initiated by the addition of pre-activated zymosan A (Complement Technology Inc, #B400) at a final concentration of 1 mg/mL, in which the reaction mixture was incubated for 70 minutes at 37° C., followed by the immediate addition of an equal volume of 50 mM EDTA in GVB to stop the activated complement reaction. The entire stopped reaction mixture was transferred to a 96-well plate (Nunc Maxisorp) and incubated for 1 hour for C9 ELISA detection. Following aspiration of the reaction mixture after coating, the plate was immediately blocked using the StartingBlock T20 buffer (ThermoFisher, #37539) for 20 minutes at RT, proceeded by a wash step with PBS containing 0.05% (v/v) Tween-20 (PBS-T). A mouse anti-human C9 monoclonal antibody (ThermoFisher,

#MA5-33373) was used as the primary antibody at 0.2 μg/mL in PBS-T and incubated for 1 hour, followed by a PBS-T wash, and the addition of a horseradish peroxidase (HRP)-conjugated goat anti-mouse IgG secondary antibody (ThermoFisher, #A16072) at 0.5 μg/mL for 45 minutes. After a final wash, the reaction was developed using Quant-aBlu Fluorogenic Peroxidase Substrate Detection (ThermoFisher, #15169), and the plate was read at 325 nm excitation and 420 nm emission wavelengths using the FlexStation 3 Microplate Reader (Molecular Devices). Percentage inhibition values were calculated by baseline correcting all values with the EDTA-containing negative control and normalizing all values to the EGTA-containing compound-free positive control. $IC_{50}$ values were calculated using a four-parameter logistic regression dose response model.

Example 89: Wieslab Assay for Alternative Complement Pathway

The ability of the compounds described herein (e.g., compounds of Formula I) to inhibit the formation of C5b-9 in the alternative pathway was examined with the Wieslab Complement Alternative Pathway kit (Svar, COMPLAP330RUO) following the manufacturer's protocol. In brief, human serum (Complement Technology, NHS) was diluted 1/18 with Diluent AP and added to compound serially diluted in DMSO (1% final (v/v)). After compound pre-incubation at room temperature for 15 min, samples were then transferred to the pre-coated plate and incubated for 60 min at 37° C. The plate was washed three times with Wash Buffer and incubated with 100 μL of Conjugate for 30 min at room temperature followed by another three times of washing. The plate was then incubated with 100 μL of Substrate Solution for another 30 min at room temperature before measuring the absorbance at 405 nm on the FlexStation 3 Microplate Reader (Molecular Devices). Absorbance was normalized to DMSO control and plotted against compound concentration to determine $IC_{50}$ values.

Example 90: Rat LPS Challenge Model for Pharmacodynamic Assessment of Compounds

Studies were performed with 9-week-old male Sprague Dawley rats (Envigo RMS LLC). Lipopolysaccharide (LPS from *Salmonella typhimurium*, Sigma, L6143) was dissolved in sterile 0.9% saline at 50 μg/mL and administrated by intraperitoneal (i.p.) injection at 1 mL per animal. Compounds described herein (e.g., compounds of Formula I) were formulated in water containing 0.5% (w/v) methylcellulose and 0.1% (v/v) Tween 80. Two hours after the injection of LPS to induce complement activity, compound or vehicle was administrated by oral gavage at various doses. Studies were terminated 4 hours after compound administration, for the duration of 6 hours. Negative or positive control animals were dosed with 1 mL of saline or LPS by i.p. injection respectively, with both control groups receiving vehicle by oral gavage. At the end of the studies, plasma and kidney tissue were collected for PD evaluation. Diluted plasma and kidney homogenate samples were analyzed using the Jess Simple Western system with a rat complement C3d antibody (R&D Systems, AF2655). The peak area of the C3d band from each sample was measured by the Compass software and normalized by total protein input. Percentage inhibition values were calculated using the average of negative and positive control animals.

Example 91: Rat Passive Heymann Nephritis Model of Membranous Nephropathy for Efficacy Assessment Studies were performed with 9-week-old male Sprague Dawley rats (Envigo RMS LLC). Passive Heymann Nephritis was induced via i.v. injection of Sheep Anti-Rat Fx1A Serum (Probetex, PTX-002S) at 6 mL/kg. Compound A, a selected compound of Formula I, was formulated in water containing 0.5% (w/v) methylcellulose and 0.1% (v/v) Tween 80. Compound A and/or vehicle was administered by oral gavage at 5 mL/kg either BID (12:12) or QD at various doses (typically 0.1-100 mg/kg), and administration was initiated either 24 hours prior to injection of Sheep Anti-Rat Fx1A Serum (prophylactic) or 6 days post injection of Sheep Anti-Rat Fx1A Serum (therapeutic) depending on desired dosing regimen. Negative or positive control animals were dosed with 6 mL/kg of 0.9% saline or Sheep Anti-Rat Fx1A Serum via i.v. injection respectively, with both control groups receiving vehicle by oral gavage. Rats were placed into metabolic caging (Lab Products) and urine was collected over the course of 24 hours at 4, 7, 10, and 14 days post injection of Sheep Anti-Rat Fx1A Serum. Diluted urine samples were analyzed using Bradford reagent (Sigma, B6916-500 mL), Creatinine colorimetric kit (Caymen Chemical, 500701) and MesoScale Rat Kidney Injury Panel 1 (MSD, K15162C) to assess proteinuria, urinary creatinine, and urinary biomarkers respectively. Studies were terminated 14 days post injection of Sheep Anti-Rat Fx1A Serum, and at the end of the studies, kidney tissue were collected for PD evaluation. Diluted kidney homogenate samples were analyzed using the Jess Simple Western system with a rat complement C3d antibody (R&D Systems, AF2655). Abundance of CFB activation product, Ba in the urine samples were also measured as a PD marker using the Simple Western with a polyclonal antisera to human CFB (cross-reacting with rat; Quidel, A311). The peak area of the C3d or Ba band from each sample was measured by the Compass software. Percentage inhibition values were calculated using the average of negative and positive control animals.

Figure 2A:
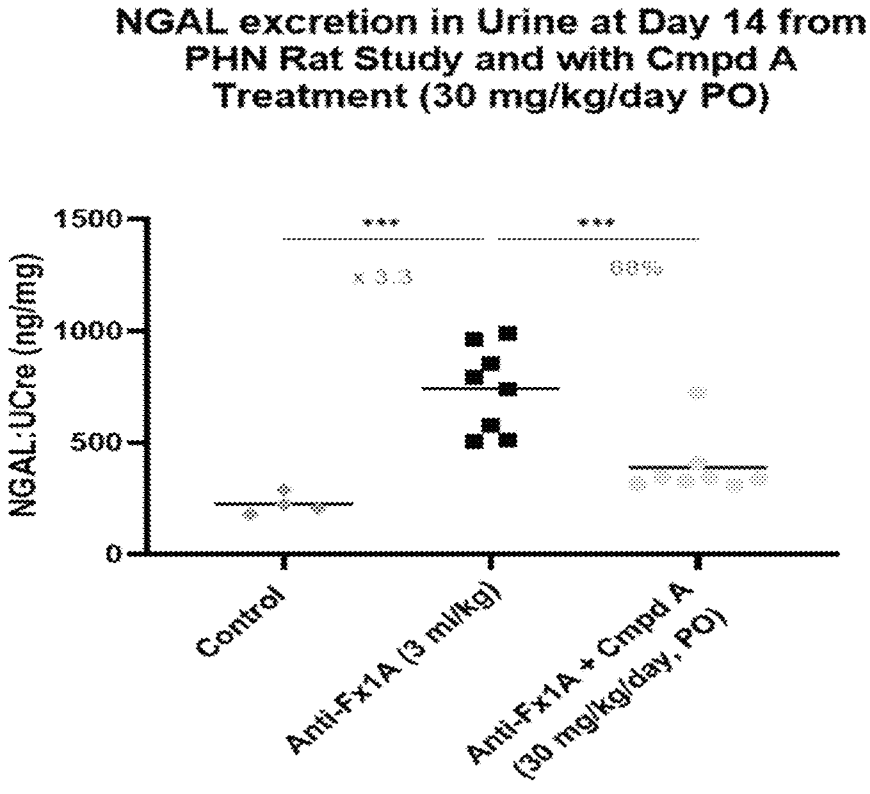
FIG. 2A depicts the kidney C3d deposition measured on day 14 of the same PHN rat study shown in FIG. 1.
Figure 2B:
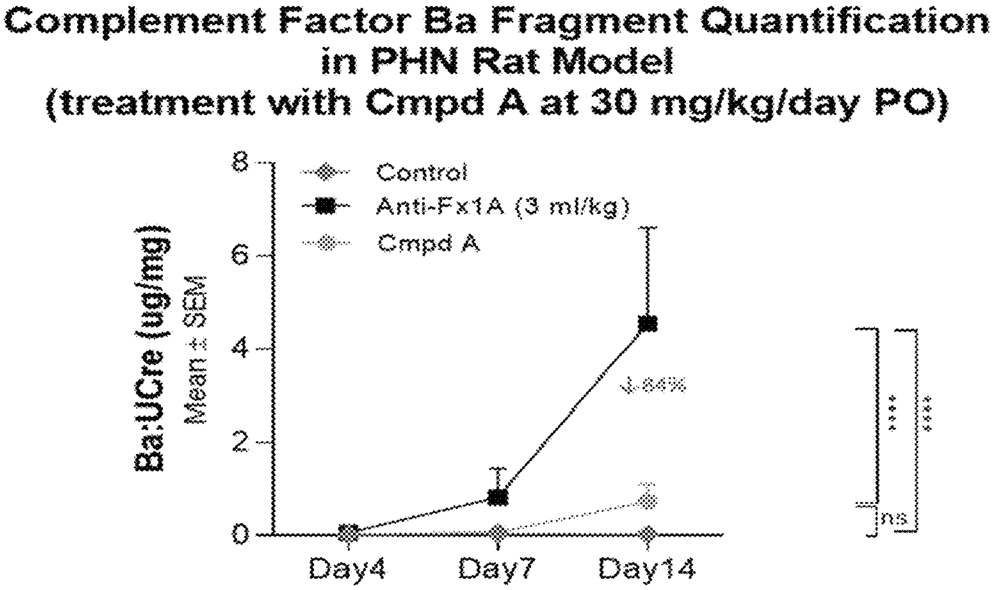
FIG. 2B depicts the urinary complement factor Ba fragment measured on day 14 of the same PHN rat study shown in FIG. 1.
Figure 3A:
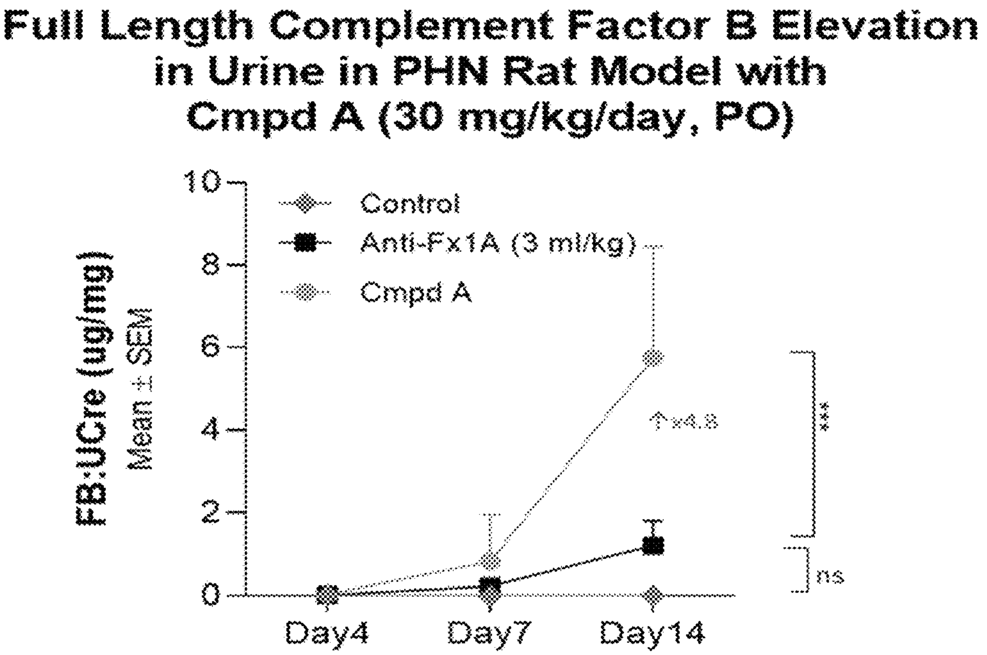
FIG. 3A depicts the urinary full-length complement factor B measured on day 14 of the PHN rat study in FIG. 1.
Figure 3B:
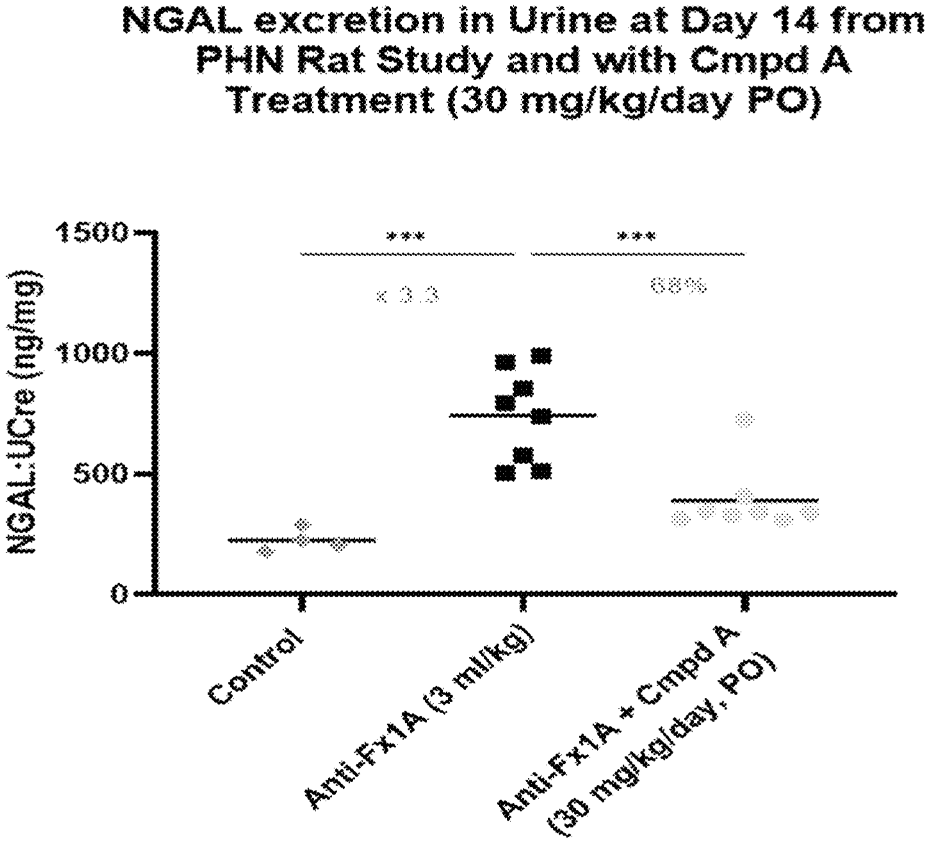
FIG. 3B depicts the urinary neutrophil gelatinase-associated lipocalin (NGAL-1) on day 14 of the same PHN rat study shown in FIG. 1.
Figure 4:
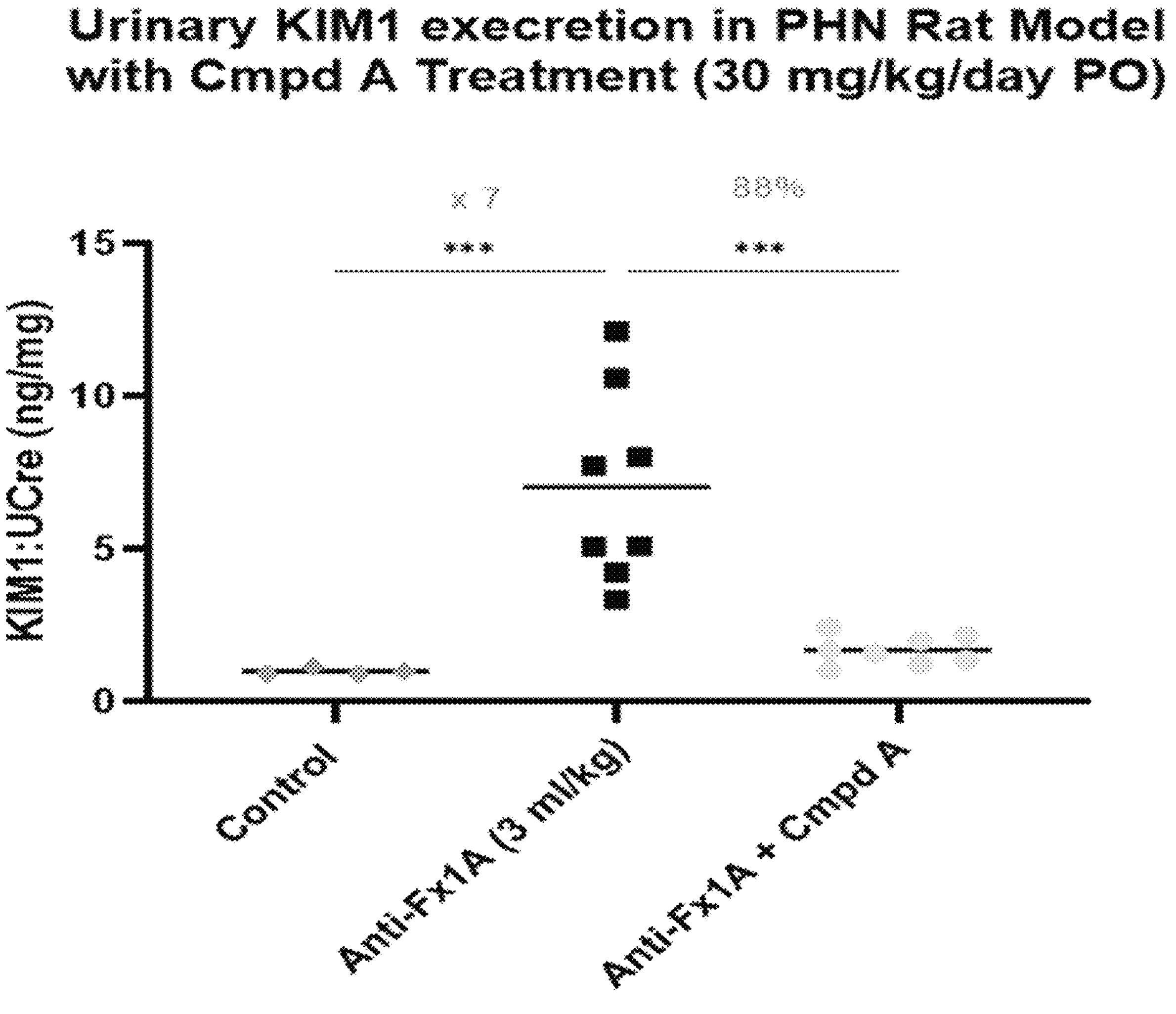
FIG. 4 depicts the urinary kidney injury molecule 1 (KIM-1) on day 14 of the PHN rat study in FIG. 1.

FIG. 1 shows that Compound A of Formula I dosed orally at 30 mg/kg/day QD reduced UPCR elevation by approx 50% over the 14-day study period vs the arm which was challenged with anti-Fx1a sera. FIG. 2A shows that administration of Compound A dosed orally at 30 mg/kg/day QD reduced the elevation in kidney C3d deposition (measured by Western analysis) by 78% versus the arm challenged with anti-Fx1a sera. FIG. 2B shows that administration of Compound A dosed orally at 30 mg/kg/day QD reduced the elevation in urinary Ba secretion (normalized to urinary creatinine) by 84% versus the arm challenged with anti-Fx1a sera. FIG. 3A shows that administration of Compound A dosed orally at 30 mg/kg/day QD increased the urinary full length complement factor B (normalized to urinary creatinine) by 4.8-fold versus the arm challenged with anti-Fx1a sera. FIG. 3B shows that administration of Compound A (dosed orally at 30 mg/kg/day QD decreased the elevation of NGAL-1 (normalized to urinary creatinine) by 68% versus the arm challenged with anti-Fx1a sera. FIG. 4 shows that administration of Compound A (dosed orally at 30 mg/kg/day QD) decreased the elevation of KIM-1 (normalized to urinary creatinine) by 88% versus the arm challenged with anti-Fx1a sera.

Example 92: Compound Permeability in a CACO-2 Cell Line

Complement Factor B (CFB) inhibitors that showed good potency in the enzymatic assay were assessed for their in vitro permeability in Caco-2 cell. Caco-2 monolayers were cultured for 21-28 days on polyethylene membranes of 96-well Corning insert plate (seeding density: 100,000 cells/cm2). Test compounds were diluted to 2 μM concentration in HBSS buffer (10 mM HEPES, pH 7.4) and added to either the apical or basolateral side of the cell monolayers and incubated at 37° C. in a cell culture incubator for 2 h. At the end of the incubation time, samples were obtained from the contralateral sides and the compound levels were assessed by liquid chromatography-tandem mass spectrometry (LC-MS/MS) assay to determine the apparent permeability coefficients Papp (A→B), Papp (B→A) and efflux ratio (ER=Papp (B→A)/Papp (A→B)).

Example 93: In Vitro Stability in Hepatocytes

Select compounds of Formula I were assessed for in vitro metabolic stability in cryopreserved hepatocyte suspensions using loss-of-parent approach. Test compounds at 0.3 μM final concentration were incubated with cryopreserved hepatocyte suspensions (rat or human; $0.1\times10^6$ cells in 0.2 mL volume) in a 96-well plate at 37° C. for up to 2 h. During the incubation, samples were obtained at different time points and analyzed by LC-MS/MS assay for the remaining parent compound. From the percent parent remaining vs. time curve, half-life, in vitro intrinsic clearance, and scaled-up clearance values were calculated. Selected compounds of Formula I were also assessed for metabolic stability in dog and monkey hepatocyte suspensions.

Example 94: CYP Inhibition Assessment of Compounds

Compounds of Formula I were first assessed in vitro for their potential to inhibit the major cytochrome P450 (CYP) enzymes CYP1A2, CYP2C9, CYP2C19, CYP2D6, and CYP3A4. Human liver microsomes (150-donor, mixed gender; 0.2 mg/mL) were incubated at 37° C. for 10 min with a mixture of respective probe substrates for each of the CYP enzymes in the presence of the test compounds at 30 μM and NADPH (cofactor; 1 mM). The reaction was quenched at the end of the incubation, and metabolite formation was assessed by LC-MS/MS, to determine the $IC_{50}$ (test compound concentration that produces 50% inhibition of the activity of a CYP enzyme). The probe substrate and the corresponding metabolite measured as well as the positive control inhibitor for each of the CYP enzymes are listed in the table below.

| CYP Enzyme | Probe Substrate | Metabolite Monitored | Positive Control |
|---|---|---|---|
| CYP1A2 | Phenacetin | Acetaminophen | α-Naphthoflavone |
| CYP2C9 | Diclofenac | 4'-hydroxy diclofenac | Sulfaphenazole |
| CYP2C19 | S-mephenytoin | 4'-hydroxy mephenytoin | (+)-N-3-benzylnirvanol |
| CYP2D6 | Dextromethorphan | Dextrorphan | Quinidine |
| CYP3A4 | Midazolam | 1'-hydroxy midazolam | Ketoconazole |

Selected compounds of Formula I were further assessed at different concentrations (e.g., 0.05-50 μM) in vitro for their potential to inhibit each of the major cytochrome P450 enzymes, such as CYP1A2, CYP2B6, CYP2C8, CYP2C9, CYP2C19, CYP2D6, and CYP3A4, directly or in a time-dependent manner (TDI). Compounds were followed up with kinact/KI determination for any CYP enzyme showing time-dependent inhibition ($IC_{50}$ shift≥1.5). The probe substrate and the corresponding metabolite measured as well as the direct and TDI positive control inhibitor for each of the CYP enzymes are listed in the table below.

| CYP Enzyme | Probe Substrate | Metabolite Monitored | Positive Control | Type of Inhibitor |
|---|---|---|---|---|
| CYP1A2 | Phenacetin | Acetaminophen | α-Naphthoflavone | Direct inhibitor |
| | | | Furafylline | TDI |
| CYP2B6 | Efavirenz | 8-hydroxy efavirenz | Orphenadrine | Direct inhibitor |
| | | | Phencyclidine | TDI |
| CYP2C8 | Amodiaquine | N-desethylamodiaquine | Montelukast | Direct inhibitor |
| | | | Gemfibrozil glucuronide | TDI |
| CYP2C9 | Diclofenac | 4'-hydroxy diclofenac | Sulfaphenazole | Direct inhibitor |
| | | | Tienilic acid | TDI |
| CYP2C19 | S-Mephenytoin | 4'-hydroxy mephenytoin | Modafinil | Direct inhibitor |
| | | | Esomeprazole | TDI |
| CYP2D6 | Dextromethorphan | Dextrorphan | Quinidine | Direct inhibitor |
| | | | Paroxetine | TDI |
| CYP3A4/5 | Testosterone | 6β-hydroxy testosterone | Ketoconazole | Direct inhibitor |
| | | | Troleandomycin | TDI |
| CYP3A4/5 | Midazolam | 1'-hydroxy midazolam | Ketoconazole | Direct inhibitor |
| | | | Troleandomycin | TDI |

Example 95: Non-Clinical Pharmacokinetic Assessment of Compounds of Formula I

Selected compounds of Formula I were evaluated for in vivo pharmacokinetics and oral bioavailability in rats. After administration of 1 mg/kg IV and 10 mg/kg PO doses in suitable formulations to rats (e.g., 60% PEG400/40% water for IV formulation, 0.5% methocel+0.1% tween 80 for PO formulation), plasma samples were obtained at different time points up to 24 h (e.g., 5 min, 15 min, 30 min, 1 h, 2 h, 4 h, 8 h and 24 h), and compound levels were quantified by LC-MS/MS. Pharmacokinetic parameters (e.g., CLp, Vdss, AUC0-24 h, % oral bioavailability) were estimated by non-compartmental analysis (NCA) of the time vs. plasma concentration data. In addition, trough concentration of the test compounds was measured in rat kidney tissues obtained at 24 h after PO administration to determine the kidney-to-plasma ratio (Kp, kidney). All compounds evaluated in rat pharmacokinetic studies were also assessed for plasma protein binding by using ultracentrifugation approach. Fraction unbound (Fu) values in rat plasma were then used to determine the unbound concentrations achieved in rat plasma.

Pharmacokinetic properties of selected compounds of Formula I were also evaluated in higher species such as beagle dogs and cynomolgus monkeys to guide human PK prediction by allometric scaling.

The embodiments described above are intended to be merely exemplary, and those skilled in the art will recognize, or will be able to ascertain using no more than routine experimentation, numerous equivalents of specific compounds, materials and procedures. All such equivalents are considered to be within the scope of the claimed subject matter and are encompassed by the appended claims. Since modifications will be apparent to those of skill in the art, it is intended that the claimed subject matter be limited only by the scope of the appended claims.

What is claimed is:

1. A compound represented by:

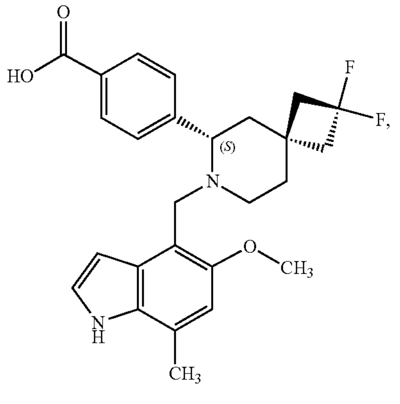

or a pharmaceutically acceptable salt thereof.

2. A pharmaceutical composition comprising a compound of claim 1, or a pharmaceutically acceptable salt thereof, and a pharmaceutically acceptable carrier.

3. The pharmaceutical composition of claim 2, wherein the pharmaceutical composition is in a solid dosage form.

4. A method of treating a disease or disorder mediated by complement factor B, comprising administering to a subject having the disease or disorder, a therapeutically effective amount of the compound of claim 1, or the pharmaceutically acceptable salt thereof, wherein the disease or disorder is age-related macular degeneration.

5. An isotopic variant of a compound represented by:

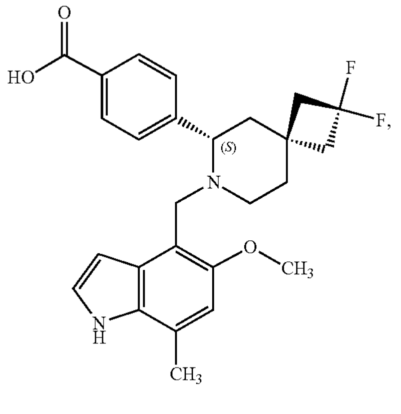

or a pharmaceutically acceptable salt thereof.

6. The pharmaceutical composition of claim 2, wherein the compound of claim 1 in the pharmaceutical composition is enantiomerically pure.

7. The pharmaceutical composition of claim 6, wherein the compound of claim 1 is more than 85% by weight in the pharmaceutical composition to the exclusion of its corresponding non-superimposable mirror image.

8. The pharmaceutical composition of claim 6, wherein the compound of claim 1 is more than 90% by weight in the pharmaceutical composition to the exclusion of its corresponding non-superimposable mirror image.

9. The pharmaceutical composition of claim 6, wherein the compound of claim 1 is more than 95% by weight in the pharmaceutical composition to the exclusion of its corresponding non-superimposable mirror image.

10. A method of treating a disease or disorder mediated by complement factor B, comprising administering to a subject having the disease or disorder the pharmaceutical composition of claim 2, wherein the disease or disorder is age-related macular degeneration.

11. A method of treating a disease or disorder mediated by complement factor B, comprising administering to a subject having the disease or disorder, a therapeutically effective amount of the compound of claim 1, or the pharmaceutically acceptable salt thereof, wherein the disease or disorder is geographic atrophy.

12. A method of treating a disease or disorder mediated by complement factor B, comprising administering to a subject having the disease or disorder the pharmaceutical composition of claim 2, wherein the disease or disorder is geographic atrophy.

13. A method of treating a disease or disorder mediated by complement factor B, comprising administering to a subject having the disease or disorder, a therapeutically effective amount of the compound of claim 1, or the pharmaceutically acceptable salt thereof, wherein the disease or disorder is focal segmental glomerulosclerosis.

14. A method of treating a disease or disorder mediated by complement factor B, comprising administering to a subject having the disease or disorder the pharmaceutical composition of claim 2, wherein the disease or disorder is focal segmental glomerulosclerosis.

15. A method of treating a disease or disorder mediated by complement factor B, comprising administering to a subject having the disease or disorder, a therapeutically effective amount of the compound of claim 1, or the pharmaceutically acceptable salt thereof, wherein the disease or disorder is diabetic nephropathy.

16. A method of treating a disease or disorder mediated by complement factor B, comprising administering to a subject having the disease or disorder the pharmaceutical composition of claim 2, wherein the disease or disorder is diabetic nephropathy.

* * * * *